US008932993B1

(12) United States Patent
Ward et al.

(10) Patent No.: US 8,932,993 B1
(45) Date of Patent: *Jan. 13, 2015

(54) METHOD OF TESTING FOR ENDOMETRIOSIS AND TREATMENT THEREFOR

(71) Applicants: Kenneth Ward, Salt Lake City, UT (US); Rakesh N. Chettier, West Jordan, UT (US); Hans Albertsen, Salt Lake City, UT (US)

(72) Inventors: Kenneth Ward, Salt Lake City, UT (US); Rakesh N. Chettier, West Jordan, UT (US); Hans Albertsen, Salt Lake City, UT (US)

(73) Assignee: Juneau Biosciences, LLC., Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 13/788,913

(22) Filed: Mar. 7, 2013

Related U.S. Application Data

(63) Continuation-in-part of application No. 12/056,754, filed on Mar. 27, 2008, now abandoned, and a continuation-in-part of application No. 12/120,322, filed on May 14, 2008, now abandoned, and a continuation-in-part of application No. 12/765,643, filed on Apr. 22, 2010, and a continuation-in-part of application No. 13/159,132, filed on Jun. 13, 2011, which is a continuation-in-part of application No. 13/071,598, filed on Mar. 25, 2011, now abandoned, application No. 13/788,913, which is a continuation-in-part of application No. 13/681,575, filed on Nov. 20, 2012, now abandoned, which is a continuation of application No. 13/602,409, filed on Sep. 4, 2012, now abandoned, application No. 13/788,913, which is a continuation-in-part of application No. 13/603,284, filed on Sep. 4, 2012, and a continuation-in-part of application No. 13/680,414, filed on Nov. 19, 2012, now abandoned, which is a continuation of application No. 13/603,297, filed on Sep. 4, 2012, now abandoned, application No. 13/788,913, which is a continuation-in-part of application No. 13/735,828, filed on Jan. 7, 2013, now abandoned, which is a continuation of application No. 13/652,018, filed on Oct. 15, 2012, now abandoned.

(60) Provisional application No. 60/943,193, filed on Jun. 11, 2007, provisional application No. 61/171,717, filed on Apr. 22, 2009, provisional application No. 61/245,808, filed on Sep. 25, 2009, provisional application No. 61/318,145, filed on Mar. 26, 2010, provisional application No. 61/530,944, filed on Sep. 3, 2011, provisional application No. 61/530,948, filed on Sep. 3, 2011, provisional application No. 61/530,945, filed on Sep. 3, 2011, provisional application No. 61/530,947, filed on Sep. 3, 2011, provisional application No. 61/547,624, filed on Oct. 14, 2011, provisional application No. 61/717,048, filed on Oct. 22, 2012, provisional application No. 61/717,053, filed on Oct. 22, 2012, provisional application No. 61/721,219, filed on Nov. 1, 2012.

(51) Int. Cl.
*C12Q 1/68* (2006.01)
*C07H 21/04* (2006.01)

(52) U.S. Cl.
CPC ........ *C12Q 1/6883* (2013.01); *C12Q 2600/156* (2013.01)
USPC .......... 506/16; 536/23.1; 536/24.5; 435/6.11; 435/6.13; 435/6.14

(58) Field of Classification Search
CPC ................... G01N 33/6893; G01N 2333/4725
USPC ............................................. 435/7.1; 436/518
See application file for complete search history.

(56) References Cited

U.S. PATENT DOCUMENTS

| | | | |
|---|---|---|---|
| 6,525,187 B1 | 2/2003 | El Shami et al. | 536/23.5 |
| 6,540,980 B1 | 4/2003 | Blumenthal et al. | 424/9.43 |
| 6,586,569 B1 | 7/2003 | Starzinski-Powitz et al. | 530/300 |
| 7,368,533 B2 | 5/2008 | El Shami et al. | 530/350 |
| 7,399,598 B2 | 7/2008 | Yang et al. | 435/7.1 |
| 2002/0127555 A1 | 9/2002 | Baban et al. | 435/6 |
| 2002/0147155 A1 | 10/2002 | Foster et al. | 514/23 |
| 2002/0192647 A1 | 12/2002 | Smith | 435/6 |
| 2003/0077589 A1 | 4/2003 | Hess-Stumpp et al. | 435/6 |
| 2003/0109018 A1 | 6/2003 | Starzinski-Powitz et al. | 435/195 |
| 2003/0124551 A1 | 7/2003 | Pappa et al. | 435/6 |
| 2003/0166014 A1 | 9/2003 | Timms | 435/7.2 |
| 2003/0219835 A1 | 11/2003 | Gosselin et al. | 435/7.2 |

(Continued)

FOREIGN PATENT DOCUMENTS

| | | | |
|---|---|---|---|
| CA | 2329527 | 5/1999 | C12Q 1/68 |
| CA | 2399259 | 8/2001 | C12Q 1/68 |

(Continued)

OTHER PUBLICATIONS

May et al (Science (1988) vol. 241, p. 1441).*

(Continued)

*Primary Examiner* — Janet Epps-Smith
(74) *Attorney, Agent, or Firm* — Michael R. Schramm

(57) ABSTRACT

The present invention relates to novel genetic markers associated with endometriosis and risk of developing endometriosis, and methods and materials for determining whether a human subject has endometriosis or is at risk of developing endometriosis and the use of such risk information in selectively administering a treatment that at least partially prevents or compensates for an endometriosis related symptom.

36 Claims, 2 Drawing Sheets

(56) References Cited

U.S. PATENT DOCUMENTS

| | | | |
|---|---|---|---|
| 2004/0048919 A1 | 3/2004 | Dreon et al. | 514/458 |
| 2004/0052787 A1 | 3/2004 | King et al. | 424/144.1 |
| 2004/0091912 A1 | 5/2004 | Smith | 435/6 |
| 2004/0210400 A1* | 10/2004 | Konvicka | 702/20 |
| 2005/0130182 A1 | 6/2005 | Messer et al. | 435/6 |
| 2005/0142580 A1 | 6/2005 | Tay et al. | 435/6 |
| 2005/0214836 A1 | 9/2005 | Nakamura et al. | 435/6 |
| 2006/0014166 A1 | 1/2006 | Cohen et al. | 435/6 |
| 2006/0057584 A1 | 3/2006 | Baban et al. | 435/6 |
| 2007/0015160 A1 | 1/2007 | Kuroda et al. | 435/6 |
| 2007/0087386 A1 | 4/2007 | Yang et al. | 435/7.1 |
| 2007/0092484 A1 | 4/2007 | Levine et al. | 424/85.1 |
| 2007/0264270 A1 | 11/2007 | Barnhart et al. | 424/184.1 |
| 2007/0287676 A1 | 12/2007 | Guo et al. | 514/43 |
| 2008/0008650 A1 | 1/2008 | Fukuda et al. | 424/9.1 |
| 2008/0187527 A1 | 8/2008 | Starzinski-Powitz et al. | 424/130 |
| 2008/0241852 A1 | 10/2008 | Messer et al. | 435/7.1 |
| 2008/0318237 A1 | 12/2008 | Giudice | 435/6 |

FOREIGN PATENT DOCUMENTS

| | | | |
|---|---|---|---|
| CA | 2497132 | 3/2004 | C12Q 1/68 |
| CA | 2596932 | 8/2006 | C12Q 1/68 |
| CA | 2607341 | 11/2006 | C12Q 1/68 |
| CA | 2681933 | 11/2007 | G01N 33/68 |
| CA | 2676415 | 10/2008 | C40B 40/06 |
| CN | 101334410 | 12/2008 | G01N 33/68 |
| JP | 2009168646 | 7/2009 | G01N 27/62 |
| WO | WO99063079 | 12/1999 | C12Q 1/68 |
| WO | WO01032920 | 5/2001 | C12Q 1/68 |
| WO | WO01062959 | 8/2001 | C12Q 1/68 |
| WO | WO2004024952 | 3/2004 | C12Q 1/68 |
| WO | WO2006091254 | 8/2006 | C12Q 1/68 |
| WO | WO2006116873 | 11/2006 | C12Q 1/68 |
| WO | WO2007126982 | 11/2007 | G01N 33/68 |
| WO | WO2008049175 | 5/2008 | G01N 33/68 |
| WO | WO2008103812 | 8/2008 | C07K 14/745 |
| WO | WO2008123901 | 10/2008 | C12Q 1/68 |
| WO | WO2009068254 | 6/2009 | G01N 33/68 |
| WO | WO20100010951 | 1/2010 | C12Q 1/68 |

OTHER PUBLICATIONS

Colette (Exper Opin Investig Drugs (2011) vol. 20, pates 917-931).*
Hegele (Arterioscler Thromb Vasc Biol. 2002;22:1058-1061).*
Lucentini J. (the Scientist (Dec. 20, 2004), p. 20).*
Benner et al (Trends in Genetics (2001) vol. 17, pp. 414-418).*
Weiser (Fertility and Sterility (2002) vol. 77, pp. 309-312).*
dbSNP ss13045391 (http://www.ncbi.nlm.nih.gov/projects/SNP/snp_ss.cgi?subsnp_id=13045391, submitted Oct. 22, 2003.*
Kennedy et al (Human reproduction (2005) vol. 20, pp. 2698-2704).*
Pennisi (E. Science (1998) vol. 281, No. 5384, pp. 1787-1789).*
U.S. Appl. No. 60/948,565, filed Jul. 9, 2007, Belouchi et al.
U.S. Appl. No. 60/899,615, filed Feb. 6, 2007, Belouchi et al.
U.S. Appl. No. 60/875,527, filed Jun. 6, 2007, Goldman et al.
U.S. Appl. No. 60/788,058, filed Apr. 3, 2007, Goldman et al.
Altinkaya SO, et al. Vascular endothelial growth factor +405 C/G polymorphism is highly associated with an increased risk of endometriosis in Turkish women. Arch Gynecol Obstet. Dec. 30, 2009.
Ammendola M, et al. Acid phosphatase locus 1 genetic polymorphism, endometriosis, and allergy. Fertil Steril. Oct. 2008;90(4):1203-1205.
Arvanitis DA, et al. CYP1A1, CYP19, and GSTM1 polymorphisms increase the risk of endometriosis. Fertil Steril. Mar. 2003;79 Suppl 1:702-709.
Asghar T, et al. The tumor necrosis factor-alpha promoter—1031C polymorphism is associated with decreased risk of endometriosis in a Japanese population. Hum Reprod. Nov. 2004;19(11):2509-2514.
Babu KA, et al. GSTM1, GSTT1 and CYP1A1 detoxification gene polymorphisms and their relationship with advanced stages of endometriosis in South Indian women. Pharmacogenet Genomics. Mar. 2005;15(3):167-172.
Bedaiwy MA, et al. Genetic polymorphism in the fibrinolytic system and endometriosis. Obstet Gynecol. Jul. 2006;108(1):162-168.
Bhanoori M, et al. The G2964A 3'-untranslated region polymorphism of the signal transducer and activator of transcription 6 gene is associated with endometriosis in South Indian women. Hum Reprod. Apr. 2007;22(4):1026-1030.
Bhanoori M, et al. The vascular endothelial growth factor (VEGF) +405G>C 5'-untranslated region polymorphism and increased risk of endometriosis in South Indian women: a case control study. Hum Reprod. Jul. 2005;20(7):1844-1849.
Bianco B, et al. +1730 G/A polymorphism of the estrogen receptor beta gene (ERbeta) may be an important genetic factor predisposing to endometriosis. Acta Obstet Gynecol Scand. 2009;88(12):1397-1401.
Borghese B, et al. Genetic polymorphisms of matrix metalloproteinase 12 and 13 genes are implicated in endometriosis progression. Hum Reprod. May 2008;23(5):1207-1213.
Caballero V, et al. Preliminary molecular genetic analysis of the Receptor Interacting Protein 140 (RIP140) in women affected by endometriosis. J Exp Clin Assist Reprod. Aug. 30, 2005;2:11.
Cayan F, et al. Association of G1057D variant of insulin receptor substrate-2 with endometriosis. Fertil Steril. Oct. 28, 2009.
Chae SJ, et al. Tumor necrosis factor (TNF)-TNF receptor gene polymorphisms and their serum levels in Korean women with endometriosis. Am J Reprod Immunol. Nov. 2008;60(5):432-439.
Chang CC, et al. The proline form of p53 codon 72 polymorphism is associated with endometriosis. Fertil Steril. Jan. 2002;77(1):43-45.
Ertunc D, et al. Glutathione-S-transferase P1 gene polymorphism and susceptibility to endometriosis. Hum Reprod. Aug. 2005;20(8):2157-2161.
Gentilini D, et al. Progesterone receptor +331G/A polymorphism in endometriosis and deep-infiltrating endometriosis. Fertil Steril. Oct. 2008;90(4):1243-1245.
Gomes Fm, et al. PTPN22 C1858T polymorphism in women with endometriosis. Am J Reprod Immunol. Mar. 1, 2010;63(3):227-232.
Govindan S, et al. Estrogen receptor-alpha gene (T/C) Pvu II polymorphism in endometriosis and uterine fibroids. Dis Markers. 2009;26(4):149-154.
Han YJ, et al. Haplotype analysis of the matrix metalloproteinase-9 gene associated with advanced-stage endometriosis. Fertil Steril. Jun. 2009;91(6):2324-2330.
Hsieh YY, et al. Angiotensin I-converting enzyme ACE 2350*G and ACE-240*T-related genotypes and alleles are associated with higher susceptibility to endometriosis. Mol Hum Reprod. Jan. 2005;11(1):11-14.
Hsieh YY, et al. Angiotensin I-converting enzyme insertion-related genotypes and allele are associated with higher susceptibility of endometriosis and leiomyoma. Mol Reprod Dev. Jul. 2007;74(7):808-814.
Hsieh YY, et al. Estrogen receptor alpha dinucleotide repeat and cytochrome P450c17alpha gene polymorphisms are associated with susceptibility to endometriosis. Fertil Steril. Mar. 2005;83(3):567-572.
Hsieh YY, et al. Glutathione S-transferase M1*null genotype but not myeloperoxidase promoter G-463A polymorphism is associated with higher susceptibility to endometriosis. Mol Hum Reprod. Oct. 2004;10(10):713-717.
Hsieh YY, et al. Interleukin-2 receptor beta (IL-2R beta)-627*C homozygote but not IL-12R beta 1 codon 378 or IL-18 105 polymorphism is associated with higher susceptibility to endometriosis. Fertil Steril. Aug. 2005;84(2):510-512.
Hsieh YY, et al. T homozygote and allele of epidermal growth factor receptor 2073 gene polymorphism are associated with higher susceptibility to endometriosis and leiomyomas. Fertil Steril. Mar. 2005;83(3):796-799.
Ivashchenko TE, et al. Analysis of the polymorphic alleles of genes encoding phase 1 and phase 2 detoxication enzymes in patients with endometriosis. Genetika. Apr. 2003;39(4):427-430.
Kim JG, et al. Association between human alpha 2-Heremans Schmidt glycoprotein (AHSG) polymorphism and endometriosis in Korean women. Fertil Steril. Dec. 2004;82(6):1497-1500.
Kim SH, et al. Association between susceptibility to advanced stage endometriosis and the genetic polymorphisms of aryl hydrocarbon

(56) References Cited

OTHER PUBLICATIONS receptor repressor and glutathione-S-transferase T1 genes, Hum Reprod. May 18, 2007;22(7):1866-1870.

Kim SH, et al. Vascular endothelial growth factor gene +405 C/G polymorphism is associated with susceptibility to advanced stage endometriosis. Hum Reprod. Oct. 2005;20(10):2904-2908.

Kitawaki J, et al. Association of HLA class I and class II alleles with susceptibility to endometriosis. Hum Immunol Nov. 2002;63(11):1033-1038.

Kitawaki J, et al. Genetic contribution of the interleukin-10 promoter polymorphism in endometriosis susceptibility. Am J Reprod Immunol. Jan. 2002;47(1):12-18.

Kitawaki J, et al. Interferon-gamma gene dinucleotide (CA) repeat and interleukin-4 promoter region (-590C/T) polymorphisms in Japanese patients with endometriosis. Hum Reprod. Aug. 2004;19(8):1765-1769.

Kitawaki J, et al. Synergistic effect of interleukin-6 promoter (IL6 -634C/G) and intercellular adhesion molecule-1 (ICAM-1 469K/E) gene polymorphisms on the risk of endometriosis in Japanese women. Am J Reprod Immunol. Oct. 2006;56(4):267-274.

Kiyomizu M, et al. Association of two polymorphisms in the peroxisome proliferator-activated receptor-gamma gene with adenomyosis, endometriosis, and leiomyomata in Japanese women. J Soc Gynecol Investig. Jul. 2006;13(5):372-377.

Lattuada D, et al. Analysis of the codon 72 polymorphism of the TP53 gene in patients with endometriosis. Mol Hum Reprod. Sep. 2004;10(9):651-654.

Lattuada D, et al. Genetics of endometriosis: a role for the progesterone receptor gene polymorphism PROGINS? Clin Endocrinol (Oxf). Aug. 2004;61(2):190-194.

Lee GH, et al. Association of tumor necrosis factor-{alpha} gene polymorphisms with advanced stage endometriosis. *Hum Reprod.* Apr. 2008;23(4):977-981.

Liu Q, et al. Association of polymorphisms -1154G/A and -2578C/A in the vascular endothelial growth factor gene with decreased risk of endometriosis in Chinese women. *Hum Reprod.* Jun. 16, 2009.

Shan K, et al. Association of three single nucleotide polymorphisms of the E-cadherin gene with endometriosis in a Chinese population. Reproduction. Aug. 2007;134(2):373-378.

Shan K, et al. The function of the SNP in the MMP1 and MMP3 promoter in susceptibility to endometriosis in China. Mol Hum Reprod. Jun. 2005;11(6):423-427.

Teramoto M, et al. Genetic contribution of tumor necrosis factor (TNF)-alpha gene promoter (-1031, -863 and -857) and TNF receptor 2 gene polymorphisms in endometriosis susceptibility. Am J Reprod Immunol. May 2004;51(5):352-357.

Tsuchiya M, et al. Analysis of the AhR, ARNT, and AhRR gene polymorphisms: genetic contribution to endometriosis susceptibility and severity. Fertil Steril. Aug. 2005;84(2):454-458.

Tsuchiya M, et al. Association between endometriosis and genetic polymorphisms of the estradiol-synthesizing enzyme genes HSD17B1 and CYP19. Hum Reprod. Apr. 2005;20(4):974-978.

Vigano P, et al. Intercellular adhesion molecule-1 (ICAM-1) gene polymorphisms in endometriosis. Mol Hum Reprod. Jan. 2003;9(1):47-52.

Vijaya Lakshmi K, et al. Tumor necrosis factor alpha -C850T polymorphism is significantly associated with endometriosis in Asian Indian women. *Fertil Steril.* Apr. 24, 2009.

Wang Z, et al. Polymorphisms in the estrogen receptor beta gene but not estrogen receptor alpha gene affect the risk of developing endometriosis in a Japanese population. Fertil Steril. Jun. 2004;81(6):1650-1656.

Wu YL, et al. Sensitive and specific real-time polymerase chain reaction assays to accurately determine copy number variations (CNVs) of human complement C4A, C4B, C4-long, C4-short, and RCCX modules: elucidation of C4 CNVs in 50 consanguineous subjects with defined HLA genotypes. J Immunol. Sep. 1, 2007;179(5):3012-3025.

Zervou S, et al. The Glu298-->Asp polymorphism of the endothelial nitric oxide synthase gene is associated with endometriosis. Fertil Steril. Dec. 2003;80(6):1524-1525.

Zhang X, et al. Interleukin-10 gene promoter polymorphisms and their protein production in peritoneal fluid in patients with endometriosis. *Mol Hum Reprod.* Feb. 2007;13(2):135-140.

Nnoaham et al, Developing Symptom-based Predictive Models of Endometriosis as a Clinical Screening Tool: Results from a Multicenter Study, Fertility and Sterility, Sep. 2012, vol. 98, No. 3, pp. 692-701e5.

Albertsen et al, GWAS Link Loci to Endometriosis, PLOS One, Mar. 2013, vol. 8, Iss. 3 e58257, pp. 1-8.

\* cited by examiner

Three Endometriosis Related Clinical Questions:

Odds Ratio

1) Menarche after age 14? (Y/N)       0.3 (0.1 – 0.6)

2) Dysmenorrhea? (Y/N)             2.6 (1.1 – 6.2)

3) Previous pregnancy? (Y/N)       0.65 (0.49 – 0.87)

SEQUENCE LISTING

<160> NUMBER OF SEQ ID NOS: 1398

<210> SEQ ID NO 1
<211> LENGTH: 33
<212> TYPE: DNA
<213> ORGANISM: Homo Sapiens

<400> SEQUENCE: 1
aaggatcatc ttggctrgag gagggatccc aac                         33

<210> SEQ ID NO 2
<211> LENGTH: 33
<212> TYPE: DNA
<213> ORGANISM: Homo Sapiens

<400> SEQUENCE: 2
cctcgcctta caactarttc ctgcctttcg tcc                         33

<210> SEQ ID NO 3
<211> LENGTH: 33
<212> TYPE: DNA
<213> ORGANISM: Homo Sapiens

<400> SEQUENCE: 3
gagaattgag ttgaaamttt aaagaaggag ttg                         33

<210> SEQ ID NO 4
<211> LENGTH: 33
<212> TYPE: DNA
<213> ORGANISM: Homo Sapiens

<400> SEQUENCE: 4
gccaaaaccc agaggcrata gtgttggttt ttc                         33

<210> SEQ ID NO 5
<211> LENGTH: 33
<212> TYPE: DNA
<213> ORGANISM: Homo Sapiens

<400> SEQUENCE: 5
ccatttaatc catagtmctc ctctctccta tct                         33

<210> SEQ ID NO 6
<211> LENGTH: 33
<212> TYPE: DNA
<213> ORGANISM: Homo Sapiens

<400> SEQUENCE: 6
gcacatgaaa gtttaartag cactactacc aga                         33

<210> SEQ ID NO 7
<211> LENGTH: 33
<212> TYPE: DNA
<213> ORGANISM: Homo Sapiens

<400> SEQUENCE: 7
tcatgaacta tgtaggraag gaagtgaaat ttg                         33

<210> SEQ ID NO 8
<211> LENGTH: 33
<212> TYPE: DNA
<213> ORGANISM: Homo Sapiens

<400> SEQUENCE: 8
gaaacaactg ctcaggrcat tttgcaaatt tac                                33

<210> SEQ ID NO 9
<211> LENGTH: 33
<212> TYPE: DNA
<213> ORGANISM: Homo Sapiens

<400> SEQUENCE: 9
atcctttctc agcaggrccc attatttctc att                                33

<210> SEQ ID NO 10
<211> LENGTH: 33
<212> TYPE: DNA
<213> ORGANISM: Homo Sapiens

<400> SEQUENCE: 10
acagatagtt cctatgrgct agacttggtc aga                                33

<210> SEQ ID NO 11
<211> LENGTH: 33
<212> TYPE: DNA
<213> ORGANISM: Homo Sapiens

<400> SEQUENCE: 11
gaactgcata gtcccarctt acaaagaatc agc                                33

<210> SEQ ID NO 12
<211> LENGTH: 33
<212> TYPE: DNA
<213> ORGANISM: Homo Sapiens

<400> SEQUENCE: 12
agagcttagt agcttcraca gaaaccacat gtg                                33

<210> SEQ ID NO 13
<211> LENGTH: 33
<212> TYPE: DNA
<213> ORGANISM: Homo Sapiens

<400> SEQUENCE: 13
agtaatagac atttacrttt cctccaggtt ttt                                33

<210> SEQ ID NO 14
<211> LENGTH: 33
<212> TYPE: DNA
<213> ORGANISM: Homo Sapiens

<400> SEQUENCE: 14
tctagagtta aatcctrtct ggggactctg ggc                                33

<210> SEQ ID NO 15
<211> LENGTH: 33
<212> TYPE: DNA
<213> ORGANISM: Homo Sapiens

<400> SEQUENCE: 15
cactcagaag agagtarcta gagtaagaag tca                                33

<210> SEQ ID NO 16
<211> LENGTH: 33
<212> TYPE: DNA
<213> ORGANISM: Homo Sapiens

<400> SEQUENCE: 16
gaaatgggaa actatcrtag ggttctttgc aga                33

<210> SEQ ID NO 17
<211> LENGTH: 33
<212> TYPE: DNA
<213> ORGANISM: Homo Sapiens

<400> SEQUENCE: 17
tgctgcaaag tgatttsgaa gttcaacctc atg                33

<210> SEQ ID NO 18
<211> LENGTH: 33
<212> TYPE: DNA
<213> ORGANISM: Homo Sapiens

<400> SEQUENCE: 18
gctgctcctg gtccctmttg taaggtcctg tga                33

<210> SEQ ID NO 19
<211> LENGTH: 33
<212> TYPE: DNA
<213> ORGANISM: Homo Sapiens

<400> SEQUENCE: 19
gatcatacga tctgtcrcaa ctgctaaatg tgc                33

<210> SEQ ID NO 20
<211> LENGTH: 33
<212> TYPE: DNA
<213> ORGANISM: Homo Sapiens

<400> SEQUENCE: 20
gagtaagaca taggagrtca aggtaggagg att                33

<210> SEQ ID NO 21
<211> LENGTH: 33
<212> TYPE: DNA
<213> ORGANISM: Homo Sapiens

<400> SEQUENCE: 21
atttatcatg ttctctrgta ggaatgctcc cca                33

<210> SEQ ID NO 22
<211> LENGTH: 33
<212> TYPE: DNA
<213> ORGANISM: Homo Sapiens

<400> SEQUENCE: 22
aaaatctcag ctccacmtca gccccaatta tct                33

<210> SEQ ID NO 23
<211> LENGTH: 33
<212> TYPE: DNA
<213> ORGANISM: Homo Sapiens

<400> SEQUENCE: 23
tatacagaaa cacaaamccc atcttggatc act                33

<210> SEQ ID NO 24
<211> LENGTH: 33
<212> TYPE: DNA
<213> ORGANISM: Homo Sapiens

```
<400> SEQUENCE: 24
tattaatctt tttcacmtca gcacagcaga act                                  33

<210> SEQ ID NO 25
<211> LENGTH: 33
<212> TYPE: DNA
<213> ORGANISM: Homo Sapiens

<400> SEQUENCE: 25
ttcgtaacta cgatgamttt ctcggttaag agt                                  33

<210> SEQ ID NO 26
<211> LENGTH: 33
<212> TYPE: DNA
<213> ORGANISM: Homo Sapiens

<400> SEQUENCE: 26
agttttgttt cacaggrcta aagcctgaac aga                                  33

<210> SEQ ID NO 27
<211> LENGTH: 33
<212> TYPE: DNA
<213> ORGANISM: Homo Sapiens

<400> SEQUENCE: 27
cgggcggcgc ggacccmaag tccgagaagc agt                                  33

<210> SEQ ID NO 28
<211> LENGTH: 33
<212> TYPE: DNA
<213> ORGANISM: Homo Sapiens

<400> SEQUENCE: 28
aaaaagaatc agaaatrtct ggtgcatgga gcc                                  33

<210> SEQ ID NO 29
<211> LENGTH: 33
<212> TYPE: DNA
<213> ORGANISM: Homo Sapiens

<400> SEQUENCE: 29
gacctccagc aggggcrtgg ccagtgggtg cca                                  33

<210> SEQ ID NO 30
<211> LENGTH: 33
<212> TYPE: DNA
<213> ORGANISM: Homo Sapiens

<400> SEQUENCE: 30
tagtttccct ggaaacrtat atctttgtac act                                  33

<210> SEQ ID NO 31
<211> LENGTH: 33
<212> TYPE: DNA
<213> ORGANISM: Homo Sapiens

<400> SEQUENCE: 31
gtgcaatgta tgaggtrtaa attaatgcag cct                                  33

<210> SEQ ID NO 32
<211> LENGTH: 33
<212> TYPE: DNA
```

<213> ORGANISM: Homo Sapiens

<400> SEQUENCE: 32
ttattttgga gtcacaraga cacttggctt ttt                    33

<210> SEQ ID NO 33
<211> LENGTH: 33
<212> TYPE: DNA
<213> ORGANISM: Homo Sapiens

<400> SEQUENCE: 33
gtgctctagc tgcaagrcag gtggaaaaag tgt                    33

<210> SEQ ID NO 34
<211> LENGTH: 33
<212> TYPE: DNA
<213> ORGANISM: Homo Sapiens

<400> SEQUENCE: 34
agccagcacc acctggrtgg ggtcattggc gag                    33

<210> SEQ ID NO 35
<211> LENGTH: 33
<212> TYPE: DNA
<213> ORGANISM: Homo Sapiens

<400> SEQUENCE: 35
gtttgctctc actcttmata caatcgccaa aat                    33

<210> SEQ ID NO 36
<211> LENGTH: 33
<212> TYPE: DNA
<213> ORGANISM: Homo Sapiens

<400> SEQUENCE: 36
taggggatct cattgcmcag taaaataggc gac                    33

<210> SEQ ID NO 37
<211> LENGTH: 33
<212> TYPE: DNA
<213> ORGANISM: Homo Sapiens

<400> SEQUENCE: 37 gttccattttt gtagccragg atataaaagc tca                   33

<210> SEQ ID NO 38
<211> LENGTH: 33
<212> TYPE: DNA
<213> ORGANISM: Homo Sapiens

<400> SEQUENCE: 38
agagacttgg gtacacmgag aggggatgtc tat                    33

<210> SEQ ID NO 39
<211> LENGTH: 33
<212> TYPE: DNA
<213> ORGANISM: Homo Sapiens

<400> SEQUENCE: 39
gggcggaggg gaggcgrgag atttctgagc tcc                    33

<210> SEQ ID NO 40
<211> LENGTH: 33

```
<212> TYPE: DNA
<213> ORGANISM: Homo Sapiens

<400> SEQUENCE: 40
cactgcttct accccamatt gacatccatc ttt                                    33

<210> SEQ ID NO 41
<211> LENGTH: 33
<212> TYPE: DNA
<213> ORGANISM: Homo Sapiens

<400> SEQUENCE: 41
tgagagaata tgacacmttc ttcctttaga gga                                    33

<210> SEQ ID NO 42
<211> LENGTH: 33
<212> TYPE: DNA
<213> ORGANISM: Homo Sapiens

<400> SEQUENCE: 42 gctataccte ccaatcrtca acctgtagaa cat                                    33

<210> SEQ ID NO 43
<211> LENGTH: 33
<212> TYPE: DNA
<213> ORGANISM: Homo Sapiens

<400> SEQUENCE: 43
tgctggtcag gatggartat gttatcagag ccc                                    33

<210> SEQ ID NO 44
<211> LENGTH: 33
<212> TYPE: DNA
<213> ORGANISM: Homo Sapiens

<400> SEQUENCE: 44
agaaccaggt agagaargct ggaggagccg cca                                    33

<210> SEQ ID NO 45
<211> LENGTH: 33
<212> TYPE: DNA
<213> ORGANISM: Homo Sapiens

<400> SEQUENCE: 45
acagcgtctc ctcatcragg ataagaccac aga                                    33

<210> SEQ ID NO 46
<211> LENGTH: 33
<212> TYPE: DNA
<213> ORGANISM: Homo Sapiens

<400> SEQUENCE: 46
tgctgcccca ccccatmctc caatttttat act                                    33

<210> SEQ ID NO 47
<211> LENGTH: 33
<212> TYPE: DNA
<213> ORGANISM: Homo Sapiens

<400> SEQUENCE: 47
aggtcaaggg caccagrttc atttcagccc tta                                    33

<210> SEQ ID NO 48
```

```
<211> LENGTH: 33
<212> TYPE: DNA
<213> ORGANISM: Homo Sapiens

<400> SEQUENCE: 48
aattcttaat gagaaartct cttggaggaa atg                                  33

<210> SEQ ID NO 49
<211> LENGTH: 33
<212> TYPE: DNA
<213> ORGANISM: Homo Sapiens

<400> SEQUENCE: 49
atgcacacag aagcccrgcc ggtatcccca cag                                  33

<210> SEQ ID NO 50
<211> LENGTH: 33
<212> TYPE: DNA
<213> ORGANISM: Homo Sapiens

<400> SEQUENCE: 50
ccctgatgat atggttrtca gaatgtattt tca                                  33

<210> SEQ ID NO 51
<211> LENGTH: 33
<212> TYPE: DNA
<213> ORGANISM: Homo Sapiens

<400> SEQUENCE: 51
ggttctccga gaggtcrctc ctggatgtag ggg                                  33

<210> SEQ ID NO 52
<211> LENGTH: 33
<212> TYPE: DNA
<213> ORGANISM: Homo Sapiens

<400> SEQUENCE: 52
actggctcat tattcgrcgt ctgtaactct ggg                                  33

<210> SEQ ID NO 53
<211> LENGTH: 33
<212> TYPE: DNA
<213> ORGANISM: Homo Sapiens

<400> SEQUENCE: 53
aatgagtgtt cttagargct gggtcggatt cct                                  33

<210> SEQ ID NO 54
<211> LENGTH: 33
<212> TYPE: DNA
<213> ORGANISM: Homo Sapiens

<400> SEQUENCE: 54
tcagacctgg gagaatrtca ggtaagctga gat                                  33

<210> SEQ ID NO 55
<211> LENGTH: 33
<212> TYPE: DNA
<213> ORGANISM: Homo Sapiens

<400> SEQUENCE: 55
gagcgcgcac tgcaccrgcc agagtgccac aca                                  33
```

```
<210> SEQ ID NO 56
<211> LENGTH: 33
<212> TYPE: DNA
<213> ORGANISM: Homo Sapiens

<400> SEQUENCE: 56
cttttcttat aggtcasagg ctagtccagc acc                              33

<210> SEQ ID NO 57
<211> LENGTH: 33
<212> TYPE: DNA
<213> ORGANISM: Homo Sapiens

<400> SEQUENCE: 57
ctcggctttg ccatcgsggg ggacatcctt gcc                              33

<210> SEQ ID NO 58
<211> LENGTH: 33
<212> TYPE: DNA
<213> ORGANISM: Homo Sapiens

<400> SEQUENCE: 58
catgttcaag tacttcrcat cctggcggta ttt                              33

<210> SEQ ID NO 59
<211> LENGTH: 33
<212> TYPE: DNA
<213> ORGANISM: Homo Sapiens

<400> SEQUENCE: 59
gttggggagt gagccarcag ttatctggag gga                              33

<210> SEQ ID NO 60
<211> LENGTH: 33
<212> TYPE: DNA
<213> ORGANISM: Homo Sapiens

<400> SEQUENCE: 60
tcagcaacag ccccctmcag agcagcagcc aga                              33

<210> SEQ ID NO 61
<211> LENGTH: 33
<212> TYPE: DNA
<213> ORGANISM: Homo Sapiens

<400> SEQUENCE: 61
catatcccat tcctggmcac atgaaatcca aaa                              33

<210> SEQ ID NO 62
<211> LENGTH: 33
<212> TYPE: DNA
<213> ORGANISM: Homo Sapiens

<400> SEQUENCE: 62
ccaagaggct cacctgmgat ccagttgccg ggg                              33

<210> SEQ ID NO 63
<211> LENGTH: 33
<212> TYPE: DNA
<213> ORGANISM: Homo Sapiens

<400> SEQUENCE: 63
aagggtcaga aaacaartaa aaggccaaga cag                              33
```

<210> SEQ ID NO 64
<211> LENGTH: 33
<212> TYPE: DNA
<213> ORGANISM: Homo Sapiens

<400> SEQUENCE: 64
caaacctcct tgagtcrgct ttaagagttt ctt                            33

<210> SEQ ID NO 65
<211> LENGTH: 33
<212> TYPE: DNA
<213> ORGANISM: Homo Sapiens

<400> SEQUENCE: 65
aactcctcaa agatctsgtg tgccctggag gcc                            33

<210> SEQ ID NO 66
<211> LENGTH: 33
<212> TYPE: DNA
<213> ORGANISM: Homo Sapiens

<400> SEQUENCE: 66
gaagtttttt acaaccraaa tctatgaccg ttg                            33

<210> SEQ ID NO 67
<211> LENGTH: 33
<212> TYPE: DNA
<213> ORGANISM: Homo Sapiens

<400> SEQUENCE: 67
cgcgcggcgc caaatcrtgg tcagagcccg gat                            33

<210> SEQ ID NO 68
<211> LENGTH: 33
<212> TYPE: DNA
<213> ORGANISM: Homo Sapiens

<400> SEQUENCE: 68
aaggaattac caagaaragc catgcatctc aca                            33

<210> SEQ ID NO 69
<211> LENGTH: 33
<212> TYPE: DNA
<213> ORGANISM: Homo Sapiens

<400> SEQUENCE: 69
ccgggaagtg cacgctrcca ccgaggagcc atc                            33

<210> SEQ ID NO 70
<211> LENGTH: 33
<212> TYPE: DNA
<213> ORGANISM: Homo Sapiens

<400> SEQUENCE: 70
gatgagatcc caagtcmaag gaagatttgc cca                            33

<210> SEQ ID NO 71
<211> LENGTH: 33
<212> TYPE: DNA
<213> ORGANISM: Homo Sapiens

<400> SEQUENCE: 71
cgaaacaaag cccatgraaa tccaaaggtt gga                            33

<210> SEQ ID NO 72
<211> LENGTH: 33
<212> TYPE: DNA
<213> ORGANISM: Homo Sapiens

<400> SEQUENCE: 72
gcttgggggc tggagarcag aatttaacat gtt                33

<210> SEQ ID NO 73
<211> LENGTH: 33
<212> TYPE: DNA
<213> ORGANISM: Homo Sapiens

<400> SEQUENCE: 73
ttcaaggccc tttgagmtct tgatggcaca tga                33

<210> SEQ ID NO 74
<211> LENGTH: 33
<212> TYPE: DNA
<213> ORGANISM: Homo Sapiens

<400> SEQUENCE: 74
agtatattag gggattrata ttacaagcaa gaa                33

<210> SEQ ID NO 75
<211> LENGTH: 33
<212> TYPE: DNA
<213> ORGANISM: Homo Sapiens

<400> SEQUENCE: 75
gctgtatgtt ataattmtct gatagaaccc aca                33

<210> SEQ ID NO 76
<211> LENGTH: 33
<212> TYPE: DNA
<213> ORGANISM: Homo Sapiens

<400> SEQUENCE: 76
gatgaaataa tagactmcag ggatttactt ttt                33

<210> SEQ ID NO 77
<211> LENGTH: 33
<212> TYPE: DNA
<213> ORGANISM: Homo Sapiens

<400> SEQUENCE: 77
actctccaaa gtcacartat tttctggaca agc                33

<210> SEQ ID NO 78
<211> LENGTH: 33
<212> TYPE: DNA
<213> ORGANISM: Homo Sapiens

<400> SEQUENCE: 78
atcaggatca taggagsact gtctgaggat cag                33

<210> SEQ ID NO 79
<211> LENGTH: 33
<212> TYPE: DNA
<213> ORGANISM: Homo Sapiens

<400> SEQUENCE: 79
acctggctag ggatacragg ccattaacca agc                     33

<210> SEQ ID NO 80
<211> LENGTH: 33
<212> TYPE: DNA
<213> ORGANISM: Homo Sapiens

<400> SEQUENCE: 80
tggttgttgc atggcayttc cagataagct gca                     33

<210> SEQ ID NO 81
<211> LENGTH: 33
<212> TYPE: DNA
<213> ORGANISM: Homo Sapiens

<400> SEQUENCE: 81
aatgtttgta tttgggrttg cccttcttac atg                     33

<210> SEQ ID NO 82
<211> LENGTH: 33
<212> TYPE: DNA
<213> ORGANISM: Homo Sapiens

<400> SEQUENCE: 82
caagttctac acttccrtaa ctcaaacgtg ttt                     33

<210> SEQ ID NO 83
<211> LENGTH: 33
<212> TYPE: DNA
<213> ORGANISM: Homo Sapiens

<400> SEQUENCE: 83
tcaattataa tcacctrtgt ggattttcct cag                     33

<210> SEQ ID NO 84
<211> LENGTH: 33
<212> TYPE: DNA
<213> ORGANISM: Homo Sapiens

<400> SEQUENCE: 84
cgaactgatc agatcgmtgc cctacacact tta                     33

<210> SEQ ID NO 85
<211> LENGTH: 33
<212> TYPE: DNA
<213> ORGANISM: Homo Sapiens

<400> SEQUENCE: 85
caaatattac tgcaatragt aatatcatac aca                     33

<210> SEQ ID NO 86
<211> LENGTH: 33
<212> TYPE: DNA
<213> ORGANISM: Homo Sapiens

<400> SEQUENCE: 86
aacagatgcc atggtaract agatgcctgg gtg                     33

<210> SEQ ID NO 87
<211> LENGTH: 33
<212> TYPE: DNA
<213> ORGANISM: Homo Sapiens

<400> SEQUENCE: 87
tctttaaggt gggttcrgag aaaggagatg gaa                         33

<210> SEQ ID NO 88
<211> LENGTH: 33
<212> TYPE: DNA
<213> ORGANISM: Homo Sapiens

<400> SEQUENCE: 88
acagacaggg tgtcatrgaa gccgcgtcat atc                         33

<210> SEQ ID NO 89
<211> LENGTH: 33
<212> TYPE: DNA
<213> ORGANISM: Homo Sapiens

<400> SEQUENCE: 89
tccaccagtg aagcaartaa tctgtggcct gct                         33

<210> SEQ ID NO 90
<211> LENGTH: 33
<212> TYPE: DNA
<213> ORGANISM: Homo Sapiens

<400> SEQUENCE: 90
caaaaaagaa gtatcarggt atatatgaag aga                         33

<210> SEQ ID NO 91
<211> LENGTH: 33
<212> TYPE: DNA
<213> ORGANISM: Homo Sapiens

<400> SEQUENCE: 91
aacagaaaat taagatmaga ttggctaaca aga                         33

<210> SEQ ID NO 92
<211> LENGTH: 33
<212> TYPE: DNA
<213> ORGANISM: Homo Sapiens

<400> SEQUENCE: 92
taaaggaatc cctgttraaa aaaaagaata agg                         33

<210> SEQ ID NO 93
<211> LENGTH: 33
<212> TYPE: DNA
<213> ORGANISM: Homo Sapiens

<400> SEQUENCE: 93
tttcctttat aaaactrtgt tactctagtc tga                         33

<210> SEQ ID NO 94
<211> LENGTH: 33
<212> TYPE: DNA
<213> ORGANISM: Homo Sapiens

<400> SEQUENCE: 94
ctaaatggtg gttcacrggg aattcatgaa act                         33

<210> SEQ ID NO 95
<211> LENGTH: 33
<212> TYPE: DNA
<213> ORGANISM: Homo Sapiens -continued

<400> SEQUENCE: 95
gggagctcag actcacrtgg tggaaagcct aaa                33

<210> SEQ ID NO 96
<211> LENGTH: 33
<212> TYPE: DNA
<213> ORGANISM: Homo Sapiens

<400> SEQUENCE: 96
atggcataac aatagtract caaagaggca aaa                33

<210> SEQ ID NO 97
<211> LENGTH: 33
<212> TYPE: DNA
<213> ORGANISM: Homo Sapiens

<400> SEQUENCE: 97
tttggaaatt taacacrtga atataaccat caa                33

<210> SEQ ID NO 98
<211> LENGTH: 33
<212> TYPE: DNA
<213> ORGANISM: Homo Sapiens

<400> SEQUENCE: 98
aacaggacta agtggcrtat aaattagggt aat                33

<210> SEQ ID NO 99
<211> LENGTH: 33
<212> TYPE: DNA
<213> ORGANISM: Homo Sapiens

<400> SEQUENCE: 99
tatatcatca gtgcccrgaa gagtacctga tgc                33

<210> SEQ ID NO 100
<211> LENGTH: 33
<212> TYPE: DNA
<213> ORGANISM: Homo Sapiens

<400> SEQUENCE: 100
accagtacca tccggtrtga tttgatggta tga                33

<210> SEQ ID NO 101
<211> LENGTH: 33
<212> TYPE: DNA
<213> ORGANISM: Homo Sapiens

<400> SEQUENCE: 101
tgatgaggcc ttctcgrgga agttttacga tgt                33

<210> SEQ ID NO 102
<211> LENGTH: 33
<212> TYPE: DNA
<213> ORGANISM: Homo Sapiens

<400> SEQUENCE: 102
tgcagctgca ggtcgcrgca ccactggggc aag                33

<210> SEQ ID NO 103
<211> LENGTH: 33
<212> TYPE: DNA
<213> ORGANISM: Homo Sapiens

```
<400> SEQUENCE: 103
actcagcccc agccccrctc actaagctca cag                              33

<210> SEQ ID NO 104
<211> LENGTH: 33
<212> TYPE: DNA
<213> ORGANISM: Homo Sapiens

<400> SEQUENCE: 104
ccattgcaaa ccacagrggt gattattttt agt                              33

<210> SEQ ID NO 105
<211> LENGTH: 33
<212> TYPE: DNA
<213> ORGANISM: Homo Sapiens

<400> SEQUENCE: 105
gggggaaagc gggaagrtct cttgctccag gaa                              33

<210> SEQ ID NO 106
<211> LENGTH: 33
<212> TYPE: DNA
<213> ORGANISM: Homo Sapiens

<400> SEQUENCE: 106
ggatgagact ccctctrtaa taaaatcaca gtc                              33

<210> SEQ ID NO 107
<211> LENGTH: 33
<212> TYPE: DNA
<213> ORGANISM: Homo Sapiens

<400> SEQUENCE: 107
ataaaattta tagtacrttt tgagcctgtg tgt                              33

<210> SEQ ID NO 108
<211> LENGTH: 33
<212> TYPE: DNA
<213> ORGANISM: Homo Sapiens

<400> SEQUENCE: 108
aaacatagca tatttcrctt gattcttgtg aca                              33

<210> SEQ ID NO 109
<211> LENGTH: 33
<212> TYPE: DNA
<213> ORGANISM: Homo Sapiens

<400> SEQUENCE: 109
tgcttcaaca atttccrttt gtgtatcgtt ggc                              33

<210> SEQ ID NO 110
<211> LENGTH: 33
<212> TYPE: DNA
<213> ORGANISM: Homo Sapiens

<400> SEQUENCE: 110
tctgtgctgt ttttcargga aaaacatctg ggt                              33

<210> SEQ ID NO 111
<211> LENGTH: 33
<212> TYPE: DNA
```

-continued

<213> ORGANISM: Homo Sapiens

<400> SEQUENCE: 111
cccaagacac tgtagcrttt acatagtagg tag        33

<210> SEQ ID NO 112
<211> LENGTH: 33
<212> TYPE: DNA
<213> ORGANISM: Homo Sapiens

<400> SEQUENCE: 112
atgatcatgt gattgawgta tctaaaccac agt        33

<210> SEQ ID NO 113
<211> LENGTH: 33
<212> TYPE: DNA
<213> ORGANISM: Homo Sapiens

<400> SEQUENCE: 113
gaacatatag acaatcrgga atgctaaaat aaa        33

<210> SEQ ID NO 114
<211> LENGTH: 33
<212> TYPE: DNA
<213> ORGANISM: Homo Sapiens

<400> SEQUENCE: 114
gactccttgc atttcartat aatgttagct ctg        33

<210> SEQ ID NO 115
<211> LENGTH: 33
<212> TYPE: DNA
<213> ORGANISM: Homo Sapiens

<400> SEQUENCE: 115
atgcattgat gaccttmaat atttattttg taa        33

<210> SEQ ID NO 116
<211> LENGTH: 33
<212> TYPE: DNA
<213> ORGANISM: Homo Sapiens

<400> SEQUENCE: 116
atatcattat gaactcmtag atttttttaac cta        33

<210> SEQ ID NO 117
<211> LENGTH: 33
<212> TYPE: DNA
<213> ORGANISM: Homo Sapiens

<400> SEQUENCE: 117
ccagcagctc atcagaraga gggatgacag aca        33

<210> SEQ ID NO 118
<211> LENGTH: 33
<212> TYPE: DNA
<213> ORGANISM: Homo Sapiens

<400> SEQUENCE: 118
acaacgcaat actactmggg aataaaaagg aaa        33

<210> SEQ ID NO 119
<211> LENGTH: 33

```
<212> TYPE: DNA
<213> ORGANISM: Homo Sapiens

<400> SEQUENCE: 119
agtagtggaa cgaaatract ttggagaaaa gga                                33

<210> SEQ ID NO 120
<211> LENGTH: 33
<212> TYPE: DNA
<213> ORGANISM: Homo Sapiens

<400> SEQUENCE: 120
tccctgcctc ctgtccrtat caatagatgt tgg                                33

<210> SEQ ID NO 121
<211> LENGTH: 33
<212> TYPE: DNA
<213> ORGANISM: Homo Sapiens

<400> SEQUENCE: 121
actgacaaca ggcttcrcca tgtaaattgc tct                                33

<210> SEQ ID NO 122
<211> LENGTH: 33
<212> TYPE: DNA
<213> ORGANISM: Homo Sapiens

<400> SEQUENCE: 122
taagatgaaa aggtctrctt tcagggtttt gtg                                33

<210> SEQ ID NO 123
<211> LENGTH: 33
<212> TYPE: DNA
<213> ORGANISM: Homo Sapiens

<400> SEQUENCE: 123
aacccagcca ttaactmttg ttagatagct tta                                33

<210> SEQ ID NO 124
<211> LENGTH: 33
<212> TYPE: DNA
<213> ORGANISM: Homo Sapiens

<400> SEQUENCE: 124
tccttttatt ctcctcrttt tatgtaattc tgt                                33

<210> SEQ ID NO 125
<211> LENGTH: 33
<212> TYPE: DNA
<213> ORGANISM: Homo Sapiens

<400> SEQUENCE: 125 acttttttgct tagtctraat taaaaaaagt ctt                               33

<210> SEQ ID NO 126
<211> LENGTH: 33
<212> TYPE: DNA
<213> ORGANISM: Homo Sapiens

<400> SEQUENCE: 126
ttacaagatt ttctttrgtt tatagaccta ctt                                33

<210> SEQ ID NO 127
```

-continued

<211> LENGTH: 33
<212> TYPE: DNA
<213> ORGANISM: Homo Sapiens

<400> SEQUENCE: 127
cttgtttggg gacacamttt caaatacaaa atg         33

<210> SEQ ID NO 128
<211> LENGTH: 33
<212> TYPE: DNA
<213> ORGANISM: Homo Sapiens

<400> SEQUENCE: 128
tttttagtat cgtagasctc tgctttgtca cag         33

<210> SEQ ID NO 129
<211> LENGTH: 33
<212> TYPE: DNA
<213> ORGANISM: Homo Sapiens

<400> SEQUENCE: 129
gactcaggtt tgaggcrttt tgcatctggt ggc         33

<210> SEQ ID NO 130
<211> LENGTH: 33
<212> TYPE: DNA
<213> ORGANISM: Homo Sapiens

<400> SEQUENCE: 130
gggaacaaat taatatrtaa actatagcct tga         33

<210> SEQ ID NO 131
<211> LENGTH: 33
<212> TYPE: DNA
<213> ORGANISM: Homo Sapiens

<400> SEQUENCE: 131
tccctgcatc ccctgcrgat aagaaaactg gca         33

<210> SEQ ID NO 132
<211> LENGTH: 33
<212> TYPE: DNA
<213> ORGANISM: Homo Sapiens

<400> SEQUENCE: 132
atagtatgtg ttcattraag atgatttggg ttt         33

<210> SEQ ID NO 133
<211> LENGTH: 33
<212> TYPE: DNA
<213> ORGANISM: Homo Sapiens

<400> SEQUENCE: 133
agatggctac cagcaaraat ggtgcaatgg cgt         33

<210> SEQ ID NO 134
<211> LENGTH: 33
<212> TYPE: DNA
<213> ORGANISM: Homo Sapiens

<400> SEQUENCE: 134
tcatttattg cttgatrgac acctctaatg tat         33

```
<210> SEQ ID NO 135
<211> LENGTH: 33
<212> TYPE: DNA
<213> ORGANISM: Homo Sapiens

<400> SEQUENCE: 135
aaaagtgtgt aattcartgc attaaataca ttc                              33

<210> SEQ ID NO 136
<211> LENGTH: 33
<212> TYPE: DNA
<213> ORGANISM: Homo Sapiens

<400> SEQUENCE: 136
gccttcccgc taaaatraga ataaggttaa gta                              33

<210> SEQ ID NO 137
<211> LENGTH: 33
<212> TYPE: DNA
<213> ORGANISM: Homo Sapiens

<400> SEQUENCE: 137
tgtcggtagg actactrgat agccacaggc aaa                              33

<210> SEQ ID NO 138
<211> LENGTH: 33
<212> TYPE: DNA
<213> ORGANISM: Homo Sapiens

<400> SEQUENCE: 138
ttgtggtctg tgtttargat aatgtggaag cta                              33

<210> SEQ ID NO 139
<211> LENGTH: 33
<212> TYPE: DNA
<213> ORGANISM: Homo Sapiens

<400> SEQUENCE: 139 ggagtgggggg gaatgcrgga gatgcccttt atg                             33

<210> SEQ ID NO 140
<211> LENGTH: 33
<212> TYPE: DNA
<213> ORGANISM: Homo Sapiens

<400> SEQUENCE: 140
atgatgctga gaatctrtga aatgacggaa gaa                              33

<210> SEQ ID NO 141
<211> LENGTH: 33
<212> TYPE: DNA
<213> ORGANISM: Homo Sapiens

<400> SEQUENCE: 141 tttattccttt ctatctract gaaattctgt att                             33

<210> SEQ ID NO 142
<211> LENGTH: 33
<212> TYPE: DNA
<213> ORGANISM: Homo Sapiens

<400> SEQUENCE: 142
acctcctgag ctcagamcaa gagtgcagcc ttt                              33
```

```
<210> SEQ ID NO 143
<211> LENGTH: 33
<212> TYPE: DNA
<213> ORGANISM: Homo Sapiens

<400> SEQUENCE: 143
gtttaatcat acatccrtgg aggaacatgt tgg                           33

<210> SEQ ID NO 144
<211> LENGTH: 33
<212> TYPE: DNA
<213> ORGANISM: Homo Sapiens

<400> SEQUENCE: 144
ctctcagggt tatgggraat tggatattaa ctg                           33

<210> SEQ ID NO 145
<211> LENGTH: 33
<212> TYPE: DNA
<213> ORGANISM: Homo Sapiens

<400> SEQUENCE: 145
actaatagtg tatgagrgtt tcattttctc tac                           33

<210> SEQ ID NO 146
<211> LENGTH: 33
<212> TYPE: DNA
<213> ORGANISM: Homo Sapiens

<400> SEQUENCE: 146
ctaactgaca ttcaacrcac tttcaaagac acc                           33

<210> SEQ ID NO 147
<211> LENGTH: 33
<212> TYPE: DNA
<213> ORGANISM: Homo Sapiens

<400> SEQUENCE: 147
ttctgcagca ccatgcrgaa ggtcccgatg agc                           33

<210> SEQ ID NO 148
<211> LENGTH: 33
<212> TYPE: DNA
<213> ORGANISM: Homo Sapiens

<400> SEQUENCE: 148
gcgaaagaac aaacaarcca tgtaatacat atg                           33

<210> SEQ ID NO 149
<211> LENGTH: 33
<212> TYPE: DNA
<213> ORGANISM: Homo Sapiens

<400> SEQUENCE: 149
gccaggtcta ggcattrttt tggtaagtga ctg                           33

<210> SEQ ID NO 150
<211> LENGTH: 33
<212> TYPE: DNA
<213> ORGANISM: Homo Sapiens

<400> SEQUENCE: 150
tttaactgct cggcccrtgt acttgatcat gga                           33
```

<210> SEQ ID NO 151
<211> LENGTH: 33
<212> TYPE: DNA
<213> ORGANISM: Homo Sapiens

<400> SEQUENCE: 151
acatgttgca taggttmtcc ctccattccc tgt                33

<210> SEQ ID NO 152
<211> LENGTH: 33
<212> TYPE: DNA
<213> ORGANISM: Homo Sapiens

<400> SEQUENCE: 152
atagctatag caccgcraat tgccacatct gta                33

<210> SEQ ID NO 153
<211> LENGTH: 33
<212> TYPE: DNA
<213> ORGANISM: Homo Sapiens

<400> SEQUENCE: 153
ttattgccat tcttgtrgaa gtaaggtggt atc                33

<210> SEQ ID NO 154
<211> LENGTH: 33
<212> TYPE: DNA
<213> ORGANISM: Homo Sapiens

<400> SEQUENCE: 154
cataagtggt ggaatcrttg ttcagaaaca tta                33

<210> SEQ ID NO 155
<211> LENGTH: 33
<212> TYPE: DNA
<213> ORGANISM: Homo Sapiens

<400> SEQUENCE: 155
tctagaaact tagtacmtcc tgttgcattg gta                33

<210> SEQ ID NO 156
<211> LENGTH: 33
<212> TYPE: DNA
<213> ORGANISM: Homo Sapiens

<400> SEQUENCE: 156
tttacatact tttcctrttg acttctccat att                33

<210> SEQ ID NO 157
<211> LENGTH: 33
<212> TYPE: DNA
<213> ORGANISM: Homo Sapiens

<400> SEQUENCE: 157
attccttctg ggatctmtta agggataaaa ccg                33

<210> SEQ ID NO 158
<211> LENGTH: 33
<212> TYPE: DNA
<213> ORGANISM: Homo Sapiens

<400> SEQUENCE: 158
caccacattc tctctcrtca gcttctcaga cat                       33

<210> SEQ ID NO 159
<211> LENGTH: 33
<212> TYPE: DNA
<213> ORGANISM: Homo Sapiens

<400> SEQUENCE: 159
aaaaattcct ccatgartct tacccagatg gag                       33

<210> SEQ ID NO 160
<211> LENGTH: 33
<212> TYPE: DNA
<213> ORGANISM: Homo Sapiens

<400> SEQUENCE: 160
gggaggttca gcagccrcca ctgcgaggag tgg                       33

<210> SEQ ID NO 161
<211> LENGTH: 33
<212> TYPE: DNA
<213> ORGANISM: Homo Sapiens

<400> SEQUENCE: 161
ccagtgcttg accctcrcca acgaccgcac tct                       33

<210> SEQ ID NO 162
<211> LENGTH: 33
<212> TYPE: DNA
<213> ORGANISM: Homo Sapiens

<400> SEQUENCE: 162
ctcctgggaa cttatamgag taaaagtctg cag                       33

<210> SEQ ID NO 163
<211> LENGTH: 33
<212> TYPE: DNA
<213> ORGANISM: Homo Sapiens

<400> SEQUENCE: 163
gcaactaaaa ttaaccrtac ttctgattgt gtc                       33

<210> SEQ ID NO 164
<211> LENGTH: 33
<212> TYPE: DNA
<213> ORGANISM: Homo Sapiens

<400> SEQUENCE: 164
tcccatccag cttaagrcat ttaaaataca att                       33

<210> SEQ ID NO 165
<211> LENGTH: 33
<212> TYPE: DNA
<213> ORGANISM: Homo Sapiens

<400> SEQUENCE: 165
aaatgcctcc ttggtcmgtt tctcccgcgt ttt                       33

<210> SEQ ID NO 166
<211> LENGTH: 33
<212> TYPE: DNA
<213> ORGANISM: Homo Sapiens

<400> SEQUENCE: 166
agcaatttat actgggraaa tatcagaagg tgt    33

<210> SEQ ID NO 167
<211> LENGTH: 33
<212> TYPE: DNA
<213> ORGANISM: Homo Sapiens

<400> SEQUENCE: 167
ggacagtaaa taagaaraaa agaactggag caa    33

<210> SEQ ID NO 168
<211> LENGTH: 33
<212> TYPE: DNA
<213> ORGANISM: Homo Sapiens

<400> SEQUENCE: 168
ttcttatggc tattttmgtg tgtactccta ctt    33

<210> SEQ ID NO 169
<211> LENGTH: 33
<212> TYPE: DNA
<213> ORGANISM: Homo Sapiens

<400> SEQUENCE: 169
taagaatcac agagagrcgg agtaatcaga ccg    33

<210> SEQ ID NO 170
<211> LENGTH: 33
<212> TYPE: DNA
<213> ORGANISM: Homo Sapiens

<400> SEQUENCE: 170
tattttgcat cccttcmata aatacaaaaa tgc    33

<210> SEQ ID NO 171
<211> LENGTH: 33
<212> TYPE: DNA
<213> ORGANISM: Homo Sapiens

<400> SEQUENCE: 171
actctgccac agacacmttc cctggagccc tcc    33

<210> SEQ ID NO 172
<211> LENGTH: 33
<212> TYPE: DNA
<213> ORGANISM: Homo Sapiens

<400> SEQUENCE: 172
tgggagaaag ggcttcract gtggtttcag aca    33

<210> SEQ ID NO 173
<211> LENGTH: 33
<212> TYPE: DNA
<213> ORGANISM: Homo Sapiens

<400> SEQUENCE: 173
ctcttcctat aaggatrcac tgttggatct agg    33

<210> SEQ ID NO 174
<211> LENGTH: 33
<212> TYPE: DNA
<213> ORGANISM: Homo Sapiens

<400> SEQUENCE: 174
gtcatgtaat tttgatracc atcaaaagga ttt                33

<210> SEQ ID NO 175
<211> LENGTH: 33
<212> TYPE: DNA
<213> ORGANISM: Homo Sapiens

<400> SEQUENCE: 175
ttgatatgaa gtgagcmtgc ataaatttca gtt                33

<210> SEQ ID NO 176
<211> LENGTH: 33
<212> TYPE: DNA
<213> ORGANISM: Homo Sapiens

<400> SEQUENCE: 176
ttatgaagat ctacttmtat tttgtcaata gta                33

<210> SEQ ID NO 177
<211> LENGTH: 33
<212> TYPE: DNA
<213> ORGANISM: Homo Sapiens

<400> SEQUENCE: 177
atttccaaat tctttarccc ttgactttgc tga                33

<210> SEQ ID NO 178
<211> LENGTH: 33
<212> TYPE: DNA
<213> ORGANISM: Homo Sapiens

<400> SEQUENCE: 178
aagaatggag attacartga ggtgatgaag acg                33

<210> SEQ ID NO 179
<211> LENGTH: 33
<212> TYPE: DNA
<213> ORGANISM: Homo Sapiens

<400> SEQUENCE: 179
gttggatctg tgacccrtgc tttctacaga gaa                33

<210> SEQ ID NO 180
<211> LENGTH: 33
<212> TYPE: DNA
<213> ORGANISM: Homo Sapiens

<400> SEQUENCE: 180
gaggtccttt ggggagygat accattaatt tgt                33

<210> SEQ ID NO 181
<211> LENGTH: 33
<212> TYPE: DNA
<213> ORGANISM: Homo Sapiens

<400> SEQUENCE: 181
tcactcaaga aaaacraga acagacaata ata                33

<210> SEQ ID NO 182
<211> LENGTH: 33
<212> TYPE: DNA
<213> ORGANISM: Homo Sapiens

<400> SEQUENCE: 182
atgtttcact aaagtarcag atgtgaaata gga    33

<210> SEQ ID NO 183
<211> LENGTH: 33
<212> TYPE: DNA
<213> ORGANISM: Homo Sapiens

<400> SEQUENCE: 183
agctgtgtgt gatagcrtgt gcctatagtt tca    33

<210> SEQ ID NO 184
<211> LENGTH: 33
<212> TYPE: DNA
<213> ORGANISM: Homo Sapiens

<400> SEQUENCE: 184
ttagaacatc acctatrctg attactccca tgc    33

<210> SEQ ID NO 185
<211> LENGTH: 33
<212> TYPE: DNA
<213> ORGANISM: Homo Sapiens

<400> SEQUENCE: 185
gagtgatttg cccatcrtgt aatggagact ggt    33

<210> SEQ ID NO 186
<211> LENGTH: 33
<212> TYPE: DNA
<213> ORGANISM: Homo Sapiens

<400> SEQUENCE: 186
ctcctcctta acatgarttg agttcacttt acc    33

<210> SEQ ID NO 187
<211> LENGTH: 33
<212> TYPE: DNA
<213> ORGANISM: Homo Sapiens

<400> SEQUENCE: 187
tgaaagagac ggttacmtag taccctgttt ctg    33

<210> SEQ ID NO 188
<211> LENGTH: 33
<212> TYPE: DNA
<213> ORGANISM: Homo Sapiens

<400> SEQUENCE: 188
caggatcccg tttaggract ttcaacaccc ttg    33

<210> SEQ ID NO 189
<211> LENGTH: 33
<212> TYPE: DNA
<213> ORGANISM: Homo Sapiens

<400> SEQUENCE: 189
ctctgtgttg atgcttmctt ccatattttg cac    33

<210> SEQ ID NO 190
<211> LENGTH: 33
<212> TYPE: DNA

<213> ORGANISM: Homo Sapiens

<400> SEQUENCE: 190
atgagagaac atcactrtag ataatttaga ctt                                33

<210> SEQ ID NO 191
<211> LENGTH: 33
<212> TYPE: DNA
<213> ORGANISM: Homo Sapiens

<400> SEQUENCE: 191
aaacatttta aaatgtragt gggataaaac atg                                33

<210> SEQ ID NO 192
<211> LENGTH: 33
<212> TYPE: DNA
<213> ORGANISM: Homo Sapiens

<400> SEQUENCE: 192
tcctgccttt gtataarcat gctatttatt cca                                33

<210> SEQ ID NO 193
<211> LENGTH: 33
<212> TYPE: DNA
<213> ORGANISM: Homo Sapiens

<400> SEQUENCE: 193
atgatgtctt gtgacarata ataaagctat ggg                                33

<210> SEQ ID NO 194
<211> LENGTH: 33
<212> TYPE: DNA
<213> ORGANISM: Homo Sapiens

<400> SEQUENCE: 194
cagtcagtgc tgtaacrtca caaatcacta atc                                33

<210> SEQ ID NO 195
<211> LENGTH: 33
<212> TYPE: DNA
<213> ORGANISM: Homo Sapiens

<400> SEQUENCE: 195
ttgtatatga gaaaaaraga ggcaattttt taa                                33

<210> SEQ ID NO 196
<211> LENGTH: 33
<212> TYPE: DNA
<213> ORGANISM: Homo Sapiens

<400> SEQUENCE: 196
atgtctattg aagcccrcct ttgacattta tga                                33

<210> SEQ ID NO 197
<211> LENGTH: 33
<212> TYPE: DNA
<213> ORGANISM: Homo Sapiens

<400> SEQUENCE: 197
ctttttcttt ttcccarttg cttcagtgat agc                                33

<210> SEQ ID NO 198
<211> LENGTH: 33

-continued

<210> SEQ ID NO 198
<211> LENGTH: 33
<212> TYPE: DNA
<213> ORGANISM: Homo Sapiens

<400> SEQUENCE: 198
aaagcaaaag gtgaagragt tatttattat cca    33

<210> SEQ ID NO 199
<211> LENGTH: 33
<212> TYPE: DNA
<213> ORGANISM: Homo Sapiens

<400> SEQUENCE: 199
aataattttc agatttmttt gaacttactt tct    33

<210> SEQ ID NO 200
<211> LENGTH: 33
<212> TYPE: DNA
<213> ORGANISM: Homo Sapiens

<400> SEQUENCE: 200
tcattgactt tgaaaaraat tccagtcatt atc    33

<210> SEQ ID NO 201
<211> LENGTH: 33
<212> TYPE: DNA
<213> ORGANISM: Homo Sapiens

<400> SEQUENCE: 201
tgaagagtta gacaatmatt tatttgagca tga    33

<210> SEQ ID NO 202
<211> LENGTH: 33
<212> TYPE: DNA
<213> ORGANISM: Homo Sapiens

<400> SEQUENCE: 202
acagaaagaa aatgccrtct tgtagtaatc cac    33

<210> SEQ ID NO 203
<211> LENGTH: 33
<212> TYPE: DNA
<213> ORGANISM: Homo Sapiens

<400> SEQUENCE: 203
cttgggaagg aacacartgg attttccctg gaa    33

<210> SEQ ID NO 204
<211> LENGTH: 33
<212> TYPE: DNA
<213> ORGANISM: Homo Sapiens

<400> SEQUENCE: 204
gcctccttgc ctacaartca aatagtagga ttt    33

<210> SEQ ID NO 205
<211> LENGTH: 33
<212> TYPE: DNA
<213> ORGANISM: Homo Sapiens

<400> SEQUENCE: 205
cagtggggtg ataggtrtgt catggaaata ata    33

<210> SEQ ID NO 206

<211> LENGTH: 33
<212> TYPE: DNA
<213> ORGANISM: Homo Sapiens

<400> SEQUENCE: 206 acaaaccttta gcgaggmata gtggtgtgat gaa                33

<210> SEQ ID NO 207
<211> LENGTH: 33
<212> TYPE: DNA
<213> ORGANISM: Homo Sapiens

<400> SEQUENCE: 207
gaatatgaaa tccaccrcac tggctgtcaa taa                33

<210> SEQ ID NO 208
<211> LENGTH: 33
<212> TYPE: DNA
<213> ORGANISM: Homo Sapiens

<400> SEQUENCE: 208
agatagagat acatatraag ctactgctgt cct                33

<210> SEQ ID NO 209
<211> LENGTH: 33
<212> TYPE: DNA
<213> ORGANISM: Homo Sapiens

<400> SEQUENCE: 209
aaaagcatac tagcaamata tattacaaag aac                33

<210> SEQ ID NO 210
<211> LENGTH: 33
<212> TYPE: DNA
<213> ORGANISM: Homo Sapiens

<400> SEQUENCE: 210
cttaatatga tacagaraag aacccaacat cac                33

<210> SEQ ID NO 211
<211> LENGTH: 33
<212> TYPE: DNA
<213> ORGANISM: Homo Sapiens

<400> SEQUENCE: 211
cgaaattgac tcaagcrttt tgtcttcaca ggt                33

<210> SEQ ID NO 212
<211> LENGTH: 33
<212> TYPE: DNA
<213> ORGANISM: Homo Sapiens

<400> SEQUENCE: 212
tgagagtcaa agaagarggg aaaactccag gaa                33

<210> SEQ ID NO 213
<211> LENGTH: 33
<212> TYPE: DNA
<213> ORGANISM: Homo Sapiens

<400> SEQUENCE: 213
gaatgtgaaa gatctgrtgt gcaaatacac gtg                33

```
<210> SEQ ID NO 214
<211> LENGTH: 33
<212> TYPE: DNA
<213> ORGANISM: Homo Sapiens

<400> SEQUENCE: 214
ccaatccttt gggttarctg atttagtagg taa                                33

<210> SEQ ID NO 215
<211> LENGTH: 33
<212> TYPE: DNA
<213> ORGANISM: Homo Sapiens

<400> SEQUENCE: 215
gttttgattt ctctggrata aatgtccaag tat                                33

<210> SEQ ID NO 216
<211> LENGTH: 33
<212> TYPE: DNA
<213> ORGANISM: Homo Sapiens

<400> SEQUENCE: 216
tgctgattct ttcaacrctt tagccagaat cat                                33

<210> SEQ ID NO 217
<211> LENGTH: 33
<212> TYPE: DNA
<213> ORGANISM: Homo Sapiens

<400> SEQUENCE: 217
gaaatgattc cataaascct gaatttatct tat                                33

<210> SEQ ID NO 218
<211> LENGTH: 33
<212> TYPE: DNA
<213> ORGANISM: Homo Sapiens

<400> SEQUENCE: 218
ctgatgtttc tgtccartct gtggctgatc aac                                33

<210> SEQ ID NO 219
<211> LENGTH: 33
<212> TYPE: DNA
<213> ORGANISM: Homo Sapiens

<400> SEQUENCE: 219
ttggatcctt ccgaagrctg gcttctttgt gag                                33

<210> SEQ ID NO 220
<211> LENGTH: 33
<212> TYPE: DNA
<213> ORGANISM: Homo Sapiens

<400> SEQUENCE: 220
tacaataaaa atctacrcaa aatactgaac aag                                33

<210> SEQ ID NO 221
<211> LENGTH: 33
<212> TYPE: DNA
<213> ORGANISM: Homo Sapiens

<400> SEQUENCE: 221
agagagaaca gttcctrtaa ttcaagtaat taa                                33
```

<210> SEQ ID NO 222
<211> LENGTH: 33
<212> TYPE: DNA
<213> ORGANISM: Homo Sapiens

<400> SEQUENCE: 222
tacagacagt ttttgtrtat ttcaacttgc cat                              33

<210> SEQ ID NO 223
<211> LENGTH: 33
<212> TYPE: DNA
<213> ORGANISM: Homo Sapiens

<400> SEQUENCE: 223
ctgggatgat aagaccrtgc attggaggac gag                              33

<210> SEQ ID NO 224
<211> LENGTH: 33
<212> TYPE: DNA
<213> ORGANISM: Homo Sapiens

<400> SEQUENCE: 224
aaacacgtgt gtgtgcrcgt gcattctcat gcg                              33

<210> SEQ ID NO 225
<211> LENGTH: 33
<212> TYPE: DNA
<213> ORGANISM: Homo Sapiens

<400> SEQUENCE: 225
tactgggtct gaaggarcat gtggaggagg cag                              33

<210> SEQ ID NO 226
<211> LENGTH: 33
<212> TYPE: DNA
<213> ORGANISM: Homo Sapiens

<400> SEQUENCE: 226
ccattcagca tttacartgg taccccaata gga                              33

<210> SEQ ID NO 227
<211> LENGTH: 33
<212> TYPE: DNA
<213> ORGANISM: Homo Sapiens

<400> SEQUENCE: 227
ttgtccccaa gttttcrtgt ttagcacaat ata                              33

<210> SEQ ID NO 228
<211> LENGTH: 33
<212> TYPE: DNA
<213> ORGANISM: Homo Sapiens

<400> SEQUENCE: 228
attcaaactc caatatrgtc ccaagtttaa aac                              33

<210> SEQ ID NO 229
<211> LENGTH: 33
<212> TYPE: DNA
<213> ORGANISM: Homo Sapiens

<400> SEQUENCE: 229
tctacattgc ttttctrtct gctatcaccc ctc                              33

```
<210> SEQ ID NO 230
<211> LENGTH: 33
<212> TYPE: DNA
<213> ORGANISM: Homo Sapiens

<400> SEQUENCE: 230
tttgtgcccc acggcgrttc tggacgcacc tgt                                     33

<210> SEQ ID NO 231
<211> LENGTH: 33
<212> TYPE: DNA
<213> ORGANISM: Homo Sapiens

<400> SEQUENCE: 231
cattaccaat agtaatrtca gaaatgaaac acc                                     33

<210> SEQ ID NO 232
<211> LENGTH: 33
<212> TYPE: DNA
<213> ORGANISM: Homo Sapiens

<400> SEQUENCE: 232
gtatttcact ccaggartgg aactgataga tct                                     33

<210> SEQ ID NO 233
<211> LENGTH: 33
<212> TYPE: DNA
<213> ORGANISM: Homo Sapiens

<400> SEQUENCE: 233
aggaggtcct catcccrtga gtcccccact cct                                     33

<210> SEQ ID NO 234
<211> LENGTH: 33
<212> TYPE: DNA
<213> ORGANISM: Homo Sapiens

<400> SEQUENCE: 234
ctacccattt tccttgragt tacgtcccct ggt                                     33

<210> SEQ ID NO 235
<211> LENGTH: 33
<212> TYPE: DNA
<213> ORGANISM: Homo Sapiens

<400> SEQUENCE: 235
gacaaggagc tggtggscca ggccaaggcg ctg                                     33

<210> SEQ ID NO 236
<211> LENGTH: 33
<212> TYPE: DNA
<213> ORGANISM: Homo Sapiens

<400> SEQUENCE: 236
cccacatcta agatacmcaa aggtcagtga cgc                                     33

<210> SEQ ID NO 237
<211> LENGTH: 33
<212> TYPE: DNA
<213> ORGANISM: Homo Sapiens

<400> SEQUENCE: 237
```

```
tgagcgttta actcctmcct ccccttactc aca                          33

<210> SEQ ID NO 238
<211> LENGTH: 33
<212> TYPE: DNA
<213> ORGANISM: Homo Sapiens

<400> SEQUENCE: 238
aggccttaag dacactrgta gactgaagga ggt                          33

<210> SEQ ID NO 239
<211> LENGTH: 33
<212> TYPE: DNA
<213> ORGANISM: Homo Sapiens

<400> SEQUENCE: 239
atccacatat ccatccrtcc ctctattctg aca                          33

<210> SEQ ID NO 240
<211> LENGTH: 33
<212> TYPE: DNA
<213> ORGANISM: Homo Sapiens

<400> SEQUENCE: 240 gctctcccttt ttccccrgca cccacctcac tcc                         33

<210> SEQ ID NO 241
<211> LENGTH: 33
<212> TYPE: DNA
<213> ORGANISM: Homo Sapiens

<400> SEQUENCE: 241
ctgaactaca cggaggrgga tgacacgggg gct                          33

<210> SEQ ID NO 242
<211> LENGTH: 33
<212> TYPE: DNA
<213> ORGANISM: Homo Sapiens

<400> SEQUENCE: 242
ggcaagccat cccggamgga cgtcagatcc tgg                          33

<210> SEQ ID NO 243
<211> LENGTH: 33
<212> TYPE: DNA
<213> ORGANISM: Homo Sapiens

<400> SEQUENCE: 243
ctgggcacgt gcttcartaa gaacagctgc tca                          33

<210> SEQ ID NO 244
<211> LENGTH: 33
<212> TYPE: DNA
<213> ORGANISM: Homo Sapiens

<400> SEQUENCE: 244
tgtgtcgggg ggtgcgmgga gagggacgag gac                          33

<210> SEQ ID NO 245
<211> LENGTH: 33
<212> TYPE: DNA
<213> ORGANISM: Homo Sapiens

<400> SEQUENCE: 245
```
ataaatccca cttggtmatg atgaatgctc ttt                33

<210> SEQ ID NO 246
<211> LENGTH: 33
<212> TYPE: DNA
<213> ORGANISM: Homo Sapiens

<400> SEQUENCE: 246
cttgaatttg tggatgrttt gtgaaatgta ata                33

<210> SEQ ID NO 247
<211> LENGTH: 33
<212> TYPE: DNA
<213> ORGANISM: Homo Sapiens

<400> SEQUENCE: 247
ttattttatg gacatartgt gtgggagctt gaa                33

<210> SEQ ID NO 248
<211> LENGTH: 33
<212> TYPE: DNA
<213> ORGANISM: Homo Sapiens

<400> SEQUENCE: 248
gaagcgcgca tgcaatrgat ccagggtgta tgc                33

<210> SEQ ID NO 249
<211> LENGTH: 33
<212> TYPE: DNA
<213> ORGANISM: Homo Sapiens

<400> SEQUENCE: 249
taacaaatag gcagaarttt tgagcaacat taa                33

<210> SEQ ID NO 250
<211> LENGTH: 33
<212> TYPE: DNA
<213> ORGANISM: Homo Sapiens

<400> SEQUENCE: 250
atattgtact ttgtatrcag aatttcaact tgg                33

<210> SEQ ID NO 251
<211> LENGTH: 33
<212> TYPE: DNA
<213> ORGANISM: Homo Sapiens

<400> SEQUENCE: 251
tttctttatc tagtggrcac ttttaggtcg att                33

<210> SEQ ID NO 252
<211> LENGTH: 33
<212> TYPE: DNA
<213> ORGANISM: Homo Sapiens

<400> SEQUENCE: 252
tttttgtgtg tatgtcrttc ttgaatacag tga                33

<210> SEQ ID NO 253
<211> LENGTH: 33
<212> TYPE: DNA
<213> ORGANISM: Homo Sapiens

<400> SEQUENCE: 253
aaggaggtaa agttaaragt taggagcaga ggg								33

<210> SEQ ID NO 254
<211> LENGTH: 33
<212> TYPE: DNA
<213> ORGANISM: Homo Sapiens

<400> SEQUENCE: 254
tgagggcacc gcccccrgcc actttccaca ctg								33

<210> SEQ ID NO 255
<211> LENGTH: 33
<212> TYPE: DNA
<213> ORGANISM: Homo Sapiens

<400> SEQUENCE: 255
ctgcctccct ggtgatrtac tccaggttaa cca								33

<210> SEQ ID NO 256
<211> LENGTH: 33
<212> TYPE: DNA
<213> ORGANISM: Homo Sapiens

<400> SEQUENCE: 256
tcacctgctc cgtgaaracc tccttgcccc tcc								33

<210> SEQ ID NO 257
<211> LENGTH: 33
<212> TYPE: DNA
<213> ORGANISM: Homo Sapiens

<400> SEQUENCE: 257
gccaggagct ggggatrtaa ggaagggga tgt								33

<210> SEQ ID NO 258
<211> LENGTH: 33
<212> TYPE: DNA
<213> ORGANISM: Homo Sapiens

<400> SEQUENCE: 258
ccagagcagc tgcgtcrctt ggcgccgggt atg								33

<210> SEQ ID NO 259
<211> LENGTH: 33
<212> TYPE: DNA
<213> ORGANISM: Homo Sapiens

<400> SEQUENCE: 259
ttacatggct ttgcgcmtcc tacctggaag gcg								33

<210> SEQ ID NO 260
<211> LENGTH: 33
<212> TYPE: DNA
<213> ORGANISM: Homo Sapiens

<400> SEQUENCE: 260
cagcgtctct ttcacargat gctctccgtg agc								33

<210> SEQ ID NO 261
<211> LENGTH: 33
<212> TYPE: DNA
<213> ORGANISM: Homo Sapiens

```
<400> SEQUENCE: 261
tgcaccatcc gacccamcca taacttttct ttt                                      33

<210> SEQ ID NO 262
<211> LENGTH: 33
<212> TYPE: DNA
<213> ORGANISM: Homo Sapiens

<400> SEQUENCE: 262
gagttccttt gcccctrtta cgacaagagg gtt                                      33

<210> SEQ ID NO 263
<211> LENGTH: 33
<212> TYPE: DNA
<213> ORGANISM: Homo Sapiens

<400> SEQUENCE: 263
gtgtatcaat tgtgtcratt tgtgcagtga gta                                      33

<210> SEQ ID NO 264
<211> LENGTH: 33
<212> TYPE: DNA
<213> ORGANISM: Homo Sapiens

<400> SEQUENCE: 264
aaacaatgaa gccaagraca gaagtgactg gac                                      33

<210> SEQ ID NO 265
<211> LENGTH: 33
<212> TYPE: DNA
<213> ORGANISM: Homo Sapiens

<400> SEQUENCE: 265
gtttttatgt cagctcracc tttgctttta agt                                      33

<210> SEQ ID NO 266
<211> LENGTH: 33
<212> TYPE: DNA
<213> ORGANISM: Homo Sapiens

<400> SEQUENCE: 266
taccagaagc acgaaarggc ctgggtctgc tgc                                      33

<210> SEQ ID NO 267
<211> LENGTH: 33
<212> TYPE: DNA
<213> ORGANISM: Homo Sapiens

<400> SEQUENCE: 267
tcttttgacc acacgcrcac acacacacac aca                                      33

<210> SEQ ID NO 268
<211> LENGTH: 33
<212> TYPE: DNA
<213> ORGANISM: Homo Sapiens

<400> SEQUENCE: 268
atggatatgc agttagraaa atgagtcatc act                                      33

<210> SEQ ID NO 269
<211> LENGTH: 33
<212> TYPE: DNA
```

<213> ORGANISM: Homo Sapiens

<400> SEQUENCE: 269 gtcgtaacett aaaatcrtat tcaaagctgt gat                33

<210> SEQ ID NO 270
<211> LENGTH: 33
<212> TYPE: DNA
<213> ORGANISM: Homo Sapiens

<400> SEQUENCE: 270
ttcataattc tactttrctg gaatcagctg aga                33

<210> SEQ ID NO 271
<211> LENGTH: 33
<212> TYPE: DNA
<213> ORGANISM: Homo Sapiens

<400> SEQUENCE: 271
aagcaaagca agcaaarcat catctgtatt tat                33

<210> SEQ ID NO 272
<211> LENGTH: 33
<212> TYPE: DNA
<213> ORGANISM: Homo Sapiens

<400> SEQUENCE: 272
attagtggag tgaactrctt ctccctgcaa tta                33

<210> SEQ ID NO 273
<211> LENGTH: 33
<212> TYPE: DNA
<213> ORGANISM: Homo Sapiens

<400> SEQUENCE: 273
aactaactgt ggctctrctt actcacgaag ttg                33

<210> SEQ ID NO 274
<211> LENGTH: 33
<212> TYPE: DNA
<213> ORGANISM: Homo Sapiens

<400> SEQUENCE: 274
tgtgaggtgt ggcacaragg taaggaatag cca                33

<210> SEQ ID NO 275
<211> LENGTH: 33
<212> TYPE: DNA
<213> ORGANISM: Homo Sapiens

<400> SEQUENCE: 275
cccagagcta cctcaarccc cctccccaag cca                33

<210> SEQ ID NO 276
<211> LENGTH: 33
<212> TYPE: DNA
<213> ORGANISM: Homo Sapiens

<400> SEQUENCE: 276
gggtaaagat gaggcamaat caagtccatc gaa                33

<210> SEQ ID NO 277
<211> LENGTH: 33

```
<212> TYPE: DNA
<213> ORGANISM: Homo Sapiens

<400> SEQUENCE: 277
gatgcaatta gagatargct ttaggaagat ctt                              33

<210> SEQ ID NO 278
<211> LENGTH: 33
<212> TYPE: DNA
<213> ORGANISM: Homo Sapiens

<400> SEQUENCE: 278
accaaggggg agagaarcaa aagaaaatta tgg                              33

<210> SEQ ID NO 279
<211> LENGTH: 33
<212> TYPE: DNA
<213> ORGANISM: Homo Sapiens

<400> SEQUENCE: 279
attttcctct taatgcrgta ctaatatatg ttg                              33

<210> SEQ ID NO 280
<211> LENGTH: 33
<212> TYPE: DNA
<213> ORGANISM: Homo Sapiens

<400> SEQUENCE: 280
gacttcacat agtgccrcct agttcttcca atg                              33

<210> SEQ ID NO 281
<211> LENGTH: 33
<212> TYPE: DNA
<213> ORGANISM: Homo Sapiens

<400> SEQUENCE: 281
cctctacccc caggctraaa aggcctgaca caa                              33

<210> SEQ ID NO 282
<211> LENGTH: 33
<212> TYPE: DNA
<213> ORGANISM: Homo Sapiens

<400> SEQUENCE: 282
ctgtgtagct atttgamgat atgctggcct gta                              33

<210> SEQ ID NO 283
<211> LENGTH: 33
<212> TYPE: DNA
<213> ORGANISM: Homo Sapiens

<400> SEQUENCE: 283
aaaaaaaaaa ataagtmctc ttaaagctag cac                              33

<210> SEQ ID NO 284
<211> LENGTH: 33
<212> TYPE: DNA
<213> ORGANISM: Homo Sapiens

<400> SEQUENCE: 284
ttctaaaaaa gcaactmctc atgagaagct gta                              33

<210> SEQ ID NO 285
```

-continued

<211> LENGTH: 33
<212> TYPE: DNA
<213> ORGANISM: Homo Sapiens

<400> SEQUENCE: 285
gttgagtcct tctcagrctt ggaatctcta aga                                    33

<210> SEQ ID NO 286
<211> LENGTH: 33
<212> TYPE: DNA
<213> ORGANISM: Homo Sapiens

<400> SEQUENCE: 286
tctcctccct ttggttraat ctttgtagct gtt                                    33

<210> SEQ ID NO 287
<211> LENGTH: 33
<212> TYPE: DNA
<213> ORGANISM: Homo Sapiens

<400> SEQUENCE: 287
ttgtttcagg tactgtrcta gttatagttt att                                    33

<210> SEQ ID NO 288
<211> LENGTH: 33
<212> TYPE: DNA
<213> ORGANISM: Homo Sapiens

<400> SEQUENCE: 288
ccagccagga tattcaragg accgaaccct ctt                                    33

<210> SEQ ID NO 289
<211> LENGTH: 33
<212> TYPE: DNA
<213> ORGANISM: Homo Sapiens

<400> SEQUENCE: 289
ttgagtgtga aagaatrtaa cagtaaaaat aaa                                    33

<210> SEQ ID NO 290
<211> LENGTH: 33
<212> TYPE: DNA
<213> ORGANISM: Homo Sapiens

<400> SEQUENCE: 290
ctacatgaga aacctgrgag ctatcttcaa atc                                    33

<210> SEQ ID NO 291
<211> LENGTH: 33
<212> TYPE: DNA
<213> ORGANISM: Homo Sapiens

<400> SEQUENCE: 291
taatgctagc cttcctrgag tctagtattt cag                                    33

<210> SEQ ID NO 292
<211> LENGTH: 33
<212> TYPE: DNA
<213> ORGANISM: Homo Sapiens

<400> SEQUENCE: 292
ctagcacgtt ttattgrcca tcattctttt cat                                    33

```
<210> SEQ ID NO 293
<211> LENGTH: 33
<212> TYPE: DNA
<213> ORGANISM: Homo Sapiens

<400> SEQUENCE: 293
gggtctcggt ggccatrttc ccgcctgtcc atg                          33

<210> SEQ ID NO 294
<211> LENGTH: 33
<212> TYPE: DNA
<213> ORGANISM: Homo Sapiens

<400> SEQUENCE: 294
ttcaaaggtc aggcaarttg attttgaaaa gaa                          33

<210> SEQ ID NO 295
<211> LENGTH: 33
<212> TYPE: DNA
<213> ORGANISM: Homo Sapiens

<400> SEQUENCE: 295
ctgcatagtg agactgmatg tttttcagga gtt                          33

<210> SEQ ID NO 296
<211> LENGTH: 33
<212> TYPE: DNA
<213> ORGANISM: Homo Sapiens

<400> SEQUENCE: 296
tgtggaagaa aaacacrtat tagttcaata aat                          33

<210> SEQ ID NO 297
<211> LENGTH: 33
<212> TYPE: DNA
<213> ORGANISM: Homo Sapiens

<400> SEQUENCE: 297
tgatgaatga taattarctt ttcctctaga gca                          33

<210> SEQ ID NO 298
<211> LENGTH: 33
<212> TYPE: DNA
<213> ORGANISM: Homo Sapiens

<400> SEQUENCE: 298
tacacttagt ctatccraaa tgacaaaaat agt                          33

<210> SEQ ID NO 299
<211> LENGTH: 33
<212> TYPE: DNA
<213> ORGANISM: Homo Sapiens

<400> SEQUENCE: 299
ttgagctttt gaagcamgtc agattggaac ttg                          33

<210> SEQ ID NO 300
<211> LENGTH: 33
<212> TYPE: DNA
<213> ORGANISM: Homo Sapiens

<400> SEQUENCE: 300
aaactgaggc tgtgaamggc tgaaaggttt cag                          33
```

```
<210> SEQ ID NO 301
<211> LENGTH: 33
<212> TYPE: DNA
<213> ORGANISM: Homo Sapiens

<400> SEQUENCE: 301
gaaccagagc ataagcrgca ttgttcatat ggt                              33

<210> SEQ ID NO 302
<211> LENGTH: 33
<212> TYPE: DNA
<213> ORGANISM: Homo Sapiens

<400> SEQUENCE: 302
attaatgttc tctcccrtat gagtcactct tca                              33

<210> SEQ ID NO 303
<211> LENGTH: 33
<212> TYPE: DNA
<213> ORGANISM: Homo Sapiens

<400> SEQUENCE: 303
aggatgaagc ttaactragg aaggtagaac caa                              33

<210> SEQ ID NO 304
<211> LENGTH: 33
<212> TYPE: DNA
<213> ORGANISM: Homo Sapiens

<400> SEQUENCE: 304
caaaagcctg aggaagrgtg aaaagaacaa agc                              33

<210> SEQ ID NO 305
<211> LENGTH: 33
<212> TYPE: DNA
<213> ORGANISM: Homo Sapiens

<400> SEQUENCE: 305
ttggaagaga aggaaraaa attttatgtg gct                               33

<210> SEQ ID NO 306
<211> LENGTH: 33
<212> TYPE: DNA
<213> ORGANISM: Homo Sapiens

<400> SEQUENCE: 306
cagcccagaa aatattraaa agataatgag caa                              33

<210> SEQ ID NO 307
<211> LENGTH: 33
<212> TYPE: DNA
<213> ORGANISM: Homo Sapiens

<400> SEQUENCE: 307
aaagtaacat cagggargtc tggaaataaa atg                              33

<210> SEQ ID NO 308
<211> LENGTH: 33
<212> TYPE: DNA
<213> ORGANISM: Homo Sapiens

<400> SEQUENCE: 308
gaaaagaaag cttacaraaa agccaaggag cgg                              33
```

```
<210> SEQ ID NO 309
<211> LENGTH: 33
<212> TYPE: DNA
<213> ORGANISM: Homo Sapiens

<400> SEQUENCE: 309
ggtcttgcca tctctcrcac acatgcatac cta                                33

<210> SEQ ID NO 310
<211> LENGTH: 33
<212> TYPE: DNA
<213> ORGANISM: Homo Sapiens

<400> SEQUENCE: 310
actcactgga gtgcccraac tgctgtccac atc                                33

<210> SEQ ID NO 311
<211> LENGTH: 33
<212> TYPE: DNA
<213> ORGANISM: Homo Sapiens

<400> SEQUENCE: 311
agaaaactgt actgacmgct acgaagtttg agc                                33

<210> SEQ ID NO 312
<211> LENGTH: 33
<212> TYPE: DNA
<213> ORGANISM: Homo Sapiens

<400> SEQUENCE: 312
cccaagccaa ctcaacrcct gcagatggct ctt                                33

<210> SEQ ID NO 313
<211> LENGTH: 33
<212> TYPE: DNA
<213> ORGANISM: Homo Sapiens

<400> SEQUENCE: 313
gcttcactgt tcttccrgtg tctagtggca aac                                33

<210> SEQ ID NO 314
<211> LENGTH: 33
<212> TYPE: DNA
<213> ORGANISM: Homo Sapiens

<400> SEQUENCE: 314
gacagttgcc ttatacrgag ggctcattaa aca                                33

<210> SEQ ID NO 315
<211> LENGTH: 33
<212> TYPE: DNA
<213> ORGANISM: Homo Sapiens

<400> SEQUENCE: 315
ggaagagtga agaagargag aagatgccca agc                                33

<210> SEQ ID NO 316
<211> LENGTH: 33
<212> TYPE: DNA
<213> ORGANISM: Homo Sapiens

<400> SEQUENCE: 316
```

```
tagtgacctt ataagargag atgtcagaaa att                                33

<210> SEQ ID NO 317
<211> LENGTH: 33
<212> TYPE: DNA
<213> ORGANISM: Homo Sapiens

<400> SEQUENCE: 317
catcatgaag ttcatgragc cgagaccacc agt                                33

<210> SEQ ID NO 318
<211> LENGTH: 33
<212> TYPE: DNA
<213> ORGANISM: Homo Sapiens

<400> SEQUENCE: 318
gaaatgatgt gtgactraac aaagagacat gca                                33

<210> SEQ ID NO 319
<211> LENGTH: 33
<212> TYPE: DNA
<213> ORGANISM: Homo Sapiens

<400> SEQUENCE: 319
ggcaaagtga ttacctraga cattagataa ctc                                33

<210> SEQ ID NO 320
<211> LENGTH: 33
<212> TYPE: DNA
<213> ORGANISM: Homo Sapiens

<400> SEQUENCE: 320
cttcccacat gacttamttt cacaggttgg aga                                33

<210> SEQ ID NO 321
<211> LENGTH: 33
<212> TYPE: DNA
<213> ORGANISM: Homo Sapiens

<400> SEQUENCE: 321
agactcctta cctctamtga aatcatccca aac                                33

<210> SEQ ID NO 322
<211> LENGTH: 33
<212> TYPE: DNA
<213> ORGANISM: Homo Sapiens

<400> SEQUENCE: 322
attgctccaa taatagrcgt gtatttctca tgt                                33

<210> SEQ ID NO 323
<211> LENGTH: 33
<212> TYPE: DNA
<213> ORGANISM: Homo Sapiens

<400> SEQUENCE: 323
tgcaatattt cctctcrctc cttatgtcta ctc                                33

<210> SEQ ID NO 324
<211> LENGTH: 33
<212> TYPE: DNA
<213> ORGANISM: Homo Sapiens

<400> SEQUENCE: 324
```

-continued taggcctcag cccccrttt aaacagaggg taa					33

<210> SEQ ID NO 325
<211> LENGTH: 33
<212> TYPE: DNA
<213> ORGANISM: Homo Sapiens

<400> SEQUENCE: 325
cacactgtta gagtgtrttt gagcatgtgg gag					33

<210> SEQ ID NO 326
<211> LENGTH: 33
<212> TYPE: DNA
<213> ORGANISM: Homo Sapiens

<400> SEQUENCE: 326
tcctgcatag gtgtccytct taaaaaataa ttg					33

<210> SEQ ID NO 327
<211> LENGTH: 33
<212> TYPE: DNA
<213> ORGANISM: Homo Sapiens

<400> SEQUENCE: 327
gatatctctt ttaacgragg ccaggtatct gta					33

<210> SEQ ID NO 328
<211> LENGTH: 33
<212> TYPE: DNA
<213> ORGANISM: Homo Sapiens

<400> SEQUENCE: 328
aaggtctcct tggccartaa gagtctgttc agt					33

<210> SEQ ID NO 329
<211> LENGTH: 33
<212> TYPE: DNA
<213> ORGANISM: Homo Sapiens

<400> SEQUENCE: 329 agattttat gtgcctratg atagtctcaa aat					33

<210> SEQ ID NO 330
<211> LENGTH: 33
<212> TYPE: DNA
<213> ORGANISM: Homo Sapiens

<400> SEQUENCE: 330
ccccactaca ctcatargca gctgatttgc aca					33

<210> SEQ ID NO 331
<211> LENGTH: 33
<212> TYPE: DNA
<213> ORGANISM: Homo Sapiens

<400> SEQUENCE: 331
tgaagataga atggcarata ccctatccta tcc					33

<210> SEQ ID NO 332
<211> LENGTH: 33
<212> TYPE: DNA
<213> ORGANISM: Homo Sapiens

```
<400> SEQUENCE: 332
gattctatcc gtctgcracc ccccacccct gca                                  33

<210> SEQ ID NO 333
<211> LENGTH: 33
<212> TYPE: DNA
<213> ORGANISM: Homo Sapiens

<400> SEQUENCE: 333
ggcaattgtg gtccttrtat ttcagacaca agc                                  33

<210> SEQ ID NO 334
<211> LENGTH: 33
<212> TYPE: DNA
<213> ORGANISM: Homo Sapiens

<400> SEQUENCE: 334
gcgggcccac cacatcmccg aggaccctgg cca                                  33

<210> SEQ ID NO 335
<211> LENGTH: 33
<212> TYPE: DNA
<213> ORGANISM: Homo Sapiens

<400> SEQUENCE: 335
aaggcctgag gcagaayaac cggggtcaag agg                                  33

<210> SEQ ID NO 336
<211> LENGTH: 33
<212> TYPE: DNA
<213> ORGANISM: Homo Sapiens

<400> SEQUENCE: 336
accatcagcc tctcacratt tttgagtagt tcc                                  33

<210> SEQ ID NO 337
<211> LENGTH: 33
<212> TYPE: DNA
<213> ORGANISM: Homo Sapiens

<400> SEQUENCE: 337
tggggctgaa gaatacmttt ctggtgtgac tca                                  33

<210> SEQ ID NO 338
<211> LENGTH: 33
<212> TYPE: DNA
<213> ORGANISM: Homo Sapiens

<400> SEQUENCE: 338
caggctggag gagcggrggc ggcaggagga gga                                  33

<210> SEQ ID NO 339
<211> LENGTH: 33
<212> TYPE: DNA
<213> ORGANISM: Homo Sapiens

<400> SEQUENCE: 339
aatgaatcaa gtcagasgca ttttttttcta ctc                                 33

<210> SEQ ID NO 340
<211> LENGTH: 33
<212> TYPE: DNA
<213> ORGANISM: Homo Sapiens
```

```
<400> SEQUENCE: 340
ttgtaaataa gtacatraga gttcttagca gga                                  33

<210> SEQ ID NO 341
<211> LENGTH: 33
<212> TYPE: DNA
<213> ORGANISM: Homo Sapiens

<400> SEQUENCE: 341
tctcatccta aaatgtrgat tctggaatat aag                                  33

<210> SEQ ID NO 342
<211> LENGTH: 33
<212> TYPE: DNA
<213> ORGANISM: Homo Sapiens

<400> SEQUENCE: 342
taaaagcact ttacatraat aattttatgt cag                                  33

<210> SEQ ID NO 343
<211> LENGTH: 33
<212> TYPE: DNA
<213> ORGANISM: Homo Sapiens

<400> SEQUENCE: 343
tgtcacttgt taatgamctt ccaatcttct aag                                  33

<210> SEQ ID NO 344
<211> LENGTH: 33
<212> TYPE: DNA
<213> ORGANISM: Homo Sapiens

<400> SEQUENCE: 344
aaagaaaata aaggacracg atgcctaaat ccc                                  33

<210> SEQ ID NO 345
<211> LENGTH: 33
<212> TYPE: DNA
<213> ORGANISM: Homo Sapiens

<400> SEQUENCE: 345
cagctggggg agaaatmatc caaaatgcaa tat                                  33

<210> SEQ ID NO 346
<211> LENGTH: 33
<212> TYPE: DNA
<213> ORGANISM: Homo Sapiens

<400> SEQUENCE: 346 attttattc agttggratg gggtggctgc aaa                                   33

<210> SEQ ID NO 347
<211> LENGTH: 33
<212> TYPE: DNA
<213> ORGANISM: Homo Sapiens

<400> SEQUENCE: 347
ttgtgctcag gcaagtrtgt tgattggata aat                                  33

<210> SEQ ID NO 348
<211> LENGTH: 33
<212> TYPE: DNA
```

-continued

<213> ORGANISM: Homo Sapiens

<400> SEQUENCE: 348
tcatttatta aaacacrgca tgattagacc act                                    33

<210> SEQ ID NO 349
<211> LENGTH: 33
<212> TYPE: DNA
<213> ORGANISM: Homo Sapiens

<400> SEQUENCE: 349
gtctctacct ttttctrccc tgctttgctc cct                                    33

<210> SEQ ID NO 350
<211> LENGTH: 33
<212> TYPE: DNA
<213> ORGANISM: Homo Sapiens

<400> SEQUENCE: 350
agggagtgga aagaaaragt gctgcaattt ttt                                    33

<210> SEQ ID NO 351
<211> LENGTH: 33
<212> TYPE: DNA
<213> ORGANISM: Homo Sapiens

<400> SEQUENCE: 351
tagtacagat ttttatrttg caatcaaatc cta                                    33

<210> SEQ ID NO 352
<211> LENGTH: 33
<212> TYPE: DNA
<213> ORGANISM: Homo Sapiens

<400> SEQUENCE: 352
tgttaccaac tgattarggt acaagtttta gga                                    33

<210> SEQ ID NO 353
<211> LENGTH: 33
<212> TYPE: DNA
<213> ORGANISM: Homo Sapiens

<400> SEQUENCE: 353
ccagaagtga aactgtrgga actgtgttct taa                                    33

<210> SEQ ID NO 354
<211> LENGTH: 33
<212> TYPE: DNA
<213> ORGANISM: Homo Sapiens

<400> SEQUENCE: 354
taggactcat tcacatrgtg atccagggtt cct                                    33

<210> SEQ ID NO 355
<211> LENGTH: 33
<212> TYPE: DNA
<213> ORGANISM: Homo Sapiens

<400> SEQUENCE: 355
gttgtttggg ctatccrtct tctcaactgt tta                                    33

<210> SEQ ID NO 356
<211> LENGTH: 33

```
<212> TYPE: DNA
<213> ORGANISM: Homo Sapiens

<400> SEQUENCE: 356
atttagtata taataamagt aacactacag cac                              33

<210> SEQ ID NO 357
<211> LENGTH: 33
<212> TYPE: DNA
<213> ORGANISM: Homo Sapiens

<400> SEQUENCE: 357
gggccccttc cttgctracc tgcagtagca tgt                              33

<210> SEQ ID NO 358
<211> LENGTH: 33
<212> TYPE: DNA
<213> ORGANISM: Homo Sapiens

<400> SEQUENCE: 358
caaagggaag tataccrcta ataaggaag gca                               33

<210> SEQ ID NO 359
<211> LENGTH: 33
<212> TYPE: DNA
<213> ORGANISM: Homo Sapiens

<400> SEQUENCE: 359
cgtggctcca ggactgrtct cagcctttgc ata                              33

<210> SEQ ID NO 360
<211> LENGTH: 33
<212> TYPE: DNA
<213> ORGANISM: Homo Sapiens

<400> SEQUENCE: 360
tatctcagat tcatgaratg gtaacttcta tgt                              33

<210> SEQ ID NO 361
<211> LENGTH: 33
<212> TYPE: DNA
<213> ORGANISM: Homo Sapiens

<400> SEQUENCE: 361
tctcaccaag gtcaccmgtg acttctagct gag                              33

<210> SEQ ID NO 362
<211> LENGTH: 33
<212> TYPE: DNA
<213> ORGANISM: Homo Sapiens

<400> SEQUENCE: 362
ctaaagagta ctgtaargtt aagggatca tgt                               33

<210> SEQ ID NO 363
<211> LENGTH: 33
<212> TYPE: DNA
<213> ORGANISM: Homo Sapiens

<400> SEQUENCE: 363
acaatgactt aacaatmcct ttcctttctg att                              33

<210> SEQ ID NO 364
```

```
<210> SEQ ID NO 364
<211> LENGTH: 33
<212> TYPE: DNA
<213> ORGANISM: Homo Sapiens

<400> SEQUENCE: 364
taaccttgat cactggrctg aagtagtgtt tgt                                    33

<210> SEQ ID NO 365
<211> LENGTH: 33
<212> TYPE: DNA
<213> ORGANISM: Homo Sapiens

<400> SEQUENCE: 365
cttaagaagg atacacraaa tatgtatgta tat                                    33

<210> SEQ ID NO 366
<211> LENGTH: 33
<212> TYPE: DNA
<213> ORGANISM: Homo Sapiens

<400> SEQUENCE: 366
ccctggcaac caaagargga gcttttacac cag                                    33

<210> SEQ ID NO 367
<211> LENGTH: 33
<212> TYPE: DNA
<213> ORGANISM: Homo Sapiens

<400> SEQUENCE: 367
ctgccttctc agagttraac ctgacataat tta                                    33

<210> SEQ ID NO 368
<211> LENGTH: 33
<212> TYPE: DNA
<213> ORGANISM: Homo Sapiens

<400> SEQUENCE: 368
gcaaatgaga ataatcrttt tttgtctttt cca                                    33

<210> SEQ ID NO 369
<211> LENGTH: 33
<212> TYPE: DNA
<213> ORGANISM: Homo Sapiens

<400> SEQUENCE: 369
ggaatgaact tctaaamtgc tgtaatctct tga                                    33

<210> SEQ ID NO 370
<211> LENGTH: 33
<212> TYPE: DNA
<213> ORGANISM: Homo Sapiens

<400> SEQUENCE: 370
tgaggtcaca tgtgctrcgg tgtgtgcgga gct                                    33

<210> SEQ ID NO 371
<211> LENGTH: 33
<212> TYPE: DNA
<213> ORGANISM: Homo Sapiens

<400> SEQUENCE: 371
tagtcaaatt cattcartgt ggctcagata tga                                    33
```

<210> SEQ ID NO 372
<211> LENGTH: 33
<212> TYPE: DNA
<213> ORGANISM: Homo Sapiens

<400> SEQUENCE: 372
atgtgaacat tttttrgac aagtttattg cta                                    33

<210> SEQ ID NO 373
<211> LENGTH: 33
<212> TYPE: DNA
<213> ORGANISM: Homo Sapiens

<400> SEQUENCE: 373
aacacagcca acatcartta agcctaattt aca                                   33

<210> SEQ ID NO 374
<211> LENGTH: 33
<212> TYPE: DNA
<213> ORGANISM: Homo Sapiens

<400> SEQUENCE: 374
ggaaaagtgg aatgccraga acagaaacta aga                                   33

<210> SEQ ID NO 375
<211> LENGTH: 33
<212> TYPE: DNA
<213> ORGANISM: Homo Sapiens

<400> SEQUENCE: 375
ctctctagag tttactrtca tctggcattc atg                                   33

<210> SEQ ID NO 376
<211> LENGTH: 33
<212> TYPE: DNA
<213> ORGANISM: Homo Sapiens

<400> SEQUENCE: 376
ctacatggaa aattgamgta gcaaggtagg tca                                   33

<210> SEQ ID NO 377
<211> LENGTH: 33
<212> TYPE: DNA
<213> ORGANISM: Homo Sapiens

<400> SEQUENCE: 377
agcctgtctc ctctggragt cttatctctc agt                                   33

<210> SEQ ID NO 378
<211> LENGTH: 33
<212> TYPE: DNA
<213> ORGANISM: Homo Sapiens

<400> SEQUENCE: 378
ttccatatcc tcgtccrcaa ttagtacgca cag                                   33

<210> SEQ ID NO 379
<211> LENGTH: 33
<212> TYPE: DNA
<213> ORGANISM: Homo Sapiens

<400> SEQUENCE: 379
catgtttact atctctrtag gtttgccttt ttg                                   33

<210> SEQ ID NO 380
<211> LENGTH: 33
<212> TYPE: DNA
<213> ORGANISM: Homo Sapiens

<400> SEQUENCE: 380
taccaaattg tatggtrtca gtgatggcag cag          33

<210> SEQ ID NO 381
<211> LENGTH: 33
<212> TYPE: DNA
<213> ORGANISM: Homo Sapiens

<400> SEQUENCE: 381
cagaactgaa ataattmtcc ataggatcct tag          33

<210> SEQ ID NO 382
<211> LENGTH: 33
<212> TYPE: DNA
<213> ORGANISM: Homo Sapiens

<400> SEQUENCE: 382
ttttaatgaa gcccctrtag gctagttgtc aag          33

<210> SEQ ID NO 383
<211> LENGTH: 33
<212> TYPE: DNA
<213> ORGANISM: Homo Sapiens

<400> SEQUENCE: 383
catctcaaac catgcarttc ctggaaatca cta          33

<210> SEQ ID NO 384
<211> LENGTH: 33
<212> TYPE: DNA
<213> ORGANISM: Homo Sapiens

<400> SEQUENCE: 384
tgcaaggaaa ccatttrcca gcctcctgca att          33

<210> SEQ ID NO 385
<211> LENGTH: 33
<212> TYPE: DNA
<213> ORGANISM: Homo Sapiens

<400> SEQUENCE: 385
ctgaaaataa gttcccrcat atatattgta gaa          33

<210> SEQ ID NO 386
<211> LENGTH: 33
<212> TYPE: DNA
<213> ORGANISM: Homo Sapiens

<400> SEQUENCE: 386
tgatgctata attcctrgat tttgtttgat ttc          33

<210> SEQ ID NO 387
<211> LENGTH: 33
<212> TYPE: DNA
<213> ORGANISM: Homo Sapiens

<400> SEQUENCE: 387
ctagagaaga tgaaggratg tgcattccag gca          33

<210> SEQ ID NO 388
<211> LENGTH: 33
<212> TYPE: DNA
<213> ORGANISM: Homo Sapiens

<400> SEQUENCE: 388
tgctcaagag cagaccrgat gagccacaca tgg  33

<210> SEQ ID NO 389
<211> LENGTH: 33
<212> TYPE: DNA
<213> ORGANISM: Homo Sapiens

<400> SEQUENCE: 389
agggatcaat tcttacrata aaattttaaa acc  33

<210> SEQ ID NO 390
<211> LENGTH: 33
<212> TYPE: DNA
<213> ORGANISM: Homo Sapiens

<400> SEQUENCE: 390
tgaaactgag taaaccrtta agaatgaatt att  33

<210> SEQ ID NO 391
<211> LENGTH: 33
<212> TYPE: DNA
<213> ORGANISM: Homo Sapiens

<400> SEQUENCE: 391
ctgcataagc cctggcrtgc taccacagcc caa  33

<210> SEQ ID NO 392
<211> LENGTH: 33
<212> TYPE: DNA
<213> ORGANISM: Homo Sapiens

<400> SEQUENCE: 392
gtgtgtccca tgtggcraga gctcaaacaa ggc  33

<210> SEQ ID NO 393
<211> LENGTH: 33
<212> TYPE: DNA
<213> ORGANISM: Homo Sapiens

<400> SEQUENCE: 393
atctaagtta aggtagraat gatgaggtca aaa  33

<210> SEQ ID NO 394
<211> LENGTH: 33
<212> TYPE: DNA
<213> ORGANISM: Homo Sapiens

<400> SEQUENCE: 394
acttcatggt gatccamtgt ctacctccag caa  33

<210> SEQ ID NO 395
<211> LENGTH: 33
<212> TYPE: DNA
<213> ORGANISM: Homo Sapiens

<400> SEQUENCE: 395

```
gtgactataa aagatgrggc cttcggcagc tcc                                33
```

\<210\> SEQ ID NO 396
\<211\> LENGTH: 33
\<212\> TYPE: DNA
\<213\> ORGANISM: Homo Sapiens

\<400\> SEQUENCE: 396

```
atattaatac gtggctmaga ttaatgacag caa                                33
```

\<210\> SEQ ID NO 397
\<211\> LENGTH: 33
\<212\> TYPE: DNA
\<213\> ORGANISM: Homo Sapiens

\<400\> SEQUENCE: 397

```
ggcaactcac agaaaargag agtttgagga tct                                33
```

\<210\> SEQ ID NO 398
\<211\> LENGTH: 33
\<212\> TYPE: DNA
\<213\> ORGANISM: Homo Sapiens

\<400\> SEQUENCE: 398

```
aaacaatgct gaggagrctt tatctttaca gtt                                33
```

\<210\> SEQ ID NO 399
\<211\> LENGTH: 33
\<212\> TYPE: DNA
\<213\> ORGANISM: Homo Sapiens

\<400\> SEQUENCE: 399

```
tcatgatgag gacgccrgaa gagatgggga gat                                33
```

\<210\> SEQ ID NO 400
\<211\> LENGTH: 33
\<212\> TYPE: DNA
\<213\> ORGANISM: Homo Sapiens

\<400\> SEQUENCE: 400

```
tggcatgctg aactgaraag acctggcttg gaa                                33
```

\<210\> SEQ ID NO 401
\<211\> LENGTH: 33
\<212\> TYPE: DNA
\<213\> ORGANISM: Homo Sapiens

\<400\> SEQUENCE: 401

```
tccctccaat tgaaggrcag gcagggactc caa                                33
```

\<210\> SEQ ID NO 402
\<211\> LENGTH: 33
\<212\> TYPE: DNA
\<213\> ORGANISM: Homo Sapiens

\<400\> SEQUENCE: 402

```
tcttgctcac ggggtcrgtg atggggaccg agt                                33
```

\<210\> SEQ ID NO 403
\<211\> LENGTH: 33
\<212\> TYPE: DNA
\<213\> ORGANISM: Homo Sapiens

\<400\> SEQUENCE: 403 agtgtttcaa ataattrtct cacttccagc tca                                33

<210> SEQ ID NO 404
<211> LENGTH: 33
<212> TYPE: DNA
<213> ORGANISM: Homo Sapiens

<400> SEQUENCE: 404
acctggagag aggggcmcag ctcagagctt tcc                                33

<210> SEQ ID NO 405
<211> LENGTH: 33
<212> TYPE: DNA
<213> ORGANISM: Homo Sapiens

<400> SEQUENCE: 405
catctgtgga tatggcmgtt ttaccctcct ggc                                33

<210> SEQ ID NO 406
<211> LENGTH: 33
<212> TYPE: DNA
<213> ORGANISM: Homo Sapiens

<400> SEQUENCE: 406
gttttgaccc cttggaraca ctcatgaaca acc                                33

<210> SEQ ID NO 407
<211> LENGTH: 33
<212> TYPE: DNA
<213> ORGANISM: Homo Sapiens

<400> SEQUENCE: 407
tgtaccccat ggttttrgca tcattgacta tta                                33

<210> SEQ ID NO 408
<211> LENGTH: 33
<212> TYPE: DNA
<213> ORGANISM: Homo Sapiens

<400> SEQUENCE: 408
aagaaaagta ttgattmctc cctttgtgcc ttt                                33

<210> SEQ ID NO 409
<211> LENGTH: 33
<212> TYPE: DNA
<213> ORGANISM: Homo Sapiens

<400> SEQUENCE: 409
aagaggatag ggaaacrttg agagaatcgg ttg                                33

<210> SEQ ID NO 410
<211> LENGTH: 33
<212> TYPE: DNA
<213> ORGANISM: Homo Sapiens

<400> SEQUENCE: 410
atgtgcccaa agccggrttc cttgaggctg ggg                                33

<210> SEQ ID NO 411
<211> LENGTH: 33
<212> TYPE: DNA
<213> ORGANISM: Homo Sapiens

<400> SEQUENCE: 411
ttttctgtgc cttcacrtgt acttacacgc aca                          33

<210> SEQ ID NO 412
<211> LENGTH: 33
<212> TYPE: DNA
<213> ORGANISM: Homo Sapiens

<400> SEQUENCE: 412
gattagtgca cttacarggg gatgaagaga cca                          33

<210> SEQ ID NO 413
<211> LENGTH: 33
<212> TYPE: DNA
<213> ORGANISM: Homo Sapiens

<400> SEQUENCE: 413
atgaataagc taacttragc cgaaatgtta aca                          33

<210> SEQ ID NO 414
<211> LENGTH: 33
<212> TYPE: DNA
<213> ORGANISM: Homo Sapiens

<400> SEQUENCE: 414
cactgcaaca ttttcaract tgaatctcac aga                          33

<210> SEQ ID NO 415
<211> LENGTH: 33
<212> TYPE: DNA
<213> ORGANISM: Homo Sapiens

<400> SEQUENCE: 415
tgccagctga ggctccrgca gacacaggtt tgc                          33

<210> SEQ ID NO 416
<211> LENGTH: 33
<212> TYPE: DNA
<213> ORGANISM: Homo Sapiens

<400> SEQUENCE: 416
agaaatggga tgtagcrtga gttgtgagtt gtt                          33

<210> SEQ ID NO 417
<211> LENGTH: 33
<212> TYPE: DNA
<213> ORGANISM: Homo Sapiens

<400> SEQUENCE: 417
gctcgcagcg ggcagtrcgt cttgaggagc acc                          33

<210> SEQ ID NO 418
<211> LENGTH: 33
<212> TYPE: DNA
<213> ORGANISM: Homo Sapiens

<400> SEQUENCE: 418
catatgtttg tgtgagmaga tctttgtaag ttt                          33

<210> SEQ ID NO 419
<211> LENGTH: 33
<212> TYPE: DNA
<213> ORGANISM: Homo Sapiens

```
<400> SEQUENCE: 419
agagtcgagt agatgargtg tgcttcaggt ttt                            33

<210> SEQ ID NO 420
<211> LENGTH: 33
<212> TYPE: DNA
<213> ORGANISM: Homo Sapiens

<400> SEQUENCE: 420
aaaatctcac aaatgcratt caagtaagtt gaa                            33

<210> SEQ ID NO 421
<211> LENGTH: 33
<212> TYPE: DNA
<213> ORGANISM: Homo Sapiens

<400> SEQUENCE: 421
tacagcagac cgaaacmatg tattttagaa tta                            33

<210> SEQ ID NO 422
<211> LENGTH: 33
<212> TYPE: DNA
<213> ORGANISM: Homo Sapiens

<400> SEQUENCE: 422
aatcactcta aacaacrcat ttaataggtt cca                            33

<210> SEQ ID NO 423
<211> LENGTH: 33
<212> TYPE: DNA
<213> ORGANISM: Homo Sapiens

<400> SEQUENCE: 423
aataaacgag agacatmtgg agaaaggaga cct                            33

<210> SEQ ID NO 424
<211> LENGTH: 33
<212> TYPE: DNA
<213> ORGANISM: Homo Sapiens

<400> SEQUENCE: 424
atctgagaaa attctcrgtc actgtcactt caa                            33

<210> SEQ ID NO 425
<211> LENGTH: 33
<212> TYPE: DNA
<213> ORGANISM: Homo Sapiens

<400> SEQUENCE: 425
cactgattag ctgatgrgac tctaccctat ata                            33

<210> SEQ ID NO 426
<211> LENGTH: 33
<212> TYPE: DNA
<213> ORGANISM: Homo Sapiens

<400> SEQUENCE: 426
ggacaggcca cacccaragg aaaacctgga gtc                            33

<210> SEQ ID NO 427
<211> LENGTH: 33
<212> TYPE: DNA
```

```
<213> ORGANISM: Homo Sapiens

<400> SEQUENCE: 427
gaacctaaac tgttgtratt ttataccaag tat                           33

<210> SEQ ID NO 428
<211> LENGTH: 33
<212> TYPE: DNA
<213> ORGANISM: Homo Sapiens

<400> SEQUENCE: 428
tttggtgaga ggagacrgct gacggagtaa gta                           33

<210> SEQ ID NO 429
<211> LENGTH: 33
<212> TYPE: DNA
<213> ORGANISM: Homo Sapiens

<400> SEQUENCE: 429 acttttgtt gtttcaraag agtggttctc ttg                            33

<210> SEQ ID NO 430
<211> LENGTH: 33
<212> TYPE: DNA
<213> ORGANISM: Homo Sapiens

<400> SEQUENCE: 430
cactttggta ttaatcrttg atcttgcagt tag                           33

<210> SEQ ID NO 431
<211> LENGTH: 33
<212> TYPE: DNA
<213> ORGANISM: Homo Sapiens

<400> SEQUENCE: 431
gacactcctt gagactrcaa accacatacc tgg                           33

<210> SEQ ID NO 432
<211> LENGTH: 33
<212> TYPE: DNA
<213> ORGANISM: Homo Sapiens

<400> SEQUENCE: 432
aaacctaaaa gatcaarttg gctaaacacg tac                           33

<210> SEQ ID NO 433
<211> LENGTH: 33
<212> TYPE: DNA
<213> ORGANISM: Homo Sapiens

<400> SEQUENCE: 433
tccgggcatt tcttggmtat ttctttaata atg                           33

<210> SEQ ID NO 434
<211> LENGTH: 33
<212> TYPE: DNA
<213> ORGANISM: Homo Sapiens

<400> SEQUENCE: 434
agaaactgag cagtgtrttg tgcagaattg gtg                           33

<210> SEQ ID NO 435
<211> LENGTH: 33
```

<212> TYPE: DNA
<213> ORGANISM: Homo Sapiens

<400> SEQUENCE: 435
cagcagaata gagaacracc aaatcaaaca aca    33

<210> SEQ ID NO 436
<211> LENGTH: 33
<212> TYPE: DNA
<213> ORGANISM: Homo Sapiens

<400> SEQUENCE: 436
atggcctgtg acatagmtag catttaataa aca    33

<210> SEQ ID NO 437
<211> LENGTH: 33
<212> TYPE: DNA
<213> ORGANISM: Homo Sapiens

<400> SEQUENCE: 437
acccataaac cattctragg gccagattaa aac    33

<210> SEQ ID NO 438
<211> LENGTH: 33
<212> TYPE: DNA
<213> ORGANISM: Homo Sapiens

<400> SEQUENCE: 438
aaatatgtta tatttamtgg cagttatctt tct    33

<210> SEQ ID NO 439
<211> LENGTH: 33
<212> TYPE: DNA
<213> ORGANISM: Homo Sapiens

<400> SEQUENCE: 439
taaagtaaac gtactcrtct tagcttagac aca    33

<210> SEQ ID NO 440
<211> LENGTH: 33
<212> TYPE: DNA
<213> ORGANISM: Homo Sapiens

<400> SEQUENCE: 440
agaaaatcaa atttttrtaa gacttaccaa aaa    33

<210> SEQ ID NO 441
<211> LENGTH: 33
<212> TYPE: DNA
<213> ORGANISM: Homo Sapiens

<400> SEQUENCE: 441
tagatggtaa ccaggcrtga agagacagct gac    33

<210> SEQ ID NO 442
<211> LENGTH: 33
<212> TYPE: DNA
<213> ORGANISM: Homo Sapiens

<400> SEQUENCE: 442
agacaagcag cgcctcrttt atgtgatgta ttt    33

<210> SEQ ID NO 443

```
<211> LENGTH: 33
<212> TYPE: DNA
<213> ORGANISM: Homo Sapiens

<400> SEQUENCE: 443
ggttaagagc tcaggayttc ccggagtcac aca                              33

<210> SEQ ID NO 444
<211> LENGTH: 33
<212> TYPE: DNA
<213> ORGANISM: Homo Sapiens

<400> SEQUENCE: 444
atttcagagg ctgcagract tctgcctgaa cct                              33

<210> SEQ ID NO 445
<211> LENGTH: 33
<212> TYPE: DNA
<213> ORGANISM: Homo Sapiens

<400> SEQUENCE: 445
atgagactga atccccrgag acctacactt gaa                              33

<210> SEQ ID NO 446
<211> LENGTH: 33
<212> TYPE: DNA
<213> ORGANISM: Homo Sapiens

<400> SEQUENCE: 446
caaacttatc acagtartca catttttaag gag                              33

<210> SEQ ID NO 447
<211> LENGTH: 33
<212> TYPE: DNA
<213> ORGANISM: Homo Sapiens

<400> SEQUENCE: 447
agtgtgttaa gctttcmtgc tcagaaatga cag                              33

<210> SEQ ID NO 448
<211> LENGTH: 33
<212> TYPE: DNA
<213> ORGANISM: Homo Sapiens

<400> SEQUENCE: 448
ccagtaccac cctttgragc tttacttgtt ttg                              33

<210> SEQ ID NO 449
<211> LENGTH: 33
<212> TYPE: DNA
<213> ORGANISM: Homo Sapiens

<400> SEQUENCE: 449
tccaacactt agggtargta agtagctagt tac                              33

<210> SEQ ID NO 450
<211> LENGTH: 33
<212> TYPE: DNA
<213> ORGANISM: Homo Sapiens

<400> SEQUENCE: 450
cacgatgtca tgtgttratt gagttgtata ctt                              33
```

<210> SEQ ID NO 451
<211> LENGTH: 33
<212> TYPE: DNA
<213> ORGANISM: Homo Sapiens

<400> SEQUENCE: 451
atgcttcacc gtctacrtcc cctaattcta acc                                    33

<210> SEQ ID NO 452
<211> LENGTH: 33
<212> TYPE: DNA
<213> ORGANISM: Homo Sapiens

<400> SEQUENCE: 452
gagagctctg tgtgccmcgt gcggcgttct cgg                                    33

<210> SEQ ID NO 453
<211> LENGTH: 33
<212> TYPE: DNA
<213> ORGANISM: Homo Sapiens

<400> SEQUENCE: 453
aaacgccctt ttatcartct tactgctggt caa                                    33

<210> SEQ ID NO 454
<211> LENGTH: 33
<212> TYPE: DNA
<213> ORGANISM: Homo Sapiens

<400> SEQUENCE: 454
cccaagcaaa tgatagmtat tgccaattaa act                                    33

<210> SEQ ID NO 455
<211> LENGTH: 33
<212> TYPE: DNA
<213> ORGANISM: Homo Sapiens

<400> SEQUENCE: 455
ccagtgactg ccaaccrtgg ccacacataa gca                                    33

<210> SEQ ID NO 456
<211> LENGTH: 33
<212> TYPE: DNA
<213> ORGANISM: Homo Sapiens

<400> SEQUENCE: 456
ctctctatac taccccrtca gtgactcgct tta                                    33

<210> SEQ ID NO 457
<211> LENGTH: 33
<212> TYPE: DNA
<213> ORGANISM: Homo Sapiens

<400> SEQUENCE: 457
tgagtctctt cactgaragg tgagctttgc tac                                    33

<210> SEQ ID NO 458
<211> LENGTH: 33
<212> TYPE: DNA
<213> ORGANISM: Homo Sapiens

<400> SEQUENCE: 458
cttacaactg tgccacrcat atctagaatc ctc                                    33

<210> SEQ ID NO 459
<211> LENGTH: 33
<212> TYPE: DNA
<213> ORGANISM: Homo Sapiens

<400> SEQUENCE: 459
accaccagga gaggttmtct ctcttcttgg agc                33

<210> SEQ ID NO 460
<211> LENGTH: 33
<212> TYPE: DNA
<213> ORGANISM: Homo Sapiens

<400> SEQUENCE: 460
cctcctccaa ctcaccrtct ccagccacag ccg                33

<210> SEQ ID NO 461
<211> LENGTH: 33
<212> TYPE: DNA
<213> ORGANISM: Homo Sapiens

<400> SEQUENCE: 461
gtagtatgaa caaaagmgcc ctgggcttgg agt                33

<210> SEQ ID NO 462
<211> LENGTH: 33
<212> TYPE: DNA
<213> ORGANISM: Homo Sapiens

<400> SEQUENCE: 462
tgtgataaat ttaatcrtag tctgtccaaa cca                33

<210> SEQ ID NO 463
<211> LENGTH: 33
<212> TYPE: DNA
<213> ORGANISM: Homo Sapiens

<400> SEQUENCE: 463
cagagtcttc ccccartct gactcttctc cat                 33

<210> SEQ ID NO 464
<211> LENGTH: 33
<212> TYPE: DNA
<213> ORGANISM: Homo Sapiens

<400> SEQUENCE: 464
tttaaataca ggagacrgga gcccaacaca taa                33

<210> SEQ ID NO 465
<211> LENGTH: 33
<212> TYPE: DNA
<213> ORGANISM: Homo Sapiens

<400> SEQUENCE: 465
tgagcctgac ctccaamacc tcagcagcag cat                33

<210> SEQ ID NO 466
<211> LENGTH: 33
<212> TYPE: DNA
<213> ORGANISM: Homo Sapiens

<400> SEQUENCE: 466
atgagggttt tagaatrtat ttgaatgctg aca                33

<210> SEQ ID NO 467
<211> LENGTH: 33
<212> TYPE: DNA
<213> ORGANISM: Homo Sapiens

<400> SEQUENCE: 467
taactccaag ttaaagrcta tttctaccac atc                33

<210> SEQ ID NO 468
<211> LENGTH: 33
<212> TYPE: DNA
<213> ORGANISM: Homo Sapiens

<400> SEQUENCE: 468
tgacactgct gacagargaa gaccccacct cca                33

<210> SEQ ID NO 469
<211> LENGTH: 33
<212> TYPE: DNA
<213> ORGANISM: Homo Sapiens

<400> SEQUENCE: 469
tctactgtgg aaacagrata gagtaacagc aaa                33

<210> SEQ ID NO 470
<211> LENGTH: 33
<212> TYPE: DNA
<213> ORGANISM: Homo Sapiens

<400> SEQUENCE: 470
atgtgattta ttttaarcct caccatttga agt                33

<210> SEQ ID NO 471
<211> LENGTH: 33
<212> TYPE: DNA
<213> ORGANISM: Homo Sapiens

<400> SEQUENCE: 471
cagaaacttc ttcaccrtgg gcaggttgct gat                33

<210> SEQ ID NO 472
<211> LENGTH: 33
<212> TYPE: DNA
<213> ORGANISM: Homo Sapiens

<400> SEQUENCE: 472
taagttgttg aaccacragc atgacagtct tta                33

<210> SEQ ID NO 473
<211> LENGTH: 33
<212> TYPE: DNA
<213> ORGANISM: Homo Sapiens

<400> SEQUENCE: 473
gaaaaccttg acaaacrgag ctggaaaacc atg                33

<210> SEQ ID NO 474
<211> LENGTH: 33
<212> TYPE: DNA
<213> ORGANISM: Homo Sapiens

<400> SEQUENCE: 474

```
cagaggatgc cagtttrctt gaatgccaaa att                    33

<210> SEQ ID NO 475
<211> LENGTH: 33
<212> TYPE: DNA
<213> ORGANISM: Homo Sapiens

<400> SEQUENCE: 475
tcattttgat cactctrtgg catttgacac ttt                    33

<210> SEQ ID NO 476
<211> LENGTH: 33
<212> TYPE: DNA
<213> ORGANISM: Homo Sapiens

<400> SEQUENCE: 476
gctggtgaga gggcacrctt actctgtgac tgg                    33

<210> SEQ ID NO 477
<211> LENGTH: 33
<212> TYPE: DNA
<213> ORGANISM: Homo Sapiens

<400> SEQUENCE: 477
aaaggaacag agccccrtta gaggaaccat agc                    33

<210> SEQ ID NO 478
<211> LENGTH: 33
<212> TYPE: DNA
<213> ORGANISM: Homo Sapiens

<400> SEQUENCE: 478
cattggagcc tacaccrctt gtgcttttct cac                    33

<210> SEQ ID NO 479
<211> LENGTH: 33
<212> TYPE: DNA
<213> ORGANISM: Homo Sapiens

<400> SEQUENCE: 479
ggtctgttcc ttccccrcga tgccgcaggc ccc                    33

<210> SEQ ID NO 480
<211> LENGTH: 33
<212> TYPE: DNA
<213> ORGANISM: Homo Sapiens

<400> SEQUENCE: 480
aatgaataca actgtamaaa ctggaaccaa acc                    33

<210> SEQ ID NO 481
<211> LENGTH: 33
<212> TYPE: DNA
<213> ORGANISM: Homo Sapiens

<400> SEQUENCE: 481
agttgagaga agccagrgtg aaattcctcc tgc                    33

<210> SEQ ID NO 482
<211> LENGTH: 33
<212> TYPE: DNA
<213> ORGANISM: Homo Sapiens

<400> SEQUENCE: 482
```
tagggataaa ataccrtga agctcatagg gat                                    33

<210> SEQ ID NO 483
<211> LENGTH: 33
<212> TYPE: DNA
<213> ORGANISM: Homo Sapiens

<400> SEQUENCE: 483
tcgtgtcctt cccaacrgct ccctcttcct tcc                                   33

<210> SEQ ID NO 484
<211> LENGTH: 33
<212> TYPE: DNA
<213> ORGANISM: Homo Sapiens

<400> SEQUENCE: 484
agaagagaga gagtaartgt attccaccaa gaa                                   33

<210> SEQ ID NO 485
<211> LENGTH: 33
<212> TYPE: DNA
<213> ORGANISM: Homo Sapiens

<400> SEQUENCE: 485
tcctgctgat ctgagcrtgt gggtcctaga ggc                                   33

<210> SEQ ID NO 486
<211> LENGTH: 33
<212> TYPE: DNA
<213> ORGANISM: Homo Sapiens

<400> SEQUENCE: 486
tttatcaaga gacattrtct atcatatagc aat                                   33

<210> SEQ ID NO 487
<211> LENGTH: 33
<212> TYPE: DNA
<213> ORGANISM: Homo Sapiens

<400> SEQUENCE: 487
ctgcaacatc agcagargct tcctgtgggt tcc                                   33

<210> SEQ ID NO 488
<211> LENGTH: 33
<212> TYPE: DNA
<213> ORGANISM: Homo Sapiens

<400> SEQUENCE: 488
ctaaggggag gtgactrgta agtttcaggt ggc                                   33

<210> SEQ ID NO 489
<211> LENGTH: 33
<212> TYPE: DNA
<213> ORGANISM: Homo Sapiens

<400> SEQUENCE: 489
tcagagagag atcaagrtaa aacgaaaaac tca                                   33

<210> SEQ ID NO 490
<211> LENGTH: 33
<212> TYPE: DNA
<213> ORGANISM: Homo Sapiens

```
<400> SEQUENCE: 490
tacaaagatt aatgatrtac aatctctggc ctt                                    33

<210> SEQ ID NO 491
<211> LENGTH: 33
<212> TYPE: DNA
<213> ORGANISM: Homo Sapiens

<400> SEQUENCE: 491
tatttcttga tgaaatrtgt aagcctccct tta                                    33

<210> SEQ ID NO 492
<211> LENGTH: 33
<212> TYPE: DNA
<213> ORGANISM: Homo Sapiens

<400> SEQUENCE: 492
tttggtgcct tcctacmgtt atggaaggaa gct                                    33

<210> SEQ ID NO 493
<211> LENGTH: 33
<212> TYPE: DNA
<213> ORGANISM: Homo Sapiens

<400> SEQUENCE: 493
cctatagtca agtaagmctg taataataaa tat                                    33

<210> SEQ ID NO 494
<211> LENGTH: 33
<212> TYPE: DNA
<213> ORGANISM: Homo Sapiens

<400> SEQUENCE: 494
gggagatctc ttacacrtga tgtttctttc aga                                    33

<210> SEQ ID NO 495
<211> LENGTH: 33
<212> TYPE: DNA
<213> ORGANISM: Homo Sapiens

<400> SEQUENCE: 495
agaaatccac ttagatrtct accctacttc ccc                                    33

<210> SEQ ID NO 496
<211> LENGTH: 33
<212> TYPE: DNA
<213> ORGANISM: Homo Sapiens

<400> SEQUENCE: 496
tttcttaaca cagcagmaaa attgttttat gtc                                    33

<210> SEQ ID NO 497
<211> LENGTH: 33
<212> TYPE: DNA
<213> ORGANISM: Homo Sapiens

<400> SEQUENCE: 497
gtagattcta atcttargcc ctttgccata gac                                    33

<210> SEQ ID NO 498
<211> LENGTH: 33
<212> TYPE: DNA
<213> ORGANISM: Homo Sapiens
```

```
<400> SEQUENCE: 498
agaaaataaa aactatrtaa tcttagatgg cac                                   33

<210> SEQ ID NO 499
<211> LENGTH: 33
<212> TYPE: DNA
<213> ORGANISM: Homo Sapiens

<400> SEQUENCE: 499
ataacactga tgatatrgat ttgaggtgag aga                                   33

<210> SEQ ID NO 500
<211> LENGTH: 33
<212> TYPE: DNA
<213> ORGANISM: Homo Sapiens

<400> SEQUENCE: 500
gggggtcaag agtggaract gcaccgaggc aag                                   33

<210> SEQ ID NO 501
<211> LENGTH: 33
<212> TYPE: DNA
<213> ORGANISM: Homo Sapiens

<400> SEQUENCE: 501
agagactttg gtctgcrccc tggggttgtc tgt                                   33

<210> SEQ ID NO 502
<211> LENGTH: 33
<212> TYPE: DNA
<213> ORGANISM: Homo Sapiens

<400> SEQUENCE: 502
ctgcacttac cgggagrgtc tctgccctca gcc                                   33

<210> SEQ ID NO 503
<211> LENGTH: 33
<212> TYPE: DNA
<213> ORGANISM: Homo Sapiens

<400> SEQUENCE: 503
agaatcaagg aataagraaa ataatgtgag ctg                                   33

<210> SEQ ID NO 504
<211> LENGTH: 33
<212> TYPE: DNA
<213> ORGANISM: Homo Sapiens

<400> SEQUENCE: 504
catcttcttc aggaagrtgt ccctaacttc tcc                                   33

<210> SEQ ID NO 505
<211> LENGTH: 33
<212> TYPE: DNA
<213> ORGANISM: Homo Sapiens

<400> SEQUENCE: 505
ttcgccctgg gatttartgc tcttctttct gct                                   33

<210> SEQ ID NO 506
<211> LENGTH: 33
<212> TYPE: DNA
```

```
<213> ORGANISM: Homo Sapiens

<400> SEQUENCE: 506
tgatgcagtg tgtgacrtct aatctccccc ata                33

<210> SEQ ID NO 507
<211> LENGTH: 33
<212> TYPE: DNA
<213> ORGANISM: Homo Sapiens

<400> SEQUENCE: 507
tatatgatat tttattrttt ttagataggg tct                33

<210> SEQ ID NO 508
<211> LENGTH: 33
<212> TYPE: DNA
<213> ORGANISM: Homo Sapiens

<400> SEQUENCE: 508
ggagcattct gggttgrcct gagcaaaggc tgc                33

<210> SEQ ID NO 509
<211> LENGTH: 33
<212> TYPE: DNA
<213> ORGANISM: Homo Sapiens

<400> SEQUENCE: 509
tctgcttatc tttcaaract catctcagcc atc                33

<210> SEQ ID NO 510
<211> LENGTH: 33
<212> TYPE: DNA
<213> ORGANISM: Homo Sapiens

<400> SEQUENCE: 510
tccagctaca ctcaacrcat ttcaccccac ccc                33

<210> SEQ ID NO 511
<211> LENGTH: 33
<212> TYPE: DNA
<213> ORGANISM: Homo Sapiens

<400> SEQUENCE: 511
tattaattgc cccagaratc tatcctcaca tcc                33

<210> SEQ ID NO 512
<211> LENGTH: 33
<212> TYPE: DNA
<213> ORGANISM: Homo Sapiens

<400> SEQUENCE: 512
tctggctccg cagcagraca cgaagtttgc att                33

<210> SEQ ID NO 513
<211> LENGTH: 33
<212> TYPE: DNA
<213> ORGANISM: Homo Sapiens

<400> SEQUENCE: 513
ggagcccttt gctgggrtgg ggatgagggt agt                33

<210> SEQ ID NO 514
<211> LENGTH: 33
```

<212> TYPE: DNA
<213> ORGANISM: Homo Sapiens

<400> SEQUENCE: 514
ctggtggcca aagtggmttt ctcccttcag ggg                33

<210> SEQ ID NO 515
<211> LENGTH: 33
<212> TYPE: DNA
<213> ORGANISM: Homo Sapiens

<400> SEQUENCE: 515
aagtctggaa tcagcaraaa tgtattacat tga                33

<210> SEQ ID NO 516
<211> LENGTH: 33
<212> TYPE: DNA
<213> ORGANISM: Homo Sapiens

<400> SEQUENCE: 516
atagaaataa gtgctaract gggagttggg aga                33

<210> SEQ ID NO 517
<211> LENGTH: 33
<212> TYPE: DNA
<213> ORGANISM: Homo Sapiens

<400> SEQUENCE: 517
gtgagagccc aggctgrggt caggaatgga aac                33

<210> SEQ ID NO 518
<211> LENGTH: 33
<212> TYPE: DNA
<213> ORGANISM: Homo Sapiens

<400> SEQUENCE: 518
gctaaaacgg gccccarttg daccgtcacc ttc                33

<210> SEQ ID NO 519
<211> LENGTH: 33
<212> TYPE: DNA
<213> ORGANISM: Homo Sapiens

<400> SEQUENCE: 519
cacttaaagc ccaaagrtgg ccggctgtgg tgg                33

<210> SEQ ID NO 520
<211> LENGTH: 33
<212> TYPE: DNA
<213> ORGANISM: Homo Sapiens

<400> SEQUENCE: 520
tgtggatctt cagcacrtct acaactccct cca                33

<210> SEQ ID NO 521
<211> LENGTH: 33
<212> TYPE: DNA
<213> ORGANISM: Homo Sapiens

<400> SEQUENCE: 521
acaaaccttc ttggaargtg gaaagttttg caa                33

<210> SEQ ID NO 522

<210> SEQ ID NO 522
<211> LENGTH: 33
<212> TYPE: DNA
<213> ORGANISM: Homo Sapiens

<400> SEQUENCE: 522
acaaaagcta ccagataaaa acactcacta tgg                                    33

<210> SEQ ID NO 523
<211> LENGTH: 33
<212> TYPE: DNA
<213> ORGANISM: Homo Sapiens

<400> SEQUENCE: 523
cctgagagat ctgagtratc aagacccagt gtt                                    33

<210> SEQ ID NO 524
<211> LENGTH: 33
<212> TYPE: DNA
<213> ORGANISM: Homo Sapiens

<400> SEQUENCE: 524
attcggtatt taatacmttt tgtgtgactg cct                                    33

<210> SEQ ID NO 525
<211> LENGTH: 33
<212> TYPE: DNA
<213> ORGANISM: Homo Sapiens

<400> SEQUENCE: 525
ctttcattta ttgaacrcct tagatatgag cta                                    33

<210> SEQ ID NO 526
<211> LENGTH: 33
<212> TYPE: DNA
<213> ORGANISM: Homo Sapiens

<400> SEQUENCE: 526
ttacagctca acaaaarcta ccagataaaa aca                                    33

<210> SEQ ID NO 527
<211> LENGTH: 33
<212> TYPE: DNA
<213> ORGANISM: Homo Sapiens

<400> SEQUENCE: 527
ggaggaagtg tggggtrtgg gtagactcct cct                                    33

<210> SEQ ID NO 528
<211> LENGTH: 33
<212> TYPE: DNA
<213> ORGANISM: Homo Sapiens

<400> SEQUENCE: 528
gtgtgtgatg cagtatrggg tagaaccagg aga                                    33

<210> SEQ ID NO 529
<211> LENGTH: 33
<212> TYPE: DNA
<213> ORGANISM: Homo Sapiens

<400> SEQUENCE: 529
ttcacacatg gaaatragg tggaaaagga gaa                                     33

```
<210> SEQ ID NO 530
<211> LENGTH: 33
<212> TYPE: DNA
<213> ORGANISM: Homo Sapiens

<400> SEQUENCE: 530
gtttgtgata aggagcrttg gggaggagat ttg                                  33

<210> SEQ ID NO 531
<211> LENGTH: 33
<212> TYPE: DNA
<213> ORGANISM: Homo Sapiens

<400> SEQUENCE: 531
tttaaggagg ctaactrctt ccacattaga tca                                  33

<210> SEQ ID NO 532
<211> LENGTH: 33
<212> TYPE: DNA
<213> ORGANISM: Homo Sapiens

<400> SEQUENCE: 532
cttttttgtc ttccccrtgc attcgccccc aca                                  33

<210> SEQ ID NO 533
<211> LENGTH: 33
<212> TYPE: DNA
<213> ORGANISM: Homo Sapiens

<400> SEQUENCE: 533
gacccaacag taagacrttt ctccttttgg taa                                  33

<210> SEQ ID NO 534
<211> LENGTH: 33
<212> TYPE: DNA
<213> ORGANISM: Homo Sapiens

<400> SEQUENCE: 534
cgttgaagaa tcagtamaat ttggagactt tga                                  33

<210> SEQ ID NO 535
<211> LENGTH: 33
<212> TYPE: DNA
<213> ORGANISM: Homo Sapiens

<400> SEQUENCE: 535
atcctgcacc ttttccmgtc aaatccccat tcc                                  33

<210> SEQ ID NO 536
<211> LENGTH: 33
<212> TYPE: DNA
<213> ORGANISM: Homo Sapiens

<400> SEQUENCE: 536
taagagaaga ctcaccrttc tgaggctgtc tga                                  33

<210> SEQ ID NO 537
<211> LENGTH: 33
<212> TYPE: DNA
<213> ORGANISM: Homo Sapiens

<400> SEQUENCE: 537
tccttcccag aaaaccrcct cagggctcac ccc                                  33
```

```
<210> SEQ ID NO 538
<211> LENGTH: 33
<212> TYPE: DNA
<213> ORGANISM: Homo Sapiens

<400> SEQUENCE: 538
gaactggaat gagaaartaa cctctaactg cta                          33

<210> SEQ ID NO 539
<211> LENGTH: 33
<212> TYPE: DNA
<213> ORGANISM: Homo Sapiens

<400> SEQUENCE: 539
agctcctact cagatarcag aactcacaaa ctt                          33

<210> SEQ ID NO 540
<211> LENGTH: 33
<212> TYPE: DNA
<213> ORGANISM: Homo Sapiens

<400> SEQUENCE: 540
ggtcaaatag taatttrttg ggtgaatgac agt                          33

<210> SEQ ID NO 541
<211> LENGTH: 33
<212> TYPE: DNA
<213> ORGANISM: Homo Sapiens

<400> SEQUENCE: 541
atttaccaga tcaaccrttc tcaatgctct tta                          33

<210> SEQ ID NO 542
<211> LENGTH: 33
<212> TYPE: DNA
<213> ORGANISM: Homo Sapiens

<400> SEQUENCE: 542
tggaagaatg tgtccargct gtgcttcccc ttt                          33

<210> SEQ ID NO 543
<211> LENGTH: 33
<212> TYPE: DNA
<213> ORGANISM: Homo Sapiens

<400> SEQUENCE: 543
ccatcacccc cggaccrtgg gctccatgcc agt                          33

<210> SEQ ID NO 544
<211> LENGTH: 33
<212> TYPE: DNA
<213> ORGANISM: Homo Sapiens

<400> SEQUENCE: 544
tcctctcctg tagaccrctg gctcatgaaa taa                          33

<210> SEQ ID NO 545
<211> LENGTH: 33
<212> TYPE: DNA
<213> ORGANISM: Homo Sapiens

<400> SEQUENCE: 545
cagactgctg gctctgrgca tctgagcagc gcc                          33
```

<210> SEQ ID NO 546
<211> LENGTH: 33
<212> TYPE: DNA
<213> ORGANISM: Homo Sapiens

<400> SEQUENCE: 546
agggttttct tgaatgrcat ttctcattgc taa                33

<210> SEQ ID NO 547
<211> LENGTH: 33
<212> TYPE: DNA
<213> ORGANISM: Homo Sapiens

<400> SEQUENCE: 547
agaatagacg tgttagraac caggttagcc tgg                33

<210> SEQ ID NO 548
<211> LENGTH: 33
<212> TYPE: DNA
<213> ORGANISM: Homo Sapiens

<400> SEQUENCE: 548
tcttgggggt cttttgrggg aacagagaac aat                33

<210> SEQ ID NO 549
<211> LENGTH: 33
<212> TYPE: DNA
<213> ORGANISM: Homo Sapiens

<400> SEQUENCE: 549
ttgatgatgg tgatatrgaa tgattaataa cca                33

<210> SEQ ID NO 550
<211> LENGTH: 33
<212> TYPE: DNA
<213> ORGANISM: Homo Sapiens

<400> SEQUENCE: 550
tgatgggaga gaaatargaa ttcaacttgt agc                33

<210> SEQ ID NO 551
<211> LENGTH: 33
<212> TYPE: DNA
<213> ORGANISM: Homo Sapiens

<400> SEQUENCE: 551
tttttccctg aaactcrgcc aaaagttttt cct                33

<210> SEQ ID NO 552
<211> LENGTH: 33
<212> TYPE: DNA
<213> ORGANISM: Homo Sapiens

<400> SEQUENCE: 552
gctatattaa aagaaartag acttcaaagc aaa                33

<210> SEQ ID NO 553
<211> LENGTH: 33
<212> TYPE: DNA
<213> ORGANISM: Homo Sapiens

<400> SEQUENCE: 553

```
aggggcctaa gcccagrtgt cagaggcaca gta                                    33

<210> SEQ ID NO 554
<211> LENGTH: 33
<212> TYPE: DNA
<213> ORGANISM: Homo Sapiens

<400> SEQUENCE: 554
gtttccagcc acctctrttt ccattccctt aaa                                    33

<210> SEQ ID NO 555
<211> LENGTH: 33
<212> TYPE: DNA
<213> ORGANISM: Homo Sapiens

<400> SEQUENCE: 555
gacgcagtct gtaggcrctt ggcaagtgtt tgc                                    33

<210> SEQ ID NO 556
<211> LENGTH: 33
<212> TYPE: DNA
<213> ORGANISM: Homo Sapiens

<400> SEQUENCE: 556
tcccctgcca ctccctrttt aatgcctttg taa                                    33

<210> SEQ ID NO 557
<211> LENGTH: 33
<212> TYPE: DNA
<213> ORGANISM: Homo Sapiens

<400> SEQUENCE: 557
gtgtgaggga ctcctcrtaa ctcctgggca agg                                    33

<210> SEQ ID NO 558
<211> LENGTH: 33
<212> TYPE: DNA
<213> ORGANISM: Homo Sapiens

<400> SEQUENCE: 558
gttgtcatga gttaccrtga ttaaagtggt gga                                    33

<210> SEQ ID NO 559
<211> LENGTH: 33
<212> TYPE: DNA
<213> ORGANISM: Homo Sapiens

<400> SEQUENCE: 559
tataatcttt gtctcartag tcaaatactt aga                                    33

<210> SEQ ID NO 560
<211> LENGTH: 33
<212> TYPE: DNA
<213> ORGANISM: Homo Sapiens

<400> SEQUENCE: 560
tccccatagc tatccarttg agccagaacc att                                    33

<210> SEQ ID NO 561
<211> LENGTH: 33
<212> TYPE: DNA
<213> ORGANISM: Homo Sapiens

<400> SEQUENCE: 561
```
tgcgatcacc tggattratg gcaactaatg ctc                                    33

<210> SEQ ID NO 562
<211> LENGTH: 33
<212> TYPE: DNA
<213> ORGANISM: Homo Sapiens

<400> SEQUENCE: 562
tctggaggtg gagtctragg atactgctct tag                                    33

<210> SEQ ID NO 563
<211> LENGTH: 33
<212> TYPE: DNA
<213> ORGANISM: Homo Sapiens

<400> SEQUENCE: 563
agtctagcca ggctccrtag aaactggagt gcc                                    33

<210> SEQ ID NO 564
<211> LENGTH: 33
<212> TYPE: DNA
<213> ORGANISM: Homo Sapiens

<400> SEQUENCE: 564
gaattttgga attcagrtat cagaaaaaag ctg                                    33

<210> SEQ ID NO 565
<211> LENGTH: 33
<212> TYPE: DNA
<213> ORGANISM: Homo Sapiens

<400> SEQUENCE: 565
agttatgtaa acaggargtg cagcatagtg tct                                    33

<210> SEQ ID NO 566
<211> LENGTH: 33
<212> TYPE: DNA
<213> ORGANISM: Homo Sapiens

<400> SEQUENCE: 566
ttctttcatc cttatgrcct ttcttgtata ggt                                    33

<210> SEQ ID NO 567
<211> LENGTH: 33
<212> TYPE: DNA
<213> ORGANISM: Homo Sapiens

<400> SEQUENCE: 567
atatatcatt ttatttratt tcccagtcac ctt                                    33

<210> SEQ ID NO 568
<211> LENGTH: 33
<212> TYPE: DNA
<213> ORGANISM: Homo Sapiens

<400> SEQUENCE: 568
cgtacccatg tgtcacragt acacatgctt ttc                                    33

<210> SEQ ID NO 569
<211> LENGTH: 33
<212> TYPE: DNA
<213> ORGANISM: Homo Sapiens

<400> SEQUENCE: 569
aatcattttt tcaaaartgt agtcttttgt gag                33

<210> SEQ ID NO 570
<211> LENGTH: 33
<212> TYPE: DNA
<213> ORGANISM: Homo Sapiens

<400> SEQUENCE: 570
aggaggtgat tagatcrtag aggttgttcc cac                33

<210> SEQ ID NO 571
<211> LENGTH: 33
<212> TYPE: DNA
<213> ORGANISM: Homo Sapiens

<400> SEQUENCE: 571
ctttgaagtc cttctgraaa atacctaaat tag                33

<210> SEQ ID NO 572
<211> LENGTH: 33
<212> TYPE: DNA
<213> ORGANISM: Homo Sapiens

<400> SEQUENCE: 572
aacccactcc actaagrcct tcagtctgtg ctc                33

<210> SEQ ID NO 573
<211> LENGTH: 33
<212> TYPE: DNA
<213> ORGANISM: Homo Sapiens

<400> SEQUENCE: 573
ctccgctgcc accgccrcca ctgctcctcc tgc                33

<210> SEQ ID NO 574
<211> LENGTH: 33
<212> TYPE: DNA
<213> ORGANISM: Homo Sapiens

<400> SEQUENCE: 574
tttgccatac taatttrgta actttagcta ggt                33

<210> SEQ ID NO 575
<211> LENGTH: 33
<212> TYPE: DNA
<213> ORGANISM: Homo Sapiens

<400> SEQUENCE: 575
gcctctagtc actaagraaa gtctaagtat ctt                33

<210> SEQ ID NO 576
<211> LENGTH: 33
<212> TYPE: DNA
<213> ORGANISM: Homo Sapiens

<400> SEQUENCE: 576
ttcaggatta gatgctraga cttcaaatca gtc                33

<210> SEQ ID NO 577
<211> LENGTH: 33
<212> TYPE: DNA
<213> ORGANISM: Homo Sapiens

```
<400> SEQUENCE: 577
acttgtttac aaaagcrtct ctataggtct gtg                                33

<210> SEQ ID NO 578
<211> LENGTH: 33
<212> TYPE: DNA
<213> ORGANISM: Homo Sapiens

<400> SEQUENCE: 578
aagataaata agacaartaa cacattaaaa agc                                33

<210> SEQ ID NO 579
<211> LENGTH: 33
<212> TYPE: DNA
<213> ORGANISM: Homo Sapiens

<400> SEQUENCE: 579
atgggcaaac ttctctmatg ctaacagtga tga                                33

<210> SEQ ID NO 580
<211> LENGTH: 33
<212> TYPE: DNA
<213> ORGANISM: Homo Sapiens

<400> SEQUENCE: 580
ctgtcttcat tcctccrgct actatcccta ccc                                33

<210> SEQ ID NO 581
<211> LENGTH: 33
<212> TYPE: DNA
<213> ORGANISM: Homo Sapiens

<400> SEQUENCE: 581
tactgccaaa cctccamtca aaatagctag ggc                                33

<210> SEQ ID NO 582
<211> LENGTH: 33
<212> TYPE: DNA
<213> ORGANISM: Homo Sapiens

<400> SEQUENCE: 582
ctgtctgcta ggagtarcat caggaagtgt ctg                                33

<210> SEQ ID NO 583
<211> LENGTH: 33
<212> TYPE: DNA
<213> ORGANISM: Homo Sapiens

<400> SEQUENCE: 583
accctagatc tttctcmttc tcttcataca cat                                33

<210> SEQ ID NO 584
<211> LENGTH: 33
<212> TYPE: DNA
<213> ORGANISM: Homo Sapiens

<400> SEQUENCE: 584
attgctagca tttattmagt gaatgaataa atg                                33

<210> SEQ ID NO 585
<211> LENGTH: 33
<212> TYPE: DNA
```

<213> ORGANISM: Homo Sapiens

<400> SEQUENCE: 585
agcctcaaag gtagcarcct ttagaaagaa aaa                33

<210> SEQ ID NO 586
<211> LENGTH: 33
<212> TYPE: DNA
<213> ORGANISM: Homo Sapiens

<400> SEQUENCE: 586
aaaaactctg tagctartat catgcttaat gat                33

<210> SEQ ID NO 587
<211> LENGTH: 33
<212> TYPE: DNA
<213> ORGANISM: Homo Sapiens

<400> SEQUENCE: 587
tttctgatgg catccartcc agagcaaatc cct                33

<210> SEQ ID NO 588
<211> LENGTH: 33
<212> TYPE: DNA
<213> ORGANISM: Homo Sapiens

<400> SEQUENCE: 588
tagtttgaaa ccctatratg ttctttgaaa cct                33

<210> SEQ ID NO 589
<211> LENGTH: 33
<212> TYPE: DNA
<213> ORGANISM: Homo Sapiens

<400> SEQUENCE: 589
agagcatcct aaatccract cttaggggaa gac                33

<210> SEQ ID NO 590
<211> LENGTH: 33
<212> TYPE: DNA
<213> ORGANISM: Homo Sapiens

<400> SEQUENCE: 590
ctgtgctgct taccatrtat ggatgagggg ttg                33

<210> SEQ ID NO 591
<211> LENGTH: 33
<212> TYPE: DNA
<213> ORGANISM: Homo Sapiens

<400> SEQUENCE: 591
aaaagactgg aggaagrcaa ttgtagctag ggc                33

<210> SEQ ID NO 592
<211> LENGTH: 33
<212> TYPE: DNA
<213> ORGANISM: Homo Sapiens

<400> SEQUENCE: 592
ggtatatggt taagatratc atacgacttg gtt                33

<210> SEQ ID NO 593
<211> LENGTH: 33

```
<212> TYPE: DNA
<213> ORGANISM: Homo Sapiens

<400> SEQUENCE: 593
tcaattgttc atttggrcaa gagtttgggt ttg                                   33

<210> SEQ ID NO 594
<211> LENGTH: 33
<212> TYPE: DNA
<213> ORGANISM: Homo Sapiens

<400> SEQUENCE: 594
tccagatttt tactatrtgt ggctgtaaaa atg                                   33

<210> SEQ ID NO 595
<211> LENGTH: 33
<212> TYPE: DNA
<213> ORGANISM: Homo Sapiens

<400> SEQUENCE: 595
taaacttaga catgaartag agaaaggagg tta                                   33

<210> SEQ ID NO 596
<211> LENGTH: 33
<212> TYPE: DNA
<213> ORGANISM: Homo Sapiens

<400> SEQUENCE: 596
ataaaggaag gtaaaarctc agaaggccaa agg                                   33

<210> SEQ ID NO 597
<211> LENGTH: 33
<212> TYPE: DNA
<213> ORGANISM: Homo Sapiens

<400> SEQUENCE: 597
catgattaaa agtatcrtct tcagacatct gct                                   33

<210> SEQ ID NO 598
<211> LENGTH: 33
<212> TYPE: DNA
<213> ORGANISM: Homo Sapiens

<400> SEQUENCE: 598
gcctggtatt ccatggrtca tgtcaaaaaa cct                                   33

<210> SEQ ID NO 599
<211> LENGTH: 33
<212> TYPE: DNA
<213> ORGANISM: Homo Sapiens

<400> SEQUENCE: 599
acactttaaa taacgtrtcc aagaaagtgg aaa                                   33

<210> SEQ ID NO 600
<211> LENGTH: 33
<212> TYPE: DNA
<213> ORGANISM: Homo Sapiens

<400> SEQUENCE: 600
tggtcattcg accttcrccc cataaatagt ggt                                   33

<210> SEQ ID NO 601
```

```
<211> LENGTH: 33
<212> TYPE: DNA
<213> ORGANISM: Homo Sapiens

<400> SEQUENCE: 601
ggccaatcta acacaarcat gactagtggg ttc                                  33

<210> SEQ ID NO 602
<211> LENGTH: 33
<212> TYPE: DNA
<213> ORGANISM: Homo Sapiens

<400> SEQUENCE: 602
tatggtctgc tgagtcrata atctatgttt tta                                  33

<210> SEQ ID NO 603
<211> LENGTH: 33
<212> TYPE: DNA
<213> ORGANISM: Homo Sapiens

<400> SEQUENCE: 603
ctgtgtataa ttcaaarcat ctccttttt gtt                                   33

<210> SEQ ID NO 604
<211> LENGTH: 33
<212> TYPE: DNA
<213> ORGANISM: Homo Sapiens

<400> SEQUENCE: 604
aacaatcaca attttcrttg atttatctcc cca                                  33

<210> SEQ ID NO 605
<211> LENGTH: 33
<212> TYPE: DNA
<213> ORGANISM: Homo Sapiens

<400> SEQUENCE: 605
gataccttat gtgaccrtag ttagtcggtg atc                                  33

<210> SEQ ID NO 606
<211> LENGTH: 33
<212> TYPE: DNA
<213> ORGANISM: Homo Sapiens

<400> SEQUENCE: 606
ttaaatatct aaatgtrtaa aacagacctg atc                                  33

<210> SEQ ID NO 607
<211> LENGTH: 33
<212> TYPE: DNA
<213> ORGANISM: Homo Sapiens

<400> SEQUENCE: 607
cgacaaggct gggatcrgtg ctctccttcc agc                                  33

<210> SEQ ID NO 608
<211> LENGTH: 33
<212> TYPE: DNA
<213> ORGANISM: Homo Sapiens

<400> SEQUENCE: 608
caattcattc tgtgccract caccctggg gtc                                   33
```

```
<210> SEQ ID NO 609
<211> LENGTH: 33
<212> TYPE: DNA
<213> ORGANISM: Homo Sapiens

<400> SEQUENCE: 609
gtctagcaat ccttgtrtat gctttaatca cag                           33

<210> SEQ ID NO 610
<211> LENGTH: 33
<212> TYPE: DNA
<213> ORGANISM: Homo Sapiens

<400> SEQUENCE: 610
caggtttagt ttgagarcca gcaaactgaa aag                           33

<210> SEQ ID NO 611
<211> LENGTH: 33
<212> TYPE: DNA
<213> ORGANISM: Homo Sapiens

<400> SEQUENCE: 611
ggaagtcaat taaaaartct aaatataaat ttg                           33

<210> SEQ ID NO 612
<211> LENGTH: 33
<212> TYPE: DNA
<213> ORGANISM: Homo Sapiens

<400> SEQUENCE: 612
gaatttaaaa atatcartac aagaaagtca tta                           33

<210> SEQ ID NO 613
<211> LENGTH: 33
<212> TYPE: DNA
<213> ORGANISM: Homo Sapiens

<400> SEQUENCE: 613
ttagcatgag ccacagraaa ggtttttgag cca                           33

<210> SEQ ID NO 614
<211> LENGTH: 33
<212> TYPE: DNA
<213> ORGANISM: Homo Sapiens

<400> SEQUENCE: 614
agtttctgtg ttttaamgga atagcctgct gtg                           33

<210> SEQ ID NO 615
<211> LENGTH: 33
<212> TYPE: DNA
<213> ORGANISM: Homo Sapiens

<400> SEQUENCE: 615
gtccggccct gctaccrcca acctttgcgt aat                           33

<210> SEQ ID NO 616
<211> LENGTH: 33
<212> TYPE: DNA
<213> ORGANISM: Homo Sapiens

<400> SEQUENCE: 616
aagtaaattg cccaagrtgg cccagctagt aaa                           33
```

```
<210> SEQ ID NO 617
<211> LENGTH: 33
<212> TYPE: DNA
<213> ORGANISM: Homo Sapiens

<400> SEQUENCE: 617
tgtctgtctc taaatcrtgt gctgttaaaa aat                                      33

<210> SEQ ID NO 618
<211> LENGTH: 33
<212> TYPE: DNA
<213> ORGANISM: Homo Sapiens

<400> SEQUENCE: 618
gctccttttt aactcartat tacctgtggt ttt                                      33

<210> SEQ ID NO 619
<211> LENGTH: 33
<212> TYPE: DNA
<213> ORGANISM: Homo Sapiens

<400> SEQUENCE: 619 tgggggtcc atgtggraaa gactgtgagt ggc                                       33

<210> SEQ ID NO 620
<211> LENGTH: 33
<212> TYPE: DNA
<213> ORGANISM: Homo Sapiens

<400> SEQUENCE: 620
tgttttatct gtggacrcta cctcgtgaga ttg                                      33

<210> SEQ ID NO 621
<211> LENGTH: 33
<212> TYPE: DNA
<213> ORGANISM: Homo Sapiens

<400> SEQUENCE: 621
ttccttgctt cttttgrccc aacattttag cgc                                      33

<210> SEQ ID NO 622
<211> LENGTH: 33
<212> TYPE: DNA
<213> ORGANISM: Homo Sapiens

<400> SEQUENCE: 622
ttctgaagta tctctaraaa gtgtctctat aaa                                      33

<210> SEQ ID NO 623
<211> LENGTH: 33
<212> TYPE: DNA
<213> ORGANISM: Homo Sapiens

<400> SEQUENCE: 623
gactgcccta gctgagrgta tgggagggag ggg                                      33

<210> SEQ ID NO 624
<211> LENGTH: 33
<212> TYPE: DNA
<213> ORGANISM: Homo Sapiens

<400> SEQUENCE: 624
tgattacccc tgttctmgga gtcgctgctt tct                                      33
```

<210> SEQ ID NO 625
<211> LENGTH: 33
<212> TYPE: DNA
<213> ORGANISM: Homo Sapiens

<400> SEQUENCE: 625
gaattgacta ctgcaamtgt gcatgatttt atc                                    33

<210> SEQ ID NO 626
<211> LENGTH: 33
<212> TYPE: DNA
<213> ORGANISM: Homo Sapiens

<400> SEQUENCE: 626
ccgaggttag gcgaagrgtc ggggcttctc tga                                    33

<210> SEQ ID NO 627
<211> LENGTH: 33
<212> TYPE: DNA
<213> ORGANISM: Homo Sapiens

<400> SEQUENCE: 627
gatggcaagc atacatrgtt ttgagtgttc cat                                    33

<210> SEQ ID NO 628
<211> LENGTH: 33
<212> TYPE: DNA
<213> ORGANISM: Homo Sapiens

<400> SEQUENCE: 628
gtagttgaat atttgcract tatatcaacc tat                                    33

<210> SEQ ID NO 629
<211> LENGTH: 33
<212> TYPE: DNA
<213> ORGANISM: Homo Sapiens

<400> SEQUENCE: 629
tgatttcggg gctttcrctt tcattatgct gtc                                    33

<210> SEQ ID NO 630
<211> LENGTH: 33
<212> TYPE: DNA
<213> ORGANISM: Homo Sapiens

<400> SEQUENCE: 630
tgagtcaaca tgaagtragg gaaatgaaaa ggg                                    33

<210> SEQ ID NO 631
<211> LENGTH: 33
<212> TYPE: DNA
<213> ORGANISM: Homo Sapiens

<400> SEQUENCE: 631
ctactgctta cttctgmctc catgtagaat aaa                                    33

<210> SEQ ID NO 632
<211> LENGTH: 33
<212> TYPE: DNA
<213> ORGANISM: Homo Sapiens

<400> SEQUENCE: 632
aaaggagcat tcacacmgct tctcttgtca tga                                      33

<210> SEQ ID NO 633
<211> LENGTH: 33
<212> TYPE: DNA
<213> ORGANISM: Homo Sapiens

<400> SEQUENCE: 633
ggcagaactt ttattgrcta ggagtttctt ttt                                      33

<210> SEQ ID NO 634
<211> LENGTH: 33
<212> TYPE: DNA
<213> ORGANISM: Homo Sapiens

<400> SEQUENCE: 634
gtgagcacat gcctctrtaa gtgattttaa aat                                      33

<210> SEQ ID NO 635
<211> LENGTH: 33
<212> TYPE: DNA
<213> ORGANISM: Homo Sapiens

<400> SEQUENCE: 635
aagagccagg gttgacrgct ctcagagaga aga                                      33

<210> SEQ ID NO 636
<211> LENGTH: 33
<212> TYPE: DNA
<213> ORGANISM: Homo Sapiens

<400> SEQUENCE: 636
gaatgtttga acatctrtag taatattgaa cca                                      33

<210> SEQ ID NO 637
<211> LENGTH: 33
<212> TYPE: DNA
<213> ORGANISM: Homo Sapiens

<400> SEQUENCE: 637
ttctacagaa atacaarctg tcttatgagt aaa                                      33

<210> SEQ ID NO 638
<211> LENGTH: 33
<212> TYPE: DNA
<213> ORGANISM: Homo Sapiens

<400> SEQUENCE: 638
agaagtaaaa cagttcrtat aaaagtgaat ttt                                      33

<210> SEQ ID NO 639
<211> LENGTH: 33
<212> TYPE: DNA
<213> ORGANISM: Homo Sapiens

<400> SEQUENCE: 639
gaaaggagga atttctrttt caagcgacac cgt                                      33

<210> SEQ ID NO 640
<211> LENGTH: 33
<212> TYPE: DNA
<213> ORGANISM: Homo Sapiens

<400> SEQUENCE: 640
ttagtatatt gtatccrgtg aatttcgcta aat                                33

<210> SEQ ID NO 641
<211> LENGTH: 33
<212> TYPE: DNA
<213> ORGANISM: Homo Sapiens

<400> SEQUENCE: 641
ctgggattac aagcatragc caccaggcct agc                                33

<210> SEQ ID NO 642
<211> LENGTH: 33
<212> TYPE: DNA
<213> ORGANISM: Homo Sapiens

<400> SEQUENCE: 642
actttggaag tgtcaargtc atggaagaca aag                                33

<210> SEQ ID NO 643
<211> LENGTH: 33
<212> TYPE: DNA
<213> ORGANISM: Homo Sapiens

<400> SEQUENCE: 643
tttaattaca gtcattrcct ttgtttttc tca                                 33

<210> SEQ ID NO 644
<211> LENGTH: 33
<212> TYPE: DNA
<213> ORGANISM: Homo Sapiens

<400> SEQUENCE: 644
atgaaaataa aaaaacmatg taaacatttg gga                                33

<210> SEQ ID NO 645
<211> LENGTH: 33
<212> TYPE: DNA
<213> ORGANISM: Homo Sapiens

<400> SEQUENCE: 645
tgataactac tggcccrtct caaggcaaga tga                                33

<210> SEQ ID NO 646
<211> LENGTH: 33
<212> TYPE: DNA
<213> ORGANISM: Homo Sapiens

<400> SEQUENCE: 646
tgagtcccaa gccaggmaca tggcatcccc tga                                33

<210> SEQ ID NO 647
<211> LENGTH: 33
<212> TYPE: DNA
<213> ORGANISM: Homo Sapiens

<400> SEQUENCE: 647
atgctgctga ggccctrggc ttctatggta gat                                33

<210> SEQ ID NO 648
<211> LENGTH: 33
<212> TYPE: DNA
<213> ORGANISM: Homo Sapiens

<400> SEQUENCE: 648
tctcgctttt gctctcrctc tcactctgta gcc                                33

<210> SEQ ID NO 649
<211> LENGTH: 33
<212> TYPE: DNA
<213> ORGANISM: Homo Sapiens

<400> SEQUENCE: 649
atttaagttt cccctcrcct atcactatgt gct                                33

<210> SEQ ID NO 650
<211> LENGTH: 33
<212> TYPE: DNA
<213> ORGANISM: Homo Sapiens

<400> SEQUENCE: 650
tagtaaatgg tattggrtga actgagtagc cat                                33

<210> SEQ ID NO 651
<211> LENGTH: 33
<212> TYPE: DNA
<213> ORGANISM: Homo Sapiens

<400> SEQUENCE: 651
ttcatttacc aatcacrtac ctttttttgtc att                               33

<210> SEQ ID NO 652
<211> LENGTH: 33
<212> TYPE: DNA
<213> ORGANISM: Homo Sapiens

<400> SEQUENCE: 652
tattggttca gccctgmaac acaggccatc ttg                                33

<210> SEQ ID NO 653
<211> LENGTH: 33
<212> TYPE: DNA
<213> ORGANISM: Homo Sapiens

<400> SEQUENCE: 653
ggaaagaaac tagtttrtct caactctgta ttc                                33

<210> SEQ ID NO 654
<211> LENGTH: 33
<212> TYPE: DNA
<213> ORGANISM: Homo Sapiens

<400> SEQUENCE: 654
gatcttctct accttgrtat aaaaatcacc tca                                33

<210> SEQ ID NO 655
<211> LENGTH: 33
<212> TYPE: DNA
<213> ORGANISM: Homo Sapiens

<400> SEQUENCE: 655
ttggttaatt tgaactmttc cctctgatat att                                33

<210> SEQ ID NO 656
<211> LENGTH: 33
<212> TYPE: DNA
<213> ORGANISM: Homo Sapiens

<400> SEQUENCE: 656
ataccaggcc atacttrgcc atcaaaagtt tga                33

<210> SEQ ID NO 657
<211> LENGTH: 33
<212> TYPE: DNA
<213> ORGANISM: Homo Sapiens

<400> SEQUENCE: 657
tgctaatctg ttccttrtaa attttcacac aaa                33

<210> SEQ ID NO 658
<211> LENGTH: 33
<212> TYPE: DNA
<213> ORGANISM: Homo Sapiens

<400> SEQUENCE: 658
gcggccggcc gccaatrgaa tcttgctcct act                33

<210> SEQ ID NO 659
<211> LENGTH: 33
<212> TYPE: DNA
<213> ORGANISM: Homo Sapiens

<400> SEQUENCE: 659
tattttcaac aaacagrata ggactatttt cac                33

<210> SEQ ID NO 660
<211> LENGTH: 33
<212> TYPE: DNA
<213> ORGANISM: Homo Sapiens

<400> SEQUENCE: 660
agagagtcta ggtgagrcac ttcatcacaa cca                33

<210> SEQ ID NO 661
<211> LENGTH: 33
<212> TYPE: DNA
<213> ORGANISM: Homo Sapiens

<400> SEQUENCE: 661
tctctctcaa aatcatrcac ttctttccac tac                33

<210> SEQ ID NO 662
<211> LENGTH: 33
<212> TYPE: DNA
<213> ORGANISM: Homo Sapiens

<400> SEQUENCE: 662
atctgatgtg caggtargaa atgtcacagg agg                33

<210> SEQ ID NO 663
<211> LENGTH: 33
<212> TYPE: DNA
<213> ORGANISM: Homo Sapiens

<400> SEQUENCE: 663
tgagggggaa agcaacrtag atactgggaa caa                33

<210> SEQ ID NO 664
<211> LENGTH: 33
<212> TYPE: DNA

<213> ORGANISM: Homo Sapiens

<400> SEQUENCE: 664
ttctggtcaa tgtgctrtat gtacatgaca aat          33

<210> SEQ ID NO 665
<211> LENGTH: 33
<212> TYPE: DNA
<213> ORGANISM: Homo Sapiens

<400> SEQUENCE: 665
ggaggaacaa aaaccarcca gtctctggac tgt          33

<210> SEQ ID NO 666
<211> LENGTH: 33
<212> TYPE: DNA
<213> ORGANISM: Homo Sapiens

<400> SEQUENCE: 666
caatttcatt tccttcrgac atatacccgg agt          33

<210> SEQ ID NO 667
<211> LENGTH: 33
<212> TYPE: DNA
<213> ORGANISM: Homo Sapiens

<400> SEQUENCE: 667
taagaaaagg aatgagraaa cttgattggt gta          33

<210> SEQ ID NO 668
<211> LENGTH: 33
<212> TYPE: DNA
<213> ORGANISM: Homo Sapiens

<400> SEQUENCE: 668
ccatgccaac aacattraga agaacaaggt tgg          33

<210> SEQ ID NO 669
<211> LENGTH: 33
<212> TYPE: DNA
<213> ORGANISM: Homo Sapiens

<400> SEQUENCE: 669
ttagagaaga aatactrtat gacacagatg agg          33

<210> SEQ ID NO 670
<211> LENGTH: 33
<212> TYPE: DNA
<213> ORGANISM: Homo Sapiens

<400> SEQUENCE: 670
gcaattccac ttctggrtat atgccacaaa gta          33

<210> SEQ ID NO 671
<211> LENGTH: 33
<212> TYPE: DNA
<213> ORGANISM: Homo Sapiens

<400> SEQUENCE: 671
cagttcagca cgggggrcag taagcgtcca gcc          33

<210> SEQ ID NO 672
<211> LENGTH: 33

```
<212> TYPE: DNA
<213> ORGANISM: Homo Sapiens

<400> SEQUENCE: 672
gaatctgtta ctctggraca cagatgcagg gtt                                33

<210> SEQ ID NO 673
<211> LENGTH: 33
<212> TYPE: DNA
<213> ORGANISM: Homo Sapiens

<400> SEQUENCE: 673
cccagcagct tacaccrcac ctccctgtta cat                                33

<210> SEQ ID NO 674
<211> LENGTH: 33
<212> TYPE: DNA
<213> ORGANISM: Homo Sapiens

<400> SEQUENCE: 674
aatgaagatt caggacracg aagcagtggt aac                                33

<210> SEQ ID NO 675
<211> LENGTH: 33
<212> TYPE: DNA
<213> ORGANISM: Homo Sapiens

<400> SEQUENCE: 675
gtaatactcc ttctacratc ctaagatggg tct                                33

<210> SEQ ID NO 676
<211> LENGTH: 33
<212> TYPE: DNA
<213> ORGANISM: Homo Sapiens

<400> SEQUENCE: 676
gaatgtctat tctctgratg agcaggggag gag                                33

<210> SEQ ID NO 677
<211> LENGTH: 33
<212> TYPE: DNA
<213> ORGANISM: Homo Sapiens

<400> SEQUENCE: 677
atggtcagct ggctttrctg ttcacaacat gtt                                33

<210> SEQ ID NO 678
<211> LENGTH: 33
<212> TYPE: DNA
<213> ORGANISM: Homo Sapiens

<400> SEQUENCE: 678
tttccagtct tatttcmggg gctggcggtg gta                                33

<210> SEQ ID NO 679
<211> LENGTH: 33
<212> TYPE: DNA
<213> ORGANISM: Homo Sapiens

<400> SEQUENCE: 679
ctttcttgtg agcttgmttt tctccacaat ttg                                33

<210> SEQ ID NO 680
```

```
<211> LENGTH: 33
<212> TYPE: DNA
<213> ORGANISM: Homo Sapiens

<400> SEQUENCE: 680
tcctgaaaag gtctcarttc tcatcagcca gcg                            33

<210> SEQ ID NO 681
<211> LENGTH: 33
<212> TYPE: DNA
<213> ORGANISM: Homo Sapiens

<400> SEQUENCE: 681
accaaacttc aagaccraac atagggaacc caa                            33

<210> SEQ ID NO 682
<211> LENGTH: 33
<212> TYPE: DNA
<213> ORGANISM: Homo Sapiens

<400> SEQUENCE: 682
ctatttgcaa gggagargaa gggcacctaa tat                            33

<210> SEQ ID NO 683
<211> LENGTH: 33
<212> TYPE: DNA
<213> ORGANISM: Homo Sapiens

<400> SEQUENCE: 683
gaagagcacc acttagrcac ttcagagacc cat                            33

<210> SEQ ID NO 684
<211> LENGTH: 33
<212> TYPE: DNA
<213> ORGANISM: Homo Sapiens

<400> SEQUENCE: 684
tgaaccagga aactgarggc tcttgtggtc cag                            33

<210> SEQ ID NO 685
<211> LENGTH: 33
<212> TYPE: DNA
<213> ORGANISM: Homo Sapiens

<400> SEQUENCE: 685
ctaccccttc aacagcratt tactacttga tcc                            33

<210> SEQ ID NO 686
<211> LENGTH: 33
<212> TYPE: DNA
<213> ORGANISM: Homo Sapiens

<400> SEQUENCE: 686
cttgaattct ttagaartca tagaaattat cct                            33

<210> SEQ ID NO 687
<211> LENGTH: 33
<212> TYPE: DNA
<213> ORGANISM: Homo Sapiens

<400> SEQUENCE: 687
ggctccctgt cctttcrccc ctcggttcct tcc                            33
```

```
<210> SEQ ID NO 688
<211> LENGTH: 33
<212> TYPE: DNA
<213> ORGANISM: Homo Sapiens

<400> SEQUENCE: 688
gagagattac ggagacrgaa gacaggcagc tgg                                    33

<210> SEQ ID NO 689
<211> LENGTH: 33
<212> TYPE: DNA
<213> ORGANISM: Homo Sapiens

<400> SEQUENCE: 689
atgaaagatg aggggaraga gagatgtgca aaa                                    33

<210> SEQ ID NO 690
<211> LENGTH: 33
<212> TYPE: DNA
<213> ORGANISM: Homo Sapiens

<400> SEQUENCE: 690
tgcaattcat ccacacmctg aaagatcctg tta                                    33

<210> SEQ ID NO 691
<211> LENGTH: 33
<212> TYPE: DNA
<213> ORGANISM: Homo Sapiens

<400> SEQUENCE: 691
tgcacctttg ttaaaaraca aatgactgta tgt                                    33

<210> SEQ ID NO 692
<211> LENGTH: 33
<212> TYPE: DNA
<213> ORGANISM: Homo Sapiens

<400> SEQUENCE: 692
catgctgccc ttttctrctg tctcaaactt gat                                    33

<210> SEQ ID NO 693
<211> LENGTH: 33
<212> TYPE: DNA
<213> ORGANISM: Homo Sapiens

<400> SEQUENCE: 693
cctgaacatt ataaacraga caagtataaa cag                                    33

<210> SEQ ID NO 694
<211> LENGTH: 33
<212> TYPE: DNA
<213> ORGANISM: Homo Sapiens

<400> SEQUENCE: 694
tcactgtctt ccatcaraaa aacaaatgat tta                                    33

<210> SEQ ID NO 695
<211> LENGTH: 33
<212> TYPE: DNA
<213> ORGANISM: Homo Sapiens

<400> SEQUENCE: 695
agggttctat tctttcraac tactccagca gtc                                    33
```

```
<210> SEQ ID NO 696
<211> LENGTH: 33
<212> TYPE: DNA
<213> ORGANISM: Homo Sapiens

<400> SEQUENCE: 696
aatcttttgc tagaatraag tcctttgcat ttt                                33

<210> SEQ ID NO 697
<211> LENGTH: 33
<212> TYPE: DNA
<213> ORGANISM: Homo Sapiens

<400> SEQUENCE: 697
tgccttcagc cgaagarttg gttttcactt tgg                                33

<210> SEQ ID NO 698
<211> LENGTH: 33
<212> TYPE: DNA
<213> ORGANISM: Homo Sapiens

<400> SEQUENCE: 698
gaatgccctt ttttcartcc tccgtgtgat tgg                                33

<210> SEQ ID NO 699
<211> LENGTH: 33
<212> TYPE: DNA
<213> ORGANISM: Homo Sapiens

<400> SEQUENCE: 699
ctgttgttaa acacatrtgc taatttcaaa ata                                33

<210> SEQ ID NO 700
<211> LENGTH: 33
<212> TYPE: DNA
<213> ORGANISM: Homo Sapiens

<400> SEQUENCE: 700
aggaggtttg tctttgrttc gcctgcacct tcc                                33

<210> SEQ ID NO 701
<211> LENGTH: 33
<212> TYPE: DNA
<213> ORGANISM: Homo Sapiens

<400> SEQUENCE: 701
gtggactagt gcctctrttt tctctaatgc ttt                                33

<210> SEQ ID NO 702
<211> LENGTH: 33
<212> TYPE: DNA
<213> ORGANISM: Homo Sapiens

<400> SEQUENCE: 702
tttctcagaa acctctraaa gccatcttct gct                                33

<210> SEQ ID NO 703
<211> LENGTH: 33
<212> TYPE: DNA
<213> ORGANISM: Homo Sapiens

<400> SEQUENCE: 703
gtcttctttc atccagsgct cctcggcctt cct                                33
```

<210> SEQ ID NO 704
<211> LENGTH: 33
<212> TYPE: DNA
<213> ORGANISM: Homo Sapiens

<400> SEQUENCE: 704
tccctcttct tcatacrcag ccactgaata gga                                    33

<210> SEQ ID NO 705
<211> LENGTH: 33
<212> TYPE: DNA
<213> ORGANISM: Homo Sapiens

<400> SEQUENCE: 705
tccctccgtc atgtaamgta ggatggcagt tac                                    33

<210> SEQ ID NO 706
<211> LENGTH: 33
<212> TYPE: DNA
<213> ORGANISM: Homo Sapiens

<400> SEQUENCE: 706
catgagtcca ctggagrtgt tttgtagact tac                                    33

<210> SEQ ID NO 707
<211> LENGTH: 33
<212> TYPE: DNA
<213> ORGANISM: Homo Sapiens

<400> SEQUENCE: 707
tacaggacct tggaaamcat gcttgaactt ctt                                    33

<210> SEQ ID NO 708
<211> LENGTH: 33
<212> TYPE: DNA
<213> ORGANISM: Homo Sapiens

<400> SEQUENCE: 708
aaatgagtga ggaccamagc tgttatgttt ttt                                    33

<210> SEQ ID NO 709
<211> LENGTH: 33
<212> TYPE: DNA
<213> ORGANISM: Homo Sapiens

<400> SEQUENCE: 709
gcaggatacc cccttgraac aagcagcgaa gat                                    33

<210> SEQ ID NO 710
<211> LENGTH: 33
<212> TYPE: DNA
<213> ORGANISM: Homo Sapiens

<400> SEQUENCE: 710
cacctgtgtg tatccarcag caagaagact gaa                                    33

<210> SEQ ID NO 711
<211> LENGTH: 33
<212> TYPE: DNA
<213> ORGANISM: Homo Sapiens

<400> SEQUENCE: 711

```
ggtttagagt aattcarttt agctgtcatt taa                          33
```

<210> SEQ ID NO 712
<211> LENGTH: 33
<212> TYPE: DNA
<213> ORGANISM: Homo Sapiens

<400> SEQUENCE: 712

```
atttttgttt tgtaggmgtg aactgctttc ttt                          33
```

<210> SEQ ID NO 713
<211> LENGTH: 33
<212> TYPE: DNA
<213> ORGANISM: Homo Sapiens

<400> SEQUENCE: 713

```
gtcctggtgg tcaaaarggc ctggacaggc atc                          33
```

<210> SEQ ID NO 714
<211> LENGTH: 33
<212> TYPE: DNA
<213> ORGANISM: Homo Sapiens

<400> SEQUENCE: 714

```
aaaagacttc ttcaaamgaa actgtgaagt ctc                          33
```

<210> SEQ ID NO 715
<211> LENGTH: 33
<212> TYPE: DNA
<213> ORGANISM: Homo Sapiens

<400> SEQUENCE: 715

```
gaagaaagtt tagtagrgct gaagtgtgca ttt                          33
```

<210> SEQ ID NO 716
<211> LENGTH: 33
<212> TYPE: DNA
<213> ORGANISM: Homo Sapiens

<400> SEQUENCE: 716

```
gtaggtagca cacaagrtaa tcatgtcagg atg                          33
```

<210> SEQ ID NO 717
<211> LENGTH: 33
<212> TYPE: DNA
<213> ORGANISM: Homo Sapiens

<400> SEQUENCE: 717

```
taatagacaa atgttgmaca atagtcaaat tct                          33
```

<210> SEQ ID NO 718
<211> LENGTH: 33
<212> TYPE: DNA
<213> ORGANISM: Homo Sapiens

<400> SEQUENCE: 718

```
tgcacatcaa tctctcrtat tttgcattta aac                          33
```

<210> SEQ ID NO 719
<211> LENGTH: 33
<212> TYPE: DNA
<213> ORGANISM: Homo Sapiens

<400> SEQUENCE: 719
acctcaggaa aggatcrtgg aacagggagg cct                                    33

<210> SEQ ID NO 720
<211> LENGTH: 33
<212> TYPE: DNA
<213> ORGANISM: Homo Sapiens

<400> SEQUENCE: 720
caagtttgtt gctttartac taccttgagt ctg                                    33

<210> SEQ ID NO 721
<211> LENGTH: 33
<212> TYPE: DNA
<213> ORGANISM: Homo Sapiens

<400> SEQUENCE: 721
gtttcctagc ttgaaamacg aagagaagaa aag                                    33

<210> SEQ ID NO 722
<211> LENGTH: 33
<212> TYPE: DNA
<213> ORGANISM: Homo Sapiens

<400> SEQUENCE: 722
tgactcacca tcaggargga tctgctgcac tgg                                    33

<210> SEQ ID NO 723
<211> LENGTH: 33
<212> TYPE: DNA
<213> ORGANISM: Homo Sapiens

<400> SEQUENCE: 723
tactgaaaaa gagaatraac aacataacag tca                                    33

<210> SEQ ID NO 724
<211> LENGTH: 33
<212> TYPE: DNA
<213> ORGANISM: Homo Sapiens

<400> SEQUENCE: 724
cttacttacc tagaggrcat atgtctgcta ctg                                    33

<210> SEQ ID NO 725
<211> LENGTH: 33
<212> TYPE: DNA
<213> ORGANISM: Homo Sapiens

<400> SEQUENCE: 725
tataattaag gttaatrgtg agattgtttg gct                                    33

<210> SEQ ID NO 726
<211> LENGTH: 33
<212> TYPE: DNA
<213> ORGANISM: Homo Sapiens

<400> SEQUENCE: 726
ttgacttatc tatggarttt ttgactattt ctg                                    33

<210> SEQ ID NO 727
<211> LENGTH: 33
<212> TYPE: DNA
<213> ORGANISM: Homo Sapiens

```
<400> SEQUENCE: 727
taacataata gaaattract gacatatgta tgg                              33

<210> SEQ ID NO 728
<211> LENGTH: 33
<212> TYPE: DNA
<213> ORGANISM: Homo Sapiens

<400> SEQUENCE: 728
atccatagaa acagacrtta attaaataac aca                              33

<210> SEQ ID NO 729
<211> LENGTH: 33
<212> TYPE: DNA
<213> ORGANISM: Homo Sapiens

<400> SEQUENCE: 729
tttcatatca gaggcarcct ctcaaccaga tgt                              33

<210> SEQ ID NO 730
<211> LENGTH: 33
<212> TYPE: DNA
<213> ORGANISM: Homo Sapiens

<400> SEQUENCE: 730
tggccagaaa gagagamaga gagacagaga cag                              33

<210> SEQ ID NO 731
<211> LENGTH: 33
<212> TYPE: DNA
<213> ORGANISM: Homo Sapiens

<400> SEQUENCE: 731
aaataggacc cttgacrcac aaaggaattt tgg                              33

<210> SEQ ID NO 732
<211> LENGTH: 33
<212> TYPE: DNA
<213> ORGANISM: Homo Sapiens

<400> SEQUENCE: 732
tggaagggcg tgctgcrgcc cggcacggcc ctg                              33

<210> SEQ ID NO 733
<211> LENGTH: 33
<212> TYPE: DNA
<213> ORGANISM: Homo Sapiens

<400> SEQUENCE: 733
acacttggta cccttgrtac atttaatagt aaa                              33

<210> SEQ ID NO 734
<211> LENGTH: 33
<212> TYPE: DNA
<213> ORGANISM: Homo Sapiens

<400> SEQUENCE: 734
ccacctgtgc gccaggrcat acactggctg cac                              33

<210> SEQ ID NO 735
<211> LENGTH: 33
<212> TYPE: DNA
<213> ORGANISM: Homo Sapiens
```

```
<400> SEQUENCE: 735
ctatcattat cgattcyacc cagcaatttc tct                                33

<210> SEQ ID NO 736
<211> LENGTH: 33
<212> TYPE: DNA
<213> ORGANISM: Homo Sapiens

<400> SEQUENCE: 736
atctgctata caacatmctc agtcccctc atc                                 33

<210> SEQ ID NO 737
<211> LENGTH: 33
<212> TYPE: DNA
<213> ORGANISM: Homo Sapiens

<400> SEQUENCE: 737
gttgaaggat ccaggartat tttcttcttg ggt                                33

<210> SEQ ID NO 738
<211> LENGTH: 33
<212> TYPE: DNA
<213> ORGANISM: Homo Sapiens

<400> SEQUENCE: 738
tgtcactttc agtatarata aaactcttta gaa                                33

<210> SEQ ID NO 739
<211> LENGTH: 33
<212> TYPE: DNA
<213> ORGANISM: Homo Sapiens

<400> SEQUENCE: 739
ctacattata aattatrctt gataccagac atc                                33

<210> SEQ ID NO 740
<211> LENGTH: 33
<212> TYPE: DNA
<213> ORGANISM: Homo Sapiens

<400> SEQUENCE: 740
actgatatca ttccctmcct gaaatatccc atg                                33

<210> SEQ ID NO 741
<211> LENGTH: 33
<212> TYPE: DNA
<213> ORGANISM: Homo Sapiens

<400> SEQUENCE: 741
ggcaaggaga gcaccartt aggaaatgtt aga                                 33

<210> SEQ ID NO 742
<211> LENGTH: 33
<212> TYPE: DNA
<213> ORGANISM: Homo Sapiens

<400> SEQUENCE: 742
gaataagaat actaacrttt atccctgca ttt                                 33

<210> SEQ ID NO 743
<211> LENGTH: 33
<212> TYPE: DNA
```

```
<213> ORGANISM: Homo Sapiens

<400> SEQUENCE: 743
caatgggatt tggtaamtat tttcttatct ttg                            33

<210> SEQ ID NO 744
<211> LENGTH: 33
<212> TYPE: DNA
<213> ORGANISM: Homo Sapiens

<400> SEQUENCE: 744
aaaaaagtac taattcrgaa aagatataaa agt                            33

<210> SEQ ID NO 745
<211> LENGTH: 33
<212> TYPE: DNA
<213> ORGANISM: Homo Sapiens

<400> SEQUENCE: 745
atcagagtat atgccamagc gggtttcgta tcc                            33

<210> SEQ ID NO 746
<211> LENGTH: 33
<212> TYPE: DNA
<213> ORGANISM: Homo Sapiens

<400> SEQUENCE: 746
tactaagcat tattctrtag atggaatata taa                            33

<210> SEQ ID NO 747
<211> LENGTH: 33
<212> TYPE: DNA
<213> ORGANISM: Homo Sapiens

<400> SEQUENCE: 747
gagacttcac tctgacrtct ttctcttttt gga                            33

<210> SEQ ID NO 748
<211> LENGTH: 33
<212> TYPE: DNA
<213> ORGANISM: Homo Sapiens

<400> SEQUENCE: 748
caagtgctct ctcaacrtgt tcaatattac taa                            33

<210> SEQ ID NO 749
<211> LENGTH: 33
<212> TYPE: DNA
<213> ORGANISM: Homo Sapiens

<400> SEQUENCE: 749
gtttctaaat atgtcaragt agatattaaa gaa                            33

<210> SEQ ID NO 750
<211> LENGTH: 33
<212> TYPE: DNA
<213> ORGANISM: Homo Sapiens

<400> SEQUENCE: 750
gcggggccgc tggacascgc ggggagttcg acg                            33

<210> SEQ ID NO 751
<211> LENGTH: 33
```

```
<212> TYPE: DNA
<213> ORGANISM: Homo Sapiens

<400> SEQUENCE: 751
ggtgttgaga ctcatartaa ctcagtaaca cct                                  33

<210> SEQ ID NO 752
<211> LENGTH: 33
<212> TYPE: DNA
<213> ORGANISM: Homo Sapiens

<400> SEQUENCE: 752
tggaaactaa aggggamtac ttatttatga ctt                                  33

<210> SEQ ID NO 753
<211> LENGTH: 33
<212> TYPE: DNA
<213> ORGANISM: Homo Sapiens

<400> SEQUENCE: 753
ctttgacccc agtggartgc tctctcctgc aaa                                  33

<210> SEQ ID NO 754
<211> LENGTH: 33
<212> TYPE: DNA
<213> ORGANISM: Homo Sapiens

<400> SEQUENCE: 754
ttagcatgtg tggaatrttt tccatattat gta                                  33

<210> SEQ ID NO 755
<211> LENGTH: 33
<212> TYPE: DNA
<213> ORGANISM: Homo Sapiens

<400> SEQUENCE: 755
accatgggat tccaatmcat tgcaagtatt tca                                  33

<210> SEQ ID NO 756
<211> LENGTH: 33
<212> TYPE: DNA
<213> ORGANISM: Homo Sapiens

<400> SEQUENCE: 756
gcagtctctc ccttgamaca tccttcccct tcc                                  33

<210> SEQ ID NO 757
<211> LENGTH: 33
<212> TYPE: DNA
<213> ORGANISM: Homo Sapiens

<400> SEQUENCE: 757
tccagacaca agtcacragt tcagggttc aca                                   33

<210> SEQ ID NO 758
<211> LENGTH: 33
<212> TYPE: DNA
<213> ORGANISM: Homo Sapiens

<400> SEQUENCE: 758
cccccaataa caggaargag attcctttgt tcc                                  33

<210> SEQ ID NO 759
```

```
<211> LENGTH: 33
<212> TYPE: DNA
<213> ORGANISM: Homo Sapiens

<400> SEQUENCE: 759
cttctttggc ttctcartgc actctgaatg aaa                              33

<210> SEQ ID NO 760
<211> LENGTH: 33
<212> TYPE: DNA
<213> ORGANISM: Homo Sapiens

<400> SEQUENCE: 760
cactgcctga gatagamgtt tgcatcttat tgg                              33

<210> SEQ ID NO 761
<211> LENGTH: 33
<212> TYPE: DNA
<213> ORGANISM: Homo Sapiens

<400> SEQUENCE: 761
tttttcttat tgattcmtag gagttctttta cat                             33

<210> SEQ ID NO 762
<211> LENGTH: 33
<212> TYPE: DNA
<213> ORGANISM: Homo Sapiens

<400> SEQUENCE: 762
tttattgata gtttacrctg ctggaaatat aat                              33

<210> SEQ ID NO 763
<211> LENGTH: 33
<212> TYPE: DNA
<213> ORGANISM: Homo Sapiens

<400> SEQUENCE: 763
agacctgaag agcaggracc ctggtggatt ttt                              33

<210> SEQ ID NO 764
<211> LENGTH: 33
<212> TYPE: DNA
<213> ORGANISM: Homo Sapiens

<400> SEQUENCE: 764
tcaagtttcc ttttgtrtcc ctggcgaact tta                              33

<210> SEQ ID NO 765
<211> LENGTH: 33
<212> TYPE: DNA
<213> ORGANISM: Homo Sapiens

<400> SEQUENCE: 765
tatggttttt ggatttmgca tttagttaat gac                              33

<210> SEQ ID NO 766
<211> LENGTH: 33
<212> TYPE: DNA
<213> ORGANISM: Homo Sapiens

<400> SEQUENCE: 766
tcctgtacag gtgcatrtgg atgtgctatg tgt                              33
```

<210> SEQ ID NO 767
<211> LENGTH: 33
<212> TYPE: DNA
<213> ORGANISM: Homo Sapiens

<400> SEQUENCE: 767
aaattctatg ccaagcrctt tcatatacaa tat                                    33

<210> SEQ ID NO 768
<211> LENGTH: 33
<212> TYPE: DNA
<213> ORGANISM: Homo Sapiens

<400> SEQUENCE: 768
gccattcttt ctattcrgtc aatatgaaag aca                                    33

<210> SEQ ID NO 769
<211> LENGTH: 33
<212> TYPE: DNA
<213> ORGANISM: Homo Sapiens

<400> SEQUENCE: 769
cctgttgtta attcccratc aatagtcccg aga                                    33

<210> SEQ ID NO 770
<211> LENGTH: 33
<212> TYPE: DNA
<213> ORGANISM: Homo Sapiens

<400> SEQUENCE: 770
gctccagggc tgggacmctt tctgagcctc ctc                                    33

<210> SEQ ID NO 771
<211> LENGTH: 33
<212> TYPE: DNA
<213> ORGANISM: Homo Sapiens

<400> SEQUENCE: 771
gatgtaggta accatcrtta tgggacccca gag                                    33

<210> SEQ ID NO 772
<211> LENGTH: 33
<212> TYPE: DNA
<213> ORGANISM: Homo Sapiens

<400> SEQUENCE: 772
gcaacagggg tactagrgca tcatgaaatt cac                                    33

<210> SEQ ID NO 773
<211> LENGTH: 33
<212> TYPE: DNA
<213> ORGANISM: Homo Sapiens

<400> SEQUENCE: 773
ctacacagtc gtgtgarcca atccctccaa ata                                    33

<210> SEQ ID NO 774
<211> LENGTH: 33
<212> TYPE: DNA
<213> ORGANISM: Homo Sapiens

<400> SEQUENCE: 774
aggctctgtg atgggcrcag gaacacactg agg                                    33

```
<210> SEQ ID NO 775
<211> LENGTH: 33
<212> TYPE: DNA
<213> ORGANISM: Homo Sapiens

<400> SEQUENCE: 775
ttgtgccgtt attaatkcca tttgttattt cat                                    33

<210> SEQ ID NO 776
<211> LENGTH: 33
<212> TYPE: DNA
<213> ORGANISM: Homo Sapiens

<400> SEQUENCE: 776
gcttgcagta gcgcgamatg gttagctacc ttc                                    33

<210> SEQ ID NO 777
<211> LENGTH: 33
<212> TYPE: DNA
<213> ORGANISM: Homo Sapiens

<400> SEQUENCE: 777
gccttgcgga ccaccartgg gaaagcagac tcc                                    33

<210> SEQ ID NO 778
<211> LENGTH: 33
<212> TYPE: DNA
<213> ORGANISM: Homo Sapiens

<400> SEQUENCE: 778
cttgatgtgt caggacmatt ttgttgctgt agg                                    33

<210> SEQ ID NO 779
<211> LENGTH: 33
<212> TYPE: DNA
<213> ORGANISM: Homo Sapiens

<400> SEQUENCE: 779
ctcgctactg atggacrttc acatttaaat ttt                                    33

<210> SEQ ID NO 780
<211> LENGTH: 33
<212> TYPE: DNA
<213> ORGANISM: Homo Sapiens

<400> SEQUENCE: 780
actgaaatat agccagmaat aaataatcat gct                                    33

<210> SEQ ID NO 781
<211> LENGTH: 33
<212> TYPE: DNA
<213> ORGANISM: Homo Sapiens

<400> SEQUENCE: 781
ctcctatatt caacagraca gcaaatgaag act                                    33

<210> SEQ ID NO 782
<211> LENGTH: 33
<212> TYPE: DNA
<213> ORGANISM: Homo Sapiens

<400> SEQUENCE: 782
atgaaaatat aaaatcratt gtggtgatgg ttt                                    33
```

<210> SEQ ID NO 783
<211> LENGTH: 33
<212> TYPE: DNA
<213> ORGANISM: Homo Sapiens

<400> SEQUENCE: 783
agctcagaaa atctcaytgg aacccttgaa gta                                33

<210> SEQ ID NO 784
<211> LENGTH: 33
<212> TYPE: DNA
<213> ORGANISM: Homo Sapiens

<400> SEQUENCE: 784
cggggtttaa gaggacraca ggtgtctgta ttg                                33

<210> SEQ ID NO 785
<211> LENGTH: 33
<212> TYPE: DNA
<213> ORGANISM: Homo Sapiens

<400> SEQUENCE: 785
atcagagcca agacccrgcc ctcaagtcct cct                                33

<210> SEQ ID NO 786
<211> LENGTH: 33
<212> TYPE: DNA
<213> ORGANISM: Homo Sapiens

<400> SEQUENCE: 786
tgtggaaggg gaggtcmgtc agccagcatt aag                                33

<210> SEQ ID NO 787
<211> LENGTH: 33
<212> TYPE: DNA
<213> ORGANISM: Homo Sapiens

<400> SEQUENCE: 787
gatttttctc tcctctraaa gagcaatttt ctc                                33

<210> SEQ ID NO 788
<211> LENGTH: 33
<212> TYPE: DNA
<213> ORGANISM: Homo Sapiens

<400> SEQUENCE: 788
acaggaaact tcaaccmagt atcaagttac taa                                33

<210> SEQ ID NO 789
<211> LENGTH: 33
<212> TYPE: DNA
<213> ORGANISM: Homo Sapiens

<400> SEQUENCE: 789
cctcttcaga gggaatrtgg tcctgtggac acc                                33

<210> SEQ ID NO 790
<211> LENGTH: 33
<212> TYPE: DNA
<213> ORGANISM: Homo Sapiens

<400> SEQUENCE: 790

```
ggacccaggg aatctcrccc tggctcttcc tcc         33
```

<210> SEQ ID NO 791
<211> LENGTH: 33
<212> TYPE: DNA
<213> ORGANISM: Homo Sapiens

<400> SEQUENCE: 791

```
cactgatatc gaatgtrtct tggagtgaga aag         33
```

<210> SEQ ID NO 792
<211> LENGTH: 33
<212> TYPE: DNA
<213> ORGANISM: Homo Sapiens

<400> SEQUENCE: 792

```
ggaattaaca gccacartgc aagcttcttg ctg         33
```

<210> SEQ ID NO 793
<211> LENGTH: 33
<212> TYPE: DNA
<213> ORGANISM: Homo Sapiens

<400> SEQUENCE: 793

```
ggatccatgg cctggcratt ccaggtctgg gtt         33
```

<210> SEQ ID NO 794
<211> LENGTH: 33
<212> TYPE: DNA
<213> ORGANISM: Homo Sapiens

<400> SEQUENCE: 794

```
tgttctaggg ccaaccrggg gatcggagga gtc         33
```

<210> SEQ ID NO 795
<211> LENGTH: 33
<212> TYPE: DNA
<213> ORGANISM: Homo Sapiens

<400> SEQUENCE: 795

```
gggcagagta cttatcrtat gtgcatacta tat         33
```

<210> SEQ ID NO 796
<211> LENGTH: 33
<212> TYPE: DNA
<213> ORGANISM: Homo Sapiens

<400> SEQUENCE: 796

```
ctcataacat tttcccrcta gaaataatgt gtg         33
```

<210> SEQ ID NO 797
<211> LENGTH: 33
<212> TYPE: DNA
<213> ORGANISM: Homo Sapiens

<400> SEQUENCE: 797

```
cttctatttt gctgttrctg ttttgcattt gag         33
```

<210> SEQ ID NO 798
<211> LENGTH: 33
<212> TYPE: DNA
<213> ORGANISM: Homo Sapiens

<400> SEQUENCE: 798
atccagtggg aaagtcrgtt gcatcctatg ttt        33

<210> SEQ ID NO 799
<211> LENGTH: 33
<212> TYPE: DNA
<213> ORGANISM: Homo Sapiens

<400> SEQUENCE: 799
tatgtttgtg gtccttrtaa ctgacttctg ctt        33

<210> SEQ ID NO 800
<211> LENGTH: 33
<212> TYPE: DNA
<213> ORGANISM: Homo Sapiens

<400> SEQUENCE: 800
tatggaaatg atatggrata cataggaatg gcg        33

<210> SEQ ID NO 801
<211> LENGTH: 33
<212> TYPE: DNA
<213> ORGANISM: Homo Sapiens

<400> SEQUENCE: 801
aatacatagc agttgcrata tccattttgg gta        33

<210> SEQ ID NO 802
<211> LENGTH: 33
<212> TYPE: DNA
<213> ORGANISM: Homo Sapiens

<400> SEQUENCE: 802
tgcttagcag ggcactrgga aatgcacttc agt        33

<210> SEQ ID NO 803
<211> LENGTH: 33
<212> TYPE: DNA
<213> ORGANISM: Homo Sapiens

<400> SEQUENCE: 803
ttaatttgca ttttcaraaa gactaccttg gct        33

<210> SEQ ID NO 804
<211> LENGTH: 33
<212> TYPE: DNA
<213> ORGANISM: Homo Sapiens

<400> SEQUENCE: 804
tgcctctaag atattgkaca cacaaatgaa gca        33

<210> SEQ ID NO 805
<211> LENGTH: 33
<212> TYPE: DNA
<213> ORGANISM: Homo Sapiens

<400> SEQUENCE: 805
actaactcca aacaagmatc aacagtaaaa tta        33

<210> SEQ ID NO 806
<211> LENGTH: 33
<212> TYPE: DNA
<213> ORGANISM: Homo Sapiens

<400> SEQUENCE: 806
tcacatatga tagattmggc aattgagtta tat    33

<210> SEQ ID NO 807
<211> LENGTH: 33
<212> TYPE: DNA
<213> ORGANISM: Homo Sapiens

<400> SEQUENCE: 807
gctgtttaaa tgtttamttg atgatggaat gtg    33

<210> SEQ ID NO 808
<211> LENGTH: 33
<212> TYPE: DNA
<213> ORGANISM: Homo Sapiens

<400> SEQUENCE: 808
gtgtgtgtga acaagcrcaa agtccatatc cag    33

<210> SEQ ID NO 809
<211> LENGTH: 33
<212> TYPE: DNA
<213> ORGANISM: Homo Sapiens

<400> SEQUENCE: 809
agtaatgcca actacaratt atgaaatatt tca    33

<210> SEQ ID NO 810
<211> LENGTH: 33
<212> TYPE: DNA
<213> ORGANISM: Homo Sapiens

<400> SEQUENCE: 810
ggagtttccc tatcccrggc tgcagtgcaa tgg    33

<210> SEQ ID NO 811
<211> LENGTH: 33
<212> TYPE: DNA
<213> ORGANISM: Homo Sapiens

<400> SEQUENCE: 811
atggggctca ctgcctrtaa cttcaaggaa gca    33

<210> SEQ ID NO 812
<211> LENGTH: 33
<212> TYPE: DNA
<213> ORGANISM: Homo Sapiens

<400> SEQUENCE: 812
ataagaaaat atccagmact gagtgtatgt tta    33

<210> SEQ ID NO 813
<211> LENGTH: 33
<212> TYPE: DNA
<213> ORGANISM: Homo Sapiens

<400> SEQUENCE: 813
tcaagtcatc agattgmatc tccccacctg cca    33

<210> SEQ ID NO 814
<211> LENGTH: 33
<212> TYPE: DNA
<213> ORGANISM: Homo Sapiens -continued

<400> SEQUENCE: 814
cgcccaccac tgtgccrgaa tgtgatgcac aca                        33

<210> SEQ ID NO 815
<211> LENGTH: 33
<212> TYPE: DNA
<213> ORGANISM: Homo Sapiens

<400> SEQUENCE: 815
agagatcaca ccccgamctc cagctcccac gtg                        33

<210> SEQ ID NO 816
<211> LENGTH: 33
<212> TYPE: DNA
<213> ORGANISM: Homo Sapiens

<400> SEQUENCE: 816
gcacaccctg aaccaargaa aacacagaag aaa                        33

<210> SEQ ID NO 817
<211> LENGTH: 33
<212> TYPE: DNA
<213> ORGANISM: Homo Sapiens

<400> SEQUENCE: 817
ggtccaaaaa tatcacrgta cttcgagaga cca                        33

<210> SEQ ID NO 818
<211> LENGTH: 33
<212> TYPE: DNA
<213> ORGANISM: Homo Sapiens

<400> SEQUENCE: 818
cacctcccca tctgtgrccc tctgtgacac acg                        33

<210> SEQ ID NO 819
<211> LENGTH: 33
<212> TYPE: DNA
<213> ORGANISM: Homo Sapiens

<400> SEQUENCE: 819
acctaccatg tttatcrgaa atctcagcct aaa                        33

<210> SEQ ID NO 820
<211> LENGTH: 33
<212> TYPE: DNA
<213> ORGANISM: Homo Sapiens

<400> SEQUENCE: 820
aatgactggc tctaaarctg ggtctctgtt cac                        33

<210> SEQ ID NO 821
<211> LENGTH: 33
<212> TYPE: DNA
<213> ORGANISM: Homo Sapiens

<400> SEQUENCE: 821
gcaatgttta aaaacarcat tttgggctgg gcg                        33

<210> SEQ ID NO 822
<211> LENGTH: 33
<212> TYPE: DNA

```
<213> ORGANISM: Homo Sapiens

<400> SEQUENCE: 822
ggtgggtgct gatgagrgaa ggcaggagat gca                                33

<210> SEQ ID NO 823
<211> LENGTH: 33
<212> TYPE: DNA
<213> ORGANISM: Homo Sapiens

<400> SEQUENCE: 823
tttatctaat ctgatgrtct ctgctctttt tat                                33

<210> SEQ ID NO 824
<211> LENGTH: 33
<212> TYPE: DNA
<213> ORGANISM: Homo Sapiens

<400> SEQUENCE: 824
cctgccgcct agggagrttg tgctctgccc ctc                                33

<210> SEQ ID NO 825
<211> LENGTH: 33
<212> TYPE: DNA
<213> ORGANISM: Homo Sapiens

<400> SEQUENCE: 825
ccactaaaat tctacartca gaatgcttgg caa                                33

<210> SEQ ID NO 826
<211> LENGTH: 33
<212> TYPE: DNA
<213> ORGANISM: Homo Sapiens

<400> SEQUENCE: 826
ctagaagccg aggacartga gatctcttct tct                                33

<210> SEQ ID NO 827
<211> LENGTH: 33
<212> TYPE: DNA
<213> ORGANISM: Homo Sapiens

<400> SEQUENCE: 827
ccctcccttt agtcagrgat tattctgggg acc                                33

<210> SEQ ID NO 828
<211> LENGTH: 33
<212> TYPE: DNA
<213> ORGANISM: Homo Sapiens

<400> SEQUENCE: 828
tgctaacagc tctaccrtga tgacaaggcc att                                33

<210> SEQ ID NO 829
<211> LENGTH: 33
<212> TYPE: DNA
<213> ORGANISM: Homo Sapiens

<400> SEQUENCE: 829
gggttactat ggtgatragg attaggataa tgg                                33

<210> SEQ ID NO 830
<211> LENGTH: 33
```

```
<212> TYPE: DNA
<213> ORGANISM: Homo Sapiens

<400> SEQUENCE: 830
tgcccccacc acaaccragg acagtgtctt gcc                                33

<210> SEQ ID NO 831
<211> LENGTH: 33
<212> TYPE: DNA
<213> ORGANISM: Homo Sapiens

<400> SEQUENCE: 831
ggacccagta tcttcarggt agcattttg aac                                 33

<210> SEQ ID NO 832
<211> LENGTH: 33
<212> TYPE: DNA
<213> ORGANISM: Homo Sapiens

<400> SEQUENCE: 832
ctgacagaag gactgcrgct gaatttcaca ttt                                33

<210> SEQ ID NO 833
<211> LENGTH: 33
<212> TYPE: DNA
<213> ORGANISM: Homo Sapiens

<400> SEQUENCE: 833
tggcctccag cactggrtcg cgccttgggg cca                                33

<210> SEQ ID NO 834
<211> LENGTH: 33
<212> TYPE: DNA
<213> ORGANISM: Homo Sapiens

<400> SEQUENCE: 834 tttttttcaat gctgacrcag agtgatttaa aaa                               33

<210> SEQ ID NO 835
<211> LENGTH: 33
<212> TYPE: DNA
<213> ORGANISM: Homo Sapiens

<400> SEQUENCE: 835
ccttgggtag ctatcargta catgcctaac ttg                                33

<210> SEQ ID NO 836
<211> LENGTH: 33
<212> TYPE: DNA
<213> ORGANISM: Homo Sapiens

<400> SEQUENCE: 836
gtgtgaccag agcagcrgtg actgctggtg tgt                                33

<210> SEQ ID NO 837
<211> LENGTH: 33
<212> TYPE: DNA
<213> ORGANISM: Homo Sapiens

<400> SEQUENCE: 837
tagggcacgg gagaagraca tcgaggccgc agg                                33

<210> SEQ ID NO 838
```

<211> LENGTH: 33
<212> TYPE: DNA
<213> ORGANISM: Homo Sapiens

<400> SEQUENCE: 838
ggcagctagg gactgargca gcgtagcata aca    33

<210> SEQ ID NO 839
<211> LENGTH: 33
<212> TYPE: DNA
<213> ORGANISM: Homo Sapiens

<400> SEQUENCE: 839
gttcgactgc aggaaarccc tacaggttgc tgg    33

<210> SEQ ID NO 840
<211> LENGTH: 33
<212> TYPE: DNA
<213> ORGANISM: Homo Sapiens

<400> SEQUENCE: 840
ctttcctggg gatgctmatt gaggttggaa aga    33

<210> SEQ ID NO 841
<211> LENGTH: 33
<212> TYPE: DNA
<213> ORGANISM: Homo Sapiens

<400> SEQUENCE: 841
ctggttttcc taatcaraga aagcttcaaa gaa    33

<210> SEQ ID NO 842
<211> LENGTH: 33
<212> TYPE: DNA
<213> ORGANISM: Homo Sapiens

<400> SEQUENCE: 842
tattagcaga ctcaccrcaa aaggatatgc cag    33

<210> SEQ ID NO 843
<211> LENGTH: 33
<212> TYPE: DNA
<213> ORGANISM: Homo Sapiens

<400> SEQUENCE: 843
acagcacaag aggatgrtga gtgggtatat agt    33

<210> SEQ ID NO 844
<211> LENGTH: 33
<212> TYPE: DNA
<213> ORGANISM: Homo Sapiens

<400> SEQUENCE: 844
gaagcccagg atgaaamagg gttgttcaat gtc    33

<210> SEQ ID NO 845
<211> LENGTH: 33
<212> TYPE: DNA
<213> ORGANISM: Homo Sapiens

<400> SEQUENCE: 845
cacagacatg caaattrgga tgtggaacca ctt    33

```
<210> SEQ ID NO 846
<211> LENGTH: 33
<212> TYPE: DNA
<213> ORGANISM: Homo Sapiens

<400> SEQUENCE: 846
gggaatagat gcagaaytgg caaagaagca aga                                33

<210> SEQ ID NO 847
<211> LENGTH: 33
<212> TYPE: DNA
<213> ORGANISM: Homo Sapiens

<400> SEQUENCE: 847
gcaggctttc atgtgtrtta actattaagg ctc                                33

<210> SEQ ID NO 848
<211> LENGTH: 33
<212> TYPE: DNA
<213> ORGANISM: Homo Sapiens

<400> SEQUENCE: 848
aacaaattcc atatgtratt aggatgtaca tgc                                33

<210> SEQ ID NO 849
<211> LENGTH: 33
<212> TYPE: DNA
<213> ORGANISM: Homo Sapiens

<400> SEQUENCE: 849 tcccctacc attcatmcat cattgatttt agg                                 33

<210> SEQ ID NO 850
<211> LENGTH: 33
<212> TYPE: DNA
<213> ORGANISM: Homo Sapiens

<400> SEQUENCE: 850
ttgtggtata tatacartaa tatcctccaa tgc                                33

<210> SEQ ID NO 851
<211> LENGTH: 33
<212> TYPE: DNA
<213> ORGANISM: Homo Sapiens

<400> SEQUENCE: 851
tggtagggga ggaagtrgta ggcagaaacc agt                                33

<210> SEQ ID NO 852
<211> LENGTH: 33
<212> TYPE: DNA
<213> ORGANISM: Homo Sapiens

<400> SEQUENCE: 852
atataaatcc catagartga agtcttttct ata                                33

<210> SEQ ID NO 853
<211> LENGTH: 33
<212> TYPE: DNA
<213> ORGANISM: Homo Sapiens

<400> SEQUENCE: 853
ccttggtcct ttactcrtgc ctctctgtac tca                                33
```

<210> SEQ ID NO 854
<211> LENGTH: 33
<212> TYPE: DNA
<213> ORGANISM: Homo Sapiens

<400> SEQUENCE: 854
aagatggtat aagtcartga tttttctgcc ttc       33

<210> SEQ ID NO 855
<211> LENGTH: 33
<212> TYPE: DNA
<213> ORGANISM: Homo Sapiens

<400> SEQUENCE: 855
gcaccctgag aattgamttg aagttctcct ctt       33

<210> SEQ ID NO 856
<211> LENGTH: 33
<212> TYPE: DNA
<213> ORGANISM: Homo Sapiens

<400> SEQUENCE: 856
acagcctaca ttgagcmaaa caaaacttga ttt       33

<210> SEQ ID NO 857
<211> LENGTH: 33
<212> TYPE: DNA
<213> ORGANISM: Homo Sapiens

<400> SEQUENCE: 857
tccagcctaa ataaatmccc acccggtttg ggg       33

<210> SEQ ID NO 858
<211> LENGTH: 33
<212> TYPE: DNA
<213> ORGANISM: Homo Sapiens

<400> SEQUENCE: 858
ggggacacaa gaggccrggg agctctcttc ccg       33

<210> SEQ ID NO 859
<211> LENGTH: 33
<212> TYPE: DNA
<213> ORGANISM: Homo Sapiens

<400> SEQUENCE: 859
agatatacgc tcaagcmcct ccaagccttt act       33

<210> SEQ ID NO 860
<211> LENGTH: 33
<212> TYPE: DNA
<213> ORGANISM: Homo Sapiens

<400> SEQUENCE: 860
ctagaaacct gcctcaratg gggaaagatt agg       33

<210> SEQ ID NO 861
<211> LENGTH: 33
<212> TYPE: DNA
<213> ORGANISM: Homo Sapiens

<400> SEQUENCE: 861
caacactgtg cctagamctt ggggccagtc tgg       33

<210> SEQ ID NO 862
<211> LENGTH: 33
<212> TYPE: DNA
<213> ORGANISM: Homo Sapiens

<400> SEQUENCE: 862
ggtgcttgag ccagtarctc agaggtaacc cct         33

<210> SEQ ID NO 863
<211> LENGTH: 33
<212> TYPE: DNA
<213> ORGANISM: Homo Sapiens

<400> SEQUENCE: 863
gtgattgtta ggggtgrcat cagcaaggac tgt         33

<210> SEQ ID NO 864
<211> LENGTH: 33
<212> TYPE: DNA
<213> ORGANISM: Homo Sapiens

<400> SEQUENCE: 864
gctgtaggca aacagtraat ccaatttcct cca         33

<210> SEQ ID NO 865
<211> LENGTH: 33
<212> TYPE: DNA
<213> ORGANISM: Homo Sapiens

<400> SEQUENCE: 865
ctgtgctcta acactgmaca ttcatgtagc ttt         33

<210> SEQ ID NO 866
<211> LENGTH: 33
<212> TYPE: DNA
<213> ORGANISM: Homo Sapiens

<400> SEQUENCE: 866
tccaggaatt cagcacmttc cagccctgga gac         33

<210> SEQ ID NO 867
<211> LENGTH: 33
<212> TYPE: DNA
<213> ORGANISM: Homo Sapiens

<400> SEQUENCE: 867
agagaggagg ggagagrtaa ctgatacatg cta         33

<210> SEQ ID NO 868
<211> LENGTH: 33
<212> TYPE: DNA
<213> ORGANISM: Homo Sapiens

<400> SEQUENCE: 868
cactgtccct gaatgcraaa taagggtgac ctt         33

<210> SEQ ID NO 869
<211> LENGTH: 33
<212> TYPE: DNA
<213> ORGANISM: Homo Sapiens

<400> SEQUENCE: 869
aagcaaacca attggaragg tgttccctgt att            33

<210> SEQ ID NO 870
<211> LENGTH: 33
<212> TYPE: DNA
<213> ORGANISM: Homo Sapiens

<400> SEQUENCE: 870
ccgatagttg gtgactrttt tatttctttg ttg            33

<210> SEQ ID NO 871
<211> LENGTH: 33
<212> TYPE: DNA
<213> ORGANISM: Homo Sapiens

<400> SEQUENCE: 871
cagaggaaaa cctgccraga ggggcaaatg gat            33

<210> SEQ ID NO 872
<211> LENGTH: 33
<212> TYPE: DNA
<213> ORGANISM: Homo Sapiens

<400> SEQUENCE: 872
tctcctttaa gatacargaa gcttggaagc gga            33

<210> SEQ ID NO 873
<211> LENGTH: 33
<212> TYPE: DNA
<213> ORGANISM: Homo Sapiens

<400> SEQUENCE: 873
cccatctgta aaatggrcac ctaccattga ttc            33

<210> SEQ ID NO 874
<211> LENGTH: 33
<212> TYPE: DNA
<213> ORGANISM: Homo Sapiens

<400> SEQUENCE: 874
gagggaatgg ccattargta aatgctcttt aga            33

<210> SEQ ID NO 875
<211> LENGTH: 33
<212> TYPE: DNA
<213> ORGANISM: Homo Sapiens

<400> SEQUENCE: 875
caggtcccac gataccrtca ggaatgtccg ttt            33

<210> SEQ ID NO 876
<211> LENGTH: 33
<212> TYPE: DNA
<213> ORGANISM: Homo Sapiens

<400> SEQUENCE: 876
agttaagaaa agtgtcrcag gctaaggaac tgg            33

<210> SEQ ID NO 877
<211> LENGTH: 33
<212> TYPE: DNA
<213> ORGANISM: Homo Sapiens

<400> SEQUENCE: 877
attgtagact tgcacgmggg gctgtatggg ctc                                   33

<210> SEQ ID NO 878
<211> LENGTH: 33
<212> TYPE: DNA
<213> ORGANISM: Homo Sapiens

<400> SEQUENCE: 878
ggggacccct gctcccrgag tgacagggga gga                                   33

<210> SEQ ID NO 879
<211> LENGTH: 33
<212> TYPE: DNA
<213> ORGANISM: Homo Sapiens

<400> SEQUENCE: 879
cgcaaccgcg tgaggcraca gaaccgacgg gca                                   33

<210> SEQ ID NO 880
<211> LENGTH: 33
<212> TYPE: DNA
<213> ORGANISM: Homo Sapiens

<400> SEQUENCE: 880
tttattaccc acagtcmccc tcggtctgaa aat                                   33

<210> SEQ ID NO 881
<211> LENGTH: 33
<212> TYPE: DNA
<213> ORGANISM: Homo Sapiens

<400> SEQUENCE: 881
tcaattttcg tccagcrttc tctgctacac tgc                                   33

<210> SEQ ID NO 882
<211> LENGTH: 33
<212> TYPE: DNA
<213> ORGANISM: Homo Sapiens

<400> SEQUENCE: 882
cacgcctggc caacctmttc accctcaatc taa                                   33

<210> SEQ ID NO 883
<211> LENGTH: 33
<212> TYPE: DNA
<213> ORGANISM: Homo Sapiens

<400> SEQUENCE: 883
tcagcatcac taataamaga aacacagcgt agt                                   33

<210> SEQ ID NO 884
<211> LENGTH: 33
<212> TYPE: DNA
<213> ORGANISM: Homo Sapiens

<400> SEQUENCE: 884
gaaaatgaga tagagaragg aaagaaataa tat                                   33

<210> SEQ ID NO 885
<211> LENGTH: 33
<212> TYPE: DNA
<213> ORGANISM: Homo Sapiens

```
<400> SEQUENCE: 885
ccctattggg ctattartag attggcattt aaa                    33

<210> SEQ ID NO 886
<211> LENGTH: 33
<212> TYPE: DNA
<213> ORGANISM: Homo Sapiens

<400> SEQUENCE: 886
attgaaaaaa gcctgtrggg gtgctttgtg cag                    33

<210> SEQ ID NO 887
<211> LENGTH: 33
<212> TYPE: DNA
<213> ORGANISM: Homo Sapiens

<400> SEQUENCE: 887
ctgttgattc taccctrtga acagctgggc tta                    33

<210> SEQ ID NO 888
<211> LENGTH: 33
<212> TYPE: DNA
<213> ORGANISM: Homo Sapiens

<400> SEQUENCE: 888
tcaagaccct gaattcmatt tttttgaata tat                    33

<210> SEQ ID NO 889
<211> LENGTH: 33
<212> TYPE: DNA
<213> ORGANISM: Homo Sapiens

<400> SEQUENCE: 889
tccagttttt atggaarcta ccatttactc tgt                    33

<210> SEQ ID NO 890
<211> LENGTH: 33
<212> TYPE: DNA
<213> ORGANISM: Homo Sapiens

<400> SEQUENCE: 890
agactcatat caaaacrcaa taagtgtgtg gca                    33

<210> SEQ ID NO 891
<211> LENGTH: 33
<212> TYPE: DNA
<213> ORGANISM: Homo Sapiens

<400> SEQUENCE: 891
tgcttctagt tagcttrtct atagcttccc tgt                    33

<210> SEQ ID NO 892
<211> LENGTH: 33
<212> TYPE: DNA
<213> ORGANISM: Homo Sapiens

<400> SEQUENCE: 892
accctacata cacatarcta aatttttttt tct                    33

<210> SEQ ID NO 893
<211> LENGTH: 33
<212> TYPE: DNA
<213> ORGANISM: Homo Sapiens
```

```
<400> SEQUENCE: 893
tgtggctcgc agatttraaa taaagcagag gtc                                    33

<210> SEQ ID NO 894
<211> LENGTH: 33
<212> TYPE: DNA
<213> ORGANISM: Homo Sapiens

<400> SEQUENCE: 894
gagagtcaca ggaaggrccc ctttacgtcg gat                                    33

<210> SEQ ID NO 895
<211> LENGTH: 33
<212> TYPE: DNA
<213> ORGANISM: Homo Sapiens

<400> SEQUENCE: 895
agtagatagt ggtccargcc tagtattttt aac                                    33

<210> SEQ ID NO 896
<211> LENGTH: 33
<212> TYPE: DNA
<213> ORGANISM: Homo Sapiens

<400> SEQUENCE: 896
tcccccagag gtgtgtrtgg ctagttagct cac                                    33

<210> SEQ ID NO 897
<211> LENGTH: 33
<212> TYPE: DNA
<213> ORGANISM: Homo Sapiens

<400> SEQUENCE: 897
attagtgtgc agttacrtag cttgggccca gac                                    33

<210> SEQ ID NO 898
<211> LENGTH: 33
<212> TYPE: DNA
<213> ORGANISM: Homo Sapiens

<400> SEQUENCE: 898
cagcacatga atatggmggc ctgctgtgtg cca                                    33

<210> SEQ ID NO 899
<211> LENGTH: 33
<212> TYPE: DNA
<213> ORGANISM: Homo Sapiens

<400> SEQUENCE: 899
ctagcctata cttaacrcat aagtttcatc cat                                    33

<210> SEQ ID NO 900
<211> LENGTH: 33
<212> TYPE: DNA
<213> ORGANISM: Homo Sapiens

<400> SEQUENCE: 900
aaaagattgg gctgaargga aagagatgag atg                                    33

<210> SEQ ID NO 901
<211> LENGTH: 33
<212> TYPE: DNA
```

<213> ORGANISM: Homo Sapiens

<400> SEQUENCE: 901
ccctcctgct gccctcrgtt tagggtttac aag                33

<210> SEQ ID NO 902
<211> LENGTH: 33
<212> TYPE: DNA
<213> ORGANISM: Homo Sapiens

<400> SEQUENCE: 902
ctcagtgaaa atggctragg ggaggagctt ttc                33

<210> SEQ ID NO 903
<211> LENGTH: 33
<212> TYPE: DNA
<213> ORGANISM: Homo Sapiens

<400> SEQUENCE: 903
tctcctcttt cacccmaca tgcaattcaa ctt                33

<210> SEQ ID NO 904
<211> LENGTH: 33
<212> TYPE: DNA
<213> ORGANISM: Homo Sapiens

<400> SEQUENCE: 904
tatatctcca tgatatrtaa tccaagatat ata                33

<210> SEQ ID NO 905
<211> LENGTH: 33
<212> TYPE: DNA
<213> ORGANISM: Homo Sapiens

<400> SEQUENCE: 905
cttatttgtg agagaasaga aacctccagg gtg                33

<210> SEQ ID NO 906
<211> LENGTH: 33
<212> TYPE: DNA
<213> ORGANISM: Homo Sapiens

<400> SEQUENCE: 906
cggtgctcca gtcgtcmtgc tgggccagca cag                33

<210> SEQ ID NO 907
<211> LENGTH: 33
<212> TYPE: DNA
<213> ORGANISM: Homo Sapiens

<400> SEQUENCE: 907
ggaggaagcg gctgtcrcag tggctgggct tag                33

<210> SEQ ID NO 908
<211> LENGTH: 33
<212> TYPE: DNA
<213> ORGANISM: Homo Sapiens

<400> SEQUENCE: 908
cttactaaag aactcartgt atgcagggaa cag                33

<210> SEQ ID NO 909
<211> LENGTH: 33

```
<212> TYPE: DNA
<213> ORGANISM: Homo Sapiens

<400> SEQUENCE: 909
ttgcatttgt tttgggract gtctgaggtt aga                              33

<210> SEQ ID NO 910
<211> LENGTH: 33
<212> TYPE: DNA
<213> ORGANISM: Homo Sapiens

<400> SEQUENCE: 910
tggcagcagt ggagatrgac agagcagaga gat                              33

<210> SEQ ID NO 911
<211> LENGTH: 33
<212> TYPE: DNA
<213> ORGANISM: Homo Sapiens

<400> SEQUENCE: 911
tgaccagtac agctgcrccc tgactggccc tgt                              33

<210> SEQ ID NO 912
<211> LENGTH: 33
<212> TYPE: DNA
<213> ORGANISM: Homo Sapiens

<400> SEQUENCE: 912
aataagcaat aataaaratg tgacttttac agc                              33

<210> SEQ ID NO 913
<211> LENGTH: 33
<212> TYPE: DNA
<213> ORGANISM: Homo Sapiens

<400> SEQUENCE: 913
tcatataact tagctargtc attgtgaaat ttt                              33

<210> SEQ ID NO 914
<211> LENGTH: 33
<212> TYPE: DNA
<213> ORGANISM: Homo Sapiens

<400> SEQUENCE: 914
catggagaac aggtgtracc taagtgcaga gcc                              33

<210> SEQ ID NO 915
<211> LENGTH: 33
<212> TYPE: DNA
<213> ORGANISM: Homo Sapiens

<400> SEQUENCE: 915
tctaccaaac atacaaraaa gagctgatat caa                              33

<210> SEQ ID NO 916
<211> LENGTH: 33
<212> TYPE: DNA
<213> ORGANISM: Homo Sapiens

<400> SEQUENCE: 916
aaatcctggt gaacacmtgt gcctttcac aga                               33

<210> SEQ ID NO 917
```

<211> LENGTH: 33
<212> TYPE: DNA
<213> ORGANISM: Homo Sapiens

<400> SEQUENCE: 917
atggtgcttt tttcaamcat acccatgacc aat                33

<210> SEQ ID NO 918
<211> LENGTH: 33
<212> TYPE: DNA
<213> ORGANISM: Homo Sapiens

<400> SEQUENCE: 918
ctcacattta aactgamgga atcataaagt aac                33

<210> SEQ ID NO 919
<211> LENGTH: 33
<212> TYPE: DNA
<213> ORGANISM: Homo Sapiens

<400> SEQUENCE: 919
aaaagaaatt ctgggtrtct ccagagaggg aat                33

<210> SEQ ID NO 920
<211> LENGTH: 33
<212> TYPE: DNA
<213> ORGANISM: Homo Sapiens

<400> SEQUENCE: 920
aaaagaagac ctttaasgct caacaacatg cat                33

<210> SEQ ID NO 921
<211> LENGTH: 33
<212> TYPE: DNA
<213> ORGANISM: Homo Sapiens

<400> SEQUENCE: 921
aatgccatct agaaagrtct tgatcagcaa ctt                33

<210> SEQ ID NO 922
<211> LENGTH: 33
<212> TYPE: DNA
<213> ORGANISM: Homo Sapiens

<400> SEQUENCE: 922
ccagccaatg ggagagrtga atgctagagg gtt                33

<210> SEQ ID NO 923
<211> LENGTH: 33
<212> TYPE: DNA
<213> ORGANISM: Homo Sapiens

<400> SEQUENCE: 923
agagctccct tcatgcratt aaagtatgac tga                33

<210> SEQ ID NO 924
<211> LENGTH: 33
<212> TYPE: DNA
<213> ORGANISM: Homo Sapiens

<400> SEQUENCE: 924
gataatctca atatagrcct cgcatggagt aag                33

<210> SEQ ID NO 925
<211> LENGTH: 33
<212> TYPE: DNA
<213> ORGANISM: Homo Sapiens

<400> SEQUENCE: 925
gttttcacca tgggagraag aaaacacaaa taa         33

<210> SEQ ID NO 926
<211> LENGTH: 33
<212> TYPE: DNA
<213> ORGANISM: Homo Sapiens

<400> SEQUENCE: 926
ggaggagggt gagcacrcct atgatacgct gag         33

<210> SEQ ID NO 927
<211> LENGTH: 33
<212> TYPE: DNA
<213> ORGANISM: Homo Sapiens

<400> SEQUENCE: 927
ctaacagata gcgcccrggt tggaggcaaa gca         33

<210> SEQ ID NO 928
<211> LENGTH: 33
<212> TYPE: DNA
<213> ORGANISM: Homo Sapiens

<400> SEQUENCE: 928
cctcttcata ttttcarctt tgtgcagtga aaa         33

<210> SEQ ID NO 929
<211> LENGTH: 33
<212> TYPE: DNA
<213> ORGANISM: Homo Sapiens

<400> SEQUENCE: 929
gtgttcactc ctttgtrtaa ttccctcccc tca         33

<210> SEQ ID NO 930
<211> LENGTH: 33
<212> TYPE: DNA
<213> ORGANISM: Homo Sapiens

<400> SEQUENCE: 930
tatctgagat gaggccrtca gtgaggacct cct         33

<210> SEQ ID NO 931
<211> LENGTH: 33
<212> TYPE: DNA
<213> ORGANISM: Homo Sapiens

<400> SEQUENCE: 931
cgacgcgctc cacctgrgcg ccgccatctt aca         33

<210> SEQ ID NO 932
<211> LENGTH: 33
<212> TYPE: DNA
<213> ORGANISM: Homo Sapiens

<400> SEQUENCE: 932
ctgaggtttc cgggatragg agagggtgtg gcg         33

<210> SEQ ID NO 933
<211> LENGTH: 33
<212> TYPE: DNA
<213> ORGANISM: Homo Sapiens

<400> SEQUENCE: 933
acaaggctgc actttcrtag ggttccatca taa                                    33

<210> SEQ ID NO 934
<211> LENGTH: 33
<212> TYPE: DNA
<213> ORGANISM: Homo Sapiens

<400> SEQUENCE: 934
ccagacccta tacatamgaa taaaatgtta cat                                    33

<210> SEQ ID NO 935
<211> LENGTH: 33
<212> TYPE: DNA
<213> ORGANISM: Homo Sapiens

<400> SEQUENCE: 935
ggcagtgaaa gtcatgmttg taccgcaatc aat                                    33

<210> SEQ ID NO 936
<211> LENGTH: 33
<212> TYPE: DNA
<213> ORGANISM: Homo Sapiens

<400> SEQUENCE: 936
atagggactc agaaaargca tcattccctt cat                                    33

<210> SEQ ID NO 937
<211> LENGTH: 33
<212> TYPE: DNA
<213> ORGANISM: Homo Sapiens

<400> SEQUENCE: 937
ccctaataaa caaactrctt aattgaacag ccc                                    33

<210> SEQ ID NO 938
<211> LENGTH: 33
<212> TYPE: DNA
<213> ORGANISM: Homo Sapiens

<400> SEQUENCE: 938
gtctcaatcc cagccargag tgaataatag atg                                    33

<210> SEQ ID NO 939
<211> LENGTH: 33
<212> TYPE: DNA
<213> ORGANISM: Homo Sapiens

<400> SEQUENCE: 939
tagaaatttg tcgaacrtgt ttgataaaat gga                                    33

<210> SEQ ID NO 940
<211> LENGTH: 33
<212> TYPE: DNA
<213> ORGANISM: Homo Sapiens

<400> SEQUENCE: 940
gtctcctgga ttgggcrtga ggagggcttt ggg                                    33

<210> SEQ ID NO 941
<211> LENGTH: 33
<212> TYPE: DNA
<213> ORGANISM: Homo Sapiens

<400> SEQUENCE: 941
aaaaaaaaat gattctrcct tatctgggat ttt                33

<210> SEQ ID NO 942
<211> LENGTH: 33
<212> TYPE: DNA
<213> ORGANISM: Homo Sapiens

<400> SEQUENCE: 942
tgcagatata ttctgargct gaactgtgtt aca                33

<210> SEQ ID NO 943
<211> LENGTH: 33
<212> TYPE: DNA
<213> ORGANISM: Homo Sapiens

<400> SEQUENCE: 943 cacttcccttt tctgacrtat cccctgatgt aag                33

<210> SEQ ID NO 944
<211> LENGTH: 33
<212> TYPE: DNA
<213> ORGANISM: Homo Sapiens

<400> SEQUENCE: 944
catccacctt atctgtrggt gactcctgct ggg                33

<210> SEQ ID NO 945
<211> LENGTH: 33
<212> TYPE: DNA
<213> ORGANISM: Homo Sapiens

<400> SEQUENCE: 945
tggaagggca gacaccrtag tccccagcta cct                33

<210> SEQ ID NO 946
<211> LENGTH: 33
<212> TYPE: DNA
<213> ORGANISM: Homo Sapiens

<400> SEQUENCE: 946
ctgcttgggc tgggtcraag gctctgctga ctg                33

<210> SEQ ID NO 947
<211> LENGTH: 33
<212> TYPE: DNA
<213> ORGANISM: Homo Sapiens

<400> SEQUENCE: 947
ttatgtcccc aaacccrcct ggggcaaggg ggt                33

<210> SEQ ID NO 948
<211> LENGTH: 33
<212> TYPE: DNA
<213> ORGANISM: Homo Sapiens

<400> SEQUENCE: 948

```
tccccggtgc tgccccrggg gagccgccca gcc                         33

<210> SEQ ID NO 949
<211> LENGTH: 33
<212> TYPE: DNA
<213> ORGANISM: Homo Sapiens

<400> SEQUENCE: 949
ttcatcctta tttggcrtta aagttaacac aaa                         33

<210> SEQ ID NO 950
<211> LENGTH: 33
<212> TYPE: DNA
<213> ORGANISM: Homo Sapiens

<400> SEQUENCE: 950
atttcaactt gaacaaraaa acaaaggcgt tag                         33

<210> SEQ ID NO 951
<211> LENGTH: 33
<212> TYPE: DNA
<213> ORGANISM: Homo Sapiens

<400> SEQUENCE: 951
tgcacaggag gctgagrtgg gagagagaaa aag                         33

<210> SEQ ID NO 952
<211> LENGTH: 33
<212> TYPE: DNA
<213> ORGANISM: Homo Sapiens

<400> SEQUENCE: 952
taatatttgg caaagcrttg ccacttaccc act                         33

<210> SEQ ID NO 953
<211> LENGTH: 33
<212> TYPE: DNA
<213> ORGANISM: Homo Sapiens

<400> SEQUENCE: 953
ctgttatagt ttccacrtca caactaactg ttt                         33

<210> SEQ ID NO 954
<211> LENGTH: 33
<212> TYPE: DNA
<213> ORGANISM: Homo Sapiens

<400> SEQUENCE: 954 aaagggatg aggagcrgat gggctgggga cac                          33

<210> SEQ ID NO 955
<211> LENGTH: 33
<212> TYPE: DNA
<213> ORGANISM: Homo Sapiens

<400> SEQUENCE: 955
gttcgacatt ttgcaartct ctttaatgtc tgg                         33

<210> SEQ ID NO 956
<211> LENGTH: 33
<212> TYPE: DNA
<213> ORGANISM: Homo Sapiens

<400> SEQUENCE: 956
```
cctttccttc caggtcrttt gagtcaagtt gaa                                    33

<210> SEQ ID NO 957
<211> LENGTH: 33
<212> TYPE: DNA
<213> ORGANISM: Homo Sapiens

<400> SEQUENCE: 957
ggctgctgta agtgacmagt tgtagttgcc tgt                                    33

<210> SEQ ID NO 958
<211> LENGTH: 33
<212> TYPE: DNA
<213> ORGANISM: Homo Sapiens

<400> SEQUENCE: 958
tagactaaaa ttaatamaga taagagttga aac                                    33

<210> SEQ ID NO 959
<211> LENGTH: 33
<212> TYPE: DNA
<213> ORGANISM: Homo Sapiens

<400> SEQUENCE: 959
attatcattt cttcttmatt tattcctagt ctg                                    33

<210> SEQ ID NO 960
<211> LENGTH: 33
<212> TYPE: DNA
<213> ORGANISM: Homo Sapiens

<400> SEQUENCE: 960
tccctataaa ggaagargta gtcagtgtgg tga                                    33

<210> SEQ ID NO 961
<211> LENGTH: 33
<212> TYPE: DNA
<213> ORGANISM: Homo Sapiens

<400> SEQUENCE: 961
tgggctgcta tttctcrtgg accaataaca aga                                    33

<210> SEQ ID NO 962
<211> LENGTH: 33
<212> TYPE: DNA
<213> ORGANISM: Homo Sapiens

<400> SEQUENCE: 962
attagtcttg ggtccaratt aatttcatga tca                                    33

<210> SEQ ID NO 963
<211> LENGTH: 33
<212> TYPE: DNA
<213> ORGANISM: Homo Sapiens

<400> SEQUENCE: 963
ctaataatct ccctagrttt tgtcctttgt cta                                    33

<210> SEQ ID NO 964
<211> LENGTH: 33
<212> TYPE: DNA
<213> ORGANISM: Homo Sapiens

<400> SEQUENCE: 964
gaattcttga ctgcctrtgt gttactcttc ttc                          33

<210> SEQ ID NO 965
<211> LENGTH: 33
<212> TYPE: DNA
<213> ORGANISM: Homo Sapiens

<400> SEQUENCE: 965
gtaaagattg ggaaaarctt gcactaactt cca                          33

<210> SEQ ID NO 966
<211> LENGTH: 33
<212> TYPE: DNA
<213> ORGANISM: Homo Sapiens

<400> SEQUENCE: 966
ctggatgttg gggagartta acttgagttc aga                          33

<210> SEQ ID NO 967
<211> LENGTH: 33
<212> TYPE: DNA
<213> ORGANISM: Homo Sapiens

<400> SEQUENCE: 967
ctcttctctg cttctgraat ggttagcagt gct                          33

<210> SEQ ID NO 968
<211> LENGTH: 33
<212> TYPE: DNA
<213> ORGANISM: Homo Sapiens

<400> SEQUENCE: 968
aagtaaagga attataract agctgctgct tca                          33

<210> SEQ ID NO 969
<211> LENGTH: 33
<212> TYPE: DNA
<213> ORGANISM: Homo Sapiens

<400> SEQUENCE: 969
gccaaagctg tcagaaraca tcctacaatg cac                          33

<210> SEQ ID NO 970
<211> LENGTH: 33
<212> TYPE: DNA
<213> ORGANISM: Homo Sapiens

<400> SEQUENCE: 970
accccttgtt gagcacrtgg atacctttga ggt                          33

<210> SEQ ID NO 971
<211> LENGTH: 33
<212> TYPE: DNA
<213> ORGANISM: Homo Sapiens

<400> SEQUENCE: 971
tatttttagt aaaatamtaa atacacacct tgt                          33

<210> SEQ ID NO 972
<211> LENGTH: 33
<212> TYPE: DNA
<213> ORGANISM: Homo Sapiens

<400> SEQUENCE: 972
tgtctcctca acccacrttt gaaaggggct cca                                    33

<210> SEQ ID NO 973
<211> LENGTH: 33
<212> TYPE: DNA
<213> ORGANISM: Homo Sapiens

<400> SEQUENCE: 973
ctggagttgc ttttggrgtc tgcattttaa caa                                    33

<210> SEQ ID NO 974
<211> LENGTH: 33
<212> TYPE: DNA
<213> ORGANISM: Homo Sapiens

<400> SEQUENCE: 974
ttttgacaga tagttgrcaa cagacatgta cag                                    33

<210> SEQ ID NO 975
<211> LENGTH: 33
<212> TYPE: DNA
<213> ORGANISM: Homo Sapiens

<400> SEQUENCE: 975
gctacaggtg tgcctgraat gtttctttac ttt                                    33

<210> SEQ ID NO 976
<211> LENGTH: 33
<212> TYPE: DNA
<213> ORGANISM: Homo Sapiens

<400> SEQUENCE: 976
aatacaacta gagagarata tatagatact taa                                    33

<210> SEQ ID NO 977
<211> LENGTH: 33
<212> TYPE: DNA
<213> ORGANISM: Homo Sapiens

<400> SEQUENCE: 977
taaaattgac cattttrcag acataatggc aag                                    33

<210> SEQ ID NO 978
<211> LENGTH: 33
<212> TYPE: DNA
<213> ORGANISM: Homo Sapiens

<400> SEQUENCE: 978
gaatgaatca tccccarttt gtttcttgct aca                                    33

<210> SEQ ID NO 979
<211> LENGTH: 33
<212> TYPE: DNA
<213> ORGANISM: Homo Sapiens

<400> SEQUENCE: 979
acctgatggg agagacrcgg ctaagtagga aag                                    33

<210> SEQ ID NO 980
<211> LENGTH: 33
<212> TYPE: DNA

```
<213> ORGANISM: Homo Sapiens

<400> SEQUENCE: 980
tcctctgaca tggatgrttg tggcattagt aac                          33

<210> SEQ ID NO 981
<211> LENGTH: 33
<212> TYPE: DNA
<213> ORGANISM: Homo Sapiens

<400> SEQUENCE: 981
atgcttcata gcttacmaag ttatttcaga gat                          33

<210> SEQ ID NO 982
<211> LENGTH: 33
<212> TYPE: DNA
<213> ORGANISM: Homo Sapiens

<400> SEQUENCE: 982
ataggactga acaacaraga attgctgata tct                          33

<210> SEQ ID NO 983
<211> LENGTH: 33
<212> TYPE: DNA
<213> ORGANISM: Homo Sapiens

<400> SEQUENCE: 983
cgcaataact gctattrtaa ctgacttaac agg                          33

<210> SEQ ID NO 984
<211> LENGTH: 33
<212> TYPE: DNA
<213> ORGANISM: Homo Sapiens

<400> SEQUENCE: 984
gaacagactt ttggtgrtga ggaggaagaa caa                          33

<210> SEQ ID NO 985
<211> LENGTH: 33
<212> TYPE: DNA
<213> ORGANISM: Homo Sapiens

<400> SEQUENCE: 985
gaagtcagtg gttctcrgtt gtattagtgg ggt                          33

<210> SEQ ID NO 986
<211> LENGTH: 33
<212> TYPE: DNA
<213> ORGANISM: Homo Sapiens

<400> SEQUENCE: 986
cctctggttt ggtgatrtca gtggaggctg ata                          33

<210> SEQ ID NO 987
<211> LENGTH: 33
<212> TYPE: DNA
<213> ORGANISM: Homo Sapiens

<400> SEQUENCE: 987
aatgcaaatg aaaacartat gagaagccac tac                          33

<210> SEQ ID NO 988
<211> LENGTH: 33
```

<212> TYPE: DNA
<213> ORGANISM: Homo Sapiens

<400> SEQUENCE: 988
tgtgctgcac aaggacract gaaacaaaag aat 33

<210> SEQ ID NO 989
<211> LENGTH: 33
<212> TYPE: DNA
<213> ORGANISM: Homo Sapiens

<400> SEQUENCE: 989
taacaagaat gacccartct atatgatcaa ctt 33

<210> SEQ ID NO 990
<211> LENGTH: 33
<212> TYPE: DNA
<213> ORGANISM: Homo Sapiens

<400> SEQUENCE: 990
catgaaagtg tcactaraaa actctaccta ctg 33

<210> SEQ ID NO 991
<211> LENGTH: 33
<212> TYPE: DNA
<213> ORGANISM: Homo Sapiens

<400> SEQUENCE: 991
ggagagagaa atatctrtca gtggaacaac tgt 33

<210> SEQ ID NO 992
<211> LENGTH: 33
<212> TYPE: DNA
<213> ORGANISM: Homo Sapiens

<400> SEQUENCE: 992
atagacactg gcccacrgtg ttgttgaaaa gaa 33

<210> SEQ ID NO 993
<211> LENGTH: 33
<212> TYPE: DNA
<213> ORGANISM: Homo Sapiens

<400> SEQUENCE: 993
cctatgatct ggtggarcac cctccctcct gaa 33

<210> SEQ ID NO 994
<211> LENGTH: 33
<212> TYPE: DNA
<213> ORGANISM: Homo Sapiens

<400> SEQUENCE: 994
tgtctgttca tacaccrgaa tatcattcag ccc 33

<210> SEQ ID NO 995
<211> LENGTH: 33
<212> TYPE: DNA
<213> ORGANISM: Homo Sapiens

<400> SEQUENCE: 995
gtgagagtag gtcactrttg aggcccccat aca 33

<210> SEQ ID NO 996

```
<211> LENGTH: 33
<212> TYPE: DNA
<213> ORGANISM: Homo Sapiens

<400> SEQUENCE: 996
tgccgctgga ggatccrgaa agagtttccg aag                                33

<210> SEQ ID NO 997
<211> LENGTH: 33
<212> TYPE: DNA
<213> ORGANISM: Homo Sapiens

<400> SEQUENCE: 997
atcacaaagc catactrcag gtacagggtc tga                                33

<210> SEQ ID NO 998
<211> LENGTH: 33
<212> TYPE: DNA
<213> ORGANISM: Homo Sapiens

<400> SEQUENCE: 998
ctcctgggtt gcccccrtcc ttgagccaat gta                                33

<210> SEQ ID NO 999
<211> LENGTH: 33
<212> TYPE: DNA
<213> ORGANISM: Homo Sapiens

<400> SEQUENCE: 999
catgtctctg aggagcsgcg ggcggcggcg cgc                                33

<210> SEQ ID NO 1000
<211> LENGTH: 33
<212> TYPE: DNA
<213> ORGANISM: Homo Sapiens

<400> SEQUENCE: 1000
cacatattgc aagctasgat attattcaat ttt                                33

<210> SEQ ID NO 1001
<211> LENGTH: 33
<212> TYPE: DNA
<213> ORGANISM: Homo Sapiens

<400> SEQUENCE: 1001
tgtcctccca gagtctrtca tctatcagga agt                                33

<210> SEQ ID NO 1002
<211> LENGTH: 33
<212> TYPE: DNA
<213> ORGANISM: Homo Sapiens

<400> SEQUENCE: 1002
aattaagaat attgggrcac ggccaggcgt ggt                                33

<210> SEQ ID NO 1003
<211> LENGTH: 33
<212> TYPE: DNA
<213> ORGANISM: Homo Sapiens

<400> SEQUENCE: 1003
ttaagtcact gcataartat ctgtcacaca aat                                33
```

```
<210> SEQ ID NO 1004
<211> LENGTH: 33
<212> TYPE: DNA
<213> ORGANISM: Homo Sapiens

<400> SEQUENCE: 1004
ccaaagctcc ctccacrgca gccaacacac cct                              33

<210> SEQ ID NO 1005
<211> LENGTH: 33
<212> TYPE: DNA
<213> ORGANISM: Homo Sapiens

<400> SEQUENCE: 1005
tctgaacaaa gatgacmgga ggagctgcct tgg                              33

<210> SEQ ID NO 1006
<211> LENGTH: 33
<212> TYPE: DNA
<213> ORGANISM: Homo Sapiens

<400> SEQUENCE: 1006
tgtgctttgg agtttgrgcg gcagaaccgc gta                              33

<210> SEQ ID NO 1007
<211> LENGTH: 33
<212> TYPE: DNA
<213> ORGANISM: Homo Sapiens

<400> SEQUENCE: 1007
tatttccccc gaataaragc cttatataat gtt                              33

<210> SEQ ID NO 1008
<211> LENGTH: 33
<212> TYPE: DNA
<213> ORGANISM: Homo Sapiens

<400> SEQUENCE: 1008
actgagtagt catcagrata tttggttgtg ttg                              33

<210> SEQ ID NO 1009
<211> LENGTH: 33
<212> TYPE: DNA
<213> ORGANISM: Homo Sapiens

<400> SEQUENCE: 1009
caagtactca ataaatrtaa acaaacctgt cat                              33

<210> SEQ ID NO 1010
<211> LENGTH: 33
<212> TYPE: DNA
<213> ORGANISM: Homo Sapiens

<400> SEQUENCE: 1010
atgaaatagt aaatacmagc cttacacttt gaa                              33

<210> SEQ ID NO 1011
<211> LENGTH: 33
<212> TYPE: DNA
<213> ORGANISM: Homo Sapiens

<400> SEQUENCE: 1011
gagctgggtt tatatgmatt gacatgaaaa gtt                              33
```

<210> SEQ ID NO 1012
<211> LENGTH: 33
<212> TYPE: DNA
<213> ORGANISM: Homo Sapiens

<400> SEQUENCE: 1012
aactggttat ttcctaragc tgagattgtg agg                               33

<210> SEQ ID NO 1013
<211> LENGTH: 33
<212> TYPE: DNA
<213> ORGANISM: Homo Sapiens

<400> SEQUENCE: 1013
attacaagtc agcagtmcaa gaaaggaaca ggg                               33

<210> SEQ ID NO 1014
<211> LENGTH: 33
<212> TYPE: DNA
<213> ORGANISM: Homo Sapiens

<400> SEQUENCE: 1014
acaaagaata taaacaragt acacagaaga agt                               33

<210> SEQ ID NO 1015
<211> LENGTH: 33
<212> TYPE: DNA
<213> ORGANISM: Homo Sapiens

<400> SEQUENCE: 1015
agtctgtctt tgcatawacc cactttccat gtc                               33

<210> SEQ ID NO 1016
<211> LENGTH: 33
<212> TYPE: DNA
<213> ORGANISM: Homo Sapiens

<400> SEQUENCE: 1016
ggcacagtca cacgccmacg aggccagccc tgc                               33

<210> SEQ ID NO 1017
<211> LENGTH: 33
<212> TYPE: DNA
<213> ORGANISM: Homo Sapiens

<400> SEQUENCE: 1017
ccttcagttt ctccctrggg cttcattatg gct                               33

<210> SEQ ID NO 1018
<211> LENGTH: 33
<212> TYPE: DNA
<213> ORGANISM: Homo Sapiens

<400> SEQUENCE: 1018
taattttaat tgatccrtca cctctactgt ttg                               33

<210> SEQ ID NO 1019
<211> LENGTH: 33
<212> TYPE: DNA
<213> ORGANISM: Homo Sapiens

<400> SEQUENCE: 1019
gtaattatta aattacrtgg aagttccttg ccc                               33

```
<210> SEQ ID NO 1020
<211> LENGTH: 33
<212> TYPE: DNA
<213> ORGANISM: Homo Sapiens

<400> SEQUENCE: 1020
tttacttacc tcttacrtag tcctaagcac aat                              33

<210> SEQ ID NO 1021
<211> LENGTH: 33
<212> TYPE: DNA
<213> ORGANISM: Homo Sapiens

<400> SEQUENCE: 1021
gaggagagct agtgaamtaa aagcctaagt ata                              33

<210> SEQ ID NO 1022
<211> LENGTH: 33
<212> TYPE: DNA
<213> ORGANISM: Homo Sapiens

<400> SEQUENCE: 1022
tttggggata tagcctrgaa atgtgtactt tta                              33

<210> SEQ ID NO 1023
<211> LENGTH: 33
<212> TYPE: DNA
<213> ORGANISM: Homo Sapiens

<400> SEQUENCE: 1023
ctgtattaca cattatmcat aatctagaaa tga                              33

<210> SEQ ID NO 1024
<211> LENGTH: 33
<212> TYPE: DNA
<213> ORGANISM: Homo Sapiens

<400> SEQUENCE: 1024
aaagctgttt gtttttraga agttctatgc tca                              33

<210> SEQ ID NO 1025
<211> LENGTH: 33
<212> TYPE: DNA
<213> ORGANISM: Homo Sapiens

<400> SEQUENCE: 1025
aacttctgtt tttactrttt tctaggcaat gtc                              33

<210> SEQ ID NO 1026
<211> LENGTH: 33
<212> TYPE: DNA
<213> ORGANISM: Homo Sapiens

<400> SEQUENCE: 1026
tggtgtctag aactgcmtct agcaagtggg agg                              33

<210> SEQ ID NO 1027
<211> LENGTH: 33
<212> TYPE: DNA
<213> ORGANISM: Homo Sapiens

<400> SEQUENCE: 1027
```

-continued tgctggacaa gtgtaargaa tctggggttt aga                                33

<210> SEQ ID NO 1028
<211> LENGTH: 33
<212> TYPE: DNA
<213> ORGANISM: Homo Sapiens

<400> SEQUENCE: 1028
gagggtttgg ctttagrctt tgttagggca agt                                33

<210> SEQ ID NO 1029
<211> LENGTH: 33
<212> TYPE: DNA
<213> ORGANISM: Homo Sapiens

<400> SEQUENCE: 1029
tagaagcaca cctagcrtat ttaaaacttg gag                                33

<210> SEQ ID NO 1030
<211> LENGTH: 33
<212> TYPE: DNA
<213> ORGANISM: Homo Sapiens

<400> SEQUENCE: 1030
acggatgaat caaaacrtta agctctctaa aag                                33

<210> SEQ ID NO 1031
<211> LENGTH: 33
<212> TYPE: DNA
<213> ORGANISM: Homo Sapiens

<400> SEQUENCE: 1031
aaataatcct tgatacrgta ctgaatattt tgt                                33

<210> SEQ ID NO 1032
<211> LENGTH: 33
<212> TYPE: DNA
<213> ORGANISM: Homo Sapiens

<400> SEQUENCE: 1032
ttatctcaaa aaaaatmtgt aggtataaat ttg                                33

<210> SEQ ID NO 1033
<211> LENGTH: 33
<212> TYPE: DNA
<213> ORGANISM: Homo Sapiens

<400> SEQUENCE: 1033
aatccatttg aaattgrcag tgtttttata ttt                                33

<210> SEQ ID NO 1034
<211> LENGTH: 33
<212> TYPE: DNA
<213> ORGANISM: Homo Sapiens

<400> SEQUENCE: 1034
cttcagtctt cgtacaraaa cacttacttt ata                                33

<210> SEQ ID NO 1035
<211> LENGTH: 33
<212> TYPE: DNA
<213> ORGANISM: Homo Sapiens

<400> SEQUENCE: 1035
cctggtaatt tgatcartca ttaagctatc ctt          33

<210> SEQ ID NO 1036
<211> LENGTH: 33
<212> TYPE: DNA
<213> ORGANISM: Homo Sapiens

<400> SEQUENCE: 1036
tgaagaattt actcacrtgg ggaaataaag gcc          33

<210> SEQ ID NO 1037
<211> LENGTH: 33
<212> TYPE: DNA
<213> ORGANISM: Homo Sapiens

<400> SEQUENCE: 1037
tgtattctct agtcagrttc tctttccagc ttg          33

<210> SEQ ID NO 1038
<211> LENGTH: 33
<212> TYPE: DNA
<213> ORGANISM: Homo Sapiens

<400> SEQUENCE: 1038
tagtatttta ggtaacratg agtaaatctt aag          33

<210> SEQ ID NO 1039
<211> LENGTH: 33
<212> TYPE: DNA
<213> ORGANISM: Homo Sapiens

<400> SEQUENCE: 1039
acagagtctg gaaatargac cgatgaaacc agg          33

<210> SEQ ID NO 1040
<211> LENGTH: 33
<212> TYPE: DNA
<213> ORGANISM: Homo Sapiens

<400> SEQUENCE: 1040
agcacaaact tttgctraat agcatgtcat cta          33

<210> SEQ ID NO 1041
<211> LENGTH: 33
<212> TYPE: DNA
<213> ORGANISM: Homo Sapiens

<400> SEQUENCE: 1041
atatcggttc tgctatrtct atgagttcct ttc          33

<210> SEQ ID NO 1042
<211> LENGTH: 33
<212> TYPE: DNA
<213> ORGANISM: Homo Sapiens

<400> SEQUENCE: 1042
aatagatgag gaagttraag tccaaaaata gtc          33

<210> SEQ ID NO 1043
<211> LENGTH: 33
<212> TYPE: DNA
<213> ORGANISM: Homo Sapiens

<400> SEQUENCE: 1043
aaagtgaatg agaacartac tgataataat agc                                    33

<210> SEQ ID NO 1044
<211> LENGTH: 33
<212> TYPE: DNA
<213> ORGANISM: Homo Sapiens

<400> SEQUENCE: 1044
tgcctgtgac acaataktga aatcttactt aaa                                    33

<210> SEQ ID NO 1045
<211> LENGTH: 33
<212> TYPE: DNA
<213> ORGANISM: Homo Sapiens

<400> SEQUENCE: 1045
atgttgaaag ggtgccrgtg ccttggtgat caa                                    33

<210> SEQ ID NO 1046
<211> LENGTH: 33
<212> TYPE: DNA
<213> ORGANISM: Homo Sapiens

<400> SEQUENCE: 1046
ttgattctta atctggrggt gtttatttcc cta                                    33

<210> SEQ ID NO 1047
<211> LENGTH: 33
<212> TYPE: DNA
<213> ORGANISM: Homo Sapiens

<400> SEQUENCE: 1047
tggcgtagat ggatatrttg ataacataga aga                                    33

<210> SEQ ID NO 1048
<211> LENGTH: 33
<212> TYPE: DNA
<213> ORGANISM: Homo Sapiens

<400> SEQUENCE: 1048
tcgtcaatgt tttaaarggt aggagttgtt aca                                    33

<210> SEQ ID NO 1049
<211> LENGTH: 33
<212> TYPE: DNA
<213> ORGANISM: Homo Sapiens

<400> SEQUENCE: 1049
ataaccgaga ccggatmggg gagtagttac ttc                                    33

<210> SEQ ID NO 1050
<211> LENGTH: 33
<212> TYPE: DNA
<213> ORGANISM: Homo Sapiens

<400> SEQUENCE: 1050
agttcataat cttccargcc tccatagtct ggt                                    33

<210> SEQ ID NO 1051
<211> LENGTH: 33
<212> TYPE: DNA
<213> ORGANISM: Homo Sapiens

<400> SEQUENCE: 1051
tagactaatg caagcamaaa atttccattt gct                33

<210> SEQ ID NO 1052
<211> LENGTH: 33
<212> TYPE: DNA
<213> ORGANISM: Homo Sapiens

<400> SEQUENCE: 1052
ggaagtctta ttcggarcaa tcagtcaaga aaa                33

<210> SEQ ID NO 1053
<211> LENGTH: 33
<212> TYPE: DNA
<213> ORGANISM: Homo Sapiens

<400> SEQUENCE: 1053
catgcaccga aatctcytca tgatggagaa ttt                33

<210> SEQ ID NO 1054
<211> LENGTH: 33
<212> TYPE: DNA
<213> ORGANISM: Homo Sapiens

<400> SEQUENCE: 1054
ggactgcaag gtaatcrtca agggactctt aga                33

<210> SEQ ID NO 1055
<211> LENGTH: 33
<212> TYPE: DNA
<213> ORGANISM: Homo Sapiens

<400> SEQUENCE: 1055
ttcatttaat tttacamgga agagtttaaa aaa                33

<210> SEQ ID NO 1056
<211> LENGTH: 33
<212> TYPE: DNA
<213> ORGANISM: Homo Sapiens

<400> SEQUENCE: 1056
tatcattgct atttccrtgt ttggtcaagg cat                33

<210> SEQ ID NO 1057
<211> LENGTH: 33
<212> TYPE: DNA
<213> ORGANISM: Homo Sapiens

<400> SEQUENCE: 1057
aaattataac aaaagaraat tttactctta taa                33

<210> SEQ ID NO 1058
<211> LENGTH: 33
<212> TYPE: DNA
<213> ORGANISM: Homo Sapiens

<400> SEQUENCE: 1058
agtgccagca ttctgarcca taattttgt gac                 33

<210> SEQ ID NO 1059
<211> LENGTH: 33
<212> TYPE: DNA

-continued

<213> ORGANISM: Homo Sapiens

<400> SEQUENCE: 1059
gggttcaaca gtctatrttt ttagcagact gtc        33

<210> SEQ ID NO 1060
<211> LENGTH: 33
<212> TYPE: DNA
<213> ORGANISM: Homo Sapiens

<400> SEQUENCE: 1060
aggcctgcct gtgtatract gtaaatattc att        33

<210> SEQ ID NO 1061
<211> LENGTH: 33
<212> TYPE: DNA
<213> ORGANISM: Homo Sapiens

<400> SEQUENCE: 1061
tcttggcttg aactgcmaat cttaaaagtt aat        33

<210> SEQ ID NO 1062
<211> LENGTH: 33
<212> TYPE: DNA
<213> ORGANISM: Homo Sapiens

<400> SEQUENCE: 1062
tgaaatattg taaatcrgtg gttttgagtg tct        33

<210> SEQ ID NO 1063
<211> LENGTH: 33
<212> TYPE: DNA
<213> ORGANISM: Homo Sapiens

<400> SEQUENCE: 1063
aaagaaaatg agagccrctg ctcgagtgaa ggg        33

<210> SEQ ID NO 1064
<211> LENGTH: 33
<212> TYPE: DNA
<213> ORGANISM: Homo Sapiens

<400> SEQUENCE: 1064
ttttcatgat ggctttrtgg ctattttttt agg        33

<210> SEQ ID NO 1065
<211> LENGTH: 33
<212> TYPE: DNA
<213> ORGANISM: Homo Sapiens

<400> SEQUENCE: 1065
aaagtactag gccagcrttc caaagaagtg ttt        33

<210> SEQ ID NO 1066
<211> LENGTH: 33
<212> TYPE: DNA
<213> ORGANISM: Homo Sapiens

<400> SEQUENCE: 1066
tgattgggaa agagtgrctg agtgtgcaag gtg        33

<210> SEQ ID NO 1067
<211> LENGTH: 33

```
<212> TYPE: DNA
<213> ORGANISM: Homo Sapiens

<400> SEQUENCE: 1067
acgttactca tcaaatrtat acaatgtagc taa                              33

<210> SEQ ID NO 1068
<211> LENGTH: 33
<212> TYPE: DNA
<213> ORGANISM: Homo Sapiens

<400> SEQUENCE: 1068
ttgtctatca gttgccrtct tccattggcc aag                              33

<210> SEQ ID NO 1069
<211> LENGTH: 33
<212> TYPE: DNA
<213> ORGANISM: Homo Sapiens

<400> SEQUENCE: 1069
ggcagagtta cacctcrtaa acaaactatt caa                              33

<210> SEQ ID NO 1070
<211> LENGTH: 33
<212> TYPE: DNA
<213> ORGANISM: Homo Sapiens

<400> SEQUENCE: 1070
agggccaagc tgccaaraac ttcttgaggt ctg                              33

<210> SEQ ID NO 1071
<211> LENGTH: 33
<212> TYPE: DNA
<213> ORGANISM: Homo Sapiens

<400> SEQUENCE: 1071
ggcagcatca aagtcaratg actgacccaa ggc                              33

<210> SEQ ID NO 1072
<211> LENGTH: 33
<212> TYPE: DNA
<213> ORGANISM: Homo Sapiens

<400> SEQUENCE: 1072
ctatgctctg gtttctrtat ttctagaact tgt                              33

<210> SEQ ID NO 1073
<211> LENGTH: 33
<212> TYPE: DNA
<213> ORGANISM: Homo Sapiens

<400> SEQUENCE: 1073
taatctttaa attgttrcat atttagcaag tgt                              33

<210> SEQ ID NO 1074
<211> LENGTH: 33
<212> TYPE: DNA
<213> ORGANISM: Homo Sapiens

<400> SEQUENCE: 1074
gctgtgctcc cagccarcag ccagaatcaa ctg                              33

<210> SEQ ID NO 1075
```

```
<211> LENGTH: 33
<212> TYPE: DNA
<213> ORGANISM: Homo Sapiens

<400> SEQUENCE: 1075
taaatctgat acaaccraaa taaacacagt ata                                    33

<210> SEQ ID NO 1076
<211> LENGTH: 33
<212> TYPE: DNA
<213> ORGANISM: Homo Sapiens

<400> SEQUENCE: 1076
cactctagaa gaccctrcaa atcagaacca gag                                    33

<210> SEQ ID NO 1077
<211> LENGTH: 33
<212> TYPE: DNA
<213> ORGANISM: Homo Sapiens

<400> SEQUENCE: 1077
gcccccaagc gtagccrggg tggatgccaa aag                                    33

<210> SEQ ID NO 1078
<211> LENGTH: 33
<212> TYPE: DNA
<213> ORGANISM: Homo Sapiens

<400> SEQUENCE: 1078
aagcctcttc aagcaarcta ctgcccatta gtg                                    33

<210> SEQ ID NO 1079
<211> LENGTH: 33
<212> TYPE: DNA
<213> ORGANISM: Homo Sapiens

<400> SEQUENCE: 1079
gttgtcaatg ctaaacraga aagggtccct gga                                    33

<210> SEQ ID NO 1080
<211> LENGTH: 33
<212> TYPE: DNA
<213> ORGANISM: Homo Sapiens

<400> SEQUENCE: 1080
tcaaaccagc cctgccrgtg cccttgtgtc cct                                    33

<210> SEQ ID NO 1081
<211> LENGTH: 33
<212> TYPE: DNA
<213> ORGANISM: Homo Sapiens

<400> SEQUENCE: 1081
cactccaggg cccccamgtg gattccccca tcg                                    33

<210> SEQ ID NO 1082
<211> LENGTH: 33
<212> TYPE: DNA
<213> ORGANISM: Homo Sapiens

<400> SEQUENCE: 1082
cattgtggga agctctmgag atggggccat cct                                    33
```

<210> SEQ ID NO 1083
<211> LENGTH: 33
<212> TYPE: DNA
<213> ORGANISM: Homo Sapiens

<400> SEQUENCE: 1083
ctgcagtgct tattctrtct cttttgtttg ttt                                    33

<210> SEQ ID NO 1084
<211> LENGTH: 33
<212> TYPE: DNA
<213> ORGANISM: Homo Sapiens

<400> SEQUENCE: 1084 atcagggggaa aagcatraac tcaaaataga tga                                   33

<210> SEQ ID NO 1085
<211> LENGTH: 33
<212> TYPE: DNA
<213> ORGANISM: Homo Sapiens

<400> SEQUENCE: 1085
aagggcgatg aatcctrggc caggctgtgc aga                                    33

<210> SEQ ID NO 1086
<211> LENGTH: 33
<212> TYPE: DNA
<213> ORGANISM: Homo Sapiens

<400> SEQUENCE: 1086
cagccagggt gtcggcrccg agctgatggg gct                                    33

<210> SEQ ID NO 1087
<211> LENGTH: 33
<212> TYPE: DNA
<213> ORGANISM: Homo Sapiens

<400> SEQUENCE: 1087
gagggtcgca ctttcamaaa tgagtcagct ggt                                    33

<210> SEQ ID NO 1088
<211> LENGTH: 33
<212> TYPE: DNA
<213> ORGANISM: Homo Sapiens

<400> SEQUENCE: 1088
cagcaagagt tattgcraag agaaacaaca aag                                    33

<210> SEQ ID NO 1089
<211> LENGTH: 33
<212> TYPE: DNA
<213> ORGANISM: Homo Sapiens

<400> SEQUENCE: 1089
ggtcctttct aaaaatrgtc accccaatcc atc                                    33

<210> SEQ ID NO 1090
<211> LENGTH: 33
<212> TYPE: DNA
<213> ORGANISM: Homo Sapiens

<400> SEQUENCE: 1090
attaatattt tatgttrcat gatttagatt tat                                    33

<210> SEQ ID NO 1091
<211> LENGTH: 33
<212> TYPE: DNA
<213> ORGANISM: Homo Sapiens

<400> SEQUENCE: 1091
tcatggaact aaaagtragc atctcaagag act                33

<210> SEQ ID NO 1092
<211> LENGTH: 33
<212> TYPE: DNA
<213> ORGANISM: Homo Sapiens

<400> SEQUENCE: 1092
agcgtatatt atcttcraag agcatttta ttt                33

<210> SEQ ID NO 1093
<211> LENGTH: 33
<212> TYPE: DNA
<213> ORGANISM: Homo Sapiens

<400> SEQUENCE: 1093
gagcatccac atccatragg ctgctgaatt cat                33

<210> SEQ ID NO 1094
<211> LENGTH: 33
<212> TYPE: DNA
<213> ORGANISM: Homo Sapiens

<400> SEQUENCE: 1094
tctccagaag atccctragc acatgtctgg atg                33

<210> SEQ ID NO 1095
<211> LENGTH: 33
<212> TYPE: DNA
<213> ORGANISM: Homo Sapiens

<400> SEQUENCE: 1095
ttcagcacta ttcagcrcct atcactgcca gct                33

<210> SEQ ID NO 1096
<211> LENGTH: 33
<212> TYPE: DNA
<213> ORGANISM: Homo Sapiens

<400> SEQUENCE: 1096
cccagacatt ttaaccrata tggccagtat aaa                33

<210> SEQ ID NO 1097
<211> LENGTH: 33
<212> TYPE: DNA
<213> ORGANISM: Homo Sapiens

<400> SEQUENCE: 1097
cgcacggcag agggccraag ccgcggtact ctc                33

<210> SEQ ID NO 1098
<211> LENGTH: 33
<212> TYPE: DNA
<213> ORGANISM: Homo Sapiens

<400> SEQUENCE: 1098
tacaaacact tgccagrttt agaaacacct gta                33

<210> SEQ ID NO 1099
<211> LENGTH: 33
<212> TYPE: DNA
<213> ORGANISM: Homo Sapiens

<400> SEQUENCE: 1099
ttatgggccc agaatgrttc cagatcagaa ttt                33

<210> SEQ ID NO 1100
<211> LENGTH: 33
<212> TYPE: DNA
<213> ORGANISM: Homo Sapiens

<400> SEQUENCE: 1100
tattgaacat tctacaratt tttataaaaa agg                33

<210> SEQ ID NO 1101
<211> LENGTH: 33
<212> TYPE: DNA
<213> ORGANISM: Homo Sapiens

<400> SEQUENCE: 1101
ttctttgtca gctaccrttg ctataaaacc ttt                33

<210> SEQ ID NO 1102
<211> LENGTH: 33
<212> TYPE: DNA
<213> ORGANISM: Homo Sapiens

<400> SEQUENCE: 1102
tgactaatta cactggrgag tccatcaaca tct                33

<210> SEQ ID NO 1103
<211> LENGTH: 33
<212> TYPE: DNA
<213> ORGANISM: Homo Sapiens

<400> SEQUENCE: 1103
tggttggaac atagccrtga cagctagcca aca                33

<210> SEQ ID NO 1104
<211> LENGTH: 33
<212> TYPE: DNA
<213> ORGANISM: Homo Sapiens

<400> SEQUENCE: 1104
caaacaaaca gaaaaartaa ccctggctat agt                33

<210> SEQ ID NO 1105
<211> LENGTH: 33
<212> TYPE: DNA
<213> ORGANISM: Homo Sapiens

<400> SEQUENCE: 1105
gaaggcccag tgggaarccg agtagtgcta cag                33

<210> SEQ ID NO 1106
<211> LENGTH: 33
<212> TYPE: DNA
<213> ORGANISM: Homo Sapiens

<400> SEQUENCE: 1106

```
atccaaatca agaaaamaat ctctgaattg cca                                    33

<210> SEQ ID NO 1107
<211> LENGTH: 33
<212> TYPE: DNA
<213> ORGANISM: Homo Sapiens

<400> SEQUENCE: 1107
ggggtaattt attgccrccg ctcgcttcac cag                                    33

<210> SEQ ID NO 1108
<211> LENGTH: 33
<212> TYPE: DNA
<213> ORGANISM: Homo Sapiens

<400> SEQUENCE: 1108
attctgcaga cacacartcc tttttgccta caa                                    33

<210> SEQ ID NO 1109
<211> LENGTH: 33
<212> TYPE: DNA
<213> ORGANISM: Homo Sapiens

<400> SEQUENCE: 1109
cgtgcactac gagtacrtga tcatggggac caa                                    33

<210> SEQ ID NO 1110
<211> LENGTH: 33
<212> TYPE: DNA
<213> ORGANISM: Homo Sapiens

<400> SEQUENCE: 1110
tggtacaggg gacagtrata gccagcacac cca                                    33

<210> SEQ ID NO 1111
<211> LENGTH: 33
<212> TYPE: DNA
<213> ORGANISM: Homo Sapiens

<400> SEQUENCE: 1111
atctgagccc ttgggtrccc ctgcctttgg aga                                    33

<210> SEQ ID NO 1112
<211> LENGTH: 33
<212> TYPE: DNA
<213> ORGANISM: Homo Sapiens

<400> SEQUENCE: 1112
tgccacttgc tgccagmcct ggctgaagca ggg                                    33

<210> SEQ ID NO 1113
<211> LENGTH: 33
<212> TYPE: DNA
<213> ORGANISM: Homo Sapiens

<400> SEQUENCE: 1113 ttgttttct gattacraca gaagacccaa caa                                     33

<210> SEQ ID NO 1114
<211> LENGTH: 33
<212> TYPE: DNA
<213> ORGANISM: Homo Sapiens

<400> SEQUENCE: 1114
```
gctcatcatg atagaartag tcatcatgga gct                          33

<210> SEQ ID NO 1115
<211> LENGTH: 33
<212> TYPE: DNA
<213> ORGANISM: Homo Sapiens

<400> SEQUENCE: 1115
gagtctcgac gggagcrttg ggagcagcgg cag                          33

<210> SEQ ID NO 1116
<211> LENGTH: 33
<212> TYPE: DNA
<213> ORGANISM: Homo Sapiens

<400> SEQUENCE: 1116
caattacaga atcatgrtgg aggtttctct gca                          33

<210> SEQ ID NO 1117
<211> LENGTH: 33
<212> TYPE: DNA
<213> ORGANISM: Homo Sapiens

<400> SEQUENCE: 1117
tgataagctg gacttcrtaa aaactataca cat                          33

<210> SEQ ID NO 1118
<211> LENGTH: 33
<212> TYPE: DNA
<213> ORGANISM: Homo Sapiens

<400> SEQUENCE: 1118
catggtaaaa tactttrgct atatttccat cag                          33

<210> SEQ ID NO 1119
<211> LENGTH: 33
<212> TYPE: DNA
<213> ORGANISM: Homo Sapiens

<400> SEQUENCE: 1119
tgaccagacg cctggtrcag actgggcctt ctt                          33

<210> SEQ ID NO 1120
<211> LENGTH: 33
<212> TYPE: DNA
<213> ORGANISM: Homo Sapiens

<400> SEQUENCE: 1120
ggatgctggt tcctccraaa acaaagagct tca                          33

<210> SEQ ID NO 1121
<211> LENGTH: 33
<212> TYPE: DNA
<213> ORGANISM: Homo Sapiens

<400> SEQUENCE: 1121
accagaaagg tgaccargac agatttttta agg                          33

<210> SEQ ID NO 1122
<211> LENGTH: 33
<212> TYPE: DNA
<213> ORGANISM: Homo Sapiens

<400> SEQUENCE: 1122
aacagtgacc tattctrgta aacacattac gaa                33

<210> SEQ ID NO 1123
<211> LENGTH: 33
<212> TYPE: DNA
<213> ORGANISM: Homo Sapiens

<400> SEQUENCE: 1123
agcaagatct cgtctcraca aaaaaaagt tta                 33

<210> SEQ ID NO 1124
<211> LENGTH: 33
<212> TYPE: DNA
<213> ORGANISM: Homo Sapiens

<400> SEQUENCE: 1124
atgaaccaac tatatgmtgt ctacaagaaa cac                33

<210> SEQ ID NO 1125
<211> LENGTH: 33
<212> TYPE: DNA
<213> ORGANISM: Homo Sapiens

<400> SEQUENCE: 1125
cggcctttgt ggtgctrttt ggtttcatcc cca                33

<210> SEQ ID NO 1126
<211> LENGTH: 33
<212> TYPE: DNA
<213> ORGANISM: Homo Sapiens

<400> SEQUENCE: 1126
tccttgagag acttccrggg caccgcttta atc                33

<210> SEQ ID NO 1127
<211> LENGTH: 33
<212> TYPE: DNA
<213> ORGANISM: Homo Sapiens

<400> SEQUENCE: 1127
aaggctctga ggttttrgta ccccagaaag att                33

<210> SEQ ID NO 1128
<211> LENGTH: 33
<212> TYPE: DNA
<213> ORGANISM: Homo Sapiens

<400> SEQUENCE: 1128
tattaccatg aactttrgta aaagttacaa ata                33

<210> SEQ ID NO 1129
<211> LENGTH: 33
<212> TYPE: DNA
<213> ORGANISM: Homo Sapiens

<400> SEQUENCE: 1129
ttagaaaatc tataacrgta aaagtacat tag                 33

<210> SEQ ID NO 1130
<211> LENGTH: 33
<212> TYPE: DNA
<213> ORGANISM: Homo Sapiens

```
<400> SEQUENCE: 1130
aaaacctctc acatgamtaa gcttacaaaa tag                              33

<210> SEQ ID NO 1131
<211> LENGTH: 33
<212> TYPE: DNA
<213> ORGANISM: Homo Sapiens

<400> SEQUENCE: 1131
ttctatagca gacattrgtc tctgaacttg ggt                              33

<210> SEQ ID NO 1132
<211> LENGTH: 33
<212> TYPE: DNA
<213> ORGANISM: Homo Sapiens

<400> SEQUENCE: 1132
ccgcagccgg gacgacracg tgcagtacct gac                              33

<210> SEQ ID NO 1133
<211> LENGTH: 33
<212> TYPE: DNA
<213> ORGANISM: Homo Sapiens

<400> SEQUENCE: 1133
ggcaggcagg gaacagrtga ttagtaacca aag                              33

<210> SEQ ID NO 1134
<211> LENGTH: 33
<212> TYPE: DNA
<213> ORGANISM: Homo Sapiens

<400> SEQUENCE: 1134
ggtgctcccg ctgaggsgcc tccgcgcctt gtg                              33

<210> SEQ ID NO 1135
<211> LENGTH: 33
<212> TYPE: DNA
<213> ORGANISM: Homo Sapiens

<400> SEQUENCE: 1135
aggtgtggga gatcccrgat gggggcctga tgc                              33

<210> SEQ ID NO 1136
<211> LENGTH: 33
<212> TYPE: DNA
<213> ORGANISM: Homo Sapiens

<400> SEQUENCE: 1136
cagcaaagtc tgaccartct aaagtaacca ctc                              33

<210> SEQ ID NO 1137
<211> LENGTH: 33
<212> TYPE: DNA
<213> ORGANISM: Homo Sapiens

<400> SEQUENCE: 1137 agggacccdtt ctaaaargtc actgtgggct ggg                             33

<210> SEQ ID NO 1138
<211> LENGTH: 33
<212> TYPE: DNA
```

```
<213> ORGANISM: Homo Sapiens

<400> SEQUENCE: 1138
gagaccagcc tacgcarcat agaacctgtc tct                              33

<210> SEQ ID NO 1139
<211> LENGTH: 33
<212> TYPE: DNA
<213> ORGANISM: Homo Sapiens

<400> SEQUENCE: 1139
agtaatactt cccatamgag atagttgtga aat                              33

<210> SEQ ID NO 1140
<211> LENGTH: 33
<212> TYPE: DNA
<213> ORGANISM: Homo Sapiens

<400> SEQUENCE: 1140
ttctgatttc acaagcrggg ctccagggca ttt                              33

<210> SEQ ID NO 1141
<211> LENGTH: 33
<212> TYPE: DNA
<213> ORGANISM: Homo Sapiens

<400> SEQUENCE: 1141
tctacaacca tgtcagraca caatctaact cct                              33

<210> SEQ ID NO 1142
<211> LENGTH: 33
<212> TYPE: DNA
<213> ORGANISM: Homo Sapiens

<400> SEQUENCE: 1142
cagaggcggc ggcggcrgca gctcaaccct cct                              33

<210> SEQ ID NO 1143
<211> LENGTH: 33
<212> TYPE: DNA
<213> ORGANISM: Homo Sapiens

<400> SEQUENCE: 1143
ctcccctgac ccaggtragg cagtgagtac ccc                              33

<210> SEQ ID NO 1144
<211> LENGTH: 33
<212> TYPE: DNA
<213> ORGANISM: Homo Sapiens

<400> SEQUENCE: 1144
atgtcctctg gagcacrccc cacagcaagt tgg                              33

<210> SEQ ID NO 1145
<211> LENGTH: 33
<212> TYPE: DNA
<213> ORGANISM: Homo Sapiens

<400> SEQUENCE: 1145
cacggcttct cggtgamcct cctggggttc tgc                              33

<210> SEQ ID NO 1146
<211> LENGTH: 33
```

<212> TYPE: DNA
<213> ORGANISM: Homo Sapiens

<400> SEQUENCE: 1146
aggctgcagg agctgcrtgc aggtgagacc ccg    33

<210> SEQ ID NO 1147
<211> LENGTH: 33
<212> TYPE: DNA
<213> ORGANISM: Homo Sapiens

<400> SEQUENCE: 1147
atcctcctca tttttcrtct aaaagcctta gtc    33

<210> SEQ ID NO 1148
<211> LENGTH: 33
<212> TYPE: DNA
<213> ORGANISM: Homo Sapiens

<400> SEQUENCE: 1148
gcccaagagc gcccacrcgt ctcccgagaa gaa    33

<210> SEQ ID NO 1149
<211> LENGTH: 33
<212> TYPE: DNA
<213> ORGANISM: Homo Sapiens

<400> SEQUENCE: 1149
gcatgcgcgc tctcagrata aacaggccct gcc    33

<210> SEQ ID NO 1150
<211> LENGTH: 33
<212> TYPE: DNA
<213> ORGANISM: Homo Sapiens

<400> SEQUENCE: 1150
aggggcacgg ggagcasagg cccctgagca gga    33

<210> SEQ ID NO 1151
<211> LENGTH: 33
<212> TYPE: DNA
<213> ORGANISM: Homo Sapiens

<400> SEQUENCE: 1151
aaaattcaaa tttttcrtgg agggcaaaca cag    33

<210> SEQ ID NO 1152
<211> LENGTH: 33
<212> TYPE: DNA
<213> ORGANISM: Homo Sapiens

<400> SEQUENCE: 1152
cccatcccct cagcttmtat tctgagctca atg    33

<210> SEQ ID NO 1153
<211> LENGTH: 33
<212> TYPE: DNA
<213> ORGANISM: Homo Sapiens

<400> SEQUENCE: 1153
gagtcacagt gatggcracc cggtattctc agc    33

<210> SEQ ID NO 1154

-continued

```
<211> LENGTH: 33
<212> TYPE: DNA
<213> ORGANISM: Homo Sapiens

<400> SEQUENCE: 1154
tgcgccatca tgccctrcgc atttcattta aat                               33

<210> SEQ ID NO 1155
<211> LENGTH: 33
<212> TYPE: DNA
<213> ORGANISM: Homo Sapiens

<400> SEQUENCE: 1155
atgagcatgt gatccartga tagtcaatga aat                               33

<210> SEQ ID NO 1156
<211> LENGTH: 33
<212> TYPE: DNA
<213> ORGANISM: Homo Sapiens

<400> SEQUENCE: 1156
gtcaaaaaaa gcatcartaa ataagtagag agt                               33

<210> SEQ ID NO 1157
<211> LENGTH: 33
<212> TYPE: DNA
<213> ORGANISM: Homo Sapiens

<400> SEQUENCE: 1157
taaatgtagt catggcmgaa agctgagtgg gtg                               33

<210> SEQ ID NO 1158
<211> LENGTH: 33
<212> TYPE: DNA
<213> ORGANISM: Homo Sapiens

<400> SEQUENCE: 1158
tgatcaggtt ttgggcragg gtctgctttt ttg                               33

<210> SEQ ID NO 1159
<211> LENGTH: 33
<212> TYPE: DNA
<213> ORGANISM: Homo Sapiens

<400> SEQUENCE: 1159
tgccagcttt acaagcsaca gaatcaccaa aac                               33

<210> SEQ ID NO 1160
<211> LENGTH: 33
<212> TYPE: DNA
<213> ORGANISM: Homo Sapiens

<400> SEQUENCE: 1160
caacaatggc accagtmctt ctccaaatca ttt                               33

<210> SEQ ID NO 1161
<211> LENGTH: 33
<212> TYPE: DNA
<213> ORGANISM: Homo Sapiens

<400> SEQUENCE: 1161
gagcaggaca tacaggragg gaaaaatgag tcc                               33
```

```
<210> SEQ ID NO 1162
<211> LENGTH: 33
<212> TYPE: DNA
<213> ORGANISM: Homo Sapiens

<400> SEQUENCE: 1162
tgtgatgtga tacttgrtag tactgaagga aac                              33

<210> SEQ ID NO 1163
<211> LENGTH: 33
<212> TYPE: DNA
<213> ORGANISM: Homo Sapiens

<400> SEQUENCE: 1163
tctaccctca gtcatargca ggaggaaata cca                              33

<210> SEQ ID NO 1164
<211> LENGTH: 33
<212> TYPE: DNA
<213> ORGANISM: Homo Sapiens

<400> SEQUENCE: 1164
gacttcctgg aggcgtrggg ggaagcggag gag                              33

<210> SEQ ID NO 1165
<211> LENGTH: 33
<212> TYPE: DNA
<213> ORGANISM: Homo Sapiens

<400> SEQUENCE: 1165
tgagatgtag agcttgrcac ctgcatataa agt                              33

<210> SEQ ID NO 1166
<211> LENGTH: 33
<212> TYPE: DNA
<213> ORGANISM: Homo Sapiens

<400> SEQUENCE: 1166
ttcctagagg ttcacartaa atctaaaaag atc                              33

<210> SEQ ID NO 1167
<211> LENGTH: 33
<212> TYPE: DNA
<213> ORGANISM: Homo Sapiens

<400> SEQUENCE: 1167
tccggcagtg tttacgragg gctggagata cac                              33

<210> SEQ ID NO 1168
<211> LENGTH: 33
<212> TYPE: DNA
<213> ORGANISM: Homo Sapiens

<400> SEQUENCE: 1168
caggtcagcc agttggraac agagttgacg gag                              33

<210> SEQ ID NO 1169
<211> LENGTH: 33
<212> TYPE: DNA
<213> ORGANISM: Homo Sapiens

<400> SEQUENCE: 1169
ttacattata catcttmggc attttttttcc ttt                             33
```

<210> SEQ ID NO 1170
<211> LENGTH: 33
<212> TYPE: DNA
<213> ORGANISM: Homo Sapiens

<400> SEQUENCE: 1170
tttctaattt aatcttrtac atgagacagc tat        33

<210> SEQ ID NO 1171
<211> LENGTH: 33
<212> TYPE: DNA
<213> ORGANISM: Homo Sapiens

<400> SEQUENCE: 1171
gcagatagga tgatacrtgt gctctgcaac cat        33

<210> SEQ ID NO 1172
<211> LENGTH: 33
<212> TYPE: DNA
<213> ORGANISM: Homo Sapiens

<400> SEQUENCE: 1172
caccagaact gaaattrttt ccagctatgt tta        33

<210> SEQ ID NO 1173
<211> LENGTH: 33
<212> TYPE: DNA
<213> ORGANISM: Homo Sapiens

<400> SEQUENCE: 1173
gaacacagaa actgcartgg cttttggacg cta        33

<210> SEQ ID NO 1174
<211> LENGTH: 33
<212> TYPE: DNA
<213> ORGANISM: Homo Sapiens

<400> SEQUENCE: 1174
cttcttccat cagggargtt atcaggctca aag        33

<210> SEQ ID NO 1175
<211> LENGTH: 33
<212> TYPE: DNA
<213> ORGANISM: Homo Sapiens

<400> SEQUENCE: 1175
atcctctgct ctcctargtt caggcaggat aga        33

<210> SEQ ID NO 1176
<211> LENGTH: 33
<212> TYPE: DNA
<213> ORGANISM: Homo Sapiens

<400> SEQUENCE: 1176
caaaccattg catcatrttt tggactgata gtt        33

<210> SEQ ID NO 1177
<211> LENGTH: 33
<212> TYPE: DNA
<213> ORGANISM: Homo Sapiens

<400> SEQUENCE: 1177
ttccccaatt attatcmgtc actcctcctc cat        33

<210> SEQ ID NO 1178
<211> LENGTH: 33
<212> TYPE: DNA
<213> ORGANISM: Homo Sapiens

<400> SEQUENCE: 1178
tggccaatcc aactgamggg gaccccttta ttg                                33

<210> SEQ ID NO 1179
<211> LENGTH: 33
<212> TYPE: DNA
<213> ORGANISM: Homo Sapiens

<400> SEQUENCE: 1179
gcagtggatc ctgaccrgcc gctgagcgcc aag                                33

<210> SEQ ID NO 1180
<211> LENGTH: 33
<212> TYPE: DNA
<213> ORGANISM: Homo Sapiens

<400> SEQUENCE: 1180
gccaggagct gtgcccrgtg cctgcagcct tca                                33

<210> SEQ ID NO 1181
<211> LENGTH: 33
<212> TYPE: DNA
<213> ORGANISM: Homo Sapiens

<400> SEQUENCE: 1181
ttaatcaaat atcgggrtta aagaatgtat caa                                33

<210> SEQ ID NO 1182
<211> LENGTH: 33
<212> TYPE: DNA
<213> ORGANISM: Homo Sapiens

<400> SEQUENCE: 1182
gcagccccag caggaargac acgataatcg att                                33

<210> SEQ ID NO 1183
<211> LENGTH: 33
<212> TYPE: DNA
<213> ORGANISM: Homo Sapiens

<400> SEQUENCE: 1183
aaggggaaac ggagccrgcc aaggacaggt gaa                                33

<210> SEQ ID NO 1184
<211> LENGTH: 33
<212> TYPE: DNA
<213> ORGANISM: Homo Sapiens

<400> SEQUENCE: 1184
acatggggaa tggggtrtgg actctatggg gtg                                33

<210> SEQ ID NO 1185
<211> LENGTH: 33
<212> TYPE: DNA
<213> ORGANISM: Homo Sapiens

<400> SEQUENCE: 1185
cccaaggcaa acctgcmtgg tgtcacgcag ggt                33

<210> SEQ ID NO 1186
<211> LENGTH: 33
<212> TYPE: DNA
<213> ORGANISM: Homo Sapiens

<400> SEQUENCE: 1186
tgctctctgg atcctgragg aagttgatcc act                33

<210> SEQ ID NO 1187
<211> LENGTH: 33
<212> TYPE: DNA
<213> ORGANISM: Homo Sapiens

<400> SEQUENCE: 1187
caggtcctca aaaacraaa cagagctatt atg                33

<210> SEQ ID NO 1188
<211> LENGTH: 33
<212> TYPE: DNA
<213> ORGANISM: Homo Sapiens

<400> SEQUENCE: 1188
cacagggcct gtggacrggg gtggctatga gat                33

<210> SEQ ID NO 1189
<211> LENGTH: 33
<212> TYPE: DNA
<213> ORGANISM: Homo Sapiens

<400> SEQUENCE: 1189
gttcttttgg atgtttrctt aggagtggaa tta                33

<210> SEQ ID NO 1190
<211> LENGTH: 33
<212> TYPE: DNA
<213> ORGANISM: Homo Sapiens

<400> SEQUENCE: 1190
caggccagag ccaggartct attgcacagt taa                33

<210> SEQ ID NO 1191
<211> LENGTH: 33
<212> TYPE: DNA
<213> ORGANISM: Homo Sapiens

<400> SEQUENCE: 1191
cattcatcaa gaagtcrgat aaagggttta aac                33

<210> SEQ ID NO 1192
<211> LENGTH: 33
<212> TYPE: DNA
<213> ORGANISM: Homo Sapiens

<400> SEQUENCE: 1192
ttaactcctt tcaaacratt tcctttgtat ctt                33

<210> SEQ ID NO 1193
<211> LENGTH: 33
<212> TYPE: DNA
<213> ORGANISM: Homo Sapiens

<400> SEQUENCE: 1193
aaatagagac acagccrgag tgctggctat gac						33

<210> SEQ ID NO 1194
<211> LENGTH: 33
<212> TYPE: DNA
<213> ORGANISM: Homo Sapiens

<400> SEQUENCE: 1194
catctctgag ttcctgmacc acttatcaag tgt						33

<210> SEQ ID NO 1195
<211> LENGTH: 33
<212> TYPE: DNA
<213> ORGANISM: Homo Sapiens

<400> SEQUENCE: 1195
gggagtgtgg acacggrgct gcactgccag gct						33

<210> SEQ ID NO 1196
<211> LENGTH: 33
<212> TYPE: DNA
<213> ORGANISM: Homo Sapiens

<400> SEQUENCE: 1196
ctctctccta cctaggrtgg cggtggtggc agc						33

<210> SEQ ID NO 1197
<211> LENGTH: 33
<212> TYPE: DNA
<213> ORGANISM: Homo Sapiens

<400> SEQUENCE: 1197
aaataaaggc ctgtggrcct cagtttcctg tgt						33

<210> SEQ ID NO 1198
<211> LENGTH: 33
<212> TYPE: DNA
<213> ORGANISM: Homo Sapiens

<400> SEQUENCE: 1198
ctgaccctga ctttgaratt tcgtctgtaa aat						33

<210> SEQ ID NO 1199
<211> LENGTH: 33
<212> TYPE: DNA
<213> ORGANISM: Homo Sapiens

<400> SEQUENCE: 1199
ggagcagccc ctcttcrtct ggcccttcca cct						33

<210> SEQ ID NO 1200
<211> LENGTH: 33
<212> TYPE: DNA
<213> ORGANISM: Homo Sapiens

<400> SEQUENCE: 1200
tattgctcat tttttrtag atgaggaaac tgc						33

<210> SEQ ID NO 1201
<211> LENGTH: 33
<212> TYPE: DNA
<213> ORGANISM: Homo Sapiens

<400> SEQUENCE: 1201
ccttgtctta gttccaracg tctccctctg tga        33

<210> SEQ ID NO 1202
<211> LENGTH: 33
<212> TYPE: DNA
<213> ORGANISM: Homo Sapiens

<400> SEQUENCE: 1202
aacaccatac agcaatragc atgaacaacc tac        33

<210> SEQ ID NO 1203
<211> LENGTH: 33
<212> TYPE: DNA
<213> ORGANISM: Homo Sapiens

<400> SEQUENCE: 1203
gcaatcttac tcctctmtga taacaaatag atc        33

<210> SEQ ID NO 1204
<211> LENGTH: 33
<212> TYPE: DNA
<213> ORGANISM: Homo Sapiens

<400> SEQUENCE: 1204
ctatgtctat aagtggraaa ggctttgttt att        33

<210> SEQ ID NO 1205
<211> LENGTH: 33
<212> TYPE: DNA
<213> ORGANISM: Homo Sapiens

<400> SEQUENCE: 1205
gaagcagatg tgtatgrttt tggagaaaca gaa        33

<210> SEQ ID NO 1206
<211> LENGTH: 33
<212> TYPE: DNA
<213> ORGANISM: Homo Sapiens

<400> SEQUENCE: 1206
gtgacttctt tcatcamcct ctggtaacca gac        33

<210> SEQ ID NO 1207
<211> LENGTH: 33
<212> TYPE: DNA
<213> ORGANISM: Homo Sapiens

<400> SEQUENCE: 1207
tctctgtttt aagggcrgtg datagggtag ggt        33

<210> SEQ ID NO 1208
<211> LENGTH: 33
<212> TYPE: DNA
<213> ORGANISM: Homo Sapiens

<400> SEQUENCE: 1208
tccttagttg gatcagrcac agactatgaa att        33

<210> SEQ ID NO 1209
<211> LENGTH: 33
<212> TYPE: DNA
<213> ORGANISM: Homo Sapiens -continued

<400> SEQUENCE: 1209
gatgaggtct gtgcatrctc ctttccccat caa							33

<210> SEQ ID NO 1210
<211> LENGTH: 33
<212> TYPE: DNA
<213> ORGANISM: Homo Sapiens

<400> SEQUENCE: 1210
ttaattctct tcctggmcag cctaacttct cct							33

<210> SEQ ID NO 1211
<211> LENGTH: 33
<212> TYPE: DNA
<213> ORGANISM: Homo Sapiens

<400> SEQUENCE: 1211
gtaaggactt tatccaraat cacttatgtg tct							33

<210> SEQ ID NO 1212
<211> LENGTH: 33
<212> TYPE: DNA
<213> ORGANISM: Homo Sapiens

<400> SEQUENCE: 1212
tgatagccat cacccargga gaatggtgaa aga							33

<210> SEQ ID NO 1213
<211> LENGTH: 33
<212> TYPE: DNA
<213> ORGANISM: Homo Sapiens

<400> SEQUENCE: 1213
ggatgtgtaa gaccctrtag ttaacataac act							33

<210> SEQ ID NO 1214
<211> LENGTH: 33
<212> TYPE: DNA
<213> ORGANISM: Homo Sapiens

<400> SEQUENCE: 1214
tgctgaactt tgtcctrgca tataattagt tac							33

<210> SEQ ID NO 1215
<211> LENGTH: 33
<212> TYPE: DNA
<213> ORGANISM: Homo Sapiens

<400> SEQUENCE: 1215
tagctaacac tactacmcaa gctaccagaa cag							33

<210> SEQ ID NO 1216
<211> LENGTH: 33
<212> TYPE: DNA
<213> ORGANISM: Homo Sapiens

<400> SEQUENCE: 1216
taatgactaa tcaggargca acgtaaccaa aag							33

<210> SEQ ID NO 1217
<211> LENGTH: 33
<212> TYPE: DNA

```
<213> ORGANISM: Homo Sapiens

<400> SEQUENCE: 1217
gacggccccc catccascct cgagctggac cac                             33

<210> SEQ ID NO 1218
<211> LENGTH: 33
<212> TYPE: DNA
<213> ORGANISM: Homo Sapiens

<400> SEQUENCE: 1218
gctgagcccc ttcagcrtag tcaggcgcgg ggc                             33

<210> SEQ ID NO 1219
<211> LENGTH: 33
<212> TYPE: DNA
<213> ORGANISM: Homo Sapiens

<400> SEQUENCE: 1219
tcatgtccta accaacrgaa tcaccctggt tcc                             33

<210> SEQ ID NO 1220
<211> LENGTH: 33
<212> TYPE: DNA
<213> ORGANISM: Homo Sapiens

<400> SEQUENCE: 1220
gccagagtct ggggccract gttccactgg gcc                             33

<210> SEQ ID NO 1221
<211> LENGTH: 33
<212> TYPE: DNA
<213> ORGANISM: Homo Sapiens

<400> SEQUENCE: 1221
ttttgaagtc aagtgcrttc ctggagatcc ggt                             33

<210> SEQ ID NO 1222
<211> LENGTH: 33
<212> TYPE: DNA
<213> ORGANISM: Homo Sapiens

<400> SEQUENCE: 1222
gagagcgaag agcaggmgga ggaacaaagg cga                             33

<210> SEQ ID NO 1223
<211> LENGTH: 33
<212> TYPE: DNA
<213> ORGANISM: Homo Sapiens

<400> SEQUENCE: 1223
atggcttgta ctaatgrctt ttgcccatta ata                             33

<210> SEQ ID NO 1224
<211> LENGTH: 33
<212> TYPE: DNA
<213> ORGANISM: Homo Sapiens

<400> SEQUENCE: 1224
aaacaaaaag atggacrtct ttcaagatca atg                             33

<210> SEQ ID NO 1225
<211> LENGTH: 33
```

```
<212> TYPE: DNA
<213> ORGANISM: Homo Sapiens

<400> SEQUENCE: 1225
ctattatgaa attctgrgtc taaagacatt gca                                    33

<210> SEQ ID NO 1226
<211> LENGTH: 33
<212> TYPE: DNA
<213> ORGANISM: Homo Sapiens

<400> SEQUENCE: 1226
ctaattctgt cagcctrctt actagaaacc aaa                                    33

<210> SEQ ID NO 1227
<211> LENGTH: 33
<212> TYPE: DNA
<213> ORGANISM: Homo Sapiens

<400> SEQUENCE: 1227
gtttttagag accacarcct gctttcttct aga                                    33

<210> SEQ ID NO 1228
<211> LENGTH: 33
<212> TYPE: DNA
<213> ORGANISM: Homo Sapiens

<400> SEQUENCE: 1228
tcctaaaagg tttcacrtca agcataagtt tct                                    33

<210> SEQ ID NO 1229
<211> LENGTH: 33
<212> TYPE: DNA
<213> ORGANISM: Homo Sapiens

<400> SEQUENCE: 1229
attatctgga gtcaggrttc ttctttagca gtg                                    33

<210> SEQ ID NO 1230
<211> LENGTH: 33
<212> TYPE: DNA
<213> ORGANISM: Homo Sapiens

<400> SEQUENCE: 1230
actcaccttg tcatcaraag agaaaggacc atg                                    33

<210> SEQ ID NO 1231
<211> LENGTH: 33
<212> TYPE: DNA
<213> ORGANISM: Homo Sapiens

<400> SEQUENCE: 1231
gggcactagg tgccacrctc accttgtcat cag                                    33

<210> SEQ ID NO 1232
<211> LENGTH: 33
<212> TYPE: DNA
<213> ORGANISM: Homo Sapiens

<400> SEQUENCE: 1232
cattactcag aattatrtct ggagcaaata aca                                    33

<210> SEQ ID NO 1233
```

-continued

```
<211> LENGTH: 33
<212> TYPE: DNA
<213> ORGANISM: Homo Sapiens

<400> SEQUENCE: 1233
cttacaccat gtttctrtca gtatcaaaca aag                                    33

<210> SEQ ID NO 1234
<211> LENGTH: 33
<212> TYPE: DNA
<213> ORGANISM: Homo Sapiens

<400> SEQUENCE: 1234
ggtttggagt ctgatcrctt ggattctggc agg                                    33

<210> SEQ ID NO 1235
<211> LENGTH: 33
<212> TYPE: DNA
<213> ORGANISM: Homo Sapiens

<400> SEQUENCE: 1235
ttcatttgaa tgaaacrggt cactttaaaa att                                    33

<210> SEQ ID NO 1236
<211> LENGTH: 33
<212> TYPE: DNA
<213> ORGANISM: Homo Sapiens

<400> SEQUENCE: 1236
ctgcaaagtt ccattaraaa gatggtggac aaa                                    33

<210> SEQ ID NO 1237
<211> LENGTH: 33
<212> TYPE: DNA
<213> ORGANISM: Homo Sapiens

<400> SEQUENCE: 1237
cctgtgcctg agatgargca ggaatctcca ggg                                    33

<210> SEQ ID NO 1238
<211> LENGTH: 33
<212> TYPE: DNA
<213> ORGANISM: Homo Sapiens

<400> SEQUENCE: 1238
tttacttttg gcctccrttg acccagatgg gga                                    33

<210> SEQ ID NO 1239
<211> LENGTH: 33
<212> TYPE: DNA
<213> ORGANISM: Homo Sapiens

<400> SEQUENCE: 1239
tttacagata ctgactrcat aaaacaacaa tcc                                    33

<210> SEQ ID NO 1240
<211> LENGTH: 33
<212> TYPE: DNA
<213> ORGANISM: Homo Sapiens

<400> SEQUENCE: 1240
caaaaggacg tactgcrtga tgctaattta taa                                    33
```

```
<210> SEQ ID NO 1241
<211> LENGTH: 33
<212> TYPE: DNA
<213> ORGANISM: Homo Sapiens

<400> SEQUENCE: 1241
acagacttaa gtgaagrccc gcattcctac ttt                                    33

<210> SEQ ID NO 1242
<211> LENGTH: 33
<212> TYPE: DNA
<213> ORGANISM: Homo Sapiens

<400> SEQUENCE: 1242
aagctaggag cattttraat atgtatttct gga                                    33

<210> SEQ ID NO 1243
<211> LENGTH: 33
<212> TYPE: DNA
<213> ORGANISM: Homo Sapiens

<400> SEQUENCE: 1243
aacactagtt gagtaartgg atacaattga ggt                                    33

<210> SEQ ID NO 1244
<211> LENGTH: 33
<212> TYPE: DNA
<213> ORGANISM: Homo Sapiens

<400> SEQUENCE: 1244
ctagacctac tgccatragt tttgtaagac aca                                    33

<210> SEQ ID NO 1245
<211> LENGTH: 33
<212> TYPE: DNA
<213> ORGANISM: Homo Sapiens

<400> SEQUENCE: 1245
caggacaggc aacacartaa cttgatacaa aag                                    33

<210> SEQ ID NO 1246
<211> LENGTH: 33
<212> TYPE: DNA
<213> ORGANISM: Homo Sapiens

<400> SEQUENCE: 1246
agtgaggctc atctgcmtgg gtgagaagcg aaa                                    33

<210> SEQ ID NO 1247
<211> LENGTH: 33
<212> TYPE: DNA
<213> ORGANISM: Homo Sapiens

<400> SEQUENCE: 1247
atgctgtagc cacttgrtaa catctttctt gaa                                    33

<210> SEQ ID NO 1248
<211> LENGTH: 33
<212> TYPE: DNA
<213> ORGANISM: Homo Sapiens

<400> SEQUENCE: 1248
aacgacttgg aaatagrcta taaatgtaga agg                                    33
```

<210> SEQ ID NO 1249
<211> LENGTH: 33
<212> TYPE: DNA
<213> ORGANISM: Homo Sapiens

<400> SEQUENCE: 1249
tttaatttaa ataatmaca ttctggggtg cca                                    33

<210> SEQ ID NO 1250
<211> LENGTH: 33
<212> TYPE: DNA
<213> ORGANISM: Homo Sapiens

<400> SEQUENCE: 1250
ccaatgacat aatatcmgac cttaaaaaaa tga                                   33

<210> SEQ ID NO 1251
<211> LENGTH: 33
<212> TYPE: DNA
<213> ORGANISM: Homo Sapiens

<400> SEQUENCE: 1251
caggtcttat ttcttcrttt acgttatgtg aaa                                   33

<210> SEQ ID NO 1252
<211> LENGTH: 33
<212> TYPE: DNA
<213> ORGANISM: Homo Sapiens

<400> SEQUENCE: 1252
gccatcccct atctctmttg aaaactgact tca                                   33

<210> SEQ ID NO 1253
<211> LENGTH: 33
<212> TYPE: DNA
<213> ORGANISM: Homo Sapiens

<400> SEQUENCE: 1253
cctctcccat gatccartca tctctcccca ggc                                   33

<210> SEQ ID NO 1254
<211> LENGTH: 33
<212> TYPE: DNA
<213> ORGANISM: Homo Sapiens

<400> SEQUENCE: 1254
gtattcaaat cttggcmaat atccaactag caa                                   33

<210> SEQ ID NO 1255
<211> LENGTH: 33
<212> TYPE: DNA
<213> ORGANISM: Homo Sapiens

<400> SEQUENCE: 1255
gaagaatgaa tgtcttrgga tacaattaag tga                                   33

<210> SEQ ID NO 1256
<211> LENGTH: 33
<212> TYPE: DNA
<213> ORGANISM: Homo Sapiens

<400> SEQUENCE: 1256
aaaccattac ataggtmtca aaatccaaat att                                   33

<210> SEQ ID NO 1257
<211> LENGTH: 33
<212> TYPE: DNA
<213> ORGANISM: Homo Sapiens

<400> SEQUENCE: 1257
aaacattttc cagagtmaag aaagagtaga aaa                                    33

<210> SEQ ID NO 1258
<211> LENGTH: 33
<212> TYPE: DNA
<213> ORGANISM: Homo Sapiens

<400> SEQUENCE: 1258
gtcattttat gagtgamaaa aagaaacaaa tgg                                    33

<210> SEQ ID NO 1259
<211> LENGTH: 33
<212> TYPE: DNA
<213> ORGANISM: Homo Sapiens

<400> SEQUENCE: 1259
aagcaatcct agctggrgta gagctggcat ttt                                    33

<210> SEQ ID NO 1260
<211> LENGTH: 33
<212> TYPE: DNA
<213> ORGANISM: Homo Sapiens

<400> SEQUENCE: 1260
aacacaatgg ggttgarcat cacctcatat tca                                    33

<210> SEQ ID NO 1261
<211> LENGTH: 33
<212> TYPE: DNA
<213> ORGANISM: Homo Sapiens

<400> SEQUENCE: 1261
acctgttctg tttgatrtgc agactgaggc tca                                    33

<210> SEQ ID NO 1262
<211> LENGTH: 33
<212> TYPE: DNA
<213> ORGANISM: Homo Sapiens

<400> SEQUENCE: 1262
atcacagatt tctgttrgtc cttttgttgg taa                                    33

<210> SEQ ID NO 1263
<211> LENGTH: 33
<212> TYPE: DNA
<213> ORGANISM: Homo Sapiens

<400> SEQUENCE: 1263
ttccaggtcc cctttcrctt cctgtgctgt tgc                                    33

<210> SEQ ID NO 1264
<211> LENGTH: 33
<212> TYPE: DNA
<213> ORGANISM: Homo Sapiens

<400> SEQUENCE: 1264
ggtcttgaca tgccagrcaa gttctctctt ggg                                    33

<210> SEQ ID NO 1265
<211> LENGTH: 33
<212> TYPE: DNA
<213> ORGANISM: Homo Sapiens

<400> SEQUENCE: 1265
agggaaagtg cttaacrtag cttgataaat gct                                    33

<210> SEQ ID NO 1266
<211> LENGTH: 33
<212> TYPE: DNA
<213> ORGANISM: Homo Sapiens

<400> SEQUENCE: 1266
cattatacta aataccragg ttaagagaat aaa                                    33

<210> SEQ ID NO 1267
<211> LENGTH: 33
<212> TYPE: DNA
<213> ORGANISM: Homo Sapiens

<400> SEQUENCE: 1267
agttactatg atttaamtgt ttcattgtgt tta                                    33

<210> SEQ ID NO 1268
<211> LENGTH: 33
<212> TYPE: DNA
<213> ORGANISM: Homo Sapiens

<400> SEQUENCE: 1268
gcttcattat atcacaraga atgagctcaa ata                                    33

<210> SEQ ID NO 1269
<211> LENGTH: 33
<212> TYPE: DNA
<213> ORGANISM: Homo Sapiens

<400> SEQUENCE: 1269
ctacctttaa gaaacargat aaaaaataat gat                                    33

<210> SEQ ID NO 1270
<211> LENGTH: 33
<212> TYPE: DNA
<213> ORGANISM: Homo Sapiens

<400> SEQUENCE: 1270
gcttttgggt acacagrccc attacataca tga                                    33

<210> SEQ ID NO 1271
<211> LENGTH: 33
<212> TYPE: DNA
<213> ORGANISM: Homo Sapiens

<400> SEQUENCE: 1271
ccaatttcct ttaaaaraga ggcttctgaa att                                    33

<210> SEQ ID NO 1272
<211> LENGTH: 33
<212> TYPE: DNA
<213> ORGANISM: Homo Sapiens

<400> SEQUENCE: 1272
atagcacctc tttctgmagc tctcgggact ctt                             33

<210> SEQ ID NO 1273
<211> LENGTH: 33
<212> TYPE: DNA
<213> ORGANISM: Homo Sapiens

<400> SEQUENCE: 1273
tcctaactgt ctaactrtat gaattccaaa agt                             33

<210> SEQ ID NO 1274
<211> LENGTH: 33
<212> TYPE: DNA
<213> ORGANISM: Homo Sapiens

<400> SEQUENCE: 1274
ttaaggcaga acaatcrtca tatctgttca gga                             33

<210> SEQ ID NO 1275
<211> LENGTH: 33
<212> TYPE: DNA
<213> ORGANISM: Homo Sapiens

<400> SEQUENCE: 1275
tacattacag aatgaaraga aaagagggct tgg                             33

<210> SEQ ID NO 1276
<211> LENGTH: 33
<212> TYPE: DNA
<213> ORGANISM: Homo Sapiens

<400> SEQUENCE: 1276
gcttgagctc tcttttragg attcatcttt gac                             33

<210> SEQ ID NO 1277
<211> LENGTH: 33
<212> TYPE: DNA
<213> ORGANISM: Homo Sapiens

<400> SEQUENCE: 1277
agaggttgca agcacargta tttgacacac tgt                             33

<210> SEQ ID NO 1278
<211> LENGTH: 33
<212> TYPE: DNA
<213> ORGANISM: Homo Sapiens

<400> SEQUENCE: 1278
tctctggctt taaacaraaa gatgactaaa act                             33

<210> SEQ ID NO 1279
<211> LENGTH: 33
<212> TYPE: DNA
<213> ORGANISM: Homo Sapiens

<400> SEQUENCE: 1279
aaaagcaaag gaggatrgca gcaaacaagt gtc                             33

<210> SEQ ID NO 1280
<211> LENGTH: 33
<212> TYPE: DNA
<213> ORGANISM: Homo Sapiens

```
<400> SEQUENCE: 1280
cccaccagca gtatacragg cttctcattt cac                                    33

<210> SEQ ID NO 1281
<211> LENGTH: 33
<212> TYPE: DNA
<213> ORGANISM: Homo Sapiens

<400> SEQUENCE: 1281
agagaaataa gtggatrtaa cagagtggat ctg                                    33

<210> SEQ ID NO 1282
<211> LENGTH: 33
<212> TYPE: DNA
<213> ORGANISM: Homo Sapiens

<400> SEQUENCE: 1282
agtggacttt ggggccrtcg tgccggatcc tcc                                    33

<210> SEQ ID NO 1283
<211> LENGTH: 33
<212> TYPE: DNA
<213> ORGANISM: Homo Sapiens

<400> SEQUENCE: 1283
cgctactcct agccccrgaa agggctcacg gtg                                    33

<210> SEQ ID NO 1284
<211> LENGTH: 33
<212> TYPE: DNA
<213> ORGANISM: Homo Sapiens

<400> SEQUENCE: 1284
aggaggcaag atcaagratt ttttttttc taa                                     33

<210> SEQ ID NO 1285
<211> LENGTH: 33
<212> TYPE: DNA
<213> ORGANISM: Homo Sapiens

<400> SEQUENCE: 1285
agcagcgcgg cctccawgcc cgccttggcc agg                                    33

<210> SEQ ID NO 1286
<211> LENGTH: 33
<212> TYPE: DNA
<213> ORGANISM: Homo Sapiens

<400> SEQUENCE: 1286
ctgggtgaca tcctacrcgg agctagtgtc aca                                    33

<210> SEQ ID NO 1287
<211> LENGTH: 33
<212> TYPE: DNA
<213> ORGANISM: Homo Sapiens

<400> SEQUENCE: 1287
ctgggcacgg ggtgccrggc tggggacgta gat                                    33

<210> SEQ ID NO 1288
<211> LENGTH: 33
<212> TYPE: DNA
<213> ORGANISM: Homo Sapiens
```

<400> SEQUENCE: 1288
ggtggggtga tgcttcraga ggctacaaga aac                                33

<210> SEQ ID NO 1289
<211> LENGTH: 33
<212> TYPE: DNA
<213> ORGANISM: Homo Sapiens

<400> SEQUENCE: 1289
gcagtgcgag gaaggcrgcg ggttccacgt cgg                                33

<210> SEQ ID NO 1290
<211> LENGTH: 33
<212> TYPE: DNA
<213> ORGANISM: Homo Sapiens

<400> SEQUENCE: 1290 cggggggtg gtacccrcgg tgcctactca tcc                                 33

<210> SEQ ID NO 1291
<211> LENGTH: 33
<212> TYPE: DNA
<213> ORGANISM: Homo Sapiens

<400> SEQUENCE: 1291
ccttttctgg tgtgtcmcca gactcttcct caa                                33

<210> SEQ ID NO 1292
<211> LENGTH: 33
<212> TYPE: DNA
<213> ORGANISM: Homo Sapiens

<400> SEQUENCE: 1292
cacccatgaa agaggcrgga ggggctctgc tcc                                33

<210> SEQ ID NO 1293
<211> LENGTH: 33
<212> TYPE: DNA
<213> ORGANISM: Homo Sapiens

<400> SEQUENCE: 1293
acctgacgag gcgtacrgaa caggccggaa cag                                33

<210> SEQ ID NO 1294
<211> LENGTH: 33
<212> TYPE: DNA
<213> ORGANISM: Homo Sapiens

<400> SEQUENCE: 1294
ttccagtgtg aacatgrcat caaagaagag gca                                33

<210> SEQ ID NO 1295
<211> LENGTH: 33
<212> TYPE: DNA
<213> ORGANISM: Homo Sapiens

<400> SEQUENCE: 1295
cccacacctc atagcargat ctcatctcta caa                                33

<210> SEQ ID NO 1296
<211> LENGTH: 33
<212> TYPE: DNA

```
<213> ORGANISM: Homo Sapiens

<400> SEQUENCE: 1296
aaaacaagca tctaccragc accctccatg agc                              33

<210> SEQ ID NO 1297
<211> LENGTH: 33
<212> TYPE: DNA
<213> ORGANISM: Homo Sapiens

<400> SEQUENCE: 1297
caagtgagag cagatamggc agcacaggga ttc                              33

<210> SEQ ID NO 1298
<211> LENGTH: 33
<212> TYPE: DNA
<213> ORGANISM: Homo Sapiens

<400> SEQUENCE: 1298
cgatattcca gagggarttg cttaaggaag ggg                              33

<210> SEQ ID NO 1299
<211> LENGTH: 33
<212> TYPE: DNA
<213> ORGANISM: Homo Sapiens

<400> SEQUENCE: 1299
tcggaggccg tcgagartcg cgtccgccgc cgt                              33

<210> SEQ ID NO 1300
<211> LENGTH: 33
<212> TYPE: DNA
<213> ORGANISM: Homo Sapiens

<400> SEQUENCE: 1300 ctaagggtg gttatcrtga caggaaggag gta                               33

<210> SEQ ID NO 1301
<211> LENGTH: 33
<212> TYPE: DNA
<213> ORGANISM: Homo Sapiens

<400> SEQUENCE: 1301
cagtagactt tcaaggrcta gtaactcgca tgc                              33

<210> SEQ ID NO 1302
<211> LENGTH: 33
<212> TYPE: DNA
<213> ORGANISM: Homo Sapiens

<400> SEQUENCE: 1302
ttcaaggcaa tgttgcmaaa ctggagaact gct                              33

<210> SEQ ID NO 1303
<211> LENGTH: 33
<212> TYPE: DNA
<213> ORGANISM: Homo Sapiens

<400> SEQUENCE: 1303
aggtgtctga tcaacgmcct cagagatgac ctg                              33

<210> SEQ ID NO 1304
<211> LENGTH: 33
```

```
<212> TYPE: DNA
<213> ORGANISM: Homo Sapiens

<400> SEQUENCE: 1304
gatttttaaa aaaagcrttg acattgtaac agt                              33

<210> SEQ ID NO 1305
<211> LENGTH: 33
<212> TYPE: DNA
<213> ORGANISM: Homo Sapiens

<400> SEQUENCE: 1305
tctcagcact ggatccrgtg ggaaaggtaa cgc                              33

<210> SEQ ID NO 1306
<211> LENGTH: 33
<212> TYPE: DNA
<213> ORGANISM: Homo Sapiens

<400> SEQUENCE: 1306
catgcccaga gtatggrtat attgggggaa tca                              33

<210> SEQ ID NO 1307
<211> LENGTH: 33
<212> TYPE: DNA
<213> ORGANISM: Homo Sapiens

<400> SEQUENCE: 1307
attgaactgt aacttamaca gagcaaacat tgt                              33

<210> SEQ ID NO 1308
<211> LENGTH: 33
<212> TYPE: DNA
<213> ORGANISM: Homo Sapiens

<400> SEQUENCE: 1308
gcctactaac agcaagrgcc tttattaata ttt                              33

<210> SEQ ID NO 1309
<211> LENGTH: 33
<212> TYPE: DNA
<213> ORGANISM: Homo Sapiens

<400> SEQUENCE: 1309
acccatgggt tctatcratt tctgccatat cct                              33

<210> SEQ ID NO 1310
<211> LENGTH: 33
<212> TYPE: DNA
<213> ORGANISM: Homo Sapiens

<400> SEQUENCE: 1310
gtgtccacct gtattaragt gttttcatgt gct                              33

<210> SEQ ID NO 1311
<211> LENGTH: 33
<212> TYPE: DNA
<213> ORGANISM: Homo Sapiens

<400> SEQUENCE: 1311
cacagttttc ccataaragc tcaaatatct ttg                              33

<210> SEQ ID NO 1312
```

-continued

<211> LENGTH: 33
<212> TYPE: DNA
<213> ORGANISM: Homo Sapiens

<400> SEQUENCE: 1312
gcctaaaggg tataatraga agagaagtaa aag                                    33

<210> SEQ ID NO 1313
<211> LENGTH: 33
<212> TYPE: DNA
<213> ORGANISM: Homo Sapiens

<400> SEQUENCE: 1313
ggctcacagc aaaactmtac cgttttgatc tgg                                    33

<210> SEQ ID NO 1314
<211> LENGTH: 33
<212> TYPE: DNA
<213> ORGANISM: Homo Sapiens

<400> SEQUENCE: 1314
gtcagatggg cctgatrtca agataaggcc tac                                    33

<210> SEQ ID NO 1315
<211> LENGTH: 33
<212> TYPE: DNA
<213> ORGANISM: Homo Sapiens

<400> SEQUENCE: 1315
tacttgcatc ccaaccrcct aaaagtgttg gtt                                    33

<210> SEQ ID NO 1316
<211> LENGTH: 33
<212> TYPE: DNA
<213> ORGANISM: Homo Sapiens

<400> SEQUENCE: 1316
tggagtccag agagaarcag cagagagagg cgc                                    33

<210> SEQ ID NO 1317
<211> LENGTH: 33
<212> TYPE: DNA
<213> ORGANISM: Homo Sapiens

<400> SEQUENCE: 1317
cttcaacctc atgttaratc agtacttata agc                                    33

<210> SEQ ID NO 1318
<211> LENGTH: 33
<212> TYPE: DNA
<213> ORGANISM: Homo Sapiens

<400> SEQUENCE: 1318
tctgcccaga tcaatarcaa tgatgacaat ggt                                    33

<210> SEQ ID NO 1319
<211> LENGTH: 33
<212> TYPE: DNA
<213> ORGANISM: Homo Sapiens

<400> SEQUENCE: 1319
ttggtctctg gtcaccraca tcctttgctc tgg                                    33

```
<210> SEQ ID NO 1320
<211> LENGTH: 33
<212> TYPE: DNA
<213> ORGANISM: Homo Sapiens

<400> SEQUENCE: 1320
tgagcctgcc caagcarggc ctgtctgatt act                                    33

<210> SEQ ID NO 1321
<211> LENGTH: 33
<212> TYPE: DNA
<213> ORGANISM: Homo Sapiens

<400> SEQUENCE: 1321
ccatacctgt acacaamcac agactccagt aaa                                    33

<210> SEQ ID NO 1322
<211> LENGTH: 33
<212> TYPE: DNA
<213> ORGANISM: Homo Sapiens

<400> SEQUENCE: 1322
ctaaatcaaa tgacaargag aaaagttagc ttt                                    33

<210> SEQ ID NO 1323
<211> LENGTH: 33
<212> TYPE: DNA
<213> ORGANISM: Homo Sapiens

<400> SEQUENCE: 1323
tctcttcccc ccacaargtc attttcttaa ttc                                    33

<210> SEQ ID NO 1324
<211> LENGTH: 33
<212> TYPE: DNA
<213> ORGANISM: Homo Sapiens

<400> SEQUENCE: 1324
ccaagaaaaa gtgcccrcaa gaaaaccaaa aca                                    33

<210> SEQ ID NO 1325
<211> LENGTH: 33
<212> TYPE: DNA
<213> ORGANISM: Homo Sapiens

<400> SEQUENCE: 1325
cacagttact caagtcraga ggcaaaaaaa aaa                                    33

<210> SEQ ID NO 1326
<211> LENGTH: 33
<212> TYPE: DNA
<213> ORGANISM: Homo Sapiens

<400> SEQUENCE: 1326
tgtgactaaa ccactcrtct gtttccccca ctc                                    33

<210> SEQ ID NO 1327
<211> LENGTH: 33
<212> TYPE: DNA
<213> ORGANISM: Homo Sapiens

<400> SEQUENCE: 1327
attaaatata tttttcrtaa taocccagct aga                                    33
```

<210> SEQ ID NO 1328
<211> LENGTH: 33
<212> TYPE: DNA
<213> ORGANISM: Homo Sapiens

<400> SEQUENCE: 1328
tattaacatt cataaamcat tcagacaatt gct                                    33

<210> SEQ ID NO 1329
<211> LENGTH: 33
<212> TYPE: DNA
<213> ORGANISM: Homo Sapiens

<400> SEQUENCE: 1329
tgcctatttc taaactmtgc tggggaaagc agg                                    33

<210> SEQ ID NO 1330
<211> LENGTH: 33
<212> TYPE: DNA
<213> ORGANISM: Homo Sapiens

<400> SEQUENCE: 1330
aggagattag ggtgttratt ttcccgttct ttc                                    33

<210> SEQ ID NO 1331
<211> LENGTH: 33
<212> TYPE: DNA
<213> ORGANISM: Homo Sapiens

<400> SEQUENCE: 1331
ataaacttgc cttactrtat acacacacat gca                                    33

<210> SEQ ID NO 1332
<211> LENGTH: 33
<212> TYPE: DNA
<213> ORGANISM: Homo Sapiens

<400> SEQUENCE: 1332
ccagggctat gaaccrtct cattctgcag cag                                     33

<210> SEQ ID NO 1333
<211> LENGTH: 33
<212> TYPE: DNA
<213> ORGANISM: Homo Sapiens

<400> SEQUENCE: 1333
ttttaggggg tgtgatrtct gctatgtgga cac                                    33

<210> SEQ ID NO 1334
<211> LENGTH: 33
<212> TYPE: DNA
<213> ORGANISM: Homo Sapiens

<400> SEQUENCE: 1334
ggattacagg catgagmcac cacatgctgc cat                                    33

<210> SEQ ID NO 1335
<211> LENGTH: 33
<212> TYPE: DNA
<213> ORGANISM: Homo Sapiens

<400> SEQUENCE: 1335
atgagttgga agaggtrtta gagtccccat cgt                                    33

<210> SEQ ID NO 1336
<211> LENGTH: 33
<212> TYPE: DNA
<213> ORGANISM: Homo Sapiens

<400> SEQUENCE: 1336
ggttttcagg aatgcaraag tctgagaaga cac                33

<210> SEQ ID NO 1337
<211> LENGTH: 33
<212> TYPE: DNA
<213> ORGANISM: Homo Sapiens

<400> SEQUENCE: 1337
taagacaaag ataaggrtct aatttcattc ttt                33

<210> SEQ ID NO 1338
<211> LENGTH: 33
<212> TYPE: DNA
<213> ORGANISM: Homo Sapiens

<400> SEQUENCE: 1338 aattttcct tagaagmctc aacctcagca tac                33

<210> SEQ ID NO 1339
<211> LENGTH: 33
<212> TYPE: DNA
<213> ORGANISM: Homo Sapiens

<400> SEQUENCE: 1339
ggggtccctt ccctgcrctc tcataagctc ccc                33

<210> SEQ ID NO 1340
<211> LENGTH: 33
<212> TYPE: DNA
<213> ORGANISM: Homo Sapiens

<400> SEQUENCE: 1340
tcgagggcta gagagtratg agagtgggtg ggg                33

<210> SEQ ID NO 1341
<211> LENGTH: 33
<212> TYPE: DNA
<213> ORGANISM: Homo Sapiens

<400> SEQUENCE: 1341
atgtatattt aaggtargct tttcttttc cct                33

<210> SEQ ID NO 1342
<211> LENGTH: 33
<212> TYPE: DNA
<213> ORGANISM: Homo Sapiens

<400> SEQUENCE: 1342
tgacatccct cctatcrggt ctttgaggga gaa                33

<210> SEQ ID NO 1343
<211> LENGTH: 33
<212> TYPE: DNA
<213> ORGANISM: Homo Sapiens

<400> SEQUENCE: 1343

```
agtggccaac actaatrtga ccttgcaggc act                                        33

<210> SEQ ID NO 1344
<211> LENGTH: 33
<212> TYPE: DNA
<213> ORGANISM: Homo Sapiens

<400> SEQUENCE: 1344
agcatatttg gcctccrtaa tgccgcttaa ggt                                        33

<210> SEQ ID NO 1345
<211> LENGTH: 33
<212> TYPE: DNA
<213> ORGANISM: Homo Sapiens

<400> SEQUENCE: 1345
taaatggcaa ttgttcrtgc aataaagaac aat                                        33

<210> SEQ ID NO 1346
<211> LENGTH: 33
<212> TYPE: DNA
<213> ORGANISM: Homo Sapiens

<400> SEQUENCE: 1346
ctcatctctt ctagccrgct ttccccttac agg                                        33

<210> SEQ ID NO 1347
<211> LENGTH: 33
<212> TYPE: DNA
<213> ORGANISM: Homo Sapiens

<400> SEQUENCE: 1347
ttccaccccc agtgatrctc agaatccagg atc                                        33

<210> SEQ ID NO 1348
<211> LENGTH: 33
<212> TYPE: DNA
<213> ORGANISM: Homo Sapiens

<400> SEQUENCE: 1348
ataaataacg atagccrgta acttacgttc act                                        33

<210> SEQ ID NO 1349
<211> LENGTH: 33
<212> TYPE: DNA
<213> ORGANISM: Homo Sapiens

<400> SEQUENCE: 1349
ctcatgctgc gctgctrtca gaggccacat ctg                                        33

<210> SEQ ID NO 1350
<211> LENGTH: 33
<212> TYPE: DNA
<213> ORGANISM: Homo Sapiens

<400> SEQUENCE: 1350
tgtgcgtggg cctcggyggc ctccactaga cgc                                        33

<210> SEQ ID NO 1351
<211> LENGTH: 33
<212> TYPE: DNA
<213> ORGANISM: Homo Sapiens

<400> SEQUENCE: 1351
```
actgggtttt gtggacmcttt tgcagaggtc ggg                                33

<210> SEQ ID NO 1352
<211> LENGTH: 33
<212> TYPE: DNA
<213> ORGANISM: Homo Sapiens

<400> SEQUENCE: 1352
gtgcctttta atatatrgac cacaagctca gag                                33

<210> SEQ ID NO 1353
<211> LENGTH: 33
<212> TYPE: DNA
<213> ORGANISM: Homo Sapiens

<400> SEQUENCE: 1353
cattgacaca ctggcamact caatactgtg cac                                33

<210> SEQ ID NO 1354
<211> LENGTH: 33
<212> TYPE: DNA
<213> ORGANISM: Homo Sapiens

<400> SEQUENCE: 1354
cccaaaagga aaccctraac ccaataagca gtc                                33

<210> SEQ ID NO 1355
<211> LENGTH: 33
<212> TYPE: DNA
<213> ORGANISM: Homo Sapiens

<400> SEQUENCE: 1355
tgttactgag gtatgcratg ccatgatttc cac                                33

<210> SEQ ID NO 1356
<211> LENGTH: 33
<212> TYPE: DNA
<213> ORGANISM: Homo Sapiens

<400> SEQUENCE: 1356
tgtaaatcac cacctcrttt tgttcctaga gct                                33

<210> SEQ ID NO 1357
<211> LENGTH: 33
<212> TYPE: DNA
<213> ORGANISM: Homo Sapiens

<400> SEQUENCE: 1357
cccttgccat aaattgraat ccagagctgt aag                                33

<210> SEQ ID NO 1358
<211> LENGTH: 33
<212> TYPE: DNA
<213> ORGANISM: Homo Sapiens

<400> SEQUENCE: 1358
acttctactc agcataraat gggccgttgc caa                                33

<210> SEQ ID NO 1359
<211> LENGTH: 33
<212> TYPE: DNA
<213> ORGANISM: Homo Sapiens

```
<400> SEQUENCE: 1359
ccataaaagg ccggctrtag actcacatgt ttt                                33

<210> SEQ ID NO 1360
<211> LENGTH: 33
<212> TYPE: DNA
<213> ORGANISM: Homo Sapiens

<400> SEQUENCE: 1360
gtttaaatga aataaarcat cctctgtttg cgg                                33

<210> SEQ ID NO 1361
<211> LENGTH: 33
<212> TYPE: DNA
<213> ORGANISM: Homo Sapiens

<400> SEQUENCE: 1361
cgcacgccac ctcttcmcca gagacgactt tgt                                33

<210> SEQ ID NO 1362
<211> LENGTH: 33
<212> TYPE: DNA
<213> ORGANISM: Homo Sapiens

<400> SEQUENCE: 1362
tggaagaaga ggtaagrtat ctccagagcc gct                                33

<210> SEQ ID NO 1363
<211> LENGTH: 33
<212> TYPE: DNA
<213> ORGANISM: Homo Sapiens

<400> SEQUENCE: 1363
gtttctccct ttgcccmcac cactaaaata cag                                33

<210> SEQ ID NO 1364
<211> LENGTH: 33
<212> TYPE: DNA
<213> ORGANISM: Homo Sapiens

<400> SEQUENCE: 1364
agtccaagca gcacctrgta attaaactga gtc                                33

<210> SEQ ID NO 1365
<211> LENGTH: 33
<212> TYPE: DNA
<213> ORGANISM: Homo Sapiens

<400> SEQUENCE: 1365
gcaaatctat acagacrgac acagattcat ggt                                33

<210> SEQ ID NO 1366
<211> LENGTH: 33
<212> TYPE: DNA
<213> ORGANISM: Homo Sapiens

<400> SEQUENCE: 1366
tctgaatctg tgtcatragc gagcctgagg gct                                33

<210> SEQ ID NO 1367
<211> LENGTH: 33
<212> TYPE: DNA
<213> ORGANISM: Homo Sapiens
```

-continued

<400> SEQUENCE: 1367
ctcagttgta tagcagratc agattctaga gtt                                33

<210> SEQ ID NO 1368
<211> LENGTH: 33
<212> TYPE: DNA
<213> ORGANISM: Homo Sapiens

<400> SEQUENCE: 1368
agaaaccagc catttgmatg cgctcaatgg aat                                33

<210> SEQ ID NO 1369
<211> LENGTH: 33
<212> TYPE: DNA
<213> ORGANISM: Homo Sapiens

<400> SEQUENCE: 1369
aaaaagctac gcccacmtcc taaccctcgg act                                33

<210> SEQ ID NO 1370
<211> LENGTH: 33
<212> TYPE: DNA
<213> ORGANISM: Homo Sapiens

<400> SEQUENCE: 1370
ggggccagcc aatgccrgca acatgaggta cag                                33

<210> SEQ ID NO 1371
<211> LENGTH: 33
<212> TYPE: DNA
<213> ORGANISM: Homo Sapiens

<400> SEQUENCE: 1371
tataaccttc caaaaamttc aacatcatct tcc                                33

<210> SEQ ID NO 1372
<211> LENGTH: 33
<212> TYPE: DNA
<213> ORGANISM: Homo Sapiens

<400> SEQUENCE: 1372
aaaggaaaag tcattcrggc tgtgataaga aag                                33

<210> SEQ ID NO 1373
<211> LENGTH: 33
<212> TYPE: DNA
<213> ORGANISM: Homo Sapiens

<400> SEQUENCE: 1373
taccactaat tccaatrctc aagaagagct gac                                33

<210> SEQ ID NO 1374
<211> LENGTH: 33
<212> TYPE: DNA
<213> ORGANISM: Homo Sapiens

<400> SEQUENCE: 1374
ccccacgtga actcgcrgca ggcagagaat cta                                33

<210> SEQ ID NO 1375
<211> LENGTH: 33
<212> TYPE: DNA

<213> ORGANISM: Homo Sapiens

<400> SEQUENCE: 1375
gggctcgttt cagaatrcgg ttgggcaagt ttg					33

<210> SEQ ID NO 1376
<211> LENGTH: 33
<212> TYPE: DNA
<213> ORGANISM: Homo Sapiens

<400> SEQUENCE: 1376
tccgtctaca gccaccmagt taaataacag cgg					33

<210> SEQ ID NO 1377
<211> LENGTH: 33
<212> TYPE: DNA
<213> ORGANISM: Homo Sapiens

<400> SEQUENCE: 1377
gttcacctcc tgatgamata aattcttgac cgt					33

<210> SEQ ID NO 1378
<211> LENGTH: 33
<212> TYPE: DNA
<213> ORGANISM: Homo Sapiens

<400> SEQUENCE: 1378
gggctatttg ataggcmcac ggcagcttgg gtt					33

<210> SEQ ID NO 1379
<211> LENGTH: 33
<212> TYPE: DNA
<213> ORGANISM: Homo Sapiens

<400> SEQUENCE: 1379
aatccatgag ttcagcmtgg tgagatcttt ccc					33

<210> SEQ ID NO 1380
<211> LENGTH: 33
<212> TYPE: DNA
<213> ORGANISM: Homo Sapiens

<400> SEQUENCE: 1380
cattgcgtcc tttcccraag agtctgttcc cat					33

<210> SEQ ID NO 1381
<211> LENGTH: 33
<212> TYPE: DNA
<213> ORGANISM: Homo Sapiens

<400> SEQUENCE: 1381
aaagaatttt cccccartgc tctagcaaat tgc					33

<210> SEQ ID NO 1382
<211> LENGTH: 33
<212> TYPE: DNA
<213> ORGANISM: Homo Sapiens

<400> SEQUENCE: 1382
ggctggtgtc tttggaraat atcaagagtc aca					33

<210> SEQ ID NO 1383
<211> LENGTH: 33

-continued

<210> SEQ ID NO 1383
<211> LENGTH: 33
<212> TYPE: DNA
<213> ORGANISM: Homo Sapiens

<400> SEQUENCE: 1383
gtcattcagc cctcccrgca accccagaaa tag                                    33

<210> SEQ ID NO 1384
<211> LENGTH: 33
<212> TYPE: DNA
<213> ORGANISM: Homo Sapiens

<400> SEQUENCE: 1384
gaagtgaccc atctggrccc cagaggcagg ggc                                    33

<210> SEQ ID NO 1385
<211> LENGTH: 33
<212> TYPE: DNA
<213> ORGANISM: Homo Sapiens

<400> SEQUENCE: 1385
cctgcagcac ccctggmcct catggggcac ttc                                    33

<210> SEQ ID NO 1386
<211> LENGTH: 33
<212> TYPE: DNA
<213> ORGANISM: Homo Sapiens

<400> SEQUENCE: 1386
ccggcggact cgcaccrtcc gaatggtcac ccg                                    33

<210> SEQ ID NO 1387
<211> LENGTH: 33
<212> TYPE: DNA
<213> ORGANISM: Homo Sapiens

<400> SEQUENCE: 1387
tgcaaaatgc ttctgaratg ggtcaaccag aag                                    33

<210> SEQ ID NO 1388
<211> LENGTH: 33
<212> TYPE: DNA
<213> ORGANISM: Homo Sapiens

<400> SEQUENCE: 1388
aaagagaggg ctgactrttg attctgtgca tac                                    33

<210> SEQ ID NO 1389
<211> LENGTH: 33
<212> TYPE: DNA
<213> ORGANISM: Homo Sapiens

<400> SEQUENCE: 1389
agagggtgcc cccaggrtcc tactgtggat cag                                    33

<210> SEQ ID NO 1390
<211> LENGTH: 33
<212> TYPE: DNA
<213> ORGANISM: Homo Sapiens

<400> SEQUENCE: 1390
gaagggagca ggtgctrtca atggaaatgg gac                                    33

<210> SEQ ID NO 1391

```
<211> LENGTH: 33
<212> TYPE: DNA
<213> ORGANISM: Homo Sapiens

<400> SEQUENCE: 1391
gaatgtcgta atcaggrcga gagctcgggg cgg                                33

<210> SEQ ID NO 1392
<211> LENGTH: 33
<212> TYPE: DNA
<213> ORGANISM: Homo Sapiens

<400> SEQUENCE: 1392
caagtctctc agtgacrggg ccgacacttg gtc                                33

<210> SEQ ID NO 1393
<211> LENGTH: 33
<212> TYPE: DNA
<213> ORGANISM: Homo Sapiens

<400> SEQUENCE: 1393
aactttctgt aaagcartgg gagttagggc aac                                33

<210> SEQ ID NO 1394
<211> LENGTH: 33
<212> TYPE: DNA
<213> ORGANISM: Homo Sapiens

<400> SEQUENCE: 1394
ctgcctctaa acccgamgtc ttcaagcctg act                                33

<210> SEQ ID NO 1395
<211> LENGTH: 33
<212> TYPE: DNA
<213> ORGANISM: Homo Sapiens

<400> SEQUENCE: 1395
gtgtcgtggc agatacmagg tctcacggaa gtc                                33

<210> SEQ ID NO 1396
<211> LENGTH: 33
<212> TYPE: DNA
<213> ORGANISM: Homo Sapiens

<400> SEQUENCE: 1396
gtgagctgca catcctrcct agaagggaca tct                                33

<210> SEQ ID NO 1397
<211> LENGTH: 33
<212> TYPE: DNA
<213> ORGANISM: Homo Sapiens

<400> SEQUENCE: 1397
tagctattcc aaataarata aacccaaag aaa                                 33

<210> SEQ ID NO 1398
<211> LENGTH: 33
<212> TYPE: DNA
<213> ORGANISM: Homo Sapiens

<400> SEQUENCE: 1398
ccaatgtatg tgaagtrgct caaatgaatt ttg                                33
```

METHOD OF TESTING FOR ENDOMETRIOSIS AND TREATMENT THEREFOR

CROSS REFERENCE TO RELATED APPLICATIONS

This nonprovisional utility patent application is a continuation-in-part of and claims the benefit under 35 USC §120 to co-pending U.S. application Ser. No. 12/056,754 filed Mar. 27, 2008, which claims the benefit under 35 USC §119(e) of U.S. provisional application No. 60/943,193, filed Jun. 11, 2007, and is a continuation-in-part of and claims the benefit under 35 USC §120 to co-pending U.S. application Ser. No. 12/120,322 filed May 14, 2008, and is a continuation-in-part of and claims the benefit under 35 USC §120 to co-pending U.S. application Ser. No. 12/765,643 filed Apr. 22, 2010, which claims the benefit under 35 USC §119(e) of U.S. provisional application No. 61/171,717, filed Apr. 22, 2009 and of U.S. provisional application No. 61/245,808, filed Sep. 25, 2009, and is a continuation-in-part of and claims the benefit under 35 USC §120 to co-pending U.S. application Ser. No. 13/159,132 filed Jun. 13, 2011, which is a continuation-in-part of and claims the benefit under 35 USC §120 to co-pending U.S. application Ser. No. 13/071,598 filed Mar. 25, 2011, which claims the benefit under 35 USC §119(e) of U.S. provisional application No. 61/318,145, filed Mar. 26, 2010, and is a continuation-in-part of and claims the benefit under 35 USC §120 to co-pending U.S. application Ser. No. 13/681,575 filed Nov. 20, 2012, which is a continuation of and claims the benefit under 35 USC §120 to co-pending U.S. application Ser. No. 13/602,409 filed Sep. 4, 2012, which claims the benefit under 35 USC §119(e) of U.S. provisional application Nos. 61/530,944 and 61/530,948, both filed Sep. 3, 2011, and is a continuation-in-part of and claims the benefit under 35 USC §120 to co-pending U.S. application Ser. No. 13/603,284 filed Sep. 4, 2012, which claims the benefit under 35 USC §119(e) of U.S. provisional application No. 61/530,945, filed Sep. 3, 2011, and is a continuation-in-part of and claims the benefit under 35 USC §120 to co-pending U.S. application Ser. No. 13/680,414 filed Nov. 19, 2012, which is a continuation of and claims the benefit under 35 USC §120 to co-pending U.S. application Ser. No. 13/603,297 filed Sep. 4, 2012, which claims the benefit under 35 USC §119(e) of U.S. provisional application No. 61/530,947, filed Sep. 3, 2011, and is a continuation-in-part of and claims the benefit under 35 USC §120 to co-pending U.S. application Ser. No. 13/735,828 filed Jan. 7, 2013, which is a continuation of and claims the benefit under 35 USC §120 to co-pending U.S. application Ser. No. 13/652,018 filed Oct. 15, 2012, which claims the benefit under 35 USC §119(e) of U.S. provisional application No. 61/547,624, filed Oct. 14, 2011, and claims the benefit under 35 USC §119(e) of U.S. provisional application Nos. 61/717,048 and 61/717,053, both filed Oct. 22, 2012, and claims the benefit under 35 USC §119(e) of U.S. provisional application No. 61/721,219, filed Nov. 1, 2012, all of which are incorporated, in their entirety, by this reference.

FIELD OF THE INVENTION

The present invention relates to endometriosis prognosis, diagnosis and therapy. In particular, the present invention relates to a novel algorithmic combination of endometriosis associated single nucleotide polymorphisms (SNPs) and Rare Variants (RVs), and endometriosis related clinical analysis to result in an endometriosis predictive and/or diagnostic test and related treatment therefor.

BACKGROUND OF THE INVENTION

Endometriosis may include autoimmune endometriosis, mild endometriosis, moderate endometriosis, severe endometriosis, superficial (peritoneal) endometriosis, deep (invasive) endometriosis, ovarian endometriosis, endometriosis-related cancers, and "endometriosis-associated conditions". For the purpose of this invention the term endometriosis is used to describe any of these conditions.

Endometriosis is most generally defined as the presence of endometrium (glands and stroma) at sites outside of the uterus (ectopic endometrial tissues rather than eutopic or within the uterus). The most common sites are the ovaries, pelvic peritoneum, uterosacral ligaments, pouch of Douglas, and rectovaginal septum although implants have been identified on the peritoneal surfaces of the abdomen (these may grow into the intestines, ureters or bladder), in the thorax, at the umbilicus, and at incision sites of prior surgeries (Child T J, Tan S L (2001) Endometriosis: aetiology, pathogenesis and treatment, Drugs 61:1735-1750; Giudice et al. (1998) Status of current research on endometriosis, The Journal of reproductive medicine 43:252-262).

Endometriosis is a common gynecologic disorder. The prevalence is difficult to know. It has been estimated that it affects approximately 14% of all women (range 1-43%), 40-60% of women with pelvic pain and 30%-50% of infertile women (Di Blasio et al. (2005) Genetics of endometriosis, Minerva ginecologica 57:225-236; Schindler AE (2004) Pathophysiology, diagnosis and treatment of endometriosis, Minerva ginecologica 56:419-435).

A non-surgical method of clinically assessing a predisposition to endometriosis is to determine the answer to three distinct endometriosis related questions, each question having an associated Odds Ratio (OR), as shown in FIG. 1. The results of answers to the FIG. 1 questions are then complied according to the endometriosis clinical factor assessment chart as shown in FIG. 2 resulting in a Raw Clinical Probability Value (RCPV). The RCPV is preferably multiplied by a Relevance Factor (RF) based on a patient's age and race to result in a Final Clinical Probability Value (FCPV). Alternatively, the RCPV may be used with data collected in population surveys.

MultiDimensional Analysis (MDA) is an analysis process that groups data into two or more categories (e.g. cases and controls or patients having a high probability of endometriosis and patients having a low probability of endometriosis).

Logistic regression analysis is a process that is used for prediction of the probability of occurrence of an event by fitting data to a logit function logistic curve.

Bayesian analysis or Bayesian interference is a method of statistical inference in which evidence is used to estimate parameters and predictions in a probability model.

It is known to treat or prevent endometriosis, especially in women who have no outwardly manifest symptoms of endometriosis, by the prophylactic administration of a therapeutic. The administered therapeutic may be any of a hormonal treatment such as an estrogen containing composition, a progesterone containing composition, a progestin containing composition, a gonadotropin releasing-hormone (GnRH) agonist, or other ovulation suppression composition, an advanced reproductive therapy or ART (ART is used to treat endometriosis related infertility and may include any fertility treatments in which the egg or sperm are "handled" in vitro as part of the treatment), or a combination thereof. In particular, the therapeutic may be administered in the form of an oral contraceptive (OC). The GnRH therapeutic may take the form of a GnRH agonist in combination with a patient specific substantially low dose of estrogen, progestin, or tibolone. Such administration of a low dose of estrogen, progestin, or tibolone in combination with a GnRH agonist to compensate potential side effects of the GnRH agonist are commonly referred to as an "add-back" therapy. It is noted that in such add-back therapy, the dosage of estrogen, progestin, or tibolone is relatively small so as to not reduce the effectiveness of the GnRH agonist.

Various genetic markers are known to have a predictive association with endometriosis. Such genetic markers and methods are disclosed for instance in U.S. patent application Ser. Nos. 12/056,754, 12/120,322, 12/566,933, 12/765,643, 13/159,132, 13/602,409, 13/603,284, 13/603,297, 13/652,018, 61/721,219, 61/717,048, and 61/717,053, all of which are incorporated herein in their entirety by this reference.

SUMMARY OF THE INVENTION

The present invention defines a method for endometriosis diagnosis/prognosis that preferably combines known endometriosis clinical factor assessment methods with endometriosis associated biomarkers such as single nucleotide polymorphisms (SNPs), indels, insertions, deletions, genomic rearrangements, Rare Variants (RVs), and more especially the biomarkers identified in table 1 (or diagnostically and predicatively functionally comparable biomarkers), preferably via a statistical assessment method such as Multi-Dimensional Scaling analysis (MDS), logistic regression, or Bayesian analysis. The markers and related statistical data shown in table 1 were discovered by analyzing a number of endometriosis cases and controls much as has been described in the prior patent applications incorporated herein by reference. It is noted that all of the biomarkers of table 1, being variations or mutations in and of the same structure (i.e. the human genome), share a single structural similarity in that all of the biomarkers of table 1 are endometriosis associated nucleotide substitutions of the same DNA sequence—the human genome DNA sequence, and that the common use of endometriosis diagnosis and prognosis of all of the biomarkers of table 1 flow from such single structural similarity. The present invention further preferably includes the treatment of a subject determined to have or be predisposed to endometriosis by administering to such subject a therapeutic such as an OC that at least partially compensates for endometriosis or that prevents or reduces the severity of endometriosis that the subject would otherwise develop or that prevents endometriosis related complications, cancers, or associated disorders. It shall be noted that preventing or cancelling a procedure, especially an invasive procedure, such as a laparoscopy, that would otherwise have been performed on a subject but for the results of a (negative) diagnosis/prognosis disclosed herein being performed on said subject, shall be consider within the scope of treatment or the "administration of a therapeutic".

It shall be noted that for the purposes of this application, a SNP is understood to be a genetic polymorphism having a Minor Allele Frequency (MAF) of at least 1% in a population (such as for instance the Caucasian population or the CEU population) and an RV is understood to be a genetic polymorphism having a Minor Allele Frequency (MAF) of less than 1% in a population (such as for instance the Caucasian population or the CEU population).

It shall be noted that "Linkage disequilibrium" or "LD" means that a particular combination of alleles (alternative nucleotides) or genetic markers at two or more different SNP (or RV) sites are non-randomly co-inherited (i.e., the combination of alleles at the different SNP (or RV) sites occurs more or less frequently in a population than the separate frequencies of occurrence of each allele or the frequency of a random formation of haplotypes from alleles in a given population). The term "LD" differs from "linkage," which describes the association of two or more loci on a chromosome with limited recombination between them. LD is also used to refer to any non-random genetic association between allele(s) at two or more different SNP (or RV) sites. Therefore, when a SNP (or RV) is in LD with other SNPs (or RVs), the particular allele of the first SNP (or RV) often predicts which alleles will be present in those SNPs (or RVs) in LD. LD is generally, but not exclusively, due to the physical proximity of the two loci along a chromosome. Hence, genotyping one of the SNP (or RV) sites will give almost the same information as genotyping the other SNP (or RV) site that is in LD. Linkage disequilibrium is caused by fitness interactions between genes or by such non-adaptive processes as population structure, inbreeding, and stochastic effects.

It shall also be noted that LD is the non-random association of alleles adjacent loci. When a particular allele at one locus is found together on the same chromosome with a specific allele at a second locus-more often than expected if the loci were segregating independently in a population-the loci are in disequilibrium. This concept of LD is formalized by one of the earliest measures of disequilibrium to be proposed (symbolized by D). D, in common with most other measures of LD, quantifies disequilibrium as the difference between the observed frequency of a two-locus haplotype and the frequency it would be expected to show if the alleles are segregating at random. A wide variety of statistics have been proposed to measure the amount of LD, and these have different strengths, depending on the context. Although the measure D has the intuitive concepts of LD, its numerical value is of little use for measuring the strength of and comparing levels of LD. This is due to the dependence of D on allele frequencies. The two most common measures are the absolute value of D' and $r^2$. The absolute value of D' is determined by dividing D by its maximum possible value, given the allele frequencies at the two loci. The case of D'=1 is known as complete LD (or CLD). The measure $r^2$ is in some ways complementary to D'. An $r^2$ value of 1 indicates complete LD as well while an $r^2$ value of 0 indicates linkage equilibrium. Complete LD demonstrates complete dependency. In other words, in complete LD the number of counts of the minor allele in loci 1 corresponds to the counts of minor allele in loci 2. Although in complete LD the alleles themselves might be different the frequency of Minor allele in loci 1 will be equal to the frequency of Minor allele in loci 2. For example, in comparing two loci such as rs1 having (A/G) and rs2 having (G/C), if it is known that rs1 and rs2 are in complete LD, and if it is known that a person carries a genotype AG on rs1, then it is known that the genotype on rs2 is GC for that person. Similarly in complete LD, if A is the minor allele of rs1 and is associated with the disease (or conversely is not associated with the disease) then the corresponding minor allele of $rs^2$ is also associated with the disease (or conversely or is not associated with the disease). Furthermore in complete LD, in any analysis of the disease, genotype for rs1 could easily be substituted for rs2 and vice versa.

In yet another embodiment, the invention also provides a kit comprising SNP detection reagents, and methods for detecting the SNPs disclosed herein by employing detection reagents and a questionnaire of non-genetic clinical factors. In one embodiment, the questionnaire would be completed by a medical professional based on medical history physical exam or other clinical findings. In yet another embodiment, the questionnaire would include any other non-genetic clinical factors known to be associated with the risk of developing endometriosis.

In yet another embodiment, the novel SNPs disclosed in '754 as well as other genetic markers are used in the selection of patients to whom a therapeutic will be administered based on the patient's assessed risk of developing endometriosis or based on the patient's assessed risk of endometriosis progression. The administered therapeutic may preferably be a patient specific gene or protein based therapy enabled and informed by SNPs discovered to be associated with endometriosis. Further, the administered therapeutic may be any of a hormonal treatment such as an estrogen containing composition, a progesterone containing composition, a progestin containing composition, a gonadotropin releasing-hormone (GnRH) agonist, or other ovulation suppression composition, or a combination thereof. In particular, the therapeutic may be administered in the form of an OC. Furthermore, the GnRH therapeutic may take the form of a GnRH agonist in combination with a patient specific substantially low dose of estrogen, progestin, or tibolone. Such administration of a low dose of estrogen, progestin, or tibolone in combination with a GnRH agonist to compensate potential side effects of the GnRH agonist are commonly referred to as an "add-back" therapy. It is noted that in such add-back therapy, the dosage of estrogen, progestin, or tibolone is relatively small so as to not reduce the effectiveness of the GnRH agonist.

It shall also be noted that unless indicated otherwise, when a genetic marker (e.g. SNP or RV) is identified as the genetic marker associated with a disease (in this instance endometriosis), it shall be understood that it is the minor allele (MA) of the particular genetic marker that is associated with the disease. Further it shall also be noted that unless indicated otherwise, if the Odds Ratio (OR) of the MA is greater than 1.0, the MA of the genetic marker (in this instance the endometriosis associated genetic marker) is correlated with an increased risk of endometriosis in a case subject as compared to a control subject and shall be considered a causative marker (C), and if the OR of the MA less than 1.0, the MA of the genetic marker is correlated with a decreased risk of endometriosis in a case subject as compared to a control subject and shall be considered a protective marker (P).

It shall also be noted that unless indicated otherwise, the phrase "functional equivalent" as used herein with respect to biomarkers shall mean that a second biomarker is substantially equivalent in its diagnostic and/or prognostic value with respect to a given disease as is a first biomarker's diagnostic and/or prognostic value with respect to the given disease. A second biomarker that is in complete LD with a first biomarker shall be expressly included within the scope of "functional equivalent" with respect to the relationship between the second biomarker to the first biomarker.

DESCRIPTION OF DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 1 depicts a "Three Endometriosis Related Clinical Questions" chart, and;

DETAILED DESCRIPTION OF THE INVENTION

Figure 2:
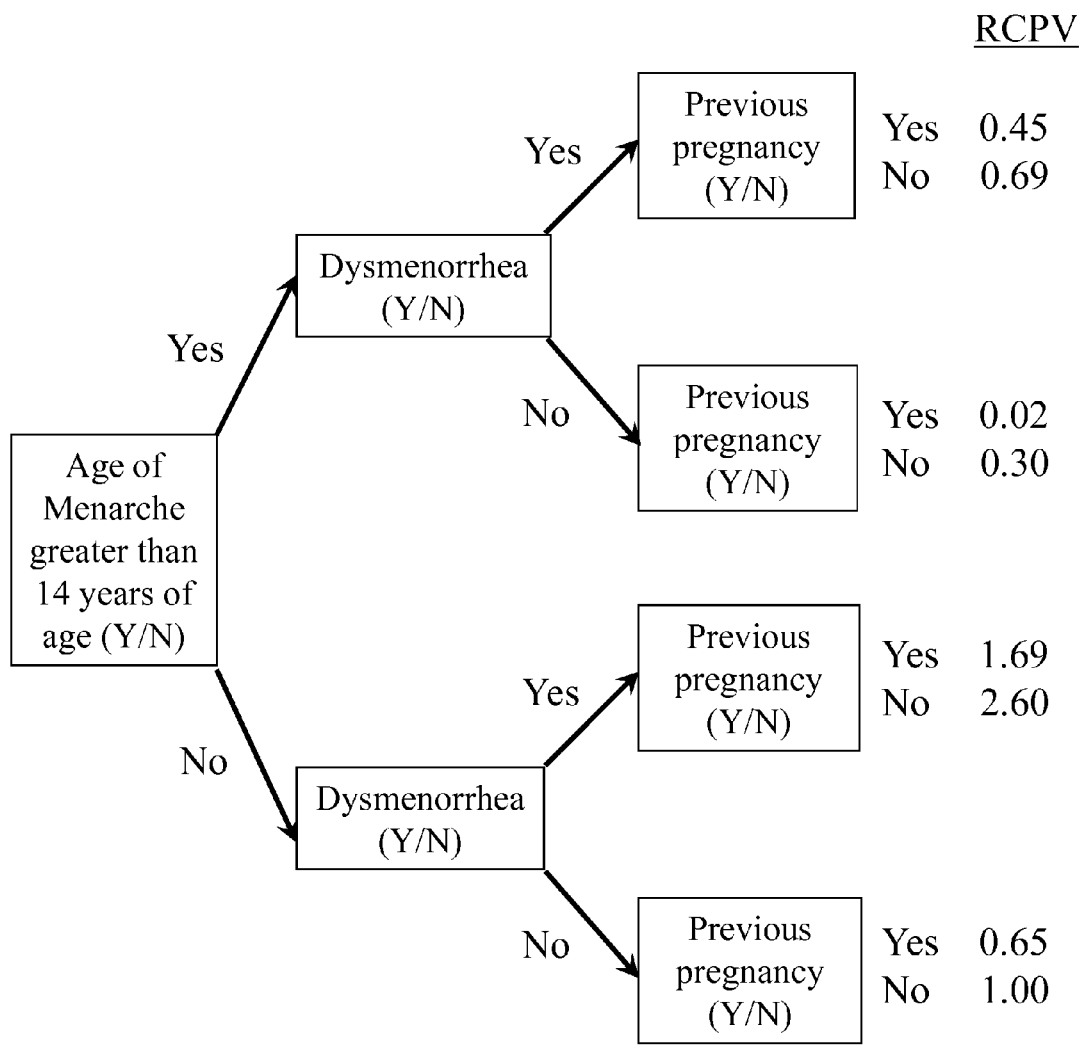
FIG. 2 depicts an "Endometriosis Clinical Factor Assessment" chart.

The method of determining predisposition to endometriosis for a patient is performed according to the following steps. In a first step, answers to the FIG. 1 questions are obtained for the patient. In a second step, an RCPV according to FIG. 2 is determined for the patient based on the answers obtained for the patient in step 1. In an optional third step, the RCPV is optionally multiplied by an RF or otherwise adjusted according to the patient's age and race or according to relevant population survey data to result in a FCPV. In a fourth step, at least one endometriosis associated biomarker preferably drawn from the biomarkers of table 1 is identified in genetic material of the patient. In a fifth step, at least one statistical analysis (preferably MDS) is performed to combine the RCPV (or the FCPV) and the predictive value of the identified genetic biomarker to result in a highly predictive endometriosis prognosis or diagnosis.

"Oral contraceptives" or OCs are contraceptives that are commonly taken orally for the principal purpose of the prevention of conception. Such contraceptives are also commonly referred to as "Oral Contraceptive Pills" or OCPs, or simply as the "Pill". Such OCs typically define a substance in pill form being comprised at least partially of estrogen, progesterone, or a combination thereof. The progesterone component may further be any of Desogestrel, Drospirenone, Ethynodiol, Levonorgestrel, Norethindrone, Norgestimate, and Norgestrel, and the estrogen component may further be any of Mestranol, Estradiol, and Ethinyl. Exemplary OCs that are commercially available are sold under the following names: ALESSE, APRI, ARANELLE, AVIANE, BREVICON, CAMILA, CESIA, CRYSELLE, CYCLESSA, DEMULEN, DESOGEN, ENPRESSE, ERRIN, ESTROSTEP, JOLIVETTE, JUNEL, KARIVA, LEENA, LESSINA, LEVLEN, LEVORA, LOESTRIN, LUTERA, MICROGESTIN, MICRONOR, MIRCETTE, MODICON, MONONESSA, NECON, NORA, NORDETTE, NORINYL, NOR-QD, NORTREL, OGESTREL, ORTHO-CEPT, ORTHO-CYCLEN, ORTHO-NOVUM, ORTHO-TRI-CYCLEN, OVCON, OVRAL, OVRETTE, PORTIA, PREVIFEM, RECLIPSEN, SOLIA, SPRINTEC, TRINESSA, TRI-NORINYL, TRIPHASIL, TRIVORA, VELIVET, YASMIN, AND ZOVIA (the preceding names are the registered trademarks of the respective providers).

"Gonadotropin releasing-hormone (GnRH) agonists" are a group of drugs that are useful in treating patients having endometriosis. Such drugs are modified versions of a naturally occurring hormone known as gonadotropin releasing hormone, which helps to control the menstrual cycle. Administration of such drugs is known to be performed in combination with an "add-back" therapy. In this case, an add-back therapy could be for instance the administration of a low dose of estrogen, progestin, or tibolone in combination with a GnRH agonist to compensate potential side effects of the GnRH agonist. It is noted that in such add-back therapy, the dosage of estrogen, progestin, or tibolone is relatively small so as to not reduce the effectiveness of the GnRH agonist.

The present invention provides SNPs associated with endometriosis, nucleic acid molecules containing SNPs, methods and reagents for the detection of the SNPs disclosed herein, uses of these SNPs for the development of detection reagents, and assays or kits that utilize such reagents. The SNPs disclosed herein are useful for diagnosing, screening for, and evaluating predisposition to endometriosis and progression of endometriosis. Additionally, such SNPs are useful in the determining individual subject treatment plans and design of clinical trials of devices for possible use in the treatment of endometriosis. Furthermore, such SNPs and their encoded products are useful targets for the development of therapeutic agents. Furthermore, such SNPs combined with other non-genetic clinical factors are useful for diagnosing, screening, evaluating predisposition to endometriosis, assessing risk of progression of endometriosis, determining individual subject treatment plans and design of clinical trials of devices for possible use in the treatment of endometriosis. Furthermore, such SNPs and are useful in the selection of recipients for an OC type therapeutic.

Therefore, the invention disclosed herein further teaches a method of selectively administering a therapeutic. Such method of administering a therapeutic preferably includes the following steps: a) Obtaining a genetic material sample of a human female subject, b) Identifying in the genetic material of the subject preferably at least one of the SNPs disclosed in '754 or alternatively identifying any other genetic marker having an association with endometriosis, c) Assessing the subject's risk of endometriosis or risk of endometriosis progression, d) Identifying the subject as having an altered risk of endometriosis or an altered risk of endometriosis progression, and e) administering to the subject a therapeutic. It is noted that the subject may be endometriosis presymptomatic or the subject may exhibit endometriosis symptoms. It is also noted that the assessment of risk may also include non-genetic clinical factors. The therapeutic may be a gene or protein based therapy adapted to the specific needs of a select patient. The therapeutic may alternatively take the form of a testosterone or a modified testosterone such as Danazol. Alternatively, the therapeutic defines a hormonal treatment therapeutic which may be administered alone or in combination with a gene therapy. For instance, the therapeutic may be an estrogen containing composition, a progesterone containing composition, a progestin containing composition, a gonadotropin releasing-hormone (GnRH) agonist, or other ovulation suppression composition, or a combination thereof. Additionally, the GnRH agonist may take the form of a GnRH agonist in combination with a patient specific substantially low dose of estrogen, progestin, or tibolone via an add-back administration. It is further noted that the therapeutic is preferably an OC. The OC preferably defines a substance in pill form that is comprised at least partially of estrogen, progesterone, or a combination thereof. The progesterone component may further be any of Desogestrel, Drospirenone, Ethynodiol, Levonorgestrel, Norethindrone, Norgestimate, and Norgestrel, and the estrogen component may further be any of Mestranol, Estradiol, and Ethinyl. Specifically, the OC may be any commercially available OC including ALESSE, APRI, ARANELLE, AVIANE, BREVICON, CAMILA, CESIA, CRYSELLE, CYCLESSA, DEMULEN, DESOGEN, ENPRESSE, ERRIN, ESTROSTEP, JOLIVETTE, JUNEL, KARIVA, LEENA, LESSINA, LEVLEN, LEVORA, LOESTRIN, LUTERA, MICROGESTIN, MICRONOR, MIRCETTE, MODICON, MONONESSA, NECON, NORA, NORDETTE, NORINYL, NOR-QD, NORTREL, OGESTREL, ORTHO-CEPT, ORTHO-CYCLEN, ORTHO-NOVUM, ORTHO-TRI-CYCLEN, OVCON, OVRAL, OVRETTE, PORTIA, PREVIFEM, RECLIPSEN, SOLIA, SPRINTEC, TRINESSA, TRI-NORINYL, TRIPHASIL, TRIVORA, VELIVET, YASMIN, AND ZOVIA (the preceding names are the registered trademarks of the respective providers). It is further noted that the therapeutic may comprise any other ovulation suppression substance. It is further noted that the therapeutic is preferably adapted to the specific subject so as to be a proper and effective amount of therapeutic for the subject. It is further noted that the administration of the therapeutic may comprise multiple sequential instances of administration of the therapeutic and that such sequence instances may occur over an extended period of time or may occur on an indefinite on-going basis.

It shall be noted that the markers of table 1 are drawn from build 37 data (or "GRCh37" as defined by the Genome Reference Consortium) and that in the header of table 1: "Set" corresponds to a particular subset (i.e. subset 01, subset 02, or subset 03) of the biomarkers of table 1, "Name" corresponds to a name for a given biomarker and where possible is the reference SNP number (rs) of the particular biomarker, but if not possible then it is the exome variant number (exm) of the particular biomarker (as assigned by Illumina, Incorporated), but if not possible then it is a "JBL" number assigned by applicant, "Chr" corresponds to the chromosome where a given biomarker is located in the human genome, "Arm" corresponds to the arm of the chromosome where a given biomarker is located in the human genome, "Cyto" corresponds to the cytoband of the arm of the chromosome where a given biomarker is located in the human genome, "Gene" corresponds to the gene where a given biomarker is located in the human genome or alternatively if the biomarker is not located within a gene, "Gene" corresponds to the nearest two genes positioned on either side of the given biomarker in the human genome, "position" corresponds to the position of a given biomarker in the human genome, "p-value" corresponds to the p-value of a given biomarker, "OR" corresponds to the Odds Ratio of a given biomarker, "Case MAF" corresponds to the case Minor Allele Frequency of a given biomarker, "Cont MAF" corresponds to the control Minor Allele Frequency of a given biomarker, "MA" corresponds to the Minor Allele of a given biomarker, and "Context Sequence" corresponds to the context sequence in which a given biomarker is located and provides a SEQ ID NO and the identification of the biomarker variation of substitution (e.g. "A/C" or "A/G", etc.). It shall be further noted that values for p-value, OR, Case MAF, and Cont MAF provided in Table 1 were derived by applicant using predetermined statistical methods and a predetermined group of cases and controls, and that while others who might analyze the same set of data may arrive at similar but not necessarily identical results if the identical analytical methods are not used. Moreover, it is believed that substantially similar results would occur based on a similar analysis performed on data drawn from different populations that used herein.

TABLES

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs7521023 | 1 | p | p13.1 | CASQ2 | 116243380 | 7.63E-05 | 1.11 | 0.435 | 0.409 | G | aagggatcatcttggct[A/G]gaggagggatccaac (SEQ ID NO: 0001) |
| 03 | rs3811012 | 1 | p | p13.1 | VANGL1 | 116234313 | 8.03E-05 | 1.11 | 0.425 | 0.399 | A | cctcgccttacaacta[A/G]ttcctgcctttcgtcc (SEQ ID NO: 0002) |
| 03 | rs1373291 | 1 | p | p13.2 | KCND3 | 112426851 | 4.79E-04 | 1.14 | 0.214 | 0.192 | A | gagaatttgagttgaaa[A/C]tttaaagaaggagttg (SEQ ID NO: 0003) |
| 03 | rs3008527 | 1 | p | p13.2 | KCND3 | 112523095 | 2.53E-03 | 0.90 | 0.253 | 0.274 | G | gccaaaaccagaggc[A/G]atagtgtgtttttc (SEQ ID NO: 0004) |
| 03 | rs3827735 | 1 | p | p13.2 | TRIM33 | 115052708 | 2.52E-04 | 1.19 | 0.130 | 0.112 | A | ccatttaatccatagt[A/C]ctcctcctctcatct (SEQ ID NO: 0005) |
| 03 | rs2640493 | 1 | p | p13.3 | KCNA2/KCNA3 | 111187885 | 2.04E-04 | 1.13 | 0.340 | 0.313 | A | gcacatgaaagtttaa[A/G]tagcactactaccaga (SEQ ID NO: 0006) |
| 03 | rs17113362 | 1 | p | p21.3 | LOC729977 | 95782971 | 7.57E-04 | 1.32 | 0.039 | 0.030 | G | tcatgaactatgtaggt[A/G]aaggaagtgaaattg (SEQ ID NO: 0007) |
| 02 | rs4658172 | 1 | p | p22.2 | BARHL2/ZNF644 | 91225594 | 1.11E-05 | 1.16 | 0.327 | 0.296 | G | gaaacaactgctcagg[A/G]catttgcaaatttac (SEQ ID NO: 0008) |
| 02 | rs6656775 | 1 | p | p22.2 | BARHL2/ZNF644 | 91219359 | 5.36E-06 | 1.16 | 0.345 | 0.311 | G | atccttctcagccagg[A/G]cccattatttctcatt (SEQ ID NO: 0009) |
| 02 | rs1526480 | 1 | p | p22.2 | BARHL2/ZNF644 | 91209986 | 7.16E-06 | 1.15 | 0.408 | 0.374 | G | acagatagttcctatg[A/G]gctagacttggtcaga (SEQ ID NO: 0010) |
| 01 | rs6699397 | 1 | p | p22.2 | BARHL2/ZNF644 | 91212216 | 3.32E-06 | 1.16 | 0.405 | 0.370 | G | gaactgcatagtccca[A/G]cttacaaagaatcagc (SEQ ID NO: 0011) |
| 03 | rs13376108 | 1 | p | p22.2 | GTF2B | 89350741 | 1.15E-02 | 1.30 | 0.024 | 0.018 | G | agagcttagtagcttc[A/G]acagaaaccaccatgtg (SEQ ID NO: 0012) |
| 03 | rs3008445 | 1 | p | p22.2 | LMO4/PKN2 | 88446605 | 2.37E-03 | 0.91 | 0.432 | 0.456 | A | agtaatagacatttac[A/G]tttcctccaggtttt (SEQ ID NO: 0013) |
| 03 | rs3008453 | 1 | p | p22.2 | LMO4/PKN2 | 88427851 | 8.00E-03 | 1.09 | 0.505 | 0.484 | A | tctagagttaaatcct[A/G]tctgggggactctgggc (SEQ ID NO: 0014) |
| 02 | rs4537535 | 1 | p | p22.2 | ZNF326/BARHL2 | 91080115 | 7.52E-03 | 1.09 | 0.503 | 0.482 | G | cactcagaagagagta[A/G]ctagaagtaagaagtca (SEQ ID NO: 0015) |
| 03 | rs7527341 | 1 | p | p31.1 | LOC729817/LPHN2 | 82009424 | 8.91E-05 | 0.95 | 0.334 | 0.347 | A | gaaatgggaaactatc[A/G]tagggttcttttgcaga (SEQ ID NO: 0016) |
| 02 | exm68565 | 1 | p | p31.1 | TNNI3K | 74808620 | 8.37E-13 | Inf | 0.005 | 0.000 | C | tgctgcaaagtgattt[C/G]gaagttcaacctcatg (SEQ ID NO: 0017) |
| 03 | rs17130484 | 1 | p | p31.3 | GPR177 | 68581840 | 2.95E-04 | 0.77 | 0.048 | 0.062 | C | gctctccggtcct[A/C]ttgtaaggtcctgtga (SEQ ID NO: 0018) |
| 03 | rs6693065 | 1 | p | p31.3 | IL12RB2 | 67800018 | 3.19E-05 | 1.08 | 0.244 | 0.231 | G | gatcatacgatctgtc[A/G]caactgctaaatgtgc (SEQ ID NO: 0019) |
| 03 | rs4255357 | 1 | p | p31.3 | PDE4B | 66399895 | 8.47E-04 | 1.11 | 0.487 | 0.461 | G | gagtaagacataggag[A/G]tcaaggtaggaaggatt (SEQ ID NO: 0020) |
| 03 | rs11208775 | 1 | p | p31.3 | PDE4B | 66410541 | 6.36E-04 | 1.11 | 0.487 | 0.460 | G | attatcatgtctct[A/G]gtaggaatgctccca (SEQ ID NO: 0021) |
| 03 | rs7554648 | 1 | p | p32.1 | FGGY/HOOK1 | 60238762 | 5.87E-03 | 1.17 | 0.087 | 0.075 | A | aaaatcagctccac[A/C]tcagcccccaattatct (SEQ ID NO: 0022) |
| 03 | rs11805025 | 1 | p | p32.2 | DAB1 | 57850717 | 4.08E-03 | 0.89 | 0.195 | 0.214 | C | tatacagaaacacaaa[A/C]cccatcttggatcact (SEQ ID NO: 0023) |
| 03 | rs778406 | 1 | p | p32.2 | USP24/LOC100288320 | 56703505 | 7.87E-05 | 1.17 | 0.067 | 0.058 | A | (SEQ ID NO: 0024) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs12758665 | 1 | p | p32.3 | USP24\|LOC100288320 | 55839117 | 3.79E-04 | 0.87 | 0.196 | 0.218 | A | tattaatcttttcac[A/C]tcagcacagcagaact (SEQ ID NO: 0025) |
| 03 | rs7520205 | 1 | p | p32.3 | USP24\|LOC100288320 | 55834309 | 1.30E-04 | 0.86 | 0.190 | 0.215 | A | ttcgtaactacgatga[A/C]ttttctcggttaagagt (SEQ ID NO: 0026) |
| 01 | exm49794 | 1 | p | p34.2 | CITED4 | 41327281 | 5.28E-60 | 21.62 | 0.056 | 0.035 | A | agtttgtttcacagg[A/G]ctaaagcctgaacaga (SEQ ID NO: 0027) |
| 03 | rs219007 | 1 | p | p34.3 | CSF3R\|GRIK3 | 37147203 | 5.68E-05 | 1.10 | 0.395 | 0.372 | A | cgggcggcgcggaccc[A/C]aagtccgagaagcagt (SEQ ID NO: 0028) |
| 02 | rs2484556 | 1 | p | p34.3 | LOC100287202\|LOC728431 | 37913283 | 4.34E-05 | 0.89 | 0.342 | 0.367 | A | aaaaagaatcagaaat[A/G]ctggtgcatggagcc (SEQ ID NO: 0029) |
| 03 | rs4970614 | 1 | p | p34.3 | POU3F1\|LOC400750 | 39135748 | 8.84E-04 | 0.84 | 0.103 | 0.120 | A | gacctccagcagggc[A/G]tggccagtgggtgcca (SEQ ID NO: 0030) |
| 01 | rs9438994 | 1 | p | p34.3 | RHBDL2 | 39388838 | 3.11E-06 | 1.23 | 0.158 | 0.132 | G | tagtttccctggaaac[A/G]tatatcttgtacact (SEQ ID NO: 0031) |
| 02 | rs6422258 | 1 | p | p34.3 | RHBDL2 | 39406644 | 9.56E-05 | 1.21 | 0.118 | 0.099 | A | gtgcaatgtatgaaggt[A/G]taaattaatgcagcct (SEQ ID NO: 0032) |
| 02 | rs4475740 | 1 | p | p34.3 | RHBDL2\|AKIRIN1 | 39425489 | 9.29E-05 | 1.23 | 0.101 | 0.084 | A | ttattttgagtcaca[A/G]agacacttggcttttt (SEQ ID NO: 0033) |
| 02 | rs1138294 | 1 | p | p36.11 | MAP3K6 | 27688633 | 2.76E-05 | 0.89 | 0.339 | 0.366 | A | gtgctctagctgcaag[A/G]caggtggaaaaggt (SEQ ID NO: 0034) |
| 03 | rs443523 | 1 | p | p36.11 | RUNX3\|SYF2 | 25403783 | 9.12E-04 | 1.12 | 0.288 | 0.265 | A | agccagccaccactgg[A/G]tgggtcattggcgag (SEQ ID NO: 0035) |
| 03 | rs292005 | 1 | p | p36.12 | HSPC157\|CDC42 | 22993335 | 1.60E-02 | 0.93 | 0.460 | 0.479 | C | gtttgtctcactctt[A/C]atacaatcgccaaaat (SEQ ID NO: 0036) |
| 03 | rs7549747 | 1 | p | p36.12 | C1QB\|EPHB2 | 22996571 | 3.37E-03 | 0.91 | 0.395 | 0.418 | G | tagggatccattgc[A/C]cagtaaaataggcgac (SEQ ID NO: 0037) |
| 03 | rs294218 | 1 | p | p36.12 | C1QB\|EPHB2 | 23033257 | 1.04E-02 | 1.09 | 0.393 | 0.373 | C | gttccattttgtagcc[A/G]aggatataaagctca (SEQ ID NO: 0038) |
| 03 | rs294214 | 1 | p | p36.12 | C1QB\|EPHB2 | 23026293 | 4.51E-03 | 1.10 | 0.315 | 0.294 | A | agagacttggtacac[A/C]gagaggggatgtcat (SEQ ID NO: 0039) |
| 03 | rs12734877 | 1 | p | p36.12 | C1QC\|C1QB | 22977883 | 9.54E-02 | 0.95 | 0.408 | 0.421 | C | gggcggagggggccg[A/G]gagatttctgagctcc (SEQ ID NO: 0040) |
| 01 | rs1534949 | 1 | p | p36.12 | CDC42\|LOC100289113 | 22426187 | 2.18E-06 | 1.16 | 0.441 | 0.405 | C | cactgcttctacccca[A/C]attgacatccatcttt (SEQ ID NO: 0041) |
| 03 | rs2473277 | 1 | p | p36.12 | HSPC157\|CDC42 | 23361845 | 1.77E-06 | 1.16 | 0.508 | 0.471 | G | tgagagaatatgacac[A/C]ttcttccttttagaga (SEQ ID NO: 0042) |
| 01 | rs4654783 | 1 | p | p36.12 | LOC100289113\|WNT4 | 22439520 | 2.16E-09 | 1.22 | 0.337 | 0.294 | A | gctataccccaatc[A/G]tcaacctgtagaacat (SEQ ID NO: 0043) |
| 01 | rs2235529 | 1 | p | p36.12 | WNT4 | 22450487 | 4.66E-12 | 1.32 | 0.189 | 0.150 | A | tgctggtcaggatgga[A/G]tatgttatcagagcc (SEQ ID NO: 0044) |
| 02 | rs7544210 | 1 | p | p36.12 | WNT4 | 22455142 | 6.02E-06 | 1.15 | 0.463 | 0.428 | G | agaaccaggtagagaa[A/G]gctggaggagccgcca (SEQ ID NO: 0045) |
| 02 | rs1046310 | 1 | p | p36.12 | WNT4\|LOC100289113 | 22443887 | 7.78E-06 | 1.15 | 0.492 | 0.457 | C | acaggtctcctcatc[A/G]aggataagaccacaga (SEQ ID NO: 0046) |
| 02 | rs3765351 | 1 | p | p36.12 | WNT4\|LOC100289113 | 22445991 | 1.14E-05 | 1.15 | 0.487 | 0.452 | G | tgcfgcccacccat[A/C]ctccaattttatact (SEQ ID NO: 0047) |
| 01 | rs12042083 | 1 | p | p36.12 | WNT4\|ZBTB40 | 22472732 | 4.84E-07 | 1.21 | 0.231 | 0.199 | A | aggtcaagggcaccag[A/G]ttcatttcagccctta (SEQ ID NO: 0048) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 01 | rs4623666 | 1 | p | p36.12 | WNT4/ZBTB40 | 22480312 | 3.96E-06 | 1.16 | 0.440 | 0.405 | G | atgcaacacagaagccc[A/G]gccggtatcccccag (SEQ ID NO: 0049) |
| 02 | rs221047 | 1 | p | p36.13 | ARHGEF19 | 16530364 | 4.01E-05 | 1.15 | 0.155 | 0.137 | G | ccctgatgatatgtt[A/G]tcagaatgtatttca (SEQ ID NO: 0050) |
| 03 | rs12088541 | 1 | p | p36.22 | MAD2L2 | 11751135 | 5.77E-04 | 0.83 | 0.093 | 0.110 | A | ggttctccgagaggtc[A/G]ctcctgatgtagggg (SEQ ID NO: 0051) |
| 03 | rs641941 | 1 | p | p36.22 | TNFRSF8/TNFRSF1B | 12206652 | 4.79E-03 | 1.09 | 0.495 | 0.473 | G | actgctcattatcg[A/G]cgtcfgtaactcgg (SEQ ID NO: 0052) |
| 03 | rs17349921 | 1 | p | p36.31 | CAMTA1 | 7170719 | 7.70E-05 | 1.09 | 0.101 | 0.094 | G | aatgagtgttcttaga[A/G]gctgggtcgattcct (SEQ ID NO: 0053) |
| 03 | rs10915329 | 1 | p | p36.32 | AJAP1/LOC100287877 | 5114102 | 2.26E-03 | 1.10 | 0.431 | 0.407 | A | tcagacctgggagaat[A/G]tcaggtaagctgagat (SEQ ID NO: 0054) |
| 01 | JBLO002 | 1 | p | p36.33 | RNF223 | 1007306 | 6.27E-05 | 6.765 | 0.020 | 0.005 | A | gagccgcactgcacc[G/A]gccagagtgccacaca (SEQ ID NO: 0055) |
| 02 | exm91506 | 1 | q | q21.1 | ANKRD35 | 145560893 | 4.73E-08 | 18.9 | 0.004 | 0.000 | C | cttttctataggtca[C/G]aaggctagtccagcac (SEQ ID NO: 0056) |
| 02 | exm90634 | 1 | q | q21.1 | PDE4DIP | 144931581 | 6.11E-12 | Inf | 0.004 | 0.000 | G | ctccggctttgccatcg[C/G]gggggacatcctgcc (SEQ ID NO: 0057) |
| 02 | exm90788 | 1 | q | q21.1 | SEC22B | 145115792 | 1.20E-13 | 3.71 | 0.011 | 0.000 | A | catgttcaagtacttc[A/G]catcctggcggtattt (SEQ ID NO: 0058) |
| 03 | rs11204684 | 1 | q | q21.3 | ENSA/GOLPH3L | 150608894 | 4.02E-04 | 1.12 | 0.481 | 0.454 | A | gttgggaagtgagccal[A/G]cagttatctggaggga (SEQ ID NO: 0059) |
| 03 | rs10888510 | 1 | q | q21.3 | LCE4A | 152681835 | 1.53E-04 | 1.56 | 0.019 | 0.012 | A | tcagcaacagcccccct[A/C]cagagcagcagca (SEQ ID NO: 0060) |
| 03 | rs4970972 | 1 | q | q21.3 | TARS2 | 150468547 | 1.65E-04 | 1.26 | 0.072 | 0.058 | A | catatcccattcctgg[A/C]cacatgaaatccaaaa (SEQ ID NO: 0061) |
| 03 | rs16838078 | 1 | q | q23.1 | ETV3L | 157069261 | 2.43E-03 | 1.31 | 0.032 | 0.025 | C | ccaagaggctcactg[A/C]gatccagttgccggg (SEQ ID NO: 0062) |
| 03 | rs4656849 | 1 | q | q23.2 | CRP1/DUSP23 | 159723521 | 2.04E-03 | 0.90 | 0.361 | 0.385 | A | aagggtcagaaaacaa[A/G]taaaaggccaagacag (SEQ ID NO: 0063) |
| 03 | rs3897374 | 1 | q | q23.3 | NOS1AP | 162168958 | 7.13E-05 | 1.03 | 0.178 | 0.174 | G | caaacctcctgagtc[A/G]gcttaagagttctt (SEQ ID NO: 0064) |
| 03 | exm129317 | 1 | q | q25.3 | RGS16 | 182571142 | 7.34E-08 | 13.65 | 0.004 | 0.000 | C | aactcctcaaagatct[C/G]gtgtgccctggaggcc (SEQ ID NO: 0065) |
| 02 | rs10921412 | 1 | q | q31.2 | CDC73/KCNT2 | 193661626 | 1.36E-03 | 1.11 | 0.361 | 0.337 | A | gaagtttttaacaacl[A/G]aaatcatgaccgttg (SEQ ID NO: 0066) |
| 02 | exm133014 | 1 | q | q31.2 | GLRX2 | 193074511 | 1.85E-17 | 4.14 | 0.023 | 0.006 | G | cgcgcggccaaatc[A/G]tggtcagagccgat (SEQ ID NO: 0067) |
| 02 | rs6701700 | 1 | q | q31.2 | RGS1/RGS13 | 192556309 | 7.80E-05 | 1.20 | 0.133 | 0.113 | A | aaggaattaccaagaa[A/G]agccatgcatctcaca (SEQ ID NO: 0068) |
| 02 | rs10489873 | 1 | q | q31.2 | RGS1/RGS13 | 192559646 | 2.31E-04 | 1.25 | 0.076 | 0.062 | A | ccgggaagtgcacgt[A/G]caccgaggagccatc (SEQ ID NO: 0069) |
| 03 | rs17466945 | 1 | q | q32.1 | CHI3L1/CHIT1 | 203183093 | 1.62E-03 | 1.16 | 0.131 | 0.116 | C | gatgagatcccaagtc[A/C]aaggaagatttgccca (SEQ ID NO: 0070) |
| 03 | rs6662930 | 1 | q | q32.1 | CNTN2 | 205041465 | 7.66E-03 | 0.92 | 0.451 | 0.472 | G | (SEQ ID NO: 0071) |
| 02 | rs880790 | 1 | q | q32.1 | IL10/IL19 | 206960216 | 1.83E-05 | 1.17 | 0.249 | 0.220 | G | cgaaacaaagcccatg[A/G]aaatccaaaggttgga (SEQ ID NO: 0072) |
| 03 | rs17434403 | 1 | q | q32.1 | RASSF5 | 206737276 | 4.07E-03 | 0.87 | 0.116 | 0.131 | C | gcttgggggctggaga[A/G]cagaatttaacatgtt (SEQ ID NO: 0073) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs4570460 | 1 | q | q32.1 | SYT2/KDM5B | 202689028 | 1.29E-03 | 1.33 | 0.034 | 0.025 | A | ttcaaggcccttgag[A/C]tcttgatggcacatga (SEQ ID NO: 0074) |
| 03 | rs6670957 | 1 | q | q32.2 | PLXNA2/LOC642587 | 209195248 | 4.01E-03 | 1.21 | 0.063 | 0.053 | A | agtataltaggggatt[A/G]atattacaagcaagaa (SEQ ID NO: 0075) |
| 02 | rs11119874 | 1 | q | q32.2 | DTL/PPP2R5A | 212357017 | 4.15E-05 | 1.11 | 0.189 | 0.173 | A | gctgtatgttataatt[A/C]tctgatagaacccaca (SEQ ID NO: 0076) |
| 02 | rs2359937 | 1 | q | q32.3 | RPS6KC1/PROX1 | 214033051 | 1.14E-02 | 0.92 | 0.478 | 0.497 | G | gatgaaataatagaact[A/C]caggagatttactttt (SEQ ID NO: 0077) |
| 02 | rs2789939 | 1 | q | q41 | DISP1/TLR5 | 223191495 | 2.07E-03 | 0.86 | 0.281 | 0.311 | C | actctccaaagtcaca[A/G]tattttctggacaagc (SEQ ID NO: 0078) |
| 02 | rs12747035 | 1 | q | q41 | PTPN14 | 214719346 | 5.58E-06 | 1.12 | 0.385 | 0.359 | G | atcaggatcataggag[C/G]actgtctgaggatcag (SEQ ID NO: 0079) |
| 02 | rs903695 | 1 | q | q42.13 | CDC42BPA/ZNF678 | 227733069 | 2.19E-03 | 1.18 | 0.211 | 0.185 | C | acctggctaggaatac[A/G]aggccattaaccaagc (SEQ ID NO: 0080) |
| 02 | rs2493142 | 1 | q | q42.2 | COG2 | 230817384 | 5.27E-03 | 1.11 | 0.262 | 0.243 | G | tggttgttgcatggca[T/C]ttccagataagctgca (SEQ ID NO: 0081) |
| 01 | rs3789649 | 1 | q | q42.2 | COG2 | 230816460 | 8.83E-07 | 1.21 | 0.227 | 0.195 | A | aatgtttgtatttgggg[A/G]tgcccttcttacatg (SEQ ID NO: 0082) |
| 02 | rs1693210 | 1 | q | q42.2 | KCNK1 | 233800613 | 1.98E-03 | 1.11 | 0.382 | 0.359 | A | caagttctacactfcc[A/G]taactcaaacgtgttt (SEQ ID NO: 0083) |
| 02 | rs7545302 | 1 | q | q43 | FMN2 | 240476158 | 9.75E-06 | 0.92 | 0.243 | 0.258 | A | tcaattataatcaccct[A/G]tgtggattttctcag (SEQ ID NO: 0084) |
| 03 | rs6699695 | 1 | q | q43 | RGS7/FH | 241539802 | 6.47E-03 | 1.10 | 0.325 | 0.305 | A | cgaactgatcagatcg[A/C]tgccctacacactta (SEQ ID NO: 0085) |
| 03 | rs9987179 | 1 | q | q44 | C1orf101/PPPDE1 | 244809936 | 7.12E-05 | 0.87 | 0.256 | 0.283 | A | caaatattactgcaat[A/G]agtaatatcatacaca (SEQ ID NO: 0086) |
| 03 | rs7548336 | 1 | q | q44 | LOC440742/C1orf100 | 244401066 | 6.04E-04 | 1.12 | 0.423 | 0.397 | G | aacagatgccatggta[A/G]actagatgcctgggtg (SEQ ID NO: 0087) |
| 03 | rs900895 | 1 | q | q44 | LOC440742/C1orf100 | 244510437 | 1.38E-03 | 1.15 | 0.156 | 0.138 | A | tctttaaggtgggttc[A/G]agagaaaggagatggaa (SEQ ID NO: 0088) |
| 03 | rs3755095 | 2 | p | p12 | CTNNA2 | 80097279 | 1.16E-03 | 1.19 | 0.098 | 0.084 | G | acagacagggtgtcaat[A/G]gaagcgcgtcatatc (SEQ ID NO: 0089) |
| 3 | rs953222 | 2 | p | p12 | CTNNA2 | 79979967 | 3.88E-03 | 1.14 | 0.135 | 0.120 | A | tccaccagtgaagcaa[A/G]taatctgtggcctgct (SEQ ID NO: 0090) |
| 03 | rs6547260 | 2 | p | p12 | CTNNA2 | 79925969 | 4.27E-04 | 1.18 | 0.137 | 0.119 | A | caaaaagaagtatca[A/G]ggtatatatgaagaga (SEQ ID NO: 0091) |
| 03 | rs1160581 | 2 | p | p12 | CTNNA2 | 80026432 | 1.33E-04 | 1.14 | 0.284 | 0.257 | G | aacagaaaattaagat[A/C]agattggctaacaaga (SEQ ID NO: 0092) |
| 03 | rs4284854 | 2 | p | p12 | CTNNA2 | 80025940 | 1.47E-04 | 1.15 | 0.264 | 0.238 | A | taaaggaatccctgtt[A/G]aaaaaaagaataagg (SEQ ID NO: 0093) |
| 03 | rs2861911 | 2 | p | p12 | CTNNA2 | 80007717 | 5.79E-03 | 1.11 | 0.208 | 0.191 | G | tttccttataaaact[A/G]tgttactctagtctga (SEQ ID NO: 0094) |
| 03 | rs1397687 | 2 | p | p12 | CTNNA2 | 80015386 | 6.22E-03 | 1.10 | 0.253 | 0.235 | A | ctaaatgggttcac[A/G]ggggaattcatgaaact (SEQ ID NO: 0095) |
| 03 | rs6732862 | 2 | p | p12 | CTNNA2 | 79918572 | 7.64E-05 | 1.16 | 0.239 | 0.213 | A | gggagctcagaactcac[A/G]tggtggaaagcctaaa (SEQ ID NO: 0096) |
| 03 | rs4852536 | 2 | p | p12 | CTNNA2 | 80104027 | 1.02E-02 | 1.16 | 0.086 | 0.076 | G | atggcataacaattagt[A/G]actcaaagaggcaaaa (SEQ ID NO: 0097) |
| | | | | | | | | | | | | tttggaaatttaacac[A/G]tgaatataaccatcaa |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs1265750 | 2 | p | p12 | CTNNA2\|LOC100289658 | 80951823 | 2.64E-02 | 1.10 | 0.169 | 0.157 | A | aacaggactaagtggc[A/G]tataaattagggtaat (SEQ ID NO: 0098) |
| 02 | rs1443896 | 2 | p | p12 | LRRTM1\|CTNNA2 | 80572750 | 8.14E-06 | 1.41 | 0.045 | 0.032 | A | tatatcatcagtgccc[A/G]gaagagtacctgatgc (SEQ ID NO: 0099) |
| 03 | rs1239102 | 2 | p | p12 | SNAR-H\|REG3G | 78873621 | 1.21E-04 | 1.13 | 0.367 | 0.338 | G | accagtaccatccgt[A/G]tgatttgatggtatga (SEQ ID NO: 0100) |
| 03 | rs11687801 | 2 | p | p12 | SNAR-H\|REG3G | 78978011 | 2.30E-04 | 1.13 | 0.329 | 0.302 | A | tgatgaaggcttctcg[A/G]gggaagttttacgatgt (SEQ ID NO: 0101) |
| 03 | exm204635 | 2 | p | p13.1 | CCDC142 | 74709541 | 8.09E-13 | Inf | 0.005 | 0.000 | A | tgcagctgcaggtgc[A/G]gcaccactgggcaag (SEQ ID NO: 0102) |
| 03 | rs879511 | 2 | p | p13.2 | SFXN5 | 73179990 | 4.99E-04 | 1.48 | 0.020 | 0.014 | G | actcagccccagcccc[A/G]ctcactaagctcacag (SEQ ID NO: 0103) |
| 03 | rs2312205 | 2 | p | p13.3 | AAK1 | 69704941 | 1.17E-02 | 1.11 | 0.188 | 0.173 | G | ccattgcaaaccacag[A/G]ggtgattattttagt (SEQ ID NO: 0104) |
| 03 | rs3771452 | 2 | p | p13.3 | ADD2 | 70936861 | 3.88E-04 | 0.89 | 0.334 | 0.360 | A | gggggaaagcgggaag[A/G]tctctgctccaggaa (SEQ ID NO: 0105) |
| 03 | rs12466648 | 2 | p | p13.3 | GFPT1 | 69560024 | 1.74E-03 | 1.13 | 0.192 | 0.173 | G | ggatgagactccctct[A/G]taataaaatcacagtc (SEQ ID NO: 0106) |
| 03 | rs12473304 | 2 | p | p13.3 | GFPT1 | 69558112 | 1.02E-03 | 1.15 | 0.178 | 0.159 | A | ataaaatttatagtac[A/G]ttttgagcctgtgtgt (SEQ ID NO: 0107) |
| 03 | rs7605572 | 2 | p | p13.3 | NFU1 | 69646504 | 2.19E-03 | 1.14 | 0.177 | 0.159 | A | aaacatagcatattcc[A/G]ctgattcttgtgaca (SEQ ID NO: 0108) |
| 03 | rs1430778 | 2 | p | p14 | ETAA1\|C1D | 68012459 | 4.27E-03 | 0.91 | 0.312 | 0.333 | G | tgcttcaacaattcc[A/G]ttgtgtgtatcgttggc (SEQ ID NO: 0109) |
| 03 | rs6727061 | 2 | p | p15 | B3GNT2\|TMEM17 | 62720684 | 3.86E-03 | 1.10 | 0.390 | 0.368 | G | tctgtgcttttca[A/G]gggaaaaacatctgggt (SEQ ID NO: 0110) |
| 03 | rs2674061 | 2 | p | p16.1 | LOC730134\|BCL11A | 59753331 | 1.58E-03 | 1.11 | 0.319 | 0.296 | A | cccaagacactgtagc[A/G]ttacatagtaggtag (SEQ ID NO: 0111) |
| 03 | rs3814360 | 2 | p | p16.3 | LOC100653325 | 47800603 | 8.19E-04 | 1.21 | 0.200 | 0.171 | T | atgatcanfgattga[A/T]tgtatctaaaccacagt (SEQ ID NO: 0112) |
| 02 | rs989373 | 2 | p | p16.3 | LOC646936\|FSHR | 49158325 | 1.12E-05 | 0.86 | 0.334 | 0.368 | A | gaacatatagcaacaatc[A/G]gggaatgctaaaataaa (SEQ ID NO: 0113) |
| 03 | rs1067352 | 2 | p | p21 | C2orf34 | 44669724 | 7.70E-04 | 0.89 | 0.290 | 0.314 | A | gactcctgcatttca[A/G]tataagttagctctg (SEQ ID NO: 0114) |
| 03 | rs1067339 | 2 | p | p21 | C2orf34 | 44624448 | 3.83E-03 | 0.91 | 0.310 | 0.331 | A | atgcattgatgacctt[A/C]aatatttatttgtaa (SEQ ID NO: 0115) |
| 03 | rs1223222 | 2 | p | p21 | C2orf34 | 44756361 | 1.30E-02 | 0.92 | 0.319 | 0.338 | C | atatcattatgaaactc[A/C]tagatttttaaccta (SEQ ID NO: 0116) |
| 03 | rs1067350 | 2 | p | p21 | C2orf34 | 44669946 | 2.56E-03 | 0.89 | 0.227 | 0.247 | A | ccaagcagctcatcagal[A/G]agagggatgacagaca (SEQ ID NO: 0117) |
| 03 | rs1067386 | 2 | p | p21 | C2orf34 | 44644257 | 3.92E-03 | 0.91 | 0.311 | 0.332 | C | acaagcaatactact[A/C]gggaataaaagggaaa (SEQ ID NO: 0118) |
| 03 | rs1067343 | 2 | p | p21 | C2orf34 | 44621042 | 4.58E-03 | 0.90 | 0.244 | 0.263 | A | agtagtggaacgaaat[A/G]actttggagaaaagga (SEQ ID NO: 0119) |
| 03 | rs1067364 | 2 | p | p21 | C2orf34 | 44655734 | 3.22E-03 | 0.90 | 0.230 | 0.250 | A | tccctgcctcctgtcc[A/C]tagatttttaaccta (SEQ ID NO: 0120) |
| 03 | rs1067405 | 2 | p | p21 | C2orf34 | 44674861 | 3.81E-03 | 0.90 | 0.240 | 0.260 | A | (SEQ ID NO: 0121) |
| 03 | rs698793 | 2 | p | p21 | C2orf34 | 44685685 | 3.74E-03 | 0.90 | 0.241 | 0.260 | G | actgacaacaggcttc[A/G]catgtaaattgctct (SEQ ID NO: 0122) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs1067370 | 2 | p | p21 | C2orf34 | 44652343 | 4.01E-03 | 0.91 | 0.310 | 0.332 | A | taagatgaaaaggtct[A/G]cttttcagggggtttgtg (SEQ ID NO: 0123) |
| 03 | rs1067406 | 2 | p | p21 | C2orf34 | 44674450 | 1.84E-03 | 0.90 | 0.302 | 0.325 | G | aaccagccattaact[A/C]ttgttagatagcttta (SEQ ID NO: 0124) |
| 03 | rs1065785 | 2 | p | p21 | C2orf34 | 44660699 | 1.98E-03 | 0.90 | 0.298 | 0.321 | A | tcctttattctcctc[A/G]ttttatgtaattcgt (SEQ ID NO: 0125) |
| 03 | rs698813 | 2 | p | p21 | C2orf34 | 44705615 | 1.49E-03 | 0.89 | 0.217 | 0.238 | A | actttttgctttagtct[A/G]aattaaaaaagtctt (SEQ ID NO: 0126) |
| 03 | rs698815 | 2 | p | p21 | C2orf34 | 44706974 | 7.55E-04 | 0.88 | 0.235 | 0.259 | C | ttacaagattttcttt[A/G]gtttatagactact (SEQ ID NO: 0127) |
| 02 | exm189795 | 2 | p | p21 | PLEKHH2 | 43903164 | 1.13E-27 | 10.09 | 0.020 | 0.002 | C | cttgtttggggacaca[A/C]tttcaaatacaaaatg (SEQ ID NO: 0128) |
| 03 | rs6712059 | 2 | p | p21 | PPM1B/SLC3A1 | 44475174 | 3.36E-03 | 0.91 | 0.375 | 0.398 | A | tttttagtatcgtagaa[C/G]ctctgctcttgtcacag (SEQ ID NO: 0129) |
| 03 | rs9309116 | 2 | p | p21 | PREPL | 44577919 | 6.27E-04 | 0.89 | 0.331 | 0.357 | G | gaactcaggtttgaggc[A/G]tttttgcatctggtggc (SEQ ID NO: 0130) |
| 03 | rs4953089 | 2 | p | p21 | PREPL | 44565024 | 6.86E-04 | 0.90 | 0.293 | 0.318 | G | gggaacaaattaatat[A/G]taaactatagccttga (SEQ ID NO: 0131) |
| 03 | rs1056865 | 2 | p | p21 | PREPL/SLC3A1 | 44546741 | 1.62E-03 | 0.90 | 0.294 | 0.318 | A | tccctgcatccctgc[A/G]gataagaaaactggca (SEQ ID NO: 0132) |
| 03 | rs698775 | 2 | p | p21 | PREPL/C2orf34 | 44588941 | 1.09E-03 | 0.89 | 0.300 | 0.324 | G | atagtatgtfcatt[A/G]aagatgatttgggttt (SEQ ID NO: 0133) |
| 03 | rs75819914 | 2 | p | p21 | PRKCE | 46078964 | 4.68E-05 | 0.88 | 0.391 | 0.423 | G | agatgctaccagcaa[A/G]aaftggtgcaatggcgt (SEQ ID NO: 0134) |
| 03 | rs2340809 | 2 | p | p21 | SLC3A1 | 44536249 | 2.28E-03 | 0.90 | 0.297 | 0.320 | A | tcatttattgcttgat[A/G]gacacctctaatgtat (SEQ ID NO: 0135) |
| 03 | rs698761 | 2 | p | p21 | SLC3A1 | 44547574 | 5.56E-04 | 0.89 | 0.293 | 0.319 | G | aaaagtgtgtaattca[A/G]tgcattaaatacattc (SEQ ID NO: 0136) |
| 03 | rs2112040 | 2 | p | p21 | SRBD1 | 45752214 | 7.29E-05 | 1.09 | 0.308 | 0.289 | G | gccttcccgctaaaat[A/G]agaataaggttaagta (SEQ ID NO: 0137) |
| 03 | rs101165323 | 2 | p | p22.2 | LOC100129149/LOC344382 | 38010296 | 1.28E-03 | 0.87 | 0.154 | 0.173 | A | tgtcggftaaggactact[A/G]gatagccacaggcaaa (SEQ ID NO: 0138) |
| 03 | rs206811 | 2 | p | p23.1 | XDH | 31636915 | 2.30E-04 | 1.13 | 0.381 | 0.354 | A | ttgtggtctgtgtfta[A/G]gataatgtggaagcta (SEQ ID NO: 0139) |
| 03 | rs206816 | 2 | p | p23.1 | XDH/SRD5A2 | 31644983 | 5.04E-04 | 1.12 | 0.408 | 0.381 | A | gggatggggggaatgc[A/G]gggagatgcccttatg (SEQ ID NO: 0140) |
| 03 | rs7575607 | 2 | p | p23.1 | XDH/SRD5A2 | 31640455 | 1.69E-03 | 1.11 | 0.413 | 0.389 | G | atgatgctgagaatct[A/G]tgaaatgacggaagaa (SEQ ID NO: 0141) |
| 03 | rs2239954 | 2 | p | p23.2 | ALK | 29856155 | 7.90E-04 | 0.89 | 0.272 | 0.296 | A | tttattccttctatct[A/G]actgaaattcgtatt (SEQ ID NO: 0142) |
| 03 | rs2239547 | 2 | p | p23.2 | ALK | 29860061 | 3.38E-05 | 0.88 | 0.239 | 0.263 | A | acctcctgagctcaga[A/C]caagagtgcagccttt (SEQ ID NO: 0143) |
| 03 | rs6734278 | 2 | p | p23.3 | KIF3C | 26202233 | 1.70E-04 | 1.21 | 0.112 | 0.095 | A | gttttaatcatacatcc[A/G]tggaggaacatgttgg (SEQ ID NO: 0144) |
| 02 | rs2384298 | 2 | p | p23.3 | KIF3C | 26156655 | 2.63E-06 | 1.15 | 0.291 | 0.263 | G | ctctcagggttagggt[A/G]aatttgatattaactg (SEQ ID NO: 0145) |
| 03 | rs13029647 | 2 | p | p23.3 | OTOF | 26731244 | 7.95E-03 | 1.09 | 0.369 | 0.349 | A | actaataagtgtatgag[A/G]gttttcattttctctac (SEQ ID NO: 0146) |
| | | | | | | | | | | | | ctaactgacattcaac[A/G]cacttcaaagacacc |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs13031859 | 2 | p | p23.3 | OTOF | 26741961 | 3.98E-05 | 0.91 | 0.464 | 0.488 | A | ttctgcagcaccatgc[A/G]gaaggtccgatgagc (SEQ ID NO: 0147) |
| 03 | rs4665181 | 2 | p | p24.1 | LOC100129278|KLHL29 | 22759343 | 2.42E-03 | 1.11 | 0.350 | 0.327 | A | gcgaaagaacaaacaa[A/G]ccatgtaatacatatg (SEQ ID NO: 0148) |
| 03 | rs851352 | 2 | p | p24.1 | NT5C1B|OSR1 | 19475331 | 5.32E-06 | 1.14 | 0.253 | 0.229 | A | gccaggtctaggcatt[A/G]ttttggtaagtgactg (SEQ ID NO: 0149) |
| 02 | rs851356 | 2 | p | p24.1 | NT5C1B|OSR1 | 19474112 | 1.05E-05 | 1.13 | 0.252 | 0.230 | G | tttaactgtcggccc[A/G]tgtactgatcatgaa (SEQ ID NO: 0150) |
| 03 | rs1871959 | 2 | p | p24.3 | TRIB2|FAM84A | 13250740 | 2.61E-04 | 1.45 | 0.025 | 0.017 | A | acatgttgcataggtt[A/C]tccctccattcctgt (SEQ ID NO: 0151) |
| 03 | rs4669910 | 2 | p | p24.3 | TRIB2|FAM84A | 13289018 | 2.44E-04 | 1.45 | 0.025 | 0.018 | A | atagctatagcaccgc[A/G]aattgccaacatcgta (SEQ ID NO: 0152) |
| 03 | rs1813530 | 2 | p | p24.3 | TRIB2|FAM84A | 13983167 | 1.46E-04 | 1.35 | 0.043 | 0.032 | G | ttattgccattctgt[A/G]gaagtaaggtgtatc (SEQ ID NO: 0153) |
| 03 | rs16860924 | 2 | p | p24.3 | TRIB2|FAM84A | 14031175 | 3.36E-04 | 1.33 | 0.042 | 0.031 | G | cataagtgggaatc[A/G]ttgttcagaaacatta (SEQ ID NO: 0154) |
| 03 | rs4669907 | 2 | p | p24.3 | TRIB2|FAM84A | 13279945 | 4.64E-04 | 1.43 | 0.025 | 0.018 | A | tctagaaacttagtac[A/C]tccctgtcattgta (SEQ ID NO: 0155) |
| 02 | rs1900854 | 2 | p | p24.3 | TRIB2|FAM84A | 14422091 | 7.04E-05 | 0.88 | 0.381 | 0.412 | G | tttacattacttttcct[A/G]ttgacttctccatatt (SEQ ID NO: 0156) |
| 03 | rs7608117 | 2 | p | p25.1 | KCNF1|C2orf50 | 11265972 | 1.99E-04 | 1.12 | 0.503 | 0.473 | A | attcttctggatct[A/C]ttaaaggataaaacg (SEQ ID NO: 0157) |
| 03 | rs1078589 | 2 | p | p25.2 | SOX11|LOC150622 | 5880342 | 1.01E-06 | 1.13 | 0.056 | 0.050 | A | ctctcgggaacttata[A/C]gagtaaaagtctgcag (SEQ ID NO: 0158) |
| 02 | rs16864121 | 2 | p | p25.2 | SOX11|LOC150622 | 5892514 | 9.24E-07 | 1.15 | 0.051 | 0.045 | G | caccacattctctctc[A/G]tcagctctcagacat (SEQ ID NO: 0159) |
| 03 | rs12714428 | 2 | p | p25.3 | LOC100128185|LOC391343 | 857713 | 2.00E-03 | 1.11 | 0.341 | 0.318 | A | aaaaattcctccatga[A/G]tcttacccagatggag (SEQ ID NO: 0160) |
| 01 | rs17025744 | 2 | q | q11.2 | TMEM131|VWA3B | 98636132 | 1.13E-06 | 1.34 | 0.075 | 0.057 | G | gggaggtcagcagcc[A/G]ccactgcgaggagtgg (SEQ ID NO: 0161) |
| 03 | rs2302621 | 2 | q | q12.1 | IL1RL2 | 102842124 | 8.49E-04 | 1.11 | 0.411 | 0.385 | C | ccagtgcttgaccctc[A/C]ccaacgaccgcactct (SEQ ID NO: 0162) |
| 02 | rs2582974 | 2 | q | q12.1 | LOC644265|LOC100287010 | 104578923 | 1.25E-05 | 0.87 | 0.376 | 0.410 | A | gcaactaaaattaacc[A/C]tacttcgattgtgtc (SEQ ID NO: 0163) |
| 03 | rs1159964 | 2 | q | q12.1 | POU3F3|LOC100128131 | 105481442 | 3.06E-03 | 1.10 | 0.428 | 0.405 | G | tcccatccagcttaag[A/G]catttaaaatacaatt (SEQ ID NO: 0164) |
| 03 | rs732278 | 2 | q | q12.1 | POU3F3|LOC100128131 | 105473698 | 3.91E-03 | 1.10 | 0.446 | 0.424 | A | aaatgcctccttggtc[A/C]gttttctcccgcgttt (SEQ ID NO: 0165) |
| 03 | rs7602289 | 2 | q | q12.1 | TMEM182|LOC644265 | 103445960 | 2.81E-04 | 0.88 | 0.256 | 0.281 | G | agcaattractgggg[A/G]aaatatcgaaggtgt (SEQ ID NO: 0166) |
| 03 | rs2420589 | 2 | q | q14.1 | DPP10 | 115722009 | 4.55E-03 | 1.10 | 0.369 | 0.347 | G | ggacagtraataagaal[A/G]aaaagaactggagcaa (SEQ ID NO: 0167) |
| 03 | rs6745631 | 2 | q | q14.1 | DPP10 | 115730919 | 4.01E-03 | 1.10 | 0.295 | 0.275 | C | ttcttafggctattt[A/C]gtgtgtactcctact (SEQ ID NO: 0168) |
| 03 | rs13429901 | 2 | q | q14.1 | DPP10 | 116279799 | 2.42E-02 | 1.11 | 0.128 | 0.117 | A | taagaatcacagagag[A/G]cggagtaatcagaccg (SEQ ID NO: 0169) |
| 03 | rs10210316 | 2 | q | q14.1 | DPP10 | 116298589 | 2.20E-02 | 1.11 | 0.128 | 0.117 | C | tatttgcatccctc[A/C]ataaatacaaaatgc (SEQ ID NO: 0170) |
| 02 | rs10206874 | 2 | q | q14.2 | INHBB|LOC84931 | 121160145 | 4.99E-05 | 0.90 | 0.463 | 0.489 | C | (SEQ ID NO: 0171) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs7570552 | 2 | q | q14.2 | MARCO\|C1QL2 | 119883331 | 7.92E-05 | 0.88 | 0.315 | 0.343 | G | actctgccacagacac[A/C]ttccctggagccctcc (SEQ ID NO: 0172) |
| 03 | rs9636365 | 2 | q | q14.2 | MARCO\|C1QL2 | 119886918 | 7.31E-05 | 0.88 | 0.316 | 0.344 | A | tgggagaaagggcttc[A/G]actgtggtttcagaca (SEQ ID NO: 0173) |
| 03 | rs12469732 | 2 | q | q14.3 | LOC339760 | 127653376 | 2.71E-03 | 1.17 | 0.105 | 0.092 | A | ctcttcctataaggat[A/G]cactgttggatctagg (SEQ ID NO: 0174) |
| 03 | rs6728117 | 2 | q | q14.3 | TSN\|LOC100288443 | 123818496 | 7.09E-03 | 0.88 | 0.120 | 0.134 | C | gtcatgtaattttgat[A/G]accatcaaaaggattt (SEQ ID NO: 0175) |
| 03 | rs13011089 | 2 | q | q14.3 | TSN\|LOC100288443 | 123828854 | 2.21E-02 | 0.90 | 0.120 | 0.132 | A | ttgatatgaagtgagc[A/G]tgcataaatttcagtt (SEQ ID NO: 0176) |
| 03 | rs309161 | 2 | q | q21.3 | DARS | 136688749 | 7.33E-05 | 1.13 | 0.164 | 0.148 | A | ttatgaagatctactt[A/C]tattttagtcaatagta (SEQ ID NO: 0177) |
| 03 | rs2322659 | 2 | q | q21.3 | LCT | 136555659 | 1.28E-03 | 1.12 | 0.271 | 0.248 | G | atttccaaattctta[A/G]ccccttgacttagctga (SEQ ID NO: 0178) |
| 03 | rs309152 | 2 | q | q21.3 | MCM6\|DARS | 136657252 | 1.81E-05 | 1.13 | 0.161 | 0.144 | G | aagaatgagattacaa[A/G]tgaggtgatgaagacg (SEQ ID NO: 0179) |
| 02 | rs10187054 | 2 | q | q21.3 | R3HDM1 | 136388473 | 1.04E-05 | 1.31 | 0.176 | 0.140 | C | gttggatctgtgaccc[A/G]tgctttcacagagaa (SEQ ID NO: 0180) |
| 03 | rs6739713 | 2 | q | q21.3 | R3HDM1\|UBXN4 | 136488978 | 3.10E-04 | 1.14 | 0.263 | 0.239 | G | gaagtcattggggag[T/C]gataccattaatttagt (SEQ ID NO: 0181) |
| 03 | rs9287442 | 2 | q | q21.3 | UBXN4 | 136522710 | 2.02E-03 | 1.12 | 0.248 | 0.227 | A | tcactcaagaaaaaac[A/G]agaacagacaataata (SEQ ID NO: 0182) |
| 03 | rs10188066 | 2 | q | q21.3 | UBXN4 | 136539513 | 2.01E-03 | 1.12 | 0.246 | 0.226 | G | atgttccactaagata[A/G]cagatgtgaaatagga (SEQ ID NO: 0183) |
| 02 | rs1900741 | 2 | q | q21.3 | ZRANB3 | 136002500 | 8.72E-05 | 1.17 | 0.216 | 0.191 | A | agctgtgtgatagc[A/G]tgtgcctatagttca (SEQ ID NO: 0184) |
| 02 | rs10221893 | 2 | q | q22.1 | CXCR4\|THSD7B | 137013606 | 2.10E-05 | 1.15 | 0.446 | 0.412 | G | ttagaacatcacctat[A/G]ctgattactcccatgc (SEQ ID NO: 0185) |
| 02 | rs6643612 | 2 | q | q22.1 | CXCR4\|THSD7B | 137006198 | 1.84E-05 | 1.15 | 0.444 | 0.411 | G | gagtgatttgcccatc[A/G]tgtaatggagactggt (SEQ ID NO: 0186) |
| 02 | rs6755074 | 2 | q | q22.2 | KYNU | 143683066 | 5.38E-04 | 0.89 | 0.360 | 0.386 | C | ctcctccttaaccatga[A/G]tttgagttcacttacc (SEQ ID NO: 0187) |
| 03 | rs11689575 | 2 | q | q22.3 | LOC100131409 | 145527778 | 1.09E-03 | 1.19 | 0.095 | 0.081 | A | tgaaagagacggttac[A/C]tagtaccegtttctg (SEQ ID NO: 0188) |
| 03 | rs7603516 | 2 | q | q22.3 | LOC100131409 | 145504693 | 1.70E-03 | 1.18 | 0.095 | 0.082 | C | caggatcccgttagg[A/G]acttcaaccccttg (SEQ ID NO: 0189) |
| 03 | rs11691685 | 2 | q | q22.3 | LOC100131409 | 145481827 | 7.74E-04 | 1.21 | 0.087 | 0.074 | G | cctgtttgatgctt[A/C]cttccatattttagcac (SEQ ID NO: 0190) |
| 03 | rs7560871 | 2 | q | q22.3 | LOC100131409\|PABPCP2 | 145616899 | 4.59E-03 | 1.18 | 0.079 | 0.067 | A | atgagaaacatcact[A/G]tagataattagactt (SEQ ID NO: 0191) |
| 03 | rs4422110 | 2 | q | q22.3 | LOC100131409\|PABPCP2 | 146114898 | 9.30E-05 | 0.89 | 0.448 | 0.478 | G | aaacattttaaaatgt[A/G]agtgggataaaaacatg (SEQ ID NO: 0192) |
| 03 | rs11690035 | 2 | q | q22.3 | LOC100131409\|PABPCP2 | 145603306 | 5.95E-03 | 1.18 | 0.080 | 0.068 | A | tcctgccttgtaaa[A/G]catgtcatttattcca (SEQ ID NO: 0193) |
| 02 | rs12621827 | 2 | q | q23.2 | LYPD6B | 149981717 | 3.03E-05 | 0.93 | 0.230 | 0.244 | A | atgatgctgtgaca[A/G]ataataaagctatggg (SEQ ID NO: 0194) |
| 01 | rs1519761 | 2 | q | q23.3 | RND3\|RBM43 | 151633204 | 4.13E-10 | 1.22 | 0.446 | 0.398 | G | cagtcagtgctgtaac[A/G]tcacaaatcactaatc (SEQ ID NO: 0195) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs12328269 | 2 | q | q23.3 | RND3\|RBM43 | 151774643 | 2.59E-04 | 1.12 | 0.445 | 0.417 | A | atgtctattgaagccc[A/G]cctttgacatttatga (SEQ ID NO: 0196) |
| 01 | rs7580162 | 2 | q | q23.3 | RND3\|RBM43 | 151655513 | 1.53E-06 | 1.18 | 0.279 | 0.246 | G | cttttctttttccca[A/G]ttgcttcagtgatagc (SEQ ID NO: 0197) |
| 01 | rs6734792 | 2 | q | q23.3 | RND3\|RBM43 | 151624882 | 6.83E-10 | 1.22 | 0.449 | 0.401 | G | aaagcaaaaggtgaag[A/G]agttatttattatcca (SEQ ID NO: 0198) |
| 01 | rs9789673 | 2 | q | q23.3 | RND3\|RBM43 | 151627106 | 1.72E-07 | 1.19 | 0.325 | 0.288 | A | aataatttcagattt[A/C]ttttgaacttactttct (SEQ ID NO: 0199) |
| 01 | rs1519768 | 2 | q | q23.3 | RND3\|RBM43 | 151648276 | 9.30E-10 | 1.22 | 0.413 | 0.366 | A | tcatttgactttgaaaa[A/G]aattccagtcattatc (SEQ ID NO: 0200) |
| 01 | rs1519754 | 2 | q | q23.3 | RND3\|RBM43 | 151619693 | 1.29E-09 | 1.21 | 0.446 | 0.400 | C | tgaagagttagacaat[A/C]atttatttgagcatga (SEQ ID NO: 0201) |
| 01 | rs6728560 | 2 | q | q23.3 | RND3\|RBM43 | 151653870 | 3.30E-06 | 1.18 | 0.278 | 0.246 | A | acagaagaaaatgcc[A/G]tcttgtagtaatcac (SEQ ID NO: 0202) |
| 01 | rs10515926 | 2 | q | q23.3 | RND3\|RBM43 | 151645865 | 6.00E-09 | 1.20 | 0.415 | 0.370 | A | cttgggaaggaacaca[A/G]tggattttcctggaa (SEQ ID NO: 0203) |
| 02 | rs12465911 | 2 | q | q23.3 | RND3\|RBM43 | 151785742 | 1.40E-05 | 1.16 | 0.300 | 0.270 | A | gcctcctgcctacaa[A/G]tcaaatagtaggattt (SEQ ID NO: 0204) |
| 01 | rs6757804 | 2 | q | q23.3 | RND3\|RBM43 | 151635832 | 3.85E-10 | 1.22 | 0.446 | 0.398 | G | cagtgtgggtgataggt[A/G]gtcatggaaataata (SEQ ID NO: 0205) |
| 03 | rs12987780 | 2 | q | q24.3 | CSRNP3 | 166470623 | 5.14E-03 | 1.09 | 0.416 | 0.395 | A | acaaaccttagcgaagt[A/C]atagtggtgtgatgaa (SEQ ID NO: 0206) |
| 03 | rs1551825 | 2 | q | q24.3 | KCNH7\|FIGN | 164340544 | 2.62E-03 | 1.10 | 0.365 | 0.343 | G | gaatatgaaatccaac[A/C]cactggctgtcaataa (SEQ ID NO: 0207) |
| 03 | rs11896706 | 2 | q | q24.3 | SCN1A\|SCN9A | 166993034 | 5.32E-04 | 0.88 | 0.238 | 0.262 | G | agataagatacatat[A/C]aagctactgctgtcct (SEQ ID NO: 0208) |
| 03 | rs7587026 | 2 | q | q24.3 | SCN1A\|SCN9A | 166978750 | 2.80E-03 | 0.90 | 0.256 | 0.277 | A | aaaagcatactagcaa[A/C]atatattacaaagaac (SEQ ID NO: 0209) |
| 02 | rs7562413 | 2 | q | q24.3 | STK39 | 168979569 | 3.66E-03 | 1.10 | 0.344 | 0.323 | A | cttaatatgatacagat[A/G]aagaaccaacactac (SEQ ID NO: 0210) |
| 03 | rs2287618 | 2 | q | q31.1 | ABCB11 | 169842809 | 5.79E-03 | 1.10 | 0.326 | 0.306 | A | cgaaattgactcaagc[A/G]ttttgtcttcacaggt (SEQ ID NO: 0211) |
| 03 | rs16864421 | 2 | q | q31.1 | LOC375295\|HNRNPA3 | 177628237 | 3.38E-04 | 1.27 | 0.060 | 0.048 | A | tgagagtcaaagaagat[A/G]gggaaaactccaggaa (SEQ ID NO: 0212) |
| 02 | exm244817 | 2 | q | q31.2 | MIR548N | 179315031 | 4.38E-62 | Inf | 0.056 | 0.010 | G | gaatgtgaaagatctg[A/G]tgtgcaaatacacgtg (SEQ ID NO: 0213) |
| 02 | rs4563185 | 2 | q | q31.3 | CWC22\|LOC729009 | 181684892 | 6.96E-04 | 1.23 | 0.168 | 0.141 | A | ccaatcattgggtta[A/G]ctgatttagtaggtaa (SEQ ID NO: 0214) |
| 03 | rs13034731 | 2 | q | q32.2 | GULP1 | 189414364 | 5.29E-04 | 0.89 | 0.356 | 0.382 | A | gttttgatttctctgg[A/G]ataaafgtccaagtat (SEQ ID NO: 0215) |
| 02 | rs2709387 | 2 | q | q33.3 | CREB1 | 208442095 | 9.76E-03 | 0.87 | 0.170 | 0.191 | A | tgctgattcttcaac[A/G]ctttagccagaatcat (SEQ ID NO: 0216) |
| 02 | rs1263628 | 2 | q | q33.3 | KLF7 | 207977132 | 8.58E-03 | 0.85 | 0.146 | 0.167 | C | gaaatgattccataaa[C/G]cctgaatttatcttat (SEQ ID NO: 0217) |
| 02 | rs7582864 | 2 | q | q33.3 | ZDBF2 | 207172627 | 3.60E-05 | 1.13 | 0.425 | 0.396 | A | ctgatgtttctgtcca[A/G]tctgtggctgatcaac (SEQ ID NO: 0218) |
| 02 | rs3732084 | 2 | q | q33.3 | ZDBF2 | 207174316 | 4.57E-05 | 1.13 | 0.417 | 0.388 | A | ctgatgtttctgtcca[A/G]tctgtggctgatcaac (SEQ ID NO: 0219) |
| 02 | rs4673350 | 2 | q | q33.3 | ZDBF2 | 207178872 | 4.33E-05 | 1.12 | 0.426 | 0.398 | G | ttggatccttccgaag[A/G]ctggcttcttgtgag (SEQ ID NO: 0220) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs1448902 | 2 | q | q33.3 | ZDBF2 | 207178422 | 3.15E-05 | 1.13 | 0.358 | 0.330 | G | tacaataaaatctac[A/G]caaaatactgaacaag (SEQ ID NO: 0221) |
| 03 | rs2033645 | 2 | q | q34 | ERBB4 | 212325378 | 2.59E-03 | 1.23 | 0.058 | 0.048 | G | agagagaacagttcct[A/G]taattcaagtaattaa (SEQ ID NO: 0222) |
| 03 | rs1250258 | 2 | q | q35 | FN1 | 216300185 | 3.96E-04 | 1.13 | 0.285 | 0.261 | G | tacagacagttttgt[A/G]tatttcaacttgccat (SEQ ID NO: 0223) |
| 03 | rs12053317 | 2 | q | q35 | WNT6 | 219733973 | 2.71E-04 | 0.85 | 0.148 | 0.170 | G | ctggaatgaataagacc[A/G]tgcattggaggacgag (SEQ ID NO: 0224) |
| 01 | rs10184043 | 2 | q | q36.1 | KCNE4|SCG2 | 224204870 | 2.30E-07 | 1.20 | 0.283 | 0.248 | A | aaacacgtgtgtgtgc[A/G]cgtgcattctcatgcg (SEQ ID NO: 0225) |
| 01 | rs10445738 | 2 | q | q36.1 | KCNE4|SCG2 | 224186245 | 8.46E-07 | 1.19 | 0.266 | 0.233 | A | tactgggtctgaagga[A/G]catgtggaggaggcag (SEQ ID NO: 0226) |
| 03 | rs17190891 | 2 | q | q36.1 | KCNE4|SCG2 | 224046645 | 4.07E-04 | 1.18 | 0.138 | 0.120 | A | ccattcagcatttaca[A/G]tggtaccccaatagga (SEQ ID NO: 0227) |
| 01 | rs1400797 | 2 | q | q36.1 | KCNE4|SCG2 | 224226772 | 4.31E-09 | 1.23 | 0.293 | 0.252 | A | ttgtcccaagttttc[A/G]tgtttagcaacaatata (SEQ ID NO: 0228) |
| 03 | rs7580493 | 2 | q | q36.3 | SPHKAP|PID1 | 229427172 | 1.51E-03 | 1.48 | 0.017 | 0.012 | A | aticaaactccaatat[A/G]gtcccaagtttaaaac (SEQ ID NO: 0229) |
| 03 | rs6431586 | 2 | q | q37.1 | INPP5D|ATG16L1 | 234119635 | 4.44E-04 | 1.19 | 0.115 | 0.099 | A | tctacattgcttttct[A/G]tctgctatcaccctc (SEQ ID NO: 0230) |
| 03 | rs10084197 | 2 | q | q37.1 | NPPC|DIS3L2 | 232810183 | 2.86E-03 | 1.11 | 0.308 | 0.286 | G | tttgtgccccaccgcg[A/G]ttctggacgcacctgt (SEQ ID NO: 0231) |
| 03 | rs838425 | 2 | q | q37.1 | PTMA|PDE6D | 232597042 | 8.82E-04 | 0.81 | 0.062 | 0.076 | G | cattaccaatagtaat[A/G]tcaggaataagaaacacc (SEQ ID NO: 0232) |
| 02 | exm284033 | 2 | q | q37.1 | ANO7 | 242154318 | 6.11E-12 | Inf | 0.004 | 0.000 | A | gtattcactccaggaa[A/G]tggaactgatagatct (SEQ ID NO: 0233) |
| 03 | rs7605254 | 2 | q | q37.3 | ASB1|LOC100287050 | 239362938 | 9.60E-03 | 0.91 | 0.274 | 0.293 | A | aggagtcctcatccc[A/G]tgagtcccccactcct (SEQ ID NO: 0234) |
| 02 | exm284661 | 2 | q | q37.3 | BOK | 242498984 | 8.95E-16 | 3.49 | 0.021 | 0.008 | G | ctaccatttccttg[A/G]agttacgtcccttggt (SEQ ID NO: 0235) |
| 03 | rs4073396 | 2 | q | q37.3 | COPS8|COL6A3 | 238111471 | 6.38E-04 | 0.88 | 0.209 | 0.232 | C | gacaaggagctgtgg[C/G]ccaggccaaggggctg (SEQ ID NO: 0236) |
| 03 | rs7585432 | 2 | q | q37.3 | CXCR7|LOC93463 | 237626734 | 1.22E-03 | 1.16 | 0.132 | 0.115 | C | cccatctaagatac[A/C]caaagtgtcagtgacgc (SEQ ID NO: 0237) |
| 03 | rs2067620 | 2 | q | q37.3 | CXCR7|LOC93463 | 237642373 | 8.83E-04 | 1.17 | 0.124 | 0.108 | G | tgaggtttaactcct[A/C]cctccccttactcaca (SEQ ID NO: 0238) |
| 03 | rs11679123 | 2 | q | q37.3 | CXCR7|LOC93463 | 237647424 | 7.96E-04 | 1.17 | 0.124 | 0.108 | A | aggccttaaggacact[A/G]gtagaactgaaggaggt (SEQ ID NO: 0239) |
| 01 | exm281099 | 2 | q | q37.3 | HDAC4 | 24005606 | 77.45E-63 | 125.80 | 0.013 | 0.001 | A | atccacatatccatcc[A/G]tccctctattctgaca (SEQ ID NO: 0240) |
| 03 | rs1796449 | 2 | q | q37.3 | HDAC4|FLJ45964 | 240420675 | 2.21E-04 | 0.89 | 0.423 | 0.452 | A | gctctccccttacccc[A/G]gcaccaccctcactcc (SEQ ID NO: 0241) |
| 03 | rs1564974 | 2 | q | q37.3 | HDAC4|FLJ45964 | 240436304 | 1.12E-03 | 0.90 | 0.441 | 0.467 | C | ctgaactacacggaggi[A/G]ggatgacacgggggct (SEQ ID NO: 0242) |
| 03 | rs1486323 | 2 | q | q37.3 | HDAC4|FLJ45964 | 240417788 | 1.64E-04 | 0.88 | 0.325 | 0.353 | G | ggcaagccatcccgga[A/C]ggacgtcagatcctgg (SEQ ID NO: 0243) |
| 03 | rs4414678 | 2 | q | q37.3 | KIF1A | 241680633 | 4.58E-04 | 1.12 | 0.372 | 0.346 | A | ctgggcacgtgcttca[A/G]taagaacagctgctca (SEQ ID NO: 0244) |
| | | | | | | | | | | | | tgtgtcggggggtgcg[A/C]ggaagagagagggacgaggac |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs1845754 | 3 | p | p11.1 | C3orf38\|EPHA3 | 88765697 | 4.79E-03 | 1.10 | 0.358 | 0.337 | A | ataaatccaacttggt[A/C]atgatgaatgctcttt (SEQ ID NO: 245) |
| 03 | rs1473624 | 3 | p | p12.2 | GBE1\|LOC100289598 | 83169976 | 1.76E-04 | 1.16 | 0.193 | 0.171 | G | cttgaatttgtggatg[A/G]ttttgtgaaatgtaata (SEQ ID NO: 246) |
| 03 | rs7618878 | 3 | p | p12.2 | GBE1\|LOC100289598 | 83089596 | 9.01E-07 | 1.13 | 0.474 | 0.444 | A | ttattttaggacata[A/G]tgtgtgggagctgaa (SEQ ID NO: 247) |
| 03 | rs1080728 | 3 | p | p12.2 | GBE1\|LOC100289598 | 83107505 | 7.42E-05 | 0.89 | 0.239 | 0.260 | A | gaagcgcatgcaat[A/G]gatccaggtgtatgc (SEQ ID NO: 248) |
| 03 | rs1995065 | 3 | p | p12.2 | GBE1\|LOC100289598 | 82913445 | 6.05E-05 | 1.11 | 0.407 | 0.383 | A | taacaaataggcagaa[A/G]ttttagagcaacattaa (SEQ ID NO: 249) |
| 02 | rs11127807 | 3 | p | p12.2 | GBE1\|LOC100289598 | 83130081 | 3.10E-07 | 1.14 | 0.474 | 0.443 | G | atattgtactttgtat[A/G]cagaatttcaacttgg (SEQ ID NO: 250) |
| 03 | rs6806032 | 3 | p | p12.2 | GBE1\|LOC100289598 | 83132865 | 7.90E-05 | 0.89 | 0.236 | 0.258 | G | tttcttatctagtgg[A/G]cacttttaggtcgatt (SEQ ID NO: 251) |
| 03 | rs2121783 | 3 | p | p13 | FOXP1 | 71174475 | 6.22E-04 | 0.90 | 0.404 | 0.431 | G | tttttgtgtgtatgtc[A/G]ttccttgaatacagtga (SEQ ID NO: 252) |
| 03 | rs9862251 | 3 | p | p14.2 | PTPRG | 61587570 | 2.48E-02 | 1.12 | 0.120 | 0.109 | G | aaggaggtaaagttaa[A/G]agttaggagcagaaggg (SEQ ID NO: 253) |
| 01 | exm321427 | 3 | p | p21.1 | SEMA3G | 52475886 | 1.55E-20 | Inf | 0.004 | 0.000 | A | tgagggcaccgcccc[A/G]gccaactttccaactg (SEQ ID NO: 254) |
| 03 | rs375544 | 3 | p | p21.2 | MAPKAPK3 | 50657826 | 1.28E-04 | 1.19 | 0.151 | 0.130 | G | ctgcctccctgtgat[A/G]tactccaggttaacca (SEQ ID NO: 255) |
| 01 | rs4688718 | 3 | p | p21.31 | CACNA2D2 | 50522063 | 4.92E-06 | 1.16 | 0.423 | 0.387 | A | tcacctgtccgtgaa[A/G]acctcctgccctcc (SEQ ID NO: 256) |
| 03 | rs2236951 | 3 | p | p21.31 | CACNA2D2 | 50421081 | 2.54E-05 | 1.17 | 0.223 | 0.197 | G | gccaggagctgggat[A/G]taaggaagggggatgt (SEQ ID NO: 257) |
| 02 | exm311992 | 3 | p | p21.31 | COL7A1 | 48623625 | 4.98E-08 | 4.22 | 0.009 | 0.002 | A | ccagaagctgcgtc[A/G]cttggccgcgggtatg (SEQ ID NO: 258) |
| 02 | rs2233474 | 3 | p | p21.31 | TUSC4\|CYB561D2 | 50388607 | 1.37E-05 | 1.21 | 0.160 | 0.136 | A | ttacatggctttgcgcl[A/C]tcctacctgaaggcg (SEQ ID NO: 259) |
| 02 | exm304730 | 3 | p | p22.1 | CYP8B1 | 42916596 | 2.38E-09 | Inf | 0.003 | 0.000 | G | cagcgtcctttcaca[A/G]gatgctctccgtgagc (SEQ ID NO: 260) |
| 03 | rs5029848 | 3 | p | p22.1 | LOC100287063 | 42110843 | 1.99E-03 | 0.91 | 0.400 | 0.424 | C | tgcaccatccgaccca[A/C]ccataacttttcttt (SEQ ID NO: 261) |
| 03 | rs7644110 | 3 | p | p22.1 | LOC100287063 | 42115488 | 1.85E-03 | 0.91 | 0.401 | 0.425 | G | gagttcatttgcccct[A/G]ttacgacaagagggtt (SEQ ID NO: 262) |
| 03 | rs1995137 | 3 | p | p22.1 | LOC100287063\|TRAK1 | 42131415 | 1.60E-03 | 0.90 | 0.405 | 0.429 | A | gtgtatcaattgtgtc[A/G]attggtgcagtgagta (SEQ ID NO: 263) |
| 03 | rs10514703 | 3 | p | p22.1 | LOC729505\|CTNNB1 | 40901256 | 7.31E-03 | 0.80 | 0.037 | 0.046 | A | aaacaattgaagccaag[A/G]acagaagtgaactggac (SEQ ID NO: 264) |
| 03 | rs6798614 | 3 | p | p22.1 | LOC729505\|CTNNB1 | 40930857 | 7.30E-03 | 0.80 | 0.037 | 0.045 | A | gttttatgtcagctc[A/G]acctttgcttttaagt (SEQ ID NO: 265) |
| 02 | exm302831 | 3 | p | p22.1 | MYRIP | 40085729 | 1.94E-08 | 34.64 | 0.004 | 0.000 | G | taccagaagcacgaaa[A/G]ggcctgggtctgctgc (SEQ ID NO: 266) |
| 03 | rs4293737 | 3 | p | p22.3 | CMTM8 | 32373530 | 1.28E-02 | 1.10 | 0.209 | 0.193 | A | tcttttgaccacgcc[A/G]caccacacacacaca (SEQ ID NO: 267) |
| 03 | rs117137777 | 3 | p | p22.3 | GPD1L\|LOC100291194 | 32245557 | 3.18E-04 | 1.21 | 0.101 | 0.085 | G | tcttttgaccacgcc[A/G]caccacacacacaca (SEQ ID NO: 268) |
| 03 | rs12493245 | 3 | p | p24.1 | EOMES\|CMC1 | 27797810 | 2.08E-03 | 1.11 | 0.370 | 0.347 | A | atggatatgcagttag[A/G]aaaatgaatgagtcatcact (SEQ ID NO: 269) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs4343572 | 3 | p | p24.2 | LOC644990/LOC100130354 | 24733019 | 1.36E-02 | 0.92 | 0.361 | 0.379 | A | gtcgtaacttaaaatc[A/G]tattcaaagctgtgat (SEQ ID NO: 0270) |
| 03 | rs4600774 | 3 | p | p24.2 | LOC644990/LOC100130354 | 24731037 | 2.65E-03 | 0.90 | 0.297 | 0.319 | A | ttcataattctactttt[A/G]ctgaatcagctgaga (SEQ ID NO: 0271) |
| 03 | rs7610222 | 3 | p | p24.2 | THRB | 24357286 | 6.07E-03 | 0.91 | 0.253 | 0.272 | A | aagcaaagcaagcaaa[A/G]catcatctgtatttat (SEQ ID NO: 0272) |
| 01 | exm2265568 | 3 | p | p24.3 | VENTXP7/UBE2E2 | 23240050 | 1.34E-08 | 2.49 | 0.004 | 0.000 | G | attagtggaagtgaact[A/G]cttctccctgcaatta (SEQ ID NO: 0273) |
| 03 | rs6442476 | 3 | p | p25.1 | C3orf20 | 14812460 | 2.43E-03 | 1.10 | 0.486 | 0.462 | G | aactaactgtggctct[A/G]cttactcacgaagttg (SEQ ID NO: 0274) |
| 03 | rs7651825 | 3 | p | p25.1 | C3orf20 | 14812118 | 4.03E-05 | 0.90 | 0.418 | 0.444 | A | tgtgaggtgcacal[A/G]aggtaaggaatagcca (SEQ ID NO: 0275) |
| 02 | rs2697149 | 3 | p | p25.3 | SLC6A1 | 11036480 | 6.59E-03 | 1.11 | 0.240 | 0.222 | C | cccagagctacctcaa[A/G]cccctcccaagcca (SEQ ID NO: 0276) |
| 03 | rs6792001 | 3 | p | p26.1 | EDEM1/GRM7 | 6106251 | 2.02E-04 | 1.16 | 0.183 | 0.161 | A | gggtaaagatgaggca[A/C]aatcaagtccatcgaa (SEQ ID NO: 0277) |
| 02 | exm285495 | 3 | p | p26.3 | CHL1 | 391100 | 7.65E-11 | 44.12 | 0.005 | 0.000 | A | gatgcaattagagata[A/G]gctttaggaagatctt (SEQ ID NO: 0278) |
| 03 | rs2044602 | 3 | p | p26.3 | CNTN4 | 2315400 | 3.66E-03 | 0.91 | 0.416 | 0.438 | A | accaaggggagaat[A/G]caaaagaaaattagg (SEQ ID NO: 0279) |
| 03 | rs16840752 | 3 | q | q12.1 | DCBLD2/COL8A1 | 98924050 | 6.69E-02 | 1.15 | 0.046 | 0.040 | A | atttcctctaatgc[A/G]gtactaatatatgttg (SEQ ID NO: 0280) |
| 03 | rs1848252 | 3 | q | q12.2 | AB13BP/IMPG2 | 100818827 | 5.34E-05 | 1.15 | 0.210 | 0.187 | G | gacttcacatagtgcc[A/G]cctagttcttccaatg (SEQ ID NO: 0281) |
| 03 | rs16843225 | 3 | q | q12.2 | AB13BP/IMPG2 | 100801257 | 1.13E-05 | 0.81 | 0.122 | 0.146 | C | ccctcaccccaggct[A/G]aaaaggctgacacaa (SEQ ID NO: 0282) |
| 03 | rs2036650 | 3 | q | q12.2 | AB13BP/IMPG2 | 100834729 | 2.07E-05 | 1.17 | 0.201 | 0.177 | C | ctgtgtagetatttga[A/C]gatatgctggcctgta (SEQ ID NO: 0283) |
| 02 | rs650567 | 3 | q | q12.3 | NFKBIZ/LOC152225 | 101594402 | 4.53E-05 | 0.88 | 0.397 | 0.428 | A | aaaaaaaaaataagt[A/C]ctcttaaagctagcac (SEQ ID NO: 0284) |
| 02 | rs641432 | 3 | q | q12.3 | NFKBIZ/LOC152225 | 101587566 | 2.88E-05 | 0.88 | 0.425 | 0.458 | A | ttctaaaaagcaact[A/C]ctcatgagaagctgta (SEQ ID NO: 0285) |
| 02 | rs16844076 | 3 | q | q12.3 | PCNP | 101296067 | 1.06E-04 | 1.32 | 0.052 | 0.040 | G | gttgagtccttccag[A/G]cttggaatcttcaaga (SEQ ID NO: 0286) |
| 02 | rs2303476 | 3 | q | q12.3 | RG9MTD1 | 101280993 | 9.87E-05 | 1.32 | 0.052 | 0.040 | G | tctcctcccttggtt[A/G]aatcttgtagctgtt (SEQ ID NO: 0287) |
| 03 | rs6793744 | 3 | q | 813.11 | CBLB/LOC344593 | 105897816 | 5.72E-05 | 1.11 | 0.057 | 0.052 | G | tgttcaggtactgt[A/G]ctagtatagtttat (SEQ ID NO: 0288) |
| 03 | rs6774644 | 3 | q | 813.12 | CBLB/LOC344593 | 106379000 | 5.37E-04 | 0.86 | 0.144 | 0.164 | G | ccagccaggatattca[A/G]aggaccgaaccctctt (SEQ ID NO: 0289) |
| 03 | rs12633892 | 3 | q | 813.12 | CBLB/LOC344593 | 106380005 | 9.96E-04 | 0.86 | 0.145 | 0.164 | G | ttgagtgtgaaagaat[A/G]taacagtaaaaataaa (SEQ ID NO: 0290) |
| 03 | rs7613153 | 3 | q | 813.12 | CBLB/LOC344593 | 106380604 | 1.03E-03 | 0.86 | 0.144 | 0.163 | A | ctacatgaaaacctg[A/G]gagctatatcttcaaatc (SEQ ID NO: 0291) |
| 02 | rs7617430 | 3 | q | q13.12 | CBLB/LOC344593 | 106392429 | 4.80E-04 | 0.85 | 0.122 | 0.141 | A | taatgctagccttcct[A/G]gagtctagtatttcag (SEQ ID NO: 0292) |
| 02 | exm337642 | 3 | q | q13.2 | CCDC80 | 112357336 | 2.19E-15 | 5.62 | 0.015 | 0.003 | A | ctagcacgttttattg[A/G]ccatcattatttcat (SEQ ID NO: 0293) |
| | | | | | | | | | | | | gggtctcggtggccat[A/G]ttcccgcctgtccatg |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs16824243 | 3 | q | q13.31 | LSAMP | 115603783 | 5.66E-04 | 0.83 | 0.091 | 0.108 | G | ttcaaaggtcaggcaa[A/G]ttgatttgaaaagaa (SEQ ID NO: 0294) |
| 03 | rs1731596 | 3 | q | q13.31 | LSAMP | 116131208 | 2.13E-04 | 1.15 | 0.218 | 0.195 | C | ctgcatagtgagactg[A/C]atgttttttcaggagtt (SEQ ID NO: 0295) |
| 03 | rs9838534 | 3 | q | q13.31 | LSAMP | 116113609 | 2.48E-04 | 1.15 | 0.218 | 0.195 | A | tgtgaagaaaaacac[A/G]tattagttcaataaat (SEQ ID NO: 0296) |
| 03 | rs6782605 | 3 | q | q13.31 | LSAMP | 116047619 | 1.55E-03 | 1.19 | 0.094 | 0.081 | A | tgatgaatgataatta[A/G]cttttcctctagagca (SEQ ID NO: 0297) |
| 03 | rs1265646 | 3 | q | q21.2 | ITGB5 | 124592700 | 6.86E-06 | 0.90 | 0.368 | 0.394 | A | tacacttagtctatcc[A/G]aaatgaccaaaatagt (SEQ ID NO: 0298) |
| 02 | exm347865 | 3 | q | q21.3 | KBTBD12 | 127642561 | 1.95E-54 | 5.97 | 0.025 | 0.007 | C | ttgagatttgaagca[A/C]gtcagattgaacttg (SEQ ID NO: 0299) |
| 03 | rs4683547 | 3 | q | q23 | SPSB4 | 140801587 | 7.54E-03 | 0.87 | 0.102 | 0.116 | A | aaactgaggctgtgaa[A/C]ggctgaagtttcag (SEQ ID NO: 0300) |
| 02 | rs12489920 | 3 | q | q26.1 | OTOL1\|LOC730129 | 162391801 | 1.21E-03 | 1.12 | 0.284 | 0.262 | A | gaaccagacataagc[A/G]gcattgttcatatgt (SEQ ID NO: 0301) |
| 02 | rs7643215 | 3 | q | q26.1 | ZBBX | 167023279 | 2.99E-05 | 0.85 | 0.221 | 0.249 | G | attaatgttctcccc[A/G]tatgagtcactctca (SEQ ID NO: 0302) |
| 02 | rs9881097 | 3 | q | q26.31 | GHSR\|VTNFSF10 | 172185376 | 5.44E-03 | 1.13 | 0.496 | 0.465 | A | aggatgaagcttaact[A/G]aggaaggtagaaccaa (SEQ ID NO: 0303) |
| 03 | rs7632772 | 3 | q | q26.32 | NAALADL\|TBL1XR1 | 176103902 | 7.34E-03 | 1.15 | 0.101 | 0.089 | G | caaaagcctgagaag[A/G]gtgaaagaacaaagc (SEQ ID NO: 0304) |
| 03 | rs1106387 | 3 | q | q26.32 | TBL1XR1\|VKCNMB2 | 177490268 | 7.34E-05 | 1.12 | 0.293 | 0.271 | A | ttgaagagaaaggaa[A/G]aaaattatgtgct (SEQ ID NO: 0305) |
| 03 | rs1106388 | 3 | q | q26.32 | TBL1XR1\|KCNMB2 | 177490311 | 8.87E-05 | 1.12 | 0.293 | 0.271 | G | agaaaactgtactgac[A/C]gctacgaagtttgagc (SEQ ID NO: 0306) |
| 02 | rs6443448 | 3 | q | q26.32 | TBL1XR1\|KCNMB2 | 177074926 | 2.16E-05 | 0.91 | 0.393 | 0.416 | G | cagccagaaaatatt[A/G]aaaagataatgagcaa (SEQ ID NO: 0307) |
| 02 | exm372681 | 3 | q | q28 | CCDC50 | 191098660 | 1.05E-21 | 19.0 | 0.012 | 0.001 | G | aaagtaacatcaggga[A/G]gtctgaaataaatg (SEQ ID NO: 0308) |
| 03 | rs890348 | 3 | q | q28 | LPP | 188241949 | 5.79E-05 | 1.08 | 0.168 | 0.158 | G | gaaaagaaagttaca[A/G]aaaagccaaggagcgg (SEQ ID NO: 0309) |
| 02 | exm376611 | 3 | q | q29 | C3orf43 | 196236401 | 6.01E-31 | Inf | 0.012 | 0.000 | A | ggtcttgccatcctc[A/G]caacacatgccataccta (SEQ ID NO: 0310) |
| 02 | rs6444670 | 3 | q | q29 | C3orf43 | 192599336 | 8.91E-06 | 0.86 | 0.360 | 0.394 | C | actcactgaagtgccc[A/G]aactgctgtccaatc (SEQ ID NO: 0311) |
| 02 | rs6799698 | 3 | q | q29 | LRRC15\|GP5 | 194105437 | 5.36E-03 | 1.21 | 0.126 | 0.106 | A | agaaaactgtactgac[A/C]gctacgaagtttgagc (SEQ ID NO: 0312) |
| 02 | rs10021613 | 4 | p | p13 | APBB2 | 41201819 | 8.45E-04 | 1.17 | 0.135 | 0.118 | G | cccagccaactcaac[A/G]cctgcagatgctctt (SEQ ID NO: 0313) |
| 03 | rs7683746 | 4 | p | p13 | APBB2 | 41203125 | 9.13E-04 | 1.17 | 0.136 | 0.119 | A | gcttcacgttcttctcc[A/G]gtgtctagtggcaaac (SEQ ID NO: 0314) |
| 02 | rs13173475 | 4 | p | p14 | FLJ16686\|KIAA1239 | 36931424 | 7.58E-05 | 1.18 | 0.171 | 0.148 | A | gacagttgcctatac[A/G]gagggctcattaaaca (SEQ ID NO: 0315) |
| 03 | rs1020808 | 4 | p | p14 | FLJ16686\|KIAA1239 | 36949073 | 1.88E-05 | 1.20 | 0.177 | 0.153 | A | ggaagagttgaagaga[A/G]gaagaagatgcccaagc (SEQ ID NO: 0316) |
| 02 | rs4832890 | 4 | p | p14 | KIAA1239 | 37264627 | 1.41E-02 | 0.92 | 0.360 | 0.379 | A | tagtgacctataaga[A/G]gagatgtcagaaatt (SEQ ID NO: 0317) |
| 03 | rs10001618 | 4 | p | p14 | KIAA1239 | 37340671 | 1.20E-02 | 1.28 | 0.027 | 0.021 | G | catcatgaagttcatg[A/G]agccgaaccaccagt (SEQ ID NO: 0318) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs3796533 | 4 | p | p14 | KLF3 | 38692806 | 9.85E-06 | 1.20 | 0.181 | 0.155 | A | gaaatgatgtgtgact[A/G]aacaaagaagacatgca (SEQ ID NO: 0319) |
| 01 | rs17582575 | 4 | p | p14 | KLF3/TLR10 | 38703734 | 2.66E-06 | 1.21 | 0.193 | 0.165 | A | gggcaaagtgattaacct[A/G]agacattagataactc (SEQ ID NO: 0320) |
| 02 | rs6838865 | 4 | p | p14 | KLF3/TLR10 | 38745883 | 2.27E-05 | 1.22 | 0.115 | 0.096 | A | cttcccacatgaacttal[A/C]ttttcacaggttggaga (SEQ ID NO: 0321) |
| 02 | rs12233656 | 4 | p | p14 | KLF3/TLR10 | 38737018 | 4.07E-05 | 1.22 | 0.096 | 0.080 | G | agactccttaacctcta[A/C]tgaaatcatcccaaac (SEQ ID NO: 0322) |
| 02 | rs6849452 | 4 | p | p14 | PCDH7/ARAP2 | 31216675 | 1.12E-04 | 1.14 | 0.311 | 0.283 | A | attgctccaataatag[A/G]cgtgtgtatttctcatgt (SEQ ID NO: 0323) |
| 03 | rs7659139 | 4 | p | p15.2 | KCNIP4/GPR125 | 22297899 | 2.66E-04 | 0.84 | 0.122 | 0.142 | G | tgcaatatttcctctc[A/G]ctcctctatgtctatcc (SEQ ID NO: 0324) |
| 02 | rs6448143 | 4 | p | p15.2 | KCNIP4/GPR125 | 22303196 | 8.02E-04 | 0.86 | 0.130 | 0.148 | G | taggctcagcccccc[A/G]ttttaaacagaggttaa (SEQ ID NO: 0325) |
| 02 | rs7697101 | 4 | p | p15.2 | KCNIP4/LOC100505912 | 22174771 | 5.99E-04 | 0.86 | 0.478 | 0.516 | C | cacactgttagagtgt[A/G]ttgagcatgtggag (SEQ ID NO: 0326) |
| 02 | exm393187 | 4 | p | p15.2 | SEL1L3 | 25834624 | 9.17E-08 | 8.41 | 0.005 | 0.001 | A | tcctgcataggtgtcc[T/C]tcttaaaaataatig (SEQ ID NO: 0327) |
| 03 | rs11721812 | 4 | p | p15.2 | SLC34A2/KIAA0746 | 25730546 | 1.49E-05 | 1.23 | 0.121 | 0.101 | A | gatatctctttttaacg[A/G]aggccaggtatctgta (SEQ ID NO: 0328) |
| 03 | rs210777 | 4 | p | p15.2 | STIM2/PCDH7 | 27432523 | 1.44E-03 | 1.14 | 0.188 | 0.170 | A | aaggctccttggcca[A/G]taagagtcgttcagt (SEQ ID NO: 0329) |
| 03 | rs7693245 | 4 | p | p15.31 | LCORL/SLIT2 | 18321896 | 2.13E-03 | 1.10 | 0.471 | 0.447 | G | agattttatgtgcct[A/G]atgatagtctcaaaat (SEQ ID NO: 0330) |
| 03 | rs4140904 | 4 | p | p15.31 | LCORL/SLIT2 | 18315992 | 2.96E-02 | 1.08 | 0.253 | 0.238 | A | ccccacactacata[A/G]gcagctgatttgcaca (SEQ ID NO: 0331) |
| 03 | rs3846386 | 4 | p | p15.33 | LOC391636/LOC441009 | 14102069 | 3.29E-03 | 1.11 | 0.269 | 0.248 | G | tgaagatagaattggca[A/G]ataccctatcctatcc (SEQ ID NO: 0332) |
| 02 | rs4689003 | 4 | p | p16.1 | PPP2R2C | 6428296 | 9.71E-05 | 1.14 | 0.182 | 0.163 | G | gattctatccgtctgc[A/G]accccccacccttgca (SEQ ID NO: 0333) |
| 02 | exm379901 | 4 | p | p16.3 | DGKQ | 961122 | 4.35E-11 | Inf | 0.004 | 0.000 | A | gccaattgtggtcctt[A/G]tatttcagacacaagc (SEQ ID NO: 0334) |
| 03 | rs4865455 | 4 | p | p16.3 | FAM53A | 1653352 | 3.18E-03 | 1.15 | 0.355 | 0.324 | C | gcgggcccaccacatc[A/C]ccgaggaccctggcca (SEQ ID NO: 0335) |
| 03 | rs12331507 | 4 | q | q12 | KDR/SRD5A3 | 56011889 | 1.83E-04 | 0.88 | 0.304 | 0.332 | A | aaggcctgaggcagaa[C/T]aaccgggtcaagagg (SEQ ID NO: 0336) |
| 03 | rs12505096 | 4 | q | q12 | KDR/SRD5A3 | 56006102 | 4.20E-05 | 0.87 | 0.269 | 0.298 | A | accatcagcctctcac[A/G]atttttgagtagttcc (SEQ ID NO: 0337) |
| 02 | exm400714 | 4 | q | q12 | KIAA1211 | 57180701 | 5.39E-15 | 7.33 | 0.012 | 0.002 | G | tggggctgaagaatac[A/C]ttttctggtgtgactca (SEQ ID NO: 0338) |
| 02 | rs6554072 | 4 | q | q12 | SCFD2 | 54079547 | 2.04E-04 | 0.84 | 0.345 | 0.384 | G | caggctggagagcggt[A/G]gggcggcaggaggagga (SEQ ID NO: 0339) |
| 03 | rs11724057 | 4 | q | q13.1 | LPHN3 | 62686490 | 7.24E-06 | 1.23 | 0.135 | 0.113 | A | aatgaatcaagtcaga[C/G]gcattttttctactc (SEQ ID NO: 0340) |
| 02 | rs7683391 | 4 | q | q13.1 | LPHN3 | 62676117 | 2.73E-04 | 1.17 | 0.154 | 0.134 | G | ttgtaaataagtacat[A/G]agagttcttagcagga (SEQ ID NO: 0341) |
| 03 | rs1901223 | 4 | q | q13.1 | LPHN3 | 62660731 | 3.78E-04 | 1.12 | 0.434 | 0.406 | A | tctcatcctaaaatgt[A/G]aattcgaatataag (SEQ ID NO: 0342) |
| | | | | | | | | | | | | taaaagcacttacat[A/G]aataatttatgtag |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs6534447 | 4 | q | q13.3 | DKFZP56400823\|RCHY1 | 76005892 | 1.62E-04 | 0.78 | 0.062 | 0.078 | A | tgtcacttgttaatga[A/C]cttccaatcttctaag (SEQ ID NO: 343) |
| 02 | exm407053 | 4 | q | q21.1 | ART3 | 76956246 | 6.81E-08 | 13.75 | 0.004 | 0.000 | G | aagaaaataaaggac[A/G]acgatgcctaaatccc (SEQ ID NO: 344) |
| 03 | rs953534 | 4 | q | q21.22 | SCDS | 83617849 | 1.47E-03 | 1.11 | 0.332 | 0.309 | A | cagctggggagaaat[A/C]atccaaaatgcaatat (SEQ ID NO: 345) |
| 03 | rs2869362 | 4 | q | q21.23 | ARHGAP24 | 86591202 | 8.95E-03 | 1.16 | 0.083 | 0.072 | A | atttttattcagttgg[A/G]atgggfgfcgcaaa (SEQ ID NO: 346) |
| 03 | rs1482090 | 4 | q | q21.23 | ARHGAP24 | 86523580 | 3.91E-03 | 1.18 | 0.086 | 0.074 | G | ttgtgtcaggcaagt[A/G]tgttgattgataaat (SEQ ID NO: 347) |
| 03 | rs1161262 | 4 | q | q21.23 | ARHGAP24 | 86508815 | 6.41E-05 | 1.19 | 0.083 | 0.070 | G | tcatttattaaaacac[A/G]gcaatgattagaaccact (SEQ ID NO: 348) |
| 03 | rs7697141 | 4 | q | q22.1 | KIAA1680 | 92457618 | 2.43E-04 | 1.26 | 0.067 | 0.054 | A | gtctctaacctttct[A/G]ccctgcttgctcct (SEQ ID NO: 349) |
| 03 | rs6847228 | 4 | q | q22.1 | TIGD2\|GPRIN3 | 90155694 | 2.76E-04 | 1.32 | 0.045 | 0.034 | A | agggagtggaaagaaa[A/G]agtgctgcaattttt (SEQ ID NO: 350) |
| 03 | rs17020045 | 4 | q | q22.2 | GRID2 | 93892487 | 2.03E-02 | 0.93 | 0.463 | 0.482 | G | tagtacagattttat[A/G]ttgcaatcaaatccta (SEQ ID NO: 351) |
| 03 | rs1354296 | 4 | q | q22.2 | GRID2 | 94075263 | 7.45E-03 | 1.09 | 0.457 | 0.436 | A | tgttaccaactgattta[A/G]ggtacaagttttagga (SEQ ID NO: 352) |
| 03 | rs11727464 | 4 | q | q22.2 | GRID2 | 94324475 | 2.55E-04 | 0.89 | 0.399 | 0.427 | A | ccagaagtgaaactgt[A/G]ggaactgtgttcttaa (SEQ ID NO: 353) |
| 03 | rs11097364 | 4 | q | q22.2 | GRID2 | 94367364 | 4.23E-05 | 0.89 | 0.453 | 0.482 | A | taggactcattcacat[A/G]tgtgatcaagggtcct (SEQ ID NO: 354) |
| 03 | rs2174558 | 4 | q | q25 | ANK2 | 113927365 | 6.72E-03 | 1.15 | 0.106 | 0.094 | A | gttgtttgggctatcc[A/G]tcttctcaactgttta (SEQ ID NO: 355) |
| 03 | rs378405 | 4 | q | q25 | DKK2\|LOC100288317 | 108000247 | 1.62E-03 | 1.13 | 0.192 | 0.173 | A | atttagtatataataa[A/C]agtaacactacagcac (SEQ ID NO: 356) |
| 03 | rs425273 | 4 | q | q25 | DKK2\|LOC100288317 | 108016162 | 2.58E-03 | 1.13 | 0.199 | 0.180 | G | gggccccttccttgct[A/G]acctgcagtagcatgt (SEQ ID NO: 357) |
| 03 | rs852269 | 4 | q | q25 | LEF1\|LOC283456 | 109236454 | 1.95E-02 | 0.90 | 0.126 | 0.139 | G | caaagggaagtatacc[A/G]ctaaataaggaaggca (SEQ ID NO: 358) |
| 03 | rs220634 | 4 | q | q25 | LEF1\|LOC283456 | 109235238 | 1.88E-02 | 0.89 | 0.124 | 0.137 | A | cgtgggtccaggactgt[A/G]tctcagccttgcata (SEQ ID NO: 359) |
| 03 | rs1476569 | 4 | q | q26 | CAMK2D\|ARSJ | 114698696 | 3.28E-03 | 1.11 | 0.305 | 0.284 | G | tatctcagattcatgat[A/G]atggtaacttcatgt (SEQ ID NO: 360) |
| 03 | rs4629529 | 4 | q | q26 | NDST4\|TRAM1L1 | 117572163 | 1.10E-03 | 0.88 | 0.221 | 0.243 | C | tctcaccaaggtcacc[A/C]gtgacttctagctgag (SEQ ID NO: 361) |
| 03 | rs1503535 | 4 | q | q27 | LOC730456\|MAD2L1 | 120898509 | 9.10E-05 | 1.13 | 0.396 | 0.367 | G | ctaaagtactgtaa[A/G]gttaaaggatcatgt (SEQ ID NO: 362) |
| 03 | rs7684836 | 4 | q | q27 | QRFPR\|ANXA5 | 122526728 | 3.27E-03 | 1.17 | 0.096 | 0.083 | A | acaatgacttaacaat[A/C]cattcctctgatt (SEQ ID NO: 363) |
| 03 | rs10857108 | 4 | q | q28.1 | FAT4\|LOC729424 | 126780071 | 2.20E-03 | 1.14 | 0.174 | 0.157 | A | taaccttgatcactggg[A/G]ctgaagtagtgtttgt (SEQ ID NO: 364) |
| 03 | rs1911014 | 4 | q | q28.1 | FAT4\|LOC729424 | 126774098 | 7.02E-03 | 1.12 | 0.172 | 0.157 | A | cttaagaaggtacac[A/G]aaatatgtatgtatat (SEQ ID NO: 365) |
| 03 | rs958632 | 4 | q | q28.3 | PABPC4L\|LOC100289626 | 136572585 | 1.39E-03 | 1.18 | 0.109 | 0.094 | A | ccctggcaaccaaaga[A/G]gaaatatgtatgtatat (SEQ ID NO: 366) |
| 02 | rs2035469 | 4 | q | q28.3 | PABPC4L\|LOC100289626 | 136288768 | 1.19E-03 | 1.16 | 0.433 | 0.398 | G | ccctggcaaccaaaga[A/G]ggagctttacaccag (SEQ ID NO: 367) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs13435856 | 4 | q | q31.1 | SLC7A11/CCRN4L | 139535299 | 3.61E-04 | 1.36 | 0.035 | 0.026 | A | ctgcctctcagagtt[A/G]aacctgacataattta (SEQ ID NO: 368) |
| 01 | rs4835378 | 4 | q | q31.22 | LOC100287219|EDNRA | 148040980 | 3.46E-06 | 1.20 | 0.216 | 0.188 | C | gcaaatgagaataatc[A/G]tttttgtcttttcca (SEQ ID NO: 369) |
| 02 | rs3749574 | 4 | q | q31.3 | LRBA | 151207127 | 1.98E-05 | 0.86 | 0.277 | 0.307 | A | ggaatgaacttctaaa[A/C]tgctgtaatctcttga (SEQ ID NO: 370) |
| 03 | rs9995821 | 4 | q | q31.3 | SFRP2|DCHS2 | 154828366 | 4.02E-04 | 1.15 | 0.211 | 0.189 | G | tgaggtcacatgtgct[A/G]cgggtgtgcggagct (SEQ ID NO: 371) |
| 02 | rs11941518 | 4 | q | q32.1 | CTSO|PDGFC | 156950378 | 6.42E-06 | 1.22 | 0.146 | 0.123 | G | tagtcaaattcattca[A/G]tgtggctcagatatga (SEQ ID NO: 372) |
| 03 | rs6536518 | 4 | q | q32.1 | RAPGEF2|FSTL5 | 161308423 | 3.53E-04 | 1.12 | 0.463 | 0.435 | A | atgtgaacatttttt[A/G]gacaagtttaftgcta (SEQ ID NO: 373) |
| 02 | rs1898871 | 4 | q | q32.1 | RAPGEF2|FSTL5 | 161402299 | 2.83E-06 | 1.11 | 0.381 | 0.358 | A | aacacagccaacatca[A/G]ttaagcctaatttaca (SEQ ID NO: 374) |
| 02 | rs1371251 | 4 | q | q32.1 | RAPGEF2|FSTL5 | 161381482 | 1.70E-05 | 1.13 | 0.458 | 0.428 | A | ggaaaagtggaatgcc[A/G]agaacagaaaactaaga (SEQ ID NO: 375) |
| 02 | rs6827968 | 4 | q | q32.1 | RAPGEF2|FSTL5 | 161399652 | 1.96E-06 | 1.12 | 0.393 | 0.366 | A | ctctctagaagtttact[A/G]tcatctggcattcatg (SEQ ID NO: 376) |
| 02 | rs13151634 | 4 | q | q32.1 | RAPGEF2|FSTL5 | 161411394 | 2.21E-07 | 1.14 | 0.480 | 0.448 | A | ctacatggaaaattga[A/C]gtagcaaggtaggtca (SEQ ID NO: 377) |
| 02 | rs4690982 | 4 | q | q32.1 | RAPGEF2|FSTL5 | 161428827 | 2.06E-05 | 1.10 | 0.394 | 0.371 | A | agcctgtcctctgg[A/G]agtctctatcctcgt (SEQ ID NO: 378) |
| 02 | rs4690983 | 4 | q | q32.1 | RAPGEF2|FSTL5 | 161429238 | 1.58E-05 | 1.10 | 0.393 | 0.370 | A | ttccatatctcgtcc[A/G]caattagtacgccacag (SEQ ID NO: 379) |
| 03 | rs1946867 | 4 | q | q32.1 | RAPGEF2|FSTL5 | 161307463 | 1.06E-04 | 0.88 | 0.446 | 0.476 | A | catgttactatctct[A/G]taggtttgccttttg (SEQ ID NO: 380) |
| 01 | rs4525928 | 4 | q | q32.1 | RAPGEF2|FSTL5 | 161421752 | 8.63E-08 | 1.15 | 0.489 | 0.454 | C | taccaaattgtatgg[A/G]tcagtgatgcagcag (SEQ ID NO: 381) |
| 03 | rs17039615 | 4 | q | q32.1 | RAPGEF2|FSTL5 | 161406478 | 8.21E-04 | 1.14 | 0.204 | 0.183 | A | cagaactgaaataatt[A/C]tccataggatccttag (SEQ ID NO: 382) |
| 03 | rs9996901 | 4 | q | q32.2 | FSTL5 | 162482595 | 7.20E-04 | 1.19 | 0.112 | 0.096 | A | tttaagtaagccct[A/G]taggctagttgtcaag (SEQ ID NO: 383) |
| 03 | rs6536728 | 4 | q | q32.2 | NPY5R|TKTL2 | 164333380 | 3.09E-03 | 1.14 | 0.155 | 0.139 | G | catctcaaaccatgca[A/G]ttcctgaaatcacta (SEQ ID NO: 384) |
| 03 | rs10024430 | 4 | q | q32.2 | NPY5R|TKTL2 | 164295108 | 1.44E-03 | 1.33 | 0.033 | 0.025 | G | tgcaaggaaaccatt[A/G]ccagcctcctgcaatt (SEQ ID NO: 385) |
| 02 | rs1534578 | 4 | q | q32.3 | ANP32C|LOC100131276 | 165514302 | 2.48E-05 | 1.16 | 0.252 | 0.226 | G | ctgaaaataagttccc[A/G]catatatattgtagaa (SEQ ID NO: 386) |
| 03 | rs1459509 | 4 | q | q32.3 | CPE|TLL1 | 166602111 | 1.15E-02 | 1.16 | 0.076 | 0.066 | A | tgatgctataattcct[A/G]tgattttgtttgattc (SEQ ID NO: 387) |
| 03 | rs7695819 | 4 | q | q33 | AADAT|LOC441052 | 171808256 | 5.63E-05 | 1.09 | 0.232 | 0.217 | A | ctagagaagatgaagg[A/G]tatgtgcattccaggca (SEQ ID NO: 388) |
| 02 | rs1432083 | 4 | q | q33 | AADAT|LOC441052 | 171813412 | 1.91E-05 | 1.14 | 0.345 | 0.317 | G | tgctcaagcagacc[A/G]gatgagccacacatgg (SEQ ID NO: 389) |
| 02 | rs2584393 | 4 | q | q34.3 | LOC100288304|LOC100288373 | 180591910 | 1.07E-03 | 1.15 | 0.176 | 0.157 | A | agggatcaattcttac[A/G]ataaaattttaaaacc (SEQ ID NO: 390) |
| 03 | rs6852438 | 4 | q | q34.3 | LOC100288304|LOC100288373 | 182061996 | 3.50E-04 | 1.14 | 0.242 | 0.219 | G | ctgcataagccctggc[A/G]tgctaccacagcccaa (SEQ ID NO: 391) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs6837023 | 4 | q | q34.3 | LOC100288304\|LOC100288373 | 180330521 | 2.38E-04 | 1.23 | 0.088 | 0.073 | A | gtgtgtcccatgtggc[A/G]agagctcaaacaggc (SEQ ID NO: 392) |
| 03 | rs4861466 | 4 | q | q34.3 | LOC100288304\|LOC100288373 | 182064722 | 2.53E-03 | 1.10 | 0.470 | 0.446 | G | atctaagttaagttag[A/G]aatgatgaggtcaaaa (SEQ ID NO: 393) |
| 03 | rs4400034 | 4 | q | q35.1 | C4orf41 | 184586738 | 6.03E-03 | 1.14 | 0.135 | 0.121 | A | acttcatgtgtgatcca[A/C]tgtctacctccagcaa (SEQ ID NO: 394) |
| 03 | rs12108497 | 4 | q | q35.1 | CCDC111 | 185571557 | 6.43E-05 | 1.12 | 0.316 | 0.291 | A | gtgactataaaagtg[A/G]ggcctctggcagtcc (SEQ ID NO: 395) |
| 03 | rs6850330 | 4 | q | q35.1 | CDKN2AIP\|ING2 | 184415303 | 2.55E-04 | 1.26 | 0.068 | 0.055 | C | atattaatagtggct[A/C]agattaatgacgcaa (SEQ ID NO: 396) |
| 02 | rs4861551 | 4 | q | q35.1 | CLDN24\|LOC100131811 | 184362068 | 6.81E-05 | 1.15 | 0.280 | 0.253 | G | ggcaactcacagaaaa[A/G]gagagtttgaggatct (SEQ ID NO: 397) |
| 03 | rs766908 | 4 | q | q35.1 | IRF2\|CASP3 | 185468885 | 4.92E-03 | 1.15 | 0.120 | 0.107 | G | aaacaatgtgaggag[A/G]ctttatcttttacagtt (SEQ ID NO: 398) |
| 02 | rs11939575 | 4 | q | q35.2 | FAT1 | 187627792 | 3.04E-05 | 0.85 | 0.187 | 0.214 | A | tcatgatgaggacgcc[A/G]gaagagatggggagt (SEQ ID NO: 399) |
| 02 | rs13123522 | 4 | q | q35.2 | FAT1 | 187627160 | 2.65E-05 | 0.85 | 0.188 | 0.215 | G | tggcatgctgaactgt[A/G]aagaccggcttgaa (SEQ ID NO: 400) |
| 03 | rs327080 | 4 | q | q35.2 | FAT1 | 187593959 | 4.71E-04 | 0.89 | 0.305 | 0.331 | G | tccctccaattgaaggt[A/C]caggcaggaggactccaa (SEQ ID NO: 401) |
| 02 | rs2279551 | 4 | q | q35.2 | TRIML2 | 189012809 | 4.98E-03 | 1.20 | 0.062 | 0.052 | A | tcttgctcacgggtc[A/G]grgatgggaccgagt (SEQ ID NO: 402) |
| 03 | rs6849766 | 4 | q | q35.2 | ZFP42\|TRIML2 | 189010521 | 2.37E-02 | 1.10 | 0.174 | 0.161 | A | agtgtttcaaataatt[A/G]tctcacttccagtca (SEQ ID NO: 403) |
| 01 | rs4611976 | 4 | q | q35.2 | ZFP42\|TRIML2 | 188990955 | 1.78E-06 | 1.39 | 0.055 | 0.040 | C | acctgaagaaggggc[A/C]cagctgacagcttttcc (SEQ ID NO: 4004) |
| 03 | rs1895435 | 5 | p | p13.2 | GDNF\|EGFLAM | 37892952 | 8.57E-04 | 1.19 | 0.104 | 0.089 | C | catctgtgatatggc[A/C]gtttttaccctcctggc (SEQ ID NO: 405) |
| 03 | rs13362367 | 5 | p | p13.3 | LOC729862\|LOC100130803 | 29329716 | 2.03E-03 | 0.89 | 0.207 | 0.227 | A | gttttgacccottggal[A/G]acactcatgaacaacc (SEQ ID NO: 406) |
| 03 | rs12109819 | 5 | p | p13.3 | PDZD2 | 32068026 | 4.13E-02 | 0.93 | 0.302 | 0.317 | A | tgtacccatggtttt[A/G]gcatcattgactatta (SEQ ID NO: 407) |
| 03 | rs2303748 | 5 | p | p14.3 | CDH12 | 21760602 | 8.97E-04 | 1.13 | 0.279 | 0.256 | C | aagaaaagtattgatt[A/C]ctccccttgtgccttt (SEQ ID NO: 408) |
| 03 | rs6555477 | 5 | p | p15.31 | ADCY2 | 7587939 | 2.36E-04 | 1.13 | 0.316 | 0.290 | A | aagaggtggggaaac[A/G]ttgaagaatcggttg (SEQ ID NO: 409) |
| 02 | exm443730 | 5 | p | p15.31 | C5orf49 | 7831992 | 2.13E-08 | 8.93 | 0.006 | 0.001 | A | atgtgcccaagccggt[A/G]ttccttgaggctgggg (SEQ ID NO: 410) |
| 03 | rs275447 | 5 | p | p15.31 | POLS\|LOC442132 | 6825016 | 3.29E-03 | 1.13 | 0.182 | 0.164 | A | ttttctgccttcac[A/G]tgcttacttacacgcaca (SEQ ID NO: 411) |
| 03 | rs13177725 | 5 | p | p15.31 | POLS\|LOC442132 | 6795764 | 1.21E-02 | 0.90 | 0.194 | 0.210 | G | gattagtgcacttaca[A/G]gggatgaagagacca (SEQ ID NO: 412) |
| 03 | rs275442 | 5 | p | p15.31 | POLS\|LOC442132 | 6827513 | 7.70E-04 | 1.11 | 0.438 | 0.412 | A | atgaataagctaactt[A/G]agccgaaatgttaaca (SEQ ID NO: 413) |
| 03 | rs37006 | 5 | p | p15.33 | CLPTM1L\|SLC6A3 | 1355058 | 2.05E-02 | 0.93 | 0.417 | 0.435 | A | cactgcaacattttca[A/G]acttgaatctcacaga (SEQ ID NO: 414) |
| 03 | rs6861105 | 5 | p | p15.33 | IRX4\|IRX2 | 1897640 | 4.38E-04 | 0.80 | 0.064 | 0.079 | G | tgccagctgaggctcc[A/G]gcagaccacaggtttgc (SEQ ID NO: 415) |
| 03 | rs12188301 | 5 | p | p15.33 | NDUFS6\|IRX4 | 1847639 | 9.14E-05 | 0.83 | 0.108 | 0.127 | A | (SEQ ID NO: 416) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | exm442113 | 5 | p | p15.33 | TERT | 1293767 | 9.52E-14 | 7.19 | 0.011 | 0.002 | A | agaatgggatgtagc[A/G]tgagttgtgagttgtt (SEQ ID NO: 0417) |
| 03 | rs7722066 | 5 | q | q11.2 | LOC257396\|FST | 52417217 | 2.80E-04 | 0.89 | 0.386 | 0.415 | A | gctcgcagcgggcagt[A/G]cgtcttgaggagcacc (SEQ ID NO: 0418) |
| 03 | rs10060367 | 5 | q | q12.3 | FLJ46010\|MAST4 | 65859130 | 3.38E-03 | 1.12 | 0.212 | 0.193 | A | catatgtttgtgag[A/C]agatatttgtaagtt (SEQ ID NO: 0419) |
| 03 | rs10056426 | 5 | q | q12.3 | MAST4 | 66203615 | 8.76E-03 | 1.15 | 0.097 | 0.085 | G | agagtcgagtagatga[A/G]gtgtgcttcaggttt (SEQ ID NO: 0420) |
| 03 | rs26923 | 5 | q | q12.3 | MAST4 | 66170504 | 5.15E-03 | 1.16 | 0.098 | 0.086 | C | aaaattcacaaatgc[A/G]attcaagtaagttgaa (SEQ ID NO: 0421) |
| 03 | rs734828 | 5 | q | q12.3 | MAST4 | 66221262 | 6.08E-03 | 1.16 | 0.101 | 0.088 | G | tacagcagaccgaaac[A/C]atgtatttagaatta (SEQ ID NO: 0422) |
| 02 | rs12521058 | 5 | q | q13.3 | LOC728723 | 76426987 | 3.31E-05 | 1.14 | 0.416 | 0.384 | A | aattcactctaaacaac[A/G]cattaataggttcca (SEQ ID NO: 0423) |
| 03 | rs7732628 | 5 | q | q13.3 | LOC728723 | 76435346 | 4.66E-04 | 0.89 | 0.413 | 0.440 | G | aataaacgaggagacat[A/C]tggagaaaggagacct (SEQ ID NO: 0424) |
| 02 | rs2972341 | 5 | q | q13.3 | LOC728723\|PDE8B | 76468843 | 1.15E-05 | 0.90 | 0.443 | 0.468 | A | atctgagaaaatttctc[A/G]gtcactgtcacttcaa (SEQ ID NO: 0425) |
| 03 | rs6862414 | 5 | q | q13.3 | LOC728723\|PDE8B | 76454559 | 9.74E-05 | 0.90 | 0.248 | 0.269 | G | cactgattagctgatg[A/G]gactctacctatata (SEQ ID NO: 0426) |
| 03 | rs16875951 | 5 | q | q14.1 | ARSB | 78101191 | 2.19E-02 | 1.11 | 0.137 | 0.125 | A | ggacaggccacaccca[A/G]aggaaaacctggagtc (SEQ ID NO: 0427) |
| 02 | rs1129770 | 5 | q | q14.1 | CMYA5 | 79086883 | 2.40E-06 | 1.10 | 0.195 | 0.181 | A | gaacctaaactgttgt[A/G]atttataccaagtat (SEQ ID NO: 0428) |
| 03 | rs293045 | 5 | q | q15 | MCTP1 | 94289131 | 7.79E-04 | 1.33 | 0.037 | 0.028 | G | tttggtgaaggagaac[A/G]gctgcgacggagtaagta (SEQ ID NO: 0429) |
| 03 | rs1990745 | 5 | q | q21.2 | NUDT12\|RAB9P1 | 103381922 | 1.59E-03 | 1.15 | 0.150 | 0.133 | A | acttttgtgtttca[A/G]aagagtggttctctg (SEQ ID NO: 0430) |
| 03 | rs10464035 | 5 | q | q21.3 | LOC100287833\|EFNA5 | 106562841 | 2.35E-03 | 1.14 | 0.167 | 0.150 | A | cacttttggtattaatc[A/G]ttgatctgcagttag (SEQ ID NO: 0431) |
| 03 | rs10455070 | 5 | q | q21.3 | LOC100287833\|EFNA5 | 106569691 | 8.74E-03 | 1.11 | 0.186 | 0.170 | A | gacactccttgagact[A/G]caaaccacctacctgg (SEQ ID NO: 0432) |
| 03 | rs4957696 | 5 | q | q21.3 | LOC100287833\|EFNA5 | 106558682 | 2.53E-03 | 1.14 | 0.168 | 0.151 | C | aaacctaaaagatcaa[A/G]ttggctaaacacgtac (SEQ ID NO: 0433) |
| 03 | rs11749864 | 5 | q | q22.2 | MCC | 112612123 | 1.06E-02 | 1.19 | 0.058 | 0.049 | G | tccgggcattttcttcatatg (SEQ ID NO: 0434) |
| 03 | rs11740353 | 5 | q | q22.2 | MCC | 112577696 | 1.12E-02 | 1.19 | 0.057 | 0.049 | A | agaaactgagcagtgt[A/G]ttgtgcagaattggtg (SEQ ID NO: 0435) |
| 03 | rs1965429 | 5 | q | q22.2 | MCC | 112679373 | 1.09E-02 | 0.92 | 0.349 | 0.368 | C | cagcagaatagagaac[A/G]accaaatcaaacacaca (SEQ ID NO: 0436) |
| 03 | rs10519343 | 5 | q | q22.2 | MCC | 112592606 | 5.94E-03 | 1.20 | 0.058 | 0.049 | A | atggcctgtgacatag[A/C]tagcattttaataaaca (SEQ ID NO: 0437) |
| 03 | rs17333442 | 5 | q | q22.2 | YTHDC2\|KCNN2 | 112947050 | 1.27E-02 | 0.88 | 0.101 | 0.113 | C | accctaaaccattct[A/G]agggccagattaaaac (SEQ ID NO: 0438) |
| 03 | rs2112614 | 5 | q | q22.3 | CCDC112\|FEM1C | 114812584 | 1.10E-03 | 1.16 | 0.135 | 0.118 | G | aaatatgttattta[A/C]tggcagttattcttct (SEQ ID NO: 0439) |
| 03 | rs9637896 | 5 | q | q22.3 | YTHDC2\|KCNN2 | 113561408 | 9.39E-05 | 1.17 | 0.132 | 0.115 | G | taaagtaaacgtactc[A/G]tcttagcttagacaca (SEQ ID NO: 0440) |
| | | | | | | | | | | | | agaaaatcaaattttt[A/G]taagacttaccaaaaa |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2896965 | 5 | q | q23.1 | HSD17B4|FAM170A | 118921139 | 2.37E-03 | 0.87 | 0.136 | 0.153 | G | tagatggtaaccagge[A/G]tgaagagacagctgac (SEQ ID NO: 0441) |
| 03 | rs37391 | 5 | q | q23.2 | CSNK1G3|ZNF608 | 123525965 | 2.95E-04 | 0.88 | 0.308 | 0.334 | G | agacaagcagccgcctc[A/G]ttttatgtgatgtattt (SEQ ID NO: 0442) |
| 02 | rs7721313 | 5 | q | q31.1 | H2AFY | 134673961 | 3.90E-02 | 1.20 | 0.076 | 0.065 | C | ggttaagagctcagga[T/C]ttcccggagtcacaca (SEQ ID NO: 0443) |
| 03 | rs40273 | 5 | q | q31.1 | TCF7 | 133482348 | 3.98E-03 | 0.80 | 0.044 | 0.054 | G | attteagaggctgcag[A/G]acttctgcctgaacct (SEQ ID NO: 0444) |
| 02 | rs165179 | 5 | q | q31.2 | UBE2D2/UBE2D2 | 138985694 | 1.26E-05 | 1.29 | 0.074 | 0.058 | G | atgaagactgaatcccc[A/G]gagacctacacttgaa (SEQ ID NO: 0445) |
| 02 | rs10476878 | 5 | q | q32 | POU4F3|TCERG1 | 145797485 | 4.95E-05 | 0.85 | 0.194 | 0.221 | G | caaacttatcacagta[A/G]tcacatttttaaggag (SEQ ID NO: 0446) |
| 03 | rs979893 | 5 | q | q32 | POU4F3|TCERG1 | 145797020 | 8.30E-04 | 0.87 | 0.179 | 0.200 | A | agtgtgttaagcttc[A/C]tgctcagaaatgacag (SEQ ID NO: 0447) |
| 03 | rs10056189 | 5 | q | q32 | POU4F3|TCERG1 | 145804118 | 4.51E-03 | 0.87 | 0.121 | 0.136 | A | ccagtaccaccattg[A/G]agcttactgtttg (SEQ ID NO: 0448) |
| 02 | rs7718446 | 5 | q | q32 | POU4F3|TCERG1 | 145749535 | 4.40E-06 | 0.87 | 0.264 | 0.292 | G | tccaacacttaggta[A/G]gtaagtagctagttac (SEQ ID NO: 0449) |
| 02 | rs11747475 | 5 | q | q32 | POU4F3|TCERG1 | 145784922 | 5.98E-05 | 0.85 | 0.194 | 0.220 | G | cacgatgtcatgtrgtt[A/G]attgagttgtatactt (SEQ ID NO: 0450) |
| 02 | rs6886412 | 5 | q | q32 | POU4F3|TCERG1 | 145777478 | 5.42E-06 | 0.86 | 0.262 | 0.291 | G | atgcttcacgtctac[A/G]tccctaattctaacc (SEQ ID NO: 0451) |
| 02 | exm494153 | 5 | q | q32 | PPARGC1B | 149213060 | 2.10E-16 | 20.56 | 0.008 | 0.000 | A | gagagctcgtgtgc[A/C]cgtgcgggcgttctcgg (SEQ ID NO: 0452) |
| 02 | exm497501 | 5 | q | q33.1 | FAT2 | 150946613 | 4.47E-11 | Inf | 0.004 | 0.000 | G | aaacgccctttatca[A/G]tcttactgctggtcaa (SEQ ID NO: 0453) |
| 03 | rs1438937 | 5 | q | q33.1 | NMUR2|GRIA1 | 152370448 | 2.03E-04 | 0.89 | 0.412 | 0.441 | A | cccaagcaaatgatag[A/C]tattgccaattaaact (SEQ ID NO: 0454) |
| 02 | rs918509 | 5 | q | q33.2 | GALNT10 | 153762653 | 4.81E-04 | 0.88 | 0.225 | 0.249 | A | ccagtgactgccaacc[A/G]tggccacacataagca (SEQ ID NO: 0455) |
| 03 | rs954929 | 5 | q | q34 | LOC285629|GABRB2 | 160380401 | 2.37E-05 | 1.07 | 0.359 | 0.343 | A | ctctctatactacccc[A/G]tcagtgactcgctta (SEQ ID NO: 0456) |
| 02 | rs7725726 | 5 | q | q35.1 | GABRP | 170215670 | 1.65E-05 | 1.24 | 0.090 | 0.074 | A | tgagtctcttcactgal[A/G]aggtgagcttgctac (SEQ ID NO: 0457) |
| 02 | rs11134653 | 5 | q | q35.1 | GABRP | 170213757 | 6.23E-05 | 1.22 | 0.087 | 0.072 | A | cttacaactgtgccac[A/G]catatctagaatcctc (SEQ ID NO: 0458) |
| 02 | rs258878 | 5 | q | q35.2 | BOD1 | 173051169 | 1.51E-02 | 0.89 | 0.357 | 0.383 | A | accacccaggagaggtt[C/A]tctctcttcttggagc (SEQ ID NO: 0459) |
| 02 | exm505619 | 5 | q | q35.2 | EIF4E1B | 176072243 | 1.70E-12 | 50.73 | 0.005 | 0.000 | A | cctctccaactcacc[A/G]tctccagccacagccg (SEQ ID NO: 0460) |
| 03 | rs11134853 | 5 | q | q35.2 | HMP19|LOC100127922 | 173970989 | 1.81E-04 | 1.18 | 0.163 | 0.142 | C | gtagtatgaacaaaag[A/C]gccctgggcttggagt (SEQ ID NO: 0461) |
| 01 | rs2770967 | 5 | q | q35.3 | LOC100289627|TRIM52 | 180678717 | 4.44E-06 | 1.28 | 0.094 | 0.075 | G | tgtgataaatttaatc[A/G]tagtctgtgtccaaacca (SEQ ID NO: 0462) |
| 03 | rs7727897 | 5 | q | q35.3 | LOC202181 | 177047009 | 8.02E-03 | 1.15 | 0.097 | 0.085 | G | cagagtcttcccca[A/G]tctgactcttctcat (SEQ ID NO: 0463) |
| 03 | rs3940643 | 5 | q | q35.3 | RASGEF1C | 179585309 | 6.16E-04 | 1.13 | 0.302 | 0.277 | A | tttaaatacaggagac[A/G]ggggagcccaacactaa (SEQ ID NO: 0464) |
| 03 | rs4440459 | 6 | p | p12.1 | ELOVL5|GCLC | 53293410 | 8.62E-04 | 1.17 | 0.136 | 0.119 | A | (SEQ ID NO: 0465) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs9370209 | 6 | p | p12.1 | ELOVL5|GCLC | 53296156 | 4.28E-05 | 1.21 | 0.142 | 0.121 | A | tgagcctgacctccaa[A/C]acctcagcagcagcat (SEQ ID NO: 0466) |
| 03 | rs6458934 | 6 | p | p12.1 | ELOVL5|GCLC | 53291466 | 2.82E-04 | 1.18 | 0.136 | 0.117 | G | atgagggttttagaat[A/G]tatttgaatgctgaca (SEQ ID NO: 0467) |
| 03 | rs12192659 | 6 | p | p12.1 | FAM83B | 54726327 | 2.63E-04 | 1.12 | 0.485 | 0.456 | A | taactccaagttaaag[A/G]ctatttctaccacatc (SEQ ID NO: 0468) |
| 03 | rs13200042 | 6 | p | p12.1 | FAM83B|HCRTR2 | 55033223 | 2.49E-03 | 0.89 | 0.212 | 0.232 | G | tgacactgtgacagal[A/G]gaagaacccacctcca (SEQ ID NO: 0469) |
| 03 | rs3134704 | 6 | p | p12.1 | HCRTR2 | 55072273 | 1.42E-02 | 0.91 | 0.219 | 0.236 | G | tctactctggaaacag[A/G]atagagtaacagcaaa (SEQ ID NO: 0470) |
| 02 | exm555738 | 6 | p | p12.2 | GSTA5 | 52696737 | 1.81E-08 | Inf | 0.003 | 0.000 | A | atgtgatttattttaa[A/G]cctcaaccatttgaagt (SEQ ID NO: 0471) |
| 03 | rs4712023 | 6 | p | p12.2 | LOC100287869|GSTA3 | 52758653 | 6.91E-05 | 1.15 | 0.072 | 0.064 | A | cagaaacttcttcacc[A/G]tgggcaggttgctgat (SEQ ID NO: 0472) |
| 03 | rs9296695 | 6 | p | p12.2 | LOC100287869|GSTA3 | 52758076 | 4.34E-05 | 1.13 | 0.069 | 0.061 | A | taagttgttgaaccac[A/G]agcatgacagtcttta (SEQ ID NO: 0473) |
| 03 | rs2505276 | 6 | p | p12.3 | TFAP2B|LOC646517 | 51087831 | 2.04E-04 | 0.89 | 0.430 | 0.459 | A | gaaaacttgcacaaac[A/G]gagctggaaaaccatg (SEQ ID NO: 0474) |
| 03 | rs9381940 | 6 | p | p12.3 | TFAP2B|LOC646517 | 51073648 | 2.14E-03 | 0.91 | 0.383 | 0.406 | A | cagaggatgccagttt[A/G]cttgaatgccaaaatt (SEQ ID NO: 0475) |
| 03 | rs3187 | 6 | p | p21.1 | CAPN11 | 44143862 | 1.57E-14 | Inf | 0.005 | 0.000 | A | tcatttgatcactct[A/G]tggcatttgacactt (SEQ ID NO: 0476) |
| 02 | rs9381299 | 6 | p | p21.1 | SLC29A1|HSP90AB1 | 44211867 | 4.19E-05 | 1.14 | 0.141 | 0.126 | G | gctggtgagagggcac[A/G]cttactctgtgactgg (SEQ ID NO: 0477) |
| 03 | rs3187 | 6 | p | p21.1 | SLC35B2 | 44222047 | 6.79E-05 | 1.20 | 0.106 | 0.091 | A | aaaggaacagagcccc[A/G]ttagagaaccatagc (SEQ ID NO: 0478) |
| 02 | exm542389 | 6 | p | p21.31 | ETV7 | 36339143 | 2.60E-19 | 8.74 | 0.002 | 0.002 | A | cattggagcctacacc[A/G]cttgtgctttctcac (SEQ ID NO: 0479) |
| 03 | rs2499724 | 6 | p | p21.31 | GRM4 | 34086671 | 1.08E-02 | 0.89 | 0.441 | 0.468 | C | ggtctgttccttcccc[C/G]cgaatgccgcaggccc (SEQ ID NO: 0480) |
| 03 | rs2451330 | 6 | p | p21.31 | GRM4|HMGA1 | 34118586 | 8.40E-05 | 0.88 | 0.380 | 0.411 | G | aatgaattacaacgta[A/C]aaactggaaccaaaac (SEQ ID NO: 0481) |
| 03 | rs914813 | 6 | p | p21.31 | GRM4|HMGA1 | 34103954 | 1.44E-05 | 0.87 | 0.358 | 0.392 | G | agttgagggaagccag[A/G]tgtgaaattcctcctgc (SEQ ID NO: 0482) |
| 02 | rs2070600 | 6 | p | p21.32 | AGER | 32151443 | 1.63E-04 | 0.73 | 0.038 | 0.051 | A | tagggataaaaatacc[A/G]tgaagtcataggat (SEQ ID NO: 0483) |
| 02 | rs176248 | 6 | p | p21.32 | BRD2|HLA-DOA | 32965942 | 2.07E-05 | 0.85 | 0.244 | 0.275 | A | tcgtgtcctcccaac[A/G]gctcctccttcttcc (SEQ ID NO: 0484) |
| 02 | rs2076524 | 6 | p | p21.32 | BTNL2 | 32370684 | 6.48E-03 | 0.91 | 0.268 | 0.287 | G | agaagagagagtaa[A/G]tgtattccaccaagaa (SEQ ID NO: 0485) |
| 03 | rs2076525 | 6 | p | p21.32 | BTNL2 | 32370616 | 4.01E-03 | 0.90 | 0.267 | 0.287 | G | tcctgctgatctgagc[A/G]tgtgggtcctagaggc (SEQ ID NO: 0486) |
| 03 | rs2395175 | 6 | p | p21.32 | BTNL2|HLA-DRA | 32405026 | 1.78E-03 | 0.87 | 0.150 | 0.168 | A | tttatcaagagacatt[A/G]tctatcatatagcaat (SEQ ID NO: 0487) |
| 03 | rs3763316 | 6 | p | p21.32 | BTNL2|HLA-DRA | 32376746 | 5.49E-03 | 0.91 | 0.267 | 0.287 | A | ctgcaacatcagcaga[A/G]gcttcctgctgggttcc (SEQ ID NO: 0488) |
| 03 | rs2073045 | 6 | p | p21.32 | C6orf10 | 32239548 | 2.82E-03 | 0.91 | 0.350 | 0.373 | A | ctaagggaggtgact[A/G]gtaagtttcaggtgc (SEQ ID NO: 0489) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2050188 | 6 | p | p21.32 | C6orf10|BTNL2 | 32339897 | 1.47E-03 | 1.11 | 0.365 | 0.341 | G | tacaaagattaatgat[A/G]tacaatctctggcctt (SEQ ID NO: 0490) |
| 03 | rs9268474 | 6 | p | p21.32 | C6orf10|BTNL2 | 32357165 | 4.56E-03 | 0.90 | 0.267 | 0.287 | G | tatttcttgatgaaat[A/G]tgtaagcctcccttta (SEQ ID NO: 0491) |
| 03 | rs9268461 | 6 | p | p21.32 | C6orf10|BTNL2 | 32351901 | 1.33E-02 | 0.92 | 0.268 | 0.286 | A | tttggtgccttcctac[A/C]gttatggaaggaagct (SEQ ID NO: 0492) |
| 03 | rs9268456 | 6 | p | p21.32 | C6orf10|BTNL2 | 32349946 | 6.07E-03 | 0.91 | 0.268 | 0.287 | A | cctatagtcaagtaag[A/C]ctgtaataataaatat (SEQ ID NO: 0493) |
| 03 | rs9268403 | 6 | p | p21.32 | C6orf10|BTNL2 | 32341473 | 6.93E-03 | 0.91 | 0.268 | 0.287 | G | gggagatcttcttacac[A/G]tgatgttttattcaga (SEQ ID NO: 0494) |
| 03 | rs9268425 | 6 | p | p21.32 | C6orf10|BTNL2 | 32344376 | 8.36E-03 | 0.91 | 0.268 | 0.287 | A | agaaatccacttagat[A/G]tctaccctacttcccc (SEQ ID NO: 0495) |
| 03 | rs9268428 | 6 | p | p21.32 | C6orf10|BTNL2 | 32344973 | 5.96E-03 | 0.91 | 0.268 | 0.287 | A | tttcttaacacagcag[A/C]aaaattgttttatgtc (SEQ ID NO: 0496) |
| 03 | rs2894252 | 6 | p | p21.32 | C6orf10|BTNL2 | 32345443 | 6.38E-03 | 0.91 | 0.268 | 0.287 | A | gtagatttctaatctta[A/G]gcccttttgccatagac (SEQ ID NO: 0497) |
| 03 | rs2395157 | 6 | p | p21.32 | C6orf10|BTNL2 | 32348145 | 6.94E-03 | 0.91 | 0.268 | 0.287 | G | agaaataaaaactat[A/G]taatcttagatggcac (SEQ ID NO: 0498) |
| 03 | rs9268454 | 6 | p | p21.32 | C6orf10|BTNL2 | 32349711 | 6.03E-03 | 0.91 | 0.268 | 0.287 | G | ataacactgatgatat[A/G]gatttgaggtgagaa (SEQ ID NO: 0499) |
| 02 | rs1061807 | 6 | p | p21.32 | EGFL8/AGPAT1 | 32136838 | 1.27E-05 | 1.18 | 0.264 | 0.234 | A | gggggtcaagagtgga[A/G]actgcaccgaggcaag (SEQ ID NO: 0500) |
| 02 | exm536563 | 6 | p | p21.32 | HLA-DQA2 | 32714067 | 3.35E-29 | Inf | 0.026 | 0.000 | A | agagactttggtctgc[A/G]ccctgggggttgctgt (SEQ ID NO: 0501) |
| 02 | exm536439 | 6 | p | p21.32 | HLA-DQB1 | 32634282 | 2.16E-08 | 5.59 | 0.007 | 0.001 | G | ctgcacttaccggaag[A/G]gtctctgccctcagcc (SEQ ID NO: 0502) |
| 03 | rs1964995 | 6 | p | p21.32 | HLA-DRA|HLA-DRB5 | 32449411 | 2.88E-03 | 0.91 | 0.417 | 0.440 | G | agaatcaaggaataag[A/G]aaaataatgtgagctg (SEQ ID NO: 0503) |
| 03 | rs9267833 | 6 | p | p21.32 | NOTCH4 | 32177900 | 8.69E-04 | 1.13 | 0.272 | 0.249 | G | catctcttcaggaag[A/G]tgtccctaactctcc (SEQ ID NO: 0504) |
| 02 | rs206015 | 6 | p | p21.32 | NOTCH4 | 32182759 | 6.17E-05 | 0.81 | 0.098 | 0.118 | A | ttcgccctgggattta[A/G]tgctcttctttctgct (SEQ ID NO: 0505) |
| 03 | rs2071277 | 6 | p | p21.32 | NOTCH4 | 32171683 | 3.77E-04 | 1.12 | 0.510 | 0.482 | G | tgatgcagtgtgtgac[A/G]tctaatctccccccata (SEQ ID NO: 0506) |
| 02 | rs206016 | 6 | p | p21.32 | NOTCH4 | 32181182 | 4.04E-05 | 0.81 | 0.096 | 0.116 | A | tatatgatatttttatt[A/G]tttttagataggggtct (SEQ ID NO: 0507) |
| 03 | rs394657 | 6 | p | p21.32 | NOTCH4 | 32187023 | 7.27E-04 | 1.11 | 0.469 | 0.442 | G | ggagcattctgggttg[A/G]cctgagcaaggctgc (SEQ ID NO: 0508) |
| 03 | rs3134799 | 6 | p | p21.32 | NOTCH4 | 32184221 | 6.64E-04 | 1.11 | 0.464 | 0.438 | A | tctgcttatctttcaa[A/G]actcatctcagccatc (SEQ ID NO: 0509) |
| 02 | rs2071286 | 6 | p | p21.32 | NOTCH4 | 32179896 | 6.41E-05 | 1.16 | 0.225 | 0.200 | A | tccagctacactcaac[A/G]catttcacccacccc (SEQ ID NO: 0510) |
| 03 | rs9357138 | 6 | p | p21.32 | NOTCH4|C6orf10 | 32219838 | 2.54E-03 | 1.14 | 0.154 | 0.138 | A | tattaattgccccaga[A/G]atctatcctcacatcc (SEQ ID NO: 0511) |
| 03 | rs9267810 | 6 | p | p21.32 | PPT2 | 32121594 | 3.97E-06 | 1.18 | 0.269 | 0.237 | G | tctgctccgcagcag[A/G]acacgaagtttgcatt (SEQ ID NO: 0512) |
| 02 | rs2269424 | 6 | p | p21.32 | PPT2|EGFL8 | 32132233 | 9.13E-06 | 1.18 | 0.265 | 0.234 | A | tctggtccgcagcag[A/G]acacgaagtttgcatt (SEQ ID NO: 0513) |
| 03 | rs35502919 | 6 | p | p21.33 | BAT2 | 31604355 | 1.15E-04 | 0.72 | 0.034 | 0.047 | A | ggagccctttgctggg[A/G]tgggggatgaggttagt (SEQ ID NO: 0514) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs3130977 | 6 | p | p21.33 | C6orf15|PSORS1C1 | 31081989 | 6.61E-04 | 0.89 | 0.310 | 0.335 | G | ctgggccaaagtgg[A/C]ttttctccctcaggggg (SEQ ID NO: 0515) |
| 02 | exm-rs407283 | 6 | p | p21.33 | C6orf25 | 31692970 | 1.15E-13 | Inf | 0.017 | 0.003 | A | aagtctggaatcagcal[A/G]aaatgtattacattga (SEQ ID NO: 0516) |
| 03 | rs3132550 | 6 | p | p21.33 | CDSN | 31086048 | 3.46E-04 | 0.87 | 0.212 | 0.236 | A | atagaataagtgcta[A/G]actggagttggaga (SEQ ID NO: 0517) |
| 03 | rs2844456 | 6 | p | p21.33 | EHMT2 | 31864674 | 1.55E-04 | 0.73 | 0.035 | 0.048 | G | gtgagagcccagcg[A/G]ggtcaggaatggaaac (SEQ ID NO: 0518) |
| 02 | rs9263582 | 6 | p | p21.33 | HCG22|C6orf15 | 31070664 | 4.06E-05 | 0.77 | 0.063 | 0.080 | A | gctaaaacggggcccca[A/G]ttggaccgtcacttc (SEQ ID NO: 0519) |
| 01 | rs35718543 | 6 | p | p21.33 | HCG27|HLA-C | 31177845 | 1.38E-06 | 1.28 | 0.106 | 0.085 | A | cacttaaagcccaaag[A/G]ggccggctgtggtgg (SEQ ID NO: 0520) |
| 03 | rs2534457 | 6 | p | p21.33 | HLA-B|MICA | 31365707 | 3.63E-03 | 0.90 | 0.292 | 0.313 | G | tgtggatcttcagcac[A/G]tctacaactccctcca (SEQ ID NO: 0521) |
| 02 | rs2853925 | 6 | p | p21.33 | HLA-C|HLA-B | 31264922 | 1.63E-05 | 0.81 | 0.112 | 0.135 | G | acaaaccttcttggaa[A/G]gtggaaagttttgcaa (SEQ ID NO: 0522) |
| 02 | rs9264869 | 6 | p | p21.33 | HLA-C|HLA-B | 31271630 | 1.33E-05 | 0.81 | 0.112 | 0.135 | G | acaaaagctaccagaf[A/G]aaaacactcactagg (SEQ ID NO: 0523) |
| 02 | rs7759127 | 6 | p | p21.33 | HLA-C|HLA-B | 31240988 | 5.21E-06 | 0.80 | 0.110 | 0.133 | C | cctgaagatcgagt[A/G]atcaagaccagtgtt (SEQ ID NO: 0524) |
| 02 | rs2524043 | 6 | p | p21.33 | HLA-C|HLA-B | 31257012 | 1.42E-05 | 0.81 | 0.112 | 0.135 | G | aftcggtattaafac[A/C]ttttgtgtgactgcct (SEQ ID NO: 0525) |
| 02 | rs2524132 | 6 | p | p21.33 | HLA-C|HLA-B | 31264912 | 1.67E-05 | 0.81 | 0.112 | 0.135 | A | ctttcatttattgaac[A/G]ccttagatatgagcta (SEQ ID NO: 0526) |
| 02 | rs364415 | 6 | p | p21.33 | HLA-C|HLA-B | 32273224 | 1.33E-05 | 0.81 | 0.112 | 0.135 | A | ttacagctcaacaaa[A/G]ctaccagataaaaaca (SEQ ID NO: 0527) |
| 02 | rs3873385 | 6 | p | p21.33 | HLA-C|HLA-B | 31269308 | 1.91E-05 | 0.84 | 0.137 | 0.159 | A | ggaggaagtgtgggt[A/G]tgggtagactcctcct (SEQ ID NO: 0528) |
| 02 | rs9264870 | 6 | p | p21.33 | HLA-C|HLA-B | 31271662 | 1.51E-05 | 0.81 | 0.113 | 0.135 | A | gtgtgtgatgcagtat[A/G]gggtagaaccaggaga (SEQ ID NO: 0529) |
| 02 | rs2524160 | 6 | p | p21.33 | HLA-C|HLA-B | 31259854 | 1.77E-05 | 0.81 | 0.113 | 0.135 | A | ttcacactggaaat[A/G]aggtggaaaaggagaa (SEQ ID NO: 0530) |
| 02 | rs2524048 | 6 | p | p21.33 | HLA-C|HLA-B | 31256561 | 1.56E-05 | 0.81 | 0.112 | 0.135 | G | gttttgtgataaggagc[A/G]ltgggggaggagatttg (SEQ ID NO: 0531) |
| 03 | rs2524050 | 6 | p | p21.33 | HLA-C|HLA-B | 31255541 | 5.39E-05 | 0.82 | 0.109 | 0.130 | G | tttaaggaggctaact[A/G]cttccacattagatca (SEQ ID NO: 0532) |
| 02 | rs2524162 | 6 | p | p21.33 | HLA-C|HLA-B | 31259750 | 4.11E-05 | 0.82 | 0.123 | 0.146 | A | cttttttgtcttcccc[A/G]tgcattcgcccccaca (SEQ ID NO: 0533) |
| 02 | rs2524115 | 6 | p | p21.33 | HLA-C|HLA-B | 31265554 | 1.44E-05 | 0.81 | 0.112 | 0.135 | A | gacccaacagtaagac[A/G]ttttctccttttgdtaa (SEQ ID NO: 0534) |
| 01 | rs2853930 | 6 | p | p21.33 | HLA-C|HLA-B | 31255424 | 3.02E-06 | 0.79 | 0.106 | 0.131 | C | cgttgaagaatcagta[A/C]aatttggagactttga (SEQ ID NO: 0535) |
| 03 | rs13220225 | 6 | p | p21.33 | IER3|DDR1 | 30747802 | 1.36E-04 | 1.17 | 0.187 | 0.165 | A | atcctgcacttttcc[A/C]gtcaaatcccattcc (SEQ ID NO: 0536) |
| 02 | rs28780111 | 6 | p | p21.33 | IER3|DDR1 | 30720311 | 4.13E-05 | 1.18 | 0.188 | 0.164 | A | taagaagactcacc[A/G]ttctgaggctgtctga (SEQ ID NO: 0537) |
| 02 | rs2535323 | 6 | p | p21.33 | IER3|DDR1 | 30718180 | 3.71E-05 | 1.18 | 0.196 | 0.171 | G | tccttcccagaaaacc[A/G]cctcagggctcaccc (SEQ ID NO: 0538) |
| | | | | | | | | | | | | gaactggaatgaagaaa[A/G]taacctcaactgcta |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs10947091 | 6 | p | p21.33 | IER3/DDR1 | 30747216 | 1.51E-03 | 1.11 | 0.322 | 0.299 | A | agtcctactcagata[A/G]cagaactcacaaactt (SEQ ID NO: 539) |
| 03 | rs986475 | 6 | p | p21.33 | LST1/NCR3 | 31556709 | 8.74E-04 | 1.19 | 0.100 | 0.086 | G | ggtcaaatagtaattt[A/G]ttgggtgaatgacagt (SEQ ID NO: 540) |
| 03 | rs6916921 | 6 | p | p21.33 | NFKBIL1 | 31520426 | 8.60E-04 | 1.19 | 0.104 | 0.088 | A | attaccagatcaaac[A/G]ttctcaatgtcttta (SEQ ID NO: 541) |
| 03 | rs9263699 | 6 | p | p21.33 | PSORS1C1 | 31093699 | 1.16E-03 | 1.14 | 0.211 | 0.191 | A | tggaagaatgtgtcca[A/G]gctgtgcttcccctt (SEQ ID NO: 542) |
| 03 | rs3815087 | 6 | p | p21.33 | PSORS1C1 | 31093587 | 6.83E-04 | 1.14 | 0.213 | 0.192 | A | ccatcaccccgacc[A/G]tgggtcatgccagt (SEQ ID NO: 543) |
| 03 | rs9263715 | 6 | p | p21.33 | PSORS1C1 | 31095801 | 6.12E-04 | 1.14 | 0.211 | 0.190 | A | tcctctctgtagacc[A/G]ctggctcatgaaataa (SEQ ID NO: 544) |
| 03 | rs9468877 | 6 | p | p21.33 | PSORS1C3 | 31142903 | 3.81E-04 | 1.16 | 0.160 | 0.141 | A | cagactgctggctctg[A/G]gcatctgagcagcgcc (SEQ ID NO: 545) |
| 03 | rs9393228 | 6 | p | p22.3 | FLJ22536 | 22112043 | 1.16E-03 | 1.11 | 0.437 | 0.412 | A | aggggtttgaatg[A/G]catttctcattgctaa (SEQ ID NO: 546) |
| 03 | rs952578 | 6 | p | p22.3 | FLJ22536 | 21884519 | 1.16E-03 | 1.11 | 0.357 | 0.333 | A | agaatagacgtgttag[A/G]aaccaggttagctgg (SEQ ID NO: 547) |
| 03 | rs199091 | 6 | p | p22.3 | LOC389370/LOC100129616 | 23533562 | 1.76E-04 | 1.13 | 0.359 | 0.331 | G | tctggggtatttg[A/G]gggaacagagaacat (SEQ ID NO: 548) |
| 01 | rs6907340 | 6 | p | p22.3 | RNF144B/ID4 | 19803768 | 3.67E-10 | 1.20 | 0.416 | 0.373 | A | ttgatgaatggtgatat[A/G]gaatgattaataacca (SEQ ID NO: 549) |
| 02 | rs7759616 | 6 | p | p22.3 | RNF144B/ID4 | 19794585 | 1.70E-05 | 1.14 | 0.521 | 0.487 | A | tgatgggagaaatat[A/G]gaattcaacttgtagc (SEQ ID NO: 550) |
| 02 | rs760794 | 6 | p | p22.3 | RNF144B/ID4 | 19790560 | 1.84E-07 | 1.17 | 0.469 | 0.431 | A | tttttccctgaaactc[A/G]gccaaaagttttcct (SEQ ID NO: 551) |
| 01 | rs6904518 | 6 | p | p22.3 | RNF144B/ID4 | 19798704 | 7.31E-10 | 1.19 | 0.426 | 0.385 | G | gctataftaaagaaa[A/G]tagacttcaaagcaaa (SEQ ID NO: 552) |
| 02 | rs7766034 | 6 | p | p22.3 | RNF144B/ID4 | 19753061 | 5.48E-06 | 1.15 | 0.464 | 0.429 | A | aggggcctaagcccag[A/G]tgtcagaggcacagta (SEQ ID NO: 553) |
| 02 | rs6916251 | 6 | p | p22.3 | RNF144B/ID4 | 19761215 | 3.39E-07 | 1.16 | 0.465 | 0.428 | G | gtttcagccacctct[A/G]tttccattccctaaa (SEQ ID NO: 554) |
| 02 | rs6920825 | 6 | p | p22.3 | RNF144B/ID4 | 19732492 | 6.00E-05 | 1.16 | 0.223 | 0.198 | G | gacgcagtctgtaggc[A/G]tctggcaagtgttgc (SEQ ID NO: 555) |
| 02 | rs6456259 | 6 | p | p22.3 | RNF144B/ID4 | 19761718 | 5.65E-05 | 1.18 | 0.180 | 0.157 | G | tccccfgccactccct[A/G]tttaatgcctttgtaa (SEQ ID NO: 556) |
| 01 | rs2206034 | 6 | p | p22.3 | RNF144B/ID4 | 19796863 | 2.22E-08 | 1.16 | 0.479 | 0.441 | A | gtgtgagggactcctc[A/G]taactcctgggcaagg (SEQ ID NO: 557) |
| 02 | rs2223361 | 6 | p | p22.3 | RNF144B/ID4 | 19790809 | 1.76E-07 | 1.17 | 0.469 | 0.431 | A | gttgtcatgaagttacc[A/G]tgattaaagtggtgga (SEQ ID NO: 558) |
| 01 | rs6903595 | 6 | p | p22.3 | RNF144B/ID4 | 19798141 | 9.39E-09 | 1.18 | 0.423 | 0.383 | A | tataatcttgtctca[A/G]tagtcaaatacttaga (SEQ ID NO: 559) |
| 02 | rs7739264 | 6 | p | p22.3 | RNF144B/ID4 | 19785588 | 3.29E-05 | 0.90 | 0.451 | 0.477 | G | tcccatagctatcca[A/G]ttgagccagaaccatt (SEQ ID NO: 560) |
| 03 | rs2842934 | 6 | p | p22.3 | TPMT | 18139214 | 2.14E-03 | 1.12 | 0.236 | 0.216 | G | tgcgatcacctggatt[A/G]atggccaactaatgctc (SEQ ID NO: 561) |
| 03 | rs2842947 | 6 | p | p22.3 | TPMT | 18132822 | 1.62E-03 | 1.12 | 0.237 | 0.216 | G | (SEQ ID NO: 562) |
| 03 | rs2842950 | 6 | p | p22.3 | TPMT | 18135178 | 3.62E-03 | 1.11 | 0.233 | 0.215 | A | tctgaggtgagtct[A/G]aggatactgctctag (SEQ ID NO: 563) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs9462160 | 6 | p | p24.1 | LOC389369\|HIVEP1 | 11834883 | 1.60E-06 | 1.12 | 0.277 | 0.254 | G | agtctagccaggctcc[A/G]tagaaactgagtgcc (SEQ ID NO: 0564) |
| 03 | rs12193156 | 6 | p | p24.1 | PHACTR1 | 13205570 | 4.07E-03 | 0.90 | 0.264 | 0.285 | G | gaattttggaattcag[A/G]tatcagaaaaaagctg (SEQ ID NO: 0565) |
| 03 | rs201051 | 6 | p | p25.1 | LY86\|RREB1 | 6721713 | 1.50E-04 | 1.15 | 0.261 | 0.236 | A | agttatgtaaacaggal[A/G]gtrgcagcatagtgtct (SEQ ID NO: 0566) |
| 02 | rs11242762 | 6 | p | p25.2 | LOC100128372\|C6orf195 | 2379182 | 2.87E-05 | 0.88 | 0.446 | 0.477 | G | ttattcatccttatg[A/G]ccttttcttgtataggt (SEQ ID NO: 0567) |
| 03 | rs9503159 | 6 | p | p25.2 | LOC100128372\|C6orf195 | 2371304 | 7.88E-05 | 0.88 | 0.445 | 0.476 | G | atatatcattttatt[A/G]atttccagtcacctt (SEQ ID NO: 0568) |
| 03 | rs4959652 | 6 | p | p25.2 | LOC100128372\|C6orf195 | 2386913 | 8.38E-05 | 1.10 | 0.420 | 0.397 | A | cgtaccatgtgtcac[A/G]agtacacatgctttc (SEQ ID NO: 0569) |
| 03 | rs1715026 | 6 | q | q11.1 | KHDRBS2 | 62515691 | 2.76E-02 | 1.08 | 0.287 | 0.271 | G | aatcattttcaaaa[A/G]tgtagtcttttgag (SEQ ID NO: 0570) |
| 03 | rs6929584 | 6 | q | q13 | BAI3\|LMBRD1 | 70382870 | 8.84E-04 | 0.83 | 0.084 | 0.099 | G | aggaggtaggtagatc[A/C]tagaggttgtcccac (SEQ ID NO: 0571) |
| 03 | rs11114785 | 6 | q | q13 | BAI3\|LMBRD1 | 70367148 | 4.75E-03 | 0.89 | 0.180 | 0.198 | A | ctttgaagtccttctg[A/G]aaaataccctaaattag (SEQ ID NO: 0572) |
| 02 | exm563585 | 6 | q | q14.2 | SNAP91 | 84303230 | 3.86E-09 | 4.18 | 0.011 | 0.003 | G | aaccactccactaagt[A/G]ccttcagtcgtgctc (SEQ ID NO: 0573) |
| 03 | rs9359587 | 6 | q | q14.3 | KIAA1009\|TBX18 | 85105960 | 4.29E-05 | 1.15 | 0.232 | 0.208 | G | ctccgctgccaccgcc[A/G]ccactgctcctctgc (SEQ ID NO: 0574) |
| 03 | rs9294298 | 6 | q | q14.3 | KIAA1009\|TBX18 | 85147411 | 8.77E-05 | 0.92 | 0.385 | 0.405 | A | tttgccatactaattt[A/G]aaagtctaagtatctt (SEQ ID NO: 0575) |
| 03 | rs4053608 | 6 | q | q15 | BACH2 | 90787599 | 2.00E-03 | 1.11 | 0.290 | 0.268 | A | gcctagtcactaagt[A/G]aaagtctaagtatctt (SEQ ID NO: 0576) |
| 03 | rs9342219 | 6 | q | q15 | BACH2 | 90756453 | 6.39E-03 | 1.10 | 0.305 | 0.285 | A | ttcaggattagatgct[A/G]agaacttcaaatcagtc (SEQ ID NO: 0577) |
| 03 | rs453561 | 6 | q | q15 | GABRR1 | 89904872 | 1.78E-03 | 1.11 | 0.404 | 0.380 | A | acttgtttaacaaaagc[A/G]tctctataggctgtg (SEQ ID NO: 0578) |
| 03 | rs6908196 | 6 | q | q16.2 | PRDM13\|MCHR2 | 100185261 | 6.25E-04 | 0.90 | 0.400 | 0.427 | C | aagataaataagaacaa[A/G]taacacattaaaaagc (SEQ ID NO: 0579) |
| 03 | rs2198337 | 6 | q | q16.3 | FLJ10088\|HACE1 | 104756256 | 1.56E-03 | 1.16 | 0.139 | 0.123 | A | atgggcaaacttctct[A/C]atgctaacagtgatga (SEQ ID NO: 0580) |
| 03 | rs9386412 | 6 | q | q16.3 | FLJ10088\|HACE1 | 104760556 | 7.99E-04 | 1.17 | 0.139 | 0.122 | A | crgtcttcattcctcc[A/G]gctactatcctacce (SEQ ID NO: 0581) |
| 03 | rs6918769 | 6 | q | q16.3 | FLJ10088\|HACE1 | 10495247 | 12.49E-03 | 1.17 | 0.100 | 0.087 | A | tactgccaaactccaa[A/C]tcaaaatagctagggc (SEQ ID NO: 0582) |
| 03 | rs404900 | 6 | q | q16.3 | FLJ10088\|HACE1 | 104765922 | 7.45E-04 | 1.16 | 0.145 | 0.127 | C | ctgtcgtctaggagta[A/G]catcaggaagtgtctg (SEQ ID NO: 0583) |
| 02 | rs2852525 | 6 | q | q16.3 | GRIK2 | 101875714 | 1.52E-05 | 0.88 | 0.433 | 0.466 | C | acctagatctttctc[A/C]ttctcttcatacacat (SEQ ID NO: 0584) |
| 03 | rs77599386 | 6 | q | q16.3 | HACE1\|LOC100129852 | 105378954 | 8.66E-05 | 0.91 | 0.302 | 0.323 | G | attgctagcatttatt[A/C]agtgaatgaataatg (SEQ ID NO: 0585) |
| 03 | rs314286 | 6 | q | q16.3 | LIN28B | 105436053 | 3.63E-04 | 0.89 | 0.309 | 0.335 | G | agcctcaaaggtagca[A/G]cctttagaaagaaaaa (SEQ ID NO: 0586) |
| 03 | rs369065 | 6 | q | q16.3 | LIN28B | 105444058 | 6.34E-04 | 0.89 | 0.314 | 0.339 | G | aaaaactctgtagcta[A/G]tatcatgcttaatgat (SEQ ID NO: 0587) |
| | | | | | | | | | | | | tttctgatggccatcca[A/G]tccagaagcaaatccct |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs314272 | 6 | q | q16.3 | LIN28B | 105462004 | 7.45E-04 | 0.90 | 0.417 | 0.443 | G | tagtttgaaacctat[A/G]atgttctttgaaacct (SEQ ID NO: 0588) |
| 03 | rs453530 | 6 | q | q16.3 | LOC100287035|SIM1 | 100829135 | 1.39E-03 | 1.34 | 0.031 | 0.024 | A | agagcatcctaaatcc[A/G]actcttagggaagac (SEQ ID NO: 0589) |
| 03 | rs7769704 | 6 | q | q22.31 | PKIB | 122998592 | 8.72E-03 | 0.92 | 0.321 | 0.340 | G | ctgtgctgcttaccat[A/G]tatggatgagggttg (SEQ ID NO: 0590) |
| 02 | rs7774820 | 6 | q | q22.31 | TRDN | 123955723 | 2.22E-05 | 1.16 | 0.051 | 0.045 | G | aaaagactgggagaag[A/G]caattgtagctaggc (SEQ ID NO: 0591) |
| 03 | rs3757169 | 6 | q | q23.3 | MAP3K5|PEX7 | 137142946 | 1.24E-03 | 1.11 | 0.434 | 0.409 | G | ggtatatggttaagat[A/G]atcatacgactgtt (SEQ ID NO: 0592) |
| 03 | rs899894 | 6 | q | q23.3 | PDE7B | 136392020 | 1.13E-03 | 1.11 | 0.409 | 0.385 | G | tcaattgttcatttgg[A/G]caagagtttggtttg (SEQ ID NO: 0593) |
| 03 | rs1013020 | 6 | q | q23.3 | PDE7B | 136394895 | 1.00E-03 | 1.11 | 0.412 | 0.387 | A | tccagattttactat[A/G]tgtggctgtaaaatg (SEQ ID NO: 0594) |
| 03 | rs844562 | 6 | q | q24.3 | SAMD5|SASH1 | 147908995 | 9.13E-05 | 1.11 | 0.438 | 0.413 | A | taaacttagacatgaa[A/G]tagaagaaggaggtta (SEQ ID NO: 0595) |
| 03 | rs2294806 | 6 | q | q24.3 | SAMD5|SASH1 | 148183190 | 1.94E-04 | 1.13 | 0.381 | 0.353 | G | ataaagaaggtaaaa[A/G]ctcagaaggccaaagg (SEQ ID NO: 0596) |
| 03 | rs6924763 | 6 | q | q24.3 | STXBP5 | 147685480 | 3.09E-03 | 1.13 | 0.173 | 0.156 | A | catgattaaagtatc[A/G]tcttcagacatctgt (SEQ ID NO: 0597) |
| 03 | rs12201953 | 6 | q | q25.1 | UST|MAP3K7IP2 | 149546620 | 4.05E-03 | 1.30 | 0.032 | 0.025 | A | gcctggtattcatgg[A/G]tcatgtcaaaaaact (SEQ ID NO: 0598) |
| 03 | rs1544041 | 6 | q | q25.3 | ARID1B | 157408118 | 1.80E-04 | 0.86 | 0.169 | 0.193 | G | acactttaaataacgtt[A/G]tccaagaaagtgaaaa (SEQ ID NO: 0599) |
| 03 | rs240863 | 6 | q | q25.3 | FNDC1|SOD2 | 159915825 | 1.87E-05 | 1.21 | 0.149 | 0.127 | A | tggtcattcgaccttc[A/G]cccccataatagtggt (SEQ ID NO: 0600) |
| 03 | rs2201886 | 6 | q | q25.3 | NOX3|ARID1B | 155999177 | 1.87E-04 | 0.89 | 0.378 | 0.407 | A | ggccaatctaacacaa[A/G]cattgactagtgggttc (SEQ ID NO: 0601) |
| 03 | rs7739122 | 6 | q | q25.3 | NOX3|ARID1B | 155998741 | 7.46E-05 | 1.10 | 0.319 | 0.298 | G | tatggtctgctgagtc[A/G]ataatctatgttttta (SEQ ID NO: 0602) |
| 03 | rs6913088 | 6 | q | q25.3 | NOX3|ARID1B | 155970936 | 3.43E-03 | 1.10 | 0.512 | 0.488 | G | ctgtgtataattcaaa[A/G]catctcattttttgtt (SEQ ID NO: 0603) |
| 02 | rs9397831 | 6 | q | q25.3 | NOX3|ARID1B | 155994436 | 3.48E-06 | 1.12 | 0.419 | 0.393 | G | aacaatcacaatttc[A/G]ttgatttatctcccca (SEQ ID NO: 0604) |
| 02 | rs16892910 | 6 | q | q26 | PARK2 | 162096342 | 1.20E-02 | 1.11 | 0.169 | 0.155 | A | gatacctatgtgacc[A/G]tagttagtcggtgatc (SEQ ID NO: 0605) |
| 02 | rs4710698 | 6 | q | q27 | C6orf208|LOC154449 | 170439874 | 2.24E-05 | 1.12 | 0.414 | 0.386 | A | ttaaatatctaaatgt[A/G]taaaacagaactgatc (SEQ ID NO: 0606) |
| 03 | rs4710879 | 6 | q | q27 | C6orf208|LOC154449 | 170426027 | 4.60E-05 | 1.12 | 0.415 | 0.389 | G | cgacaaggctgggatc[A/G]tgtgctctccttccagc (SEQ ID NO: 0607) |
| 02 | rs4710811 | 6 | q | q27 | C6orf208|LOC154449 | 170369459 | 1.02E-04 | 1.17 | 0.182 | 0.160 | A | caattcattctgtgcc[A/G]actcacccctgggggtc (SEQ ID NO: 0608) |
| 03 | rs698626 | 7 | p | p11.2 | LOC389493|LOC441228 | 56282855 | 1.27E-02 | 0.92 | 0.454 | 0.474 | A | gtctagcaatccttgt[A/G]tatgctttaatcacag (SEQ ID NO: 0609) |
| 03 | rs9690458 | 7 | p | p12.1 | DKFZp564N2472|FLJ45974 | 53360479 | 1.32E-03 | 1.20 | 0.082 | 0.070 | G | casgttagtttgaga[A/G]ccagcaaactgaaaag (SEQ ID NO: 0610) |
| 02 | rs4326334 | 7 | p | p12.1 | LOC100131871|DKFZp564N2472 | 52996013 | 1.19E-05 | 0.87 | 0.411 | 0.445 | G | ggaagtcaattaaaaa[A/G]tctaaatataaatttg (SEQ ID NO: 0611) |
| 02 | rs1358603 | 7 | p | p12.1 | LOC100131871|DKFZp564N2472 | 52757480 | 5.71E-05 | 1.14 | 0.501 | 0.469 | A | ggaagtcaattaaaaa[A/G]tctaaatataaatttg (SEQ ID NO: 0612) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs6967460 | 7 | p | p12.1 | LOC100131871\|DKFZp564N2472 | 52950472 | 3.33E-04 | 1.25 | 0.068 | 0.055 | G | gaatttaaaatatca[A/G]tacaagaaagtcatta (SEQ ID NO: 0613) |
| 01 | exm2264261 | 7 | p | p12.3 | TNS3\|C7orf65 | 47641920 | 4.47E-11 | Inf | 0.011 | 0.001 | C | ttagcatgaggccacag[A/G]aaaggttttgagcca (SEQ ID NO: 0614) |
| 03 | rs1434960 | 7 | p | p13 | DDX56 | 44612992 | 3.58E-04 | 1.38 | 0.032 | 0.023 | G | agttctgtgtttaa[A/C]ggaatagcctgctg (SEQ ID NO: 0615) |
| 03 | rs11535191 | 7 | p | p14.1 | ELMO1\|GPR141 | 37747276 | 1.18E-03 | 0.87 | 0.171 | 0.191 | G | gtccggcctgctacc[A/G]ccaaccttgcgtaat (SEQ ID NO: 0616) |
| 03 | rs1364729 | 7 | p | p14.1 | ELMO1\|GPR141 | 37618173 | 1.26E-03 | 0.87 | 0.163 | 0.182 | G | aagtaaatgcccaag[A/G]tggcccagctagtaaa (SEQ ID NO: 0617) |
| 03 | rs3801216 | 7 | p | p14.1 | GLI3 | 42233283 | 1.54E-04 | 1.13 | 0.403 | 0.374 | A | tgtctgtctcaaatc[A/G]tgtgctgttaaaaat (SEQ ID NO: 0618) |
| 03 | rs2392465 | 7 | p | p14.2 | AOAH\|ELMO1 | 36800555 | 4.78E-03 | 0.92 | 0.446 | 0.468 | G | gctccttttaactca[A/G]tattacctgtggtttt (SEQ ID NO: 0619) |
| 03 | rs10488088 | 7 | p | p14.3 | C7orf41 | 30182813 | 5.48E-04 | 0.85 | 0.117 | 0.135 | G | tgggggtccatgtggl[A/G]aaagactgtgagtggc (SEQ ID NO: 0620) |
| 02 | rs2270221 | 7 | p | p14.3 | PDE1C | 31904027 | 5.19E-07 | 1.20 | 0.302 | 0.266 | A | tgttatctgtggac[A/G]ctacctcgtgagatfg (SEQ ID NO: 0621) |
| 03 | rs38523 | 7 | p | p15.1 | JAZF1\|LOC100128081 | 28039797 | 1.38E-02 | 0.92 | 0.350 | 0.368 | G | ttccttgcttcttttg[A/G]cccaacattttagcgc (SEQ ID NO: 0622) |
| 03 | rs6949451 | 7 | p | p15.2 | HOXA10 | 27215041 | 1.84E-04 | 1.12 | 0.493 | 0.464 | A | ttctgaagtatctcta[A/G]aaagtgtctctataa (SEQ ID NO: 0623) |
| 02 | rs11773804 | 7 | p | p15.2 | LOC100289444 | 27206688 | 1.84E-05 | 1.15 | 0.444 | 0.411 | C | gactgcctagctgaag[A/G]gtatggaagggaggg (SEQ ID NO: 0624) |
| 02 | rs7795246 | 7 | p | p15.3 | CDCA7L\|RAPGEF5 | 22047162 | 7.08E-03 | 1.09 | 0.489 | 0.468 | A | tgattaccccgttct[A/C]ggagtgctgctttct (SEQ ID NO: 0625) |
| 03 | rs2285942 | 7 | p | p15.3 | DNAH11 | 21582917 | 6.99E-02 | 0.92 | 0.134 | 0.144 | A | gaattgactactgcaa[A/C]tgtcatgatttatc (SEQ ID NO: 0626) |
| 03 | rs12534005 | 7 | p | p15.3 | IGF2BP3 | 23502518 | 6.44E-04 | 0.85 | 0.122 | 0.141 | G | ccgaggttaggcgaag[A/G]gtcgggggcttctga (SEQ ID NO: 0627) |
| 02 | rs11772760 | 7 | p | p15.3 | RAPGEF5 | 22246644 | 1.88E-05 | 1.15 | 0.357 | 0.326 | G | gattggcaagcatacat[A/G]gttttgagtgttccat (SEQ ID NO: 0628) |
| 02 | rs6461639 | 7 | p | p15.3 | RAPGEF5 | 22186955 | 2.47E-05 | 1.12 | 0.382 | 0.356 | A | gtagttgaatatttgc[A/G]acttatatcaacctat (SEQ ID NO: 0629) |
| 02 | rs2723512 | 7 | p | p15.3 | AHR\|SNX13 | 17815402 | 7.51E-05 | 1.19 | 0.133 | 0.114 | A | tgatttcgggcttc[A/G]ctttcattagctgtc (SEQ ID NO: 0630) |
| 03 | rs697521 | 7 | p | p21.1 | BZW2\|TSPAN13 | 16764156 | 7.81E-04 | 1.18 | 0.116 | 0.100 | A | tgagtcaacatgaagt[A/G]agggaaatgaaaaggg (SEQ ID NO: 0631) |
| 03 | rs17437739 | 7 | p | p21.1 | FERD3L\|TWISTNB | 19437424 | 1.41E-03 | 1.11 | 0.457 | 0.432 | A | ctactgcttacttctg[A/C]ctccatgtagaataaa (SEQ ID NO: 0632) |
| 03 | rs4286843 | 7 | p | p21.1 | FERD3L\|TWISTNB | 19463247 | 9.35E-03 | 1.09 | 0.484 | 0.464 | A | aaaggagcattcacac[A/C]gcttctctgtcatga (SEQ ID NO: 0633) |
| 03 | rs9648255 | 7 | p | p21.1 | FERD3L\|TWISTNB | 19450683 | 1.38E-02 | 0.93 | 0.465 | 0.484 | G | ggcagaactttattg[A/G]ctaggagtttcttt (SEQ ID NO: 0634) |
| 03 | rs6461452 | 7 | p | p21.1 | FERD3L\|TWISTNB | 19691229 | 7.69E-05 | 1.11 | 0.316 | 0.294 | A | gtggcacatgcctct[A/G]taagtgatttaaaat (SEQ ID NO: 0635) |
| 03 | rs17140423 | 7 | p | p21.1 | HDAC9 | 19007884 | 2.44E-04 | 1.13 | 0.314 | 0.288 | G | aagaccaggtgac[A/G]gctctcagagagaaga (SEQ ID NO: 0636) gaatgtttgaacatct[A/G]tagtaatattgaacca |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs6955426 | 7 | p | p21.2 | DGKB | 14310702 | 1.05E-02 | 1.12 | 0.138 | 0.124 | A | ttctacagaaatacaa[A/G]ctgtcttatgagtaaa (SEQ ID NO: 637) |
| 03 | rs17614094 | 7 | p | p21.3 | PHF14\|THSD7A | 11328154 | 2.72E-04 | 1.19 | 0.133 | 0.115 | A | agaagtaaaacagttc[A/G]tataaaagtgaatttt (SEQ ID NO: 638) |
| 03 | rs10261632 | 7 | p | p21.3 | PHF14\|THSD7A | 11383722 | 1.79E-04 | 1.13 | 0.402 | 0.373 | A | gaaaggaggaatttct[A/G]tttcaagcgcacacgt (SEQ ID NO: 639) |
| 02 | rs2895215 | 7 | p | p22.3 | ELFN1\|MAD1L1 | 1837636 | 2.11E-05 | 1.16 | 0.251 | 0.224 | A | ttagtatattgtatcc[A/G]gtgaattttcgctaaat (SEQ ID NO: 640) |
| 03 | rs160646 | 7 | q | q11.21 | ASL | 65556280 | 1.98E-04 | 1.19 | 0.126 | 0.107 | A | ctgggattacaagcat[A/G]agccacccaggcctagc (SEQ ID NO: 641) |
| 03 | rs419603 | 7 | q | q11.21 | CRCP | 65597341 | 2.04E-04 | 1.19 | 0.126 | 0.108 | A | actttggaagtgtcaa[A/G]gtcatgaagaagacaaag (SEQ ID NO: 642) |
| 03 | rs2243480 | 7 | q | q11.21 | CRCP | 65599196 | 2.24E-04 | 1.19 | 0.126 | 0.108 | A | tttaattacagtcatt[A/G]ccttgttttttctca (SEQ ID NO: 643) |
| 02 | rs1039664 | 7 | q | q11.21 | GUSB\|ASL | 65449716 | 7.60E-05 | 1.21 | 0.124 | 0.104 | C | atgaaaattaaaaaac[A/C]atgtaaacatttggga (SEQ ID NO: 644) |
| 03 | rs1267818 | 7 | q | q11.21 | KCTD7 | 66107024 | 3.02E-04 | 1.19 | 0.125 | 0.108 | A | tgataactactggccc[A/G]tctcaaggcaagatga (SEQ ID NO: 645) |
| 03 | rs1267817 | 7 | q | q11.21 | KCTD7\|LOC100289135 | 66110040 | 3.00E-04 | 1.19 | 0.125 | 0.108 | A | tgagtcccaagccaggt[A/G]acatggcatccctga (SEQ ID NO: 646) |
| 03 | rs6460260 | 7 | q | q11.21 | LOC100131973 | 65215455 | 4.87E-05 | 1.22 | 0.124 | 0.104 | A | atgctgctgaggccct[A/G]gggcttcatgtagat (SEQ ID NO: 647) |
| 03 | rs2178742 | 7 | q | q11.21 | LOC100289135\|RABGEF1 | 66197799 | 1.84E-04 | 1.20 | 0.126 | 0.107 | A | tctcgcttttgctct[A/G]cctctcactcgtagcc (SEQ ID NO: 648) |
| 03 | rs35315599 | 7 | q | q11.21 | RABGEF1 | 66254767 | 1.56E-04 | 1.20 | 0.126 | 0.108 | A | atttaagtttcccctc[A/G]cctatcatcatgtgct (SEQ ID NO: 649) |
| 02 | rs35391607 | 7 | q | q11.21 | VKORC1L1 | 65360829 | 7.76E-05 | 1.21 | 0.124 | 0.105 | A | tagtaaatggtattgg[A/G]tgaactgagtagccat (SEQ ID NO: 650) |
| 02 | rs6949812 | 7 | q | q11.21 | VKORC1L1 | 65387101 | 8.77E-05 | 1.21 | 0.124 | 0.105 | A | ttcatttaccaatcac[A/G]taccttttttgtcatt (SEQ ID NO: 651) |
| 02 | rs11983901 | 7 | q | 811.22 | STAG3L4\|AUTS2 | 68571255 | 6.12E-03 | 0.82 | 0.050 | 0.060 | C | tattggttcagccctg[A/C]aacacaggccatctg (SEQ ID NO: 652) |
| 03 | rs5745774 | 7 | q | q11.11 | LOC100128317\|HGF | 81330627 | 2.04E-02 | 1.17 | 0.057 | 0.049 | A | ggaaagaaactagtt[A/G]tctcaactctgtattc (SEQ ID NO: 653) |
| 03 | rs17166931 | 7 | q | 821.13 | C7orf62\|ZNF804B | 88760129 | 1.81E-04 | 1.41 | 0.032 | 0.023 | A | gatctctctaccttg[A/G]tataaaaatcaactca (SEQ ID NO: 654) |
| 03 | rs10255948 | 7 | q | q21.13 | ZNF804B\|DPY19L2P4 | 89536358 | 2.57E-03 | 1.10 | 0.449 | 0.425 | A | ttggttaatttgaact[A/C]ttccctctgatatatt (SEQ ID NO: 655) |
| 03 | rs4466326 | 7 | q | q21.13 | ZNF804B\|DPY19L2P4 | 89645073 | 3.30E-04 | 0.89 | 0.373 | 0.401 | A | ataccaggccatactt[A/G]gccatcaaaagtttga (SEQ ID NO: 656) |
| 03 | rs2214213 | 7 | q | q21.3 | CALCR | 93078060 | 3.44E-03 | 1.10 | 0.445 | 0.423 | A | tgctaatctgttccft[A/G]taaattttcacacaaa (SEQ ID NO: 657) |
| 03 | rs2240293 | 7 | q | q21.3 | LOC402679 | 96622720 | 1.19E-03 | 0.90 | 0.460 | 0.485 | G | gcggccggccgccaat[A/G]gaatcttgctcctact (SEQ ID NO: 658) |
| 03 | rs10282336 | 7 | q | q21.3 | OCM2\|LMTK2 | 97731700 | 2.78E-04 | 1.26 | 0.065 | 0.052 | A | tatttcaacaaacag[A/G]ataggactatttcac (SEQ ID NO: 659) |
| 03 | rs12533957 | 7 | q | q21.3 | SLC25A13 | 95805504 | 1.14E-03 | 1.26 | 0.051 | 0.041 | A | (SEQ ID NO: 660) |
| 03 | rs4727590 | 7 | q | q22.2 | ORC5L\|LHFPL3 | 103879276 | 1.50E-03 | 1.15 | 0.144 | 0.128 | G | agagagtctaggtgag[A/G]cacttcattcacaaccca (SEQ ID NO: 661) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs212438 | 7 | q | q22.3 | ATXN7L1/FLJ23834 | 105528339 | 2.50E-03 | 1.13 | 0.204 | 0.185 | G | tctctctcaaaatcat[A/G]cacttttccactac (SEQ ID NO: 0662) |
| 02 | rs2111201 | 7 | q | q31.1 | NRCAM | 107965942 | 2.99E-05 | 1.13 | 0.316 | 0.291 | A | atctgatgtgcaggta[A/G]gaaaatgtcacggagg (SEQ ID NO: 0663) |
| 03 | rs4142284 | 7 | q | q31.1 | NRCAM | 107940173 | 5.92E-05 | 1.12 | 0.315 | 0.290 | A | tgagggaaagcaac[A/G]tagatactgggaacaa (SEQ ID NO: 0664) |
| 03 | rs2267887 | 7 | q | q31.1 | NRCAM | 107968803 | 3.06E-04 | 1.12 | 0.423 | 0.395 | G | ttctggtcaatgtgct[A/G]tatgtacatgacaaat (SEQ ID NO: 0665) |
| 02 | rs10215206 | 7 | q | q31.1 | PNPLA8 | 108117088 | 2.07E-05 | 1.18 | 0.205 | 0.179 | A | ggaggaacaaaaacca[A/G]ccagtctctggactgt (SEQ ID NO: 0666) |
| 02 | rs10249427 | 7 | q | q31.1 | PNPLA8 | 108116481 | 3.62E-04 | 1.15 | 0.200 | 0.178 | G | caatttcatttcctc[A/G]gacatataccggagt (SEQ ID NO: 0667) |
| 03 | rs40851 | 7 | q | q31.1 | PNPLA8 | 108145121 | 1.08E-03 | 0.90 | 0.385 | 0.410 | A | taagaaaaggaatgag[A/G]aaaacttgattggtgta (SEQ ID NO: 0668) |
| 03 | rs3823855 | 7 | q | q31.32 | CADPS2 | 122057923 | 7.65E-04 | 1.12 | 0.318 | 0.294 | A | ccatgccaacaacatt[A/G]agaagaacaaggttgg (SEQ ID NO: 0669) |
| 03 | rs1582258 | 7 | q | q31.33 | GRM8 | 126122354 | 1.22E-02 | 0.92 | 0.352 | 0.371 | G | ttagaagaaataact[A/G]tatgacacagatgagg (SEQ ID NO: 0670) |
| 02 | exm657854 | 7 | q | q32.2 | CPA1 | 130023245 | 1.18E-11 | 47.29 | 0.005 | 0.000 | A | gcaattccacttctgg[A/G]tatgtgccaaaagta (SEQ ID NO: 0671) |
| 03 | rs13234407 | 7 | q | q32.3 | KLF14/FLJ43663 | 130438214 | 4.72E-05 | 0.89 | 0.461 | 0.491 | A | cagttcagcacgggg[A/G]cagtaagcgtccagcc (SEQ ID NO: 0672) |
| 03 | rs7795357 | 7 | q | q32.3 | KLF14/FLJ43663 | 130458874 | 2.68E-03 | 1.22 | 0.058 | 0.048 | G | gaatcgttactctgg[A/G]acacagatgcagggtt (SEQ ID NO: 0673) |
| 03 | rs157950 | 7 | q | q32.3 | LOC100506860 | 130601205 | 9.29E-03 | 1.26 | 0.075 | 0.060 | G | cccagcagcttacacc[A/G]cacctccctgttcat (SEQ ID NO: 0674) |
| 03 | rs13228664 | 7 | q | q32.3 | MKLN1 | 131132340 | 4.56E-03 | 0.91 | 0.442 | 0.464 | G | aatgaagattcaggat[A/G]acgaagcagtrggtaac (SEQ ID NO: 0675) |
| 02 | rs4725613 | 7 | q | q34 | CLCN1 | 143025985 | 1.63E-03 | 1.10 | 0.474 | 0.450 | G | gtaatactcctctac[A/G]atcctaagatgggtct (SEQ ID NO: 0676) |
| 03 | rs6973542 | 7 | q | q35 | CNTNAP2 | 147029028 | 3.45E-03 | 0.91 | 0.399 | 0.422 | G | gaatgtctattctctg[A/G]atgagcagggaggag (SEQ ID NO: 0677) |
| 02 | rs2262270 | 7 | q | q36.1 | FABP5P3/XRCC2 | 152211627 | 4.47E-11 | Inf | 0.010 | 0.002 | A | atgtgcagctgctt[A/G]ctgttcaacacatgtt (SEQ ID NO: 0678) |
| 02 | exm674318 | 7 | q | q36.1 | MLL3 | 151882672 | 4.52E-15 | 3.24 | 0.026 | 0.008 | A | tttccagtcttattc[A/C]gggggctggcggtggta (SEQ ID NO: 0679) |
| 03 | rs4609156 | 8 | p | p12 | LOC642513/NRG1 | 31133658 | 2.74E-03 | 1.10 | 0.478 | 0.454 | G | ctttctgtgagcttg[A/C]ttttctccacaattg (SEQ ID NO: 0680) |
| 03 | rs16879927 | 8 | p | p12 | NRG1 | 32612705 | 4.22E-04 | 0.82 | 0.088 | 0.105 | G | tcctgaaaggtctca[A/G]ttctctcatcagccagcg (SEQ ID NO: 0681) |
| 03 | rs17671468 | 8 | p | p12 | NRG1/FUT10 | 32633362 | 7.92E-04 | 0.83 | 0.089 | 0.105 | A | accaaacttcaagacc[A/G]aacataggaacccaa (SEQ ID NO: 0682) |
| 03 | rs4732639 | 8 | p | p21.2 | DPYSL2/ADRA1A | 26605110 | 8.05E-04 | 1.12 | 0.305 | 0.282 | G | ctatttgcaggagal[A/G]gaaggcacctaatat (SEQ ID NO: 0683) |
| 03 | rs7826422 | 8 | p | p21.2 | DPYSL2/ADRA1A | 26602648 | 2.88E-04 | 1.25 | 0.073 | 0.059 | A | gaagagcaccacttag[A/G]cacttcagagaccat (SEQ ID NO: 0684) |
| 03 | rs10503799 | 8 | p | p21.2 | DPYSL2/ADRA1A | 26605624 | 2.69E-04 | 1.25 | 0.073 | 0.059 | A | tgaacaggaaactga[A/G]ggctcttgtggtccag (SEQ ID NO: 0685) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs7013854 | 8 | p | p21.2 | EBF2 | 25733066 | 1.20E-04 | 1.17 | 0.185 | 0.163 | G | cttgaattcttttagaal[A/G]tcatagaaattatcct (SEQ ID NO: 0686) |
| 03 | rs920300 | 8 | p | p21.2 | NKX3-1|NKX2-6 | 23554565 | 2.33E-03 | 1.11 | 0.266 | 0.246 | G | ggtccctgtccttc[A/G]ccctcggttccttcc (SEQ ID NO: 0687) |
| 03 | rs12543268 | 8 | p | p21.2 | NKX3-1|NKX2-6 | 23556615 | 6.68E-05 | 0.90 | 0.358 | 0.383 | A | gagagattacggagac[A/G]gaagacaggcagctgg (SEQ ID NO: 0688) |
| 03 | rs977262 | 8 | p | p21.3 | LOC100128993|SH2D4A | 19081781 | 7.08E-04 | 1.12 | 0.301 | 0.277 | G | atgaaagatgagggal[A/G]agagagatgtgcaaaa (SEQ ID NO: 0689) |
| 03 | rs7012411 | 8 | p | p22 | TUSC3|MSR1 | 15788332 | 1.41E-03 | 0.90 | 0.470 | 0.496 | A | tgcaattcattccacac[A/C]ctgaaagatcctgtta (SEQ ID NO: 0690) |
| 03 | rs2980418 | 8 | p | p23.1 | FLJ10661|PRAGMIN | 8114228 | 3.75E-02 | 1.09 | 0.194 | 0.181 | G | tgcaccttgttaaaa[A/G]acaaatgactgtatgt (SEQ ID NO: 0691) |
| 03 | rs7014329 | 8 | p | p23.1 | LOC340357 | 12626394 | 5.44E-02 | 0.94 | 0.478 | 0.493 | A | catgctgcccttttct[A/G]ctgtctcaaacttgat (SEQ ID NO: 0692) |
| 03 | rs7011215 | 8 | p | p23.1 | MSRA|LOC346702 | 10312694 | 5.53E-05 | 1.13 | 0.359 | 0.332 | G | cctgaacattataaac[A/G]agacaagtataaacag (SEQ ID NO: 0693) |
| 03 | rs7816211 | 8 | p | p23.2 | CSMD1 | 3980317 | 7.75E-03 | 1.10 | 0.235 | 0.218 | G | tcactgtcttccatca[A/G]aaaaacaaatgatttta (SEQ ID NO: 0694) |
| 03 | rs2617009 | 8 | p | p23.2 | CSMD1 | 4496463 | 2.32E-02 | 0.92 | 0.202 | 0.217 | A | agggttcattcttc[A/G]aactactccagcagtc (SEQ ID NO: 0695) |
| 03 | rs4523281 | 8 | p | p23.2 | CSMD1 | 3496633 | 1.28E-04 | 1.33 | 0.049 | 0.038 | A | aatcttttgctagaal[A/G]aagtcctttgcatttt (SEQ ID NO: 0696) |
| 02 | exm678864 | 8 | p | p23.2 | CSMD1 | 3216809 | 1.26E-07 | Inf | 0.003 | 0.000 | G | tgccttcagccgaaga[A/G]ltgtggttttcacttgg (SEQ ID NO: 0697) |
| 03 | rs2724974 | 8 | p | p23.2 | CSMD1 | 4494520 | 4.03E-03 | 0.90 | 0.224 | 0.244 | G | gaatgccctttttcal[A/G]ltcctccgtgtgattgg (SEQ ID NO: 0698) |
| 03 | rs17071029 | 8 | p | p23.2 | CSMD1 | 4536253 | 2.02E-03 | 1.14 | 0.166 | 0.148 | A | ctgttgttaaacacat[A/G]tgtctaatttcaaaata (SEQ ID NO: 0699) |
| 03 | rs17073854 | 8 | p | p23.2 | CSMD1|LOC100287015 | 5377735 | 7.16E-03 | 1.16 | 0.095 | 0.083 | A | aggaggttgtctttg[A/G]ttgcctgcaacttcc (SEQ ID NO: 0700) |
| 03 | rs6990815 | 8 | p | p23.2 | CSMD1|LOC100287015 | 5713881 | 5.53E-03 | 1.27 | 0.036 | 0.029 | A | gtggactagtgcctct[A/G]ttttctctaatgcttt (SEQ ID NO: 0701) |
| 03 | rs17073881 | 8 | p | p23.2 | CSMD1|LOC100287015 | 5380363 | 6.09E-03 | 1.16 | 0.094 | 0.082 | G | tttctcagaaacctct[A/G]aaagccatctctgct (SEQ ID NO: 0702) |
| 02 | exm2173787 | 8 | p | 811.22 | PXDNL | 52233381 | 2.20E-09 | Inf | 0.003 | 0.000 | G | gtctctttcatccag[C/G]gctcctgcggccttct (SEQ ID NO: 0703) |
| 03 | rs1812576 | 8 | q | q12.2 | LOC100130298|RLBP1L1 | 62173034 | 3.45E-03 | 1.14 | 0.149 | 0.134 | G | tccctctttcatac[A/G]cagccactgaatagga (SEQ ID NO: 0704) |
| 03 | rs1866694 | 8 | q | q12.2 | LOC100130298|RLBP1L1 | 62172668 | 1.61E-03 | 1.13 | 0.209 | 0.189 | A | tccctccgcattgtaal[A/C]gtaggatggcagttac (SEQ ID NO: 0705) |
| 03 | rs17802118 | 8 | q | q12.3 | LOC100287835|NKAIN3 | 62694154 | 9.69E-03 | 1.10 | 0.265 | 0.247 | A | catgagtccactggag[A/G]tgttttgtagacttac (SEQ ID NO: 0706) |
| 02 | rs896486 | 8 | q | q12.3 | NKAIN3 | 63415467 | 3.74E-05 | 1.14 | 0.283 | 0.258 | A | tacaggacctgaat[A/C]catgcttgaacttctt (SEQ ID NO: 0707) |
| 03 | rs10217013 | 8 | q | q12.3 | YTHDF3|LOC100130155 | 64878574 | 2.00E-03 | 1.11 | 0.377 | 0.354 | A | aaatgagtgaggacca[A/C]agctgttatgtttttt (SEQ ID NO: 0708) |
| 03 | rs4268113 | 8 | q | q13.2 | C8orf34 | 69509456 | 3.04E-04 | 0.89 | 0.399 | 0.427 | G | (SEQ ID NO: 0709) |
| 03 | rs638853 | 8 | q | q13.2 | C8orf34|LOC100129096 | 70014344 | 5.33E-03 | 1.13 | 0.150 | 0.135 | A | gcaggataccccctg[A/G]aacaagcagcgaagat (SEQ ID NO: 0710) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs10957982 | 8 | q | q21.13 | ZBTB10|ZNF704 | 81455763 | 1.45E-04 | 1.16 | 0.202 | 0.179 | G | cacctgtgtgtatcca[A/G]cagcaagaagactgaa (SEQ ID NO: 0711) |
| 02 | exm710751 | 8 | q | q22.1 | INTS8 | 95878387 | 2.72E-17 | 9.20 | 0.012 | 0.001 | C | ggtttagtaattca[A/G]tttagctgtcatttaa (SEQ ID NO: 0712) |
| 03 | rs16896060 | 8 | q | q22.1 | MTDH | 98667777 | 4.96E-04 | 1.46 | 0.022 | 0.015 | A | atttttgttttgtagg[A/C]gtgaactgcttttctt (SEQ ID NO: 0713) |
| 03 | rs2618137 | 8 | q | q22.1 | RUNX1T1|C8orf83 | 93567028 | 2.40E-03 | 0.78 | 0.039 | 0.050 | C | gtcctggtggtcaaaa[A/G]ggcctggacaggcatc (SEQ ID NO: 0714) |
| 03 | rs2704253 | 8 | q | q22.1 | SDC2|PGCP | 97651358 | 1.77E-04 | 1.18 | 0.148 | 0.128 | G | aaaagactttcttcaaa[A/C]gaaacgtgaagtctc (SEQ ID NO: 0715) |
| 03 | rs4735529 | 8 | q | q22.1 | POP1 | 99139610 | 1.84E-03 | 0.91 | 0.459 | 0.483 | G | gaagaaagtttagtag[A/G]gctgaagtgtgcattt (SEQ ID NO: 0716) |
| 03 | rs17476650 | 8 | q | q23.2 | KCNV1|CSMD3 | 111101361 | 1.92E-04 | 1.19 | 0.129 | 0.111 | A | gtagtagcacacaag[A/G]taatcatgtcaggatg (SEQ ID NO: 0717) |
| 03 | rs7010965 | 8 | q | q23.3 | CSMD3|TRPS1 | 116299406 | 2.20E-02 | 1.14 | 0.084 | 0.075 | A | taatagacaaatgftg[A/C]acaatagtcaaattct (SEQ ID NO: 0718) |
| 03 | rs16887231 | 8 | q | q23.3 | CSMD3|TRPS1 | 116253370 | 1.32E-02 | 1.15 | 0.084 | 0.074 | G | tgcaatcaatcctc[A/G]tatttgcatttaaac (SEQ ID NO: 0719) |
| 03 | rs4871240 | 8 | q | q24.13 | HAS2AS|LOC100131552 | 123297701 | 1.02E-02 | 0.92 | 0.445 | 0.465 | G | acctcaggaaaggca[A/G]tggaacagggaggcct (SEQ ID NO: 0720) |
| 02 | rs13274301 | 8 | q | q24.21 | PVT1 | 128988045 | 7.96E-05 | 0.82 | 0.103 | 0.123 | C | caagtttgttgcttta[A/G]tactaccttgagtctg (SEQ ID NO: 0721) |
| 03 | rs7826937 | 8 | q | q24.21 | PVT1|LOC100287906 | 129264171 | 1.01E-02 | 0.92 | 0.345 | 0.365 | G | gtttcctagctgaaa[A/G]acgaagaagaagaaag (SEQ ID NO: 0722) |
| 03 | rs491614 | 8 | q | q24.22 | ADCY8|EFR3A | 132719817 | 1.19E-03 | 1.11 | 0.463 | 0.438 | G | tgactcaccatcagga[A/G]ggatcgtcgtcactg (SEQ ID NO: 0723) |
| 03 | rs581534 | 8 | q | q24.22 | ADCY8|EFR3A | 132711614 | 1.67E-02 | 1.15 | 0.085 | 0.075 | G | tactgaaaagaagaat[A/G]aacaacatcaacagtca (SEQ ID NO: 0724) |
| 02 | rs6999964 | 8 | q | q24.22 | ADCY8|EFR3A | 132862920 | 1.68E-05 | 1.14 | 0.216 | 0.195 | A | cttacttacctagaagg[A/G]catatgtctgctactg (SEQ ID NO: 0725) |
| 02 | rs4433159 | 8 | q | q24.22 | ASAP1|ADCY8 | 131571963 | 1.28E-03 | 1.17 | 0.320 | 0.287 | G | tataattaaggttaat[A/G]grgagattgtttggct (SEQ ID NO: 0726) |
| 03 | rs16904553 | 8 | q | q24.22 | EFR3A | 132947786 | 2.70E-03 | 1.12 | 0.212 | 0.194 | A | ttgacttatctatgga[G/A]tttttgactatttctg (SEQ ID NO: 0727) |
| 02 | rs6985794 | 8 | q | q24.22 | LOC100129104|ZFAT | 134689013 | 9.73E-02 | 1.08 | 0.129 | 0.121 | G | taacataagaaaatt[A/G]actgacatatgtatgg (SEQ ID NO: 0728) |
| 03 | rs12548244 | 8 | q | q24.23 | KHDRBS3|FLJ45872 | 137112133 | 7.19E-04 | 0.90 | 0.368 | 0.395 | G | atccatgaaacagac[A/G]ttaattaaataacaca (SEQ ID NO: 0729) |
| 03 | rs2317547 | 8 | q | q24.23 | KHDRBS3|FLJ45872 | 136933622 | 3.97E-03 | 1.10 | 0.337 | 0.316 | C | tttcatatcagaggca[A/G]cctctccaaccagatgt (SEQ ID NO: 0730) |
| 03 | rs10505647 | 8 | q | q24.23 | KHDRBS3|FLJ45872 | 137056293 | 1.23E-03 | 0.90 | 0.311 | 0.334 | A | tggccagaaagagaga[A/C]agagagacagagacag (SEQ ID NO: 0731) |
| 02 | exm728471 | 8 | q | q24.3 | EPPK1 | 144940658 | 3.25E-16 | Inf | 0.006 | 0.000 | A | aaataggaaccctgac[A/G]cacaaaggaaatttgg (SEQ ID NO: 0732) |
| 03 | rs903965 | 8 | q | q24.3 | FLJ43860|NCRNA00051 | 142698496 | 1.18E-03 | 1.44 | 0.020 | 0.014 | A | tggaagggctgct[A/G]gcccggcacgcccctg (SEQ ID NO: 0733) |
| 03 | rs3819495 | 8 | q | q24.3 | GML | 143923250 | 1.12E-02 | 1.16 | 0.085 | 0.075 | A | ccacctgtgccaggl[A/G]catacactgctgcac (SEQ ID NO: 0734) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs10971957 | 9 | p | p13.3 | DCAF12\|UBAP1 | 34151463 | 7.13E-03 | 1.13 | 0.415 | 0.386 | C | ctatcattatcgatt c[C/T]accagcaatttct (SEQ ID NO: 0735) |
| 02 | rs10972684 | 9 | p | p13.3 | OR2S2\|RECK | 36003635 | 5.21E-03 | 0.85 | 0.167 | 0.190 | A | atctgctatacaacat[C/A]ctcagtcccctcatc (SEQ ID NO: 0736) |
| 03 | rs12726 | 9 | p | p13.3 | UNC13B | 35404840 | 4.45E-04 | 1.13 | 0.263 | 0.240 | A | gttgaaggatccagga[A/G]tatttcttcttggt (SEQ ID NO: 0737) |
| 03 | rs2383733 | 9 | p | p21.2 | C9orf72\|LINGO2 | 27869510 | 7.13E-03 | 1.17 | 0.079 | 0.068 | A | tgtcactttcagtata[A/G]ataaaactttagaa (SEQ ID NO: 0738) |
| 03 | rs10811800 | 9 | p | p21.3 | DMRTA1\|LOC402360 | 22906729 | 2.19E-03 | 1.10 | 0.420 | 0.396 | A | ctacattataaattat[A/G]cttgatacacagacatc (SEQ ID NO: 0739) |
| 03 | rs1381923 | 9 | p | p21.3 | DMRTA1\|LOC402360 | 22909348 | 7.90E-03 | 0.92 | 0.448 | 0.469 | C | actgtatcattccct[A/C]cctgaaatatcccatg (SEQ ID NO: 0740) |
| 03 | rs10116397 | 9 | p | p21.3 | DMRTA1\|LOC402360 | 23570688 | 3.01E-04 | 1.25 | 0.071 | 0.057 | G | ggcaggaagcacca[A/G]tttaggaaatgttaga (SEQ ID NO: 0741) |
| 03 | rs2149913 | 9 | p | p21.3 | ELAVL2\|TUSC1 | 24573717 | 6.46E-04 | 0.89 | 0.318 | 0.343 | A | gaataagaatactaac[A/G]tttatccccctgcattt (SEQ ID NO: 0742) |
| 03 | rs2026590 | 9 | p | p21.3 | ELAVL2\|TUSC1 | 24833789 | 4.21E-04 | 1.14 | 0.240 | 0.217 | A | caatggaatttggtaa[A/C]tatttcttatctttg (SEQ ID NO: 0743) |
| 03 | rs11788362 | 9 | p | p21.3 | ELAVL2\|TUSC1 | 24493958 | 1.79E-03 | 0.89 | 0.216 | 0.237 | A | aaaaagtactaattc[A/G]gaaaagatataaagt (SEQ ID NO: 0744) |
| 03 | rs10511626 | 9 | p | p22.2 | BNC2 | 16764989 | 3.61E-02 | 0.90 | 0.110 | 0.120 | A | atcagagtatatgcca[A/C]agccggggttcgtatcc (SEQ ID NO: 0745) |
| 03 | rs1442514 | 9 | p | p22.2 | CNTLN | 17419319 | 3.13E-05 | 1.25 | 0.094 | 0.076 | A | tactaagcattattct[A/G]tagatgaatatataa (SEQ ID NO: 0746) |
| 03 | rs2772695 | 9 | p | p22.2 | SH3GL2\|ADAMTSL1 | 17985166 | 4.54E-03 | 1.13 | 0.166 | 0.150 | A | gagacttcactctgac[A/G]tatttctcttttgga (SEQ ID NO: 0747) |
| 03 | rs10810211 | 9 | p | p22.3 | ZDHHC21 | 14676870 | 1.30E-02 | 1.23 | 0.037 | 0.030 | G | caagtctctccaac[A/G]tgtcaattactaa (SEQ ID NO: 0748) |
| 02 | rs12236892 | 9 | p | p24.1 | C9orf123\|PTPRD | 7834442 | 5.91E-05 | 1.30 | 0.063 | 0.050 | G | gtttctaaatatgtca[A/G]agtagatattaaagaa (SEQ ID NO: 0749) |
| 02 | exm7737779 | 9 | p | p24.1 | ERMP1 | 5832719 | 4.28E-24 | 4.87 | 0.028 | 0.006 | G | gcggggccgctggaca[C/G]cgcgggggagttcgacg (SEQ ID NO: 0750) |
| 02 | rs10975519 | 9 | p | p24.1 | IL33 | 6253571 | 6.06E-07 | 1.18 | 0.338 | 0.302 | A | ggtgttgagactcata[A/G]taactcagtaaccact (SEQ ID NO: 0751) |
| 01 | rs1332290 | 9 | p | p24.1 | IL33 | 6255881 | 6.96E-07 | 1.17 | 0.391 | 0.354 | A | tggaaactaaagggga[A/C]tacttatttatgactt (SEQ ID NO: 0752) |
| 02 | rs10975516 | 9 | p | p24.1 | IL33 | 6247693 | 2.31E-05 | 1.15 | 0.335 | 0.304 | A | ctttgaccccagtgga[A/G]tgctctctctgcaaa (SEQ ID NO: 0753) |
| 01 | rs1048274 | 9 | p | p24.1 | IL33 | 6256292 | 3.99E-06 | 1.17 | 0.333 | 0.300 | A | ttagcatgtgtggaat[A/G]tttccatattagta (SEQ ID NO: 0754) |
| 01 | rs1330383 | 9 | p | p24.1 | IL33 | 6251507 | 4.64E-06 | 1.17 | 0.333 | 0.300 | A | accatgggattccaat[A/C]cattgcaagtatttca (SEQ ID NO: 0755) |
| 02 | rs10815398 | 9 | p | p24.1 | IL33\|LOC645969 | 6272766 | 6.98E-06 | 1.16 | 0.393 | 0.359 | C | gctctccccttga[A/C]acatccttccccttcc (SEQ ID NO: 0756) |
| 02 | rs10815402 | 9 | p | p24.1 | LOC645969\|TPD52L3 | 6293715 | 5.40E-06 | 1.17 | 0.305 | 0.273 | A | gcagtctccccttga[A/C]acatccttccccttcc (SEQ ID NO: 0757) |
| 03 | rs10975539 | 9 | p | p24.1 | LOC645969\|TPD52L3 | 6308729 | 9.21E-04 | 0.88 | 0.213 | 0.235 | A | tccagacacaagtcac[A/G]agttcaggggttcaca (SEQ ID NO: 0758) |
| 03 | rs12551256 | 9 | p | p24.1 | RANBP6\|IL33 | 6231239 | 1.64E-04 | 1.13 | 0.491 | 0.462 | G | cccccaataacaggaa[A/G]gagattccttgttcc (SEQ ID NO: 0759) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs1052335 | 9 | p | p24.1 | TPD52L3 | 6330380 | 2.74E-05 | 1.19 | 0.220 | 0.192 | C | cttattggcttctca[A/G]tgccactctgaatgaaa (SEQ ID NO: 0760) |
| 03 | rs4741806 | 9 | p | p24.2 | KIAA0020\|RFX3 | 3099009 | 1.23E-03 | 0.82 | 0.074 | 0.088 | C | cactgcctgaagatagaa[A/C]tgtttgcattcattattgg (SEQ ID NO: 0761) |
| 02 | rs7021672 | 9 | p | p24.2 | KIAA0020\|RFX3 | 3097453 | 9.19E-05 | 0.86 | 0.205 | 0.231 | A | ttttttcattgattc[A/C]taggagttcttacat (SEQ ID NO: 0762) |
| 02 | rs2986687 | 9 | p | p24.2 | RFX3 | 3301887 | 5.31E-05 | 1.19 | 0.124 | 0.106 | A | tttattgatragtttac[A/G]ctgctggaaatataat (SEQ ID NO: 0763) |
| 03 | rs3012708 | 9 | p | p24.2 | RFX3 | 3322283 | 1.71E-03 | 1.14 | 0.184 | 0.165 | G | agacctgaagagcagg[A/G]acccctggtggatttt (SEQ ID NO: 0764) |
| 03 | rs7868484 | 9 | p | p24.3 | SMARCA2 | 2141357 | 7.19E-05 | 1.14 | 0.300 | 0.273 | A | tcaagtttcctttgt[A/G]tccctgcgaactta (SEQ ID NO: 0765) |
| 02 | rs10746847 | 9 | q | q21.12 | TRPM3 | 73170382 | 3.23E-05 | 0.89 | 0.416 | 0.446 | G | tatgttttggattt[A/C]gccatttagttaattgac (SEQ ID NO: 0766) |
| 03 | rs10746850 | 9 | q | q21.12 | TRPM3 | 73183281 | 7.86E-05 | 0.90 | 0.443 | 0.469 | G | tcctgtacaggtgccat[A/G]tggatgtgctatgtgt (SEQ ID NO: 0767) |
| 02 | rs3739776 | 9 | q | q21.12 | TRPM3 | 73151970 | 1.35E-05 | 0.88 | 0.414 | 0.445 | G | aaattctatgccaagc[A/G]ctttcatatacaatat (SEQ ID NO: 0768) |
| 02 | rs6560143 | 9 | q | q21.12 | TRPM3 | 73168680 | 4.19E-05 | 0.89 | 0.415 | 0.444 | G | gccattctttcattc[A/G]gtcaatatgaaagaca (SEQ ID NO: 0769) |
| 03 | rs10119759 | 9 | q | q21.31 | PSAT1\|TLE4 | 82018583 | 6.22E-02 | 0.94 | 0.305 | 0.319 | C | cctgtgttaattccc[A/G]atcaatagtcccgaga (SEQ ID NO: 0770) |
| 03 | rs9314677 | 9 | q | q21.31 | PSAT1\|TLE4 | 82018917 | 3.29E-03 | 1.10 | 0.347 | 0.325 | G | gctccagggctgggac[A/C]ctttctgagcctcctc (SEQ ID NO: 0771) |
| 02 | rs2378380 | 9 | q | q21.31 | PSAT1\|TLE4 | 82032456 | 3.22E-02 | 0.93 | 0.300 | 0.316 | A | gatgtaaggtaaccatc[A/G]ttatgggacccagag (SEQ ID NO: 0772) |
| 03 | rs3897745 | 9 | q | q21.32 | TLE1 | 84215944 | 1.22E-03 | 0.88 | 0.182 | 0.202 | A | gcaacaggggtaactag[A/G]gcatcatcatgaaattcac (SEQ ID NO: 0773) |
| 02 | rs9410282 | 9 | q | q22.1 | LOC286238\|C9orf47 | 91318984 | 3.33E-04 | 0.89 | 0.418 | 0.446 | A | ctacacagtcgtgtga[A/G]ccaatccctcccaaata (SEQ ID NO: 0774) |
| 02 | rs944485 | 9 | q | q22.1 | SHC3 | 91679818 | 4.83E-04 | 1.17 | 0.411 | 0.374 | T | aggctcgtgatggggc[A/G]caggaaacaactgagg (SEQ ID NO: 0775) |
| 03 | exm764237 | 9 | q | q22.32 | C9orf102 | 98684662 | 4.73E-08 | 18.90 | 0.004 | 0.000 | A | ttgtgccgttattaaat[T/G]ccattttgttatttcat (SEQ ID NO: 0776) |
| 03 | exm768001 | 9 | q | q31.1 | GRIN3A | 104335619 | 4.40E-10 | 3.17 | 0.017 | 0.005 | G | gctgcaggaccacca[A/G]tgggaaagcagactcc (SEQ ID NO: 0777) |
| 02 | rs698459 | 9 | q | q31.1 | LOC347281\|OR13F1 | 107234158 | 1.22E-03 | 0.89 | 0.282 | 0.306 | C | gccttgccggaccacca[A/G]tgggaaagcagactcc (SEQ ID NO: 0778) |
| 02 | rs2808374 | 9 | q | q31.2 | LOC100128086\|RAD23B | 109987079 | 4.12E-03 | 1.11 | 0.280 | 0.260 | G | cttgatgtgtcaggac[A/C]attttgttgctgtagg (SEQ ID NO: 0779) |
| 03 | rs7864733 | 9 | q | q31.2 | LOC644620 | 109427261 | 9.34E-03 | 0.92 | 0.474 | 0.494 | C | ctcgtactgatggac[A/G]ttcacatttaaattt (SEQ ID NO: 0780) |
| 03 | rs16934033 | 9 | q | q33.1 | ASTN2 | 119657927 | 2.09E-04 | 1.55 | 0.019 | 0.012 | A | actgaaatattagccag[A/C]aattaataatcatgct (SEQ ID NO: 0781) |
| 02 | rs1990422 | 9 | q | q33.1 | DBC1\|CDK5RAP2 | 122244046 | 5.73E-05 | 1.15 | 0.240 | 0.216 | G | ctcctatttcaacag[A/G]acagcaaatgaagact (SEQ ID NO: 0782) |
| 02 | rs10513376 | 9 | q | q33.2 | DAB2IP | 124354826 | 3.47E-04 | 0.84 | 0.294 | 0.331 | C | atgaaatataaaatc[A/G]atrgtgtgatggttt (SEQ ID NO: 0783) agctcgaaaatctca[T/C]tgggaaccctgaagta |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs10985200 | 9 | q | q33.2 | GSN | 124043867 | 5.48E-05 | 1.14 | 0.497 | 0.465 | A | cggggtttaagaggac[A/G]acaggtgtctgtattg (SEQ ID NO: 0784) |
| 03 | rs3810942 | 9 | q | q33.2 | GSN/LOC100128064 | 124044995 | 1.76E-04 | 1.13 | 0.490 | 0.461 | A | atcaggccaagaccc[A/G]gccctcaagtcctcct (SEQ ID NO: 0785) |
| 03 | rs10156486 | 9 | q | q33.2 | LOC729012|OR5C1 | 125538981 | 5.27E-03 | 0.65 | 0.010 | 0.016 | C | tgtgaagggaggtc[A/C]gtcagccagcattaag (SEQ ID NO: 0786) |
| 02 | rs4556152 | 9 | q | q33.2 | RAB14|GSN | 124016909 | 6.03E-05 | 1.14 | 0.503 | 0.471 | A | gatttttctctcctct[A/G]aaagagcaatttctc (SEQ ID NO: 0787) |
| 03 | rs10760160 | 9 | q | q33.2 | RAB14|GSN | 124003326 | 3.42E-04 | 1.12 | 0.490 | 0.462 | C | acaggaaacttcaacc[A/C]agtatcaagttactaa (SEQ ID NO: 0788) |
| 03 | rs10760159 | 9 | q | q33.2 | RAB14|GSN | 123998342 | 2.45E-04 | 1.12 | 0.489 | 0.460 | A | ccctccagagggaat[A/G]tggtcctgtggacacc (SEQ ID NO: 0789) |
| 02 | rs2239696 | 9 | q | q33.2 | RAB14|GSN| | 124029155 | 2.82E-05 | 1.14 | 0.502 | 0.469 | G | ggaccecaggaatctc[A/G]ccctggctcttcctcc (SEQ ID NO: 0790) |
| 01 | rs34250136 | 9 | q | q33.3 | DENND1A|LHX2 | 126772954 | 3.07E-06 | 1.71 | 0.020 | 0.012 | A | cactgatatcgaatgt[A/G]tcttgagtgagaaag (SEQ ID NO: 0791) |
| 03 | rs10217721 | 9 | q | q33.3 | PBX3|FAM125B | 128810846 | 2.46E-02 | 1.07 | 0.455 | 0.437 | G | ggaattaacagccaca[A/G]tgcaagcttcttgctg (SEQ ID NO: 0792) |
| 03 | rs7861741 | 9 | q | q33.3 | PBX3|FAM125B | 128810469 | 1.28E-02 | 1.08 | 0.459 | 0.440 | G | ggatcatggcctggc[A/G]attccaggtctgggtt (SEQ ID NO: 0793) |
| 03 | rs7023572 | 9 | q | q34.13 | C9orf171 | 135414981 | 5.87E-05 | 1.05 | 0.356 | 0.344 | G | tgttctagggccaacc[A/G]gggggatcggaggagtc (SEQ ID NO: 0794) |
| 02 | rs10508855 | 10 | p | p11.21 | FZD8|ANKRD30A | 37070799 | 4.47E-06 | 1.30 | 0.050 | 0.039 | A | gggcagagtactattc[A/G]tatgtgcatactatat (SEQ ID NO: 0795) |
| 03 | rs17615892 | 10 | p | p11.21 | FZD8|ANKRD30A | 36635409 | 3.86E-03 | 0.89 | 0.172 | 0.190 | G | tatggaaatgatatgg[A/G]atacataggaaatgcg (SEQ ID NO: 0796) |
| 03 | rs17627587 | 10 | p | p11.21 | FZD8|ANKRD30A | 36688414 | 1.64E-03 | 0.87 | 0.143 | 0.161 | A | ctcataacatttccc[A/G]ctagaaataatgtgtg (SEQ ID NO: 0797) |
| 03 | rs3124188 | 10 | p | p11.23 | LOC645954 | 30955825 | 2.05E-03 | 0.89 | 0.232 | 0.253 | G | cttctattttgctgtt[A/G]ctgttttgcatttgag (SEQ ID NO: 0798) |
| 03 | rs17747622 | 10 | p | p12.1 | ABI1 | 27044752 | 2.15E-04 | 0.77 | 0.050 | 0.065 | A | atccagtgggaaagtc[A/G]gttgcatcctatgtt (SEQ ID NO: 0799) |
| 03 | rs10826406 | 10 | p | p12.1 | MPP7 | 28433708 | 4.41E-03 | 1.15 | 0.115 | 0.102 | A | tatgttgrggtcctt[A/G]taactgacttctgctt (SEQ ID NO: 0800) |
| 03 | rs11006995 | 10 | p | p12.1 | MPP7/LOC100288110 | 28585496 | 2.13E-02 | 1.16 | 0.069 | 0.060 | A | aattaacatagcagttgc[A/G]atatccatttgggta (SEQ ID NO: 0801) |
| 03 | rs16927305 | 10 | p | p12.1 | PDSS1 | 27023402 | 4.94E-03 | 1.16 | 0.096 | 0.083 | A | tgcttagcagggcact[A/G]gggaaatgcacttcagt (SEQ ID NO: 0802) |
| 03 | rs4748738 | 10 | p | p12.31 | NEBL | 21219406 | 2.28E-03 | 1.11 | 0.350 | 0.328 | A | ttaatttgcattttca[A/G]aaagactaccttgct (SEQ ID NO: 0803) |
| 02 | rs11012384 | 10 | p | p12.31 | NEBL | 21198380 | 4.04E-02 | 1.10 | 0.397 | 0.375 | G | tgcctctaagatattg[G/T]acacacaaatgaagca (SEQ ID NO: 0804) |
| 03 | rs17464580 | 10 | p | p12.33 | STAM | 17750968 | 9.33E-04 | 0.79 | 0.051 | 0.064 | C | actaactccaaacaag[A/C]atcaacagtaaaatta (SEQ ID NO: 0805) |
| 01 | rs11256106 | 10 | p | p14 | GATA3|SFTA1P | 9222228 | 1.98E-07 | 1.24 | 0.171 | 0.143 | C | tcacatatgatagatt[A/C]ggcaattgagttat (SEQ ID NO: 0806) |
| 02 | rs1001019 | 10 | p | p14 | GATA3|SFTA1P | 9243785 | 9.54E-06 | 1.19 | 0.198 | 0.171 | A | gctgtttaaatgttta[A/C]ttgatgatgaattg (SEQ ID NO: 0807) |
| 02 | rs7911451 | 10 | p | p14 | GATA3|SFTA1P | 9248331 | 1.56E-05 | 1.18 | 0.206 | 0.180 | A | gctgtttaaatgttta[A/C]ttgatgatgaattg (SEQ ID NO: 0808) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2387739 | 10 | p | p14 | LOC439949\|SFMBT2 | 6813564 | 1.55E-04 | 1.16 | 0.214 | 0.191 | G | gtgtgtggaacaagc[A/G]caaagtccatatccag (SEQ ID NO: 0809) |
| 03 | rs11257215 | 10 | p | p14 | LOC439951\|ECHDC3 | 11697403 | 3.79E-05 | 1.13 | 0.287 | 0.262 | G | agtaatgccaactaca[A/G]attatgaaatatttca (SEQ ID NO: 0810) |
| 03 | rs4881466 | 10 | p | p15.1 | CALML5\|LOC100132159 | 5542109 | 2.16E-04 | 1.14 | 0.289 | 0.263 | A | ggagtttcccatccc[A/G]ggctgcagtgcaatgg (SEQ ID NO: 0811) |
| 03 | rs10904508 | 10 | p | p15.1 | NET1\|CALMLS | 5503610 | 4.32E-04 | 0.89 | 0.298 | 0.324 | A | atggggctcactgcct[A/G]taacttcaaggaagca (SEQ ID NO: 0812) |
| 02 | rs11253141 | 10 | p | p15.1 | UCN3\|TUBAL3 | 5422196 | 5.46E-05 | 0.88 | 0.361 | 0.392 | C | ataagaaaatatccag[A/C]actgagtgtatgttta (SEQ ID NO: 0813) |
| 03 | rs2279208 | 10 | p | p15.2 | PFKP | 3171043 | 1.52E-03 | 0.86 | 0.133 | 0.151 | A | tcaagtcatcagattg[A/C]atctcccaactgcca (SEQ ID NO: 0814) |
| 03 | rs2388558 | 10 | p | p15.2 | PITRM1 | 3180689 | 1.72E-03 | 0.89 | 0.240 | 0.262 | A | cgcccaccactgtgcc[A/G]gaatgtgatgcacaca (SEQ ID NO: 0815) |
| 03 | rs4881111 | 10 | p | p15.2 | PITRM1 | 3190265 | 4.38E-03 | 1.09 | 0.490 | 0.467 | A | agagatcaaccccgga[A/C]ctccagctcccagtg (SEQ ID NO: 0816) |
| 03 | rs9423709 | 10 | p | p15.2 | PITRM1 | 3202682 | 3.65E-03 | 0.89 | 0.211 | 0.230 | A | gcacacccctgaaccaa[A/G]gaaaaacacagaagaaa (SEQ ID NO: 0817) |
| 03 | rs7898695 | 10 | p | p15.2 | PITRM1 | 3184507 | 3.61E-03 | 1.10 | 0.429 | 0.406 | A | ggtccaaaatatcac[A/G]gtracttcgaggacca (SEQ ID NO: 0818) |
| 03 | rs4881109 | 10 | p | p15.2 | PITRM1 | 3185237 | 1.42E-03 | 0.89 | 0.233 | 0.255 | G | cacctcccatcgtg[A/G]ccctctgtgacacacg (SEQ ID NO: 0819) |
| 03 | rs4881110 | 10 | p | p15.2 | PITRM1 | 3185393 | 3.57E-03 | 0.90 | 0.244 | 0.264 | G | acctaccatgtttatc[A/G]gaaatctcagcctaaa (SEQ ID NO: 0820) |
| 03 | rs12763675 | 10 | p | p15.3 | DIP2C\|LARP5 | 744591 | 6.79E-04 | 0.89 | 0.335 | 0.360 | A | aatgactggctctaaa[A/G]ctgggtctgttcac (SEQ ID NO: 0821) |
| 03 | rs12572078 | 10 | p | p15.3 | NCRNA00168\|ADARB2 | 1669110 | 5.49E-05 | 1.16 | 0.268 | 0.240 | A | gcaatgtttaaaaaca[A/G]catttgggctgggcg (SEQ ID NO: 0822) |
| 03 | rs1875005 | 10 | p | p15.3 | NCRNA00168\|ADARB2 | 1661398 | 8.56E-04 | 0.90 | 0.450 | 0.476 | A | ggtgggtgctgatgag[A/G]gaaggcaggagatgca (SEQ ID NO: 0823) |
| 03 | rs2802477 | 10 | q | q11.21 | HNRNPA3P1\|LOC100130539 | 44696034 | 1.83E-03 | 0.90 | 0.390 | 0.414 | G | tttatctaatctgatg[A/G]tctcgctatttat (SEQ ID NO: 0824) |
| 02 | rs11238956 | 10 | q | q11.21 | HNRNPA3P1\|LOC100130539 | 44749854 | 1.09E-05 | 0.87 | 0.316 | 0.348 | G | cctgccgctaggag[A/G]ttgtgctgtcccctc (SEQ ID NO: 0825) |
| 03 | rs268309 | 10 | q | q11.21 | HNRNPA3P1\|LOC100130539 | 44611148 | 3.62E-03 | 1.28 | 0.035 | 0.028 | A | ccactaaaattcaca[A/G]tcagaatgcttggcaa (SEQ ID NO: 0826) |
| 02 | rs2503853 | 10 | q | q11.21 | RASGEF1A\|FXYD4 | 43750260 | 2.57E-05 | 1.18 | 0.207 | 0.181 | A | ctagaagccgaggaca[A/G]tgagatctctcttct (SEQ ID NO: 0827) |
| 03 | rs3844600 | 10 | q | q11.22 | ARHGAP22 | 49683897 | 3.00E-02 | 1.09 | 0.224 | 0.211 | A | ccctccctttagtcag[A/G]gattattctgggggac (SEQ ID NO: 0828) |
| 03 | rs1345107 | 10 | q | q11.22 | ARHGAP22 | 49794481 | 3.07E-04 | 1.15 | 0.204 | 0.182 | A | tgctaacagctctacc[A/G]tgatgacaaggccatt (SEQ IDNo.0829) |
| 03 | rs1806437 | 10 | q | q11.22 | ARHGAP22 | 49798463 | 4.29E-04 | 0.89 | 0.359 | 0.386 | A | gggttactactgtgat[A/G]aggattaggatatagg (SEQ ID NO: 0830) |
| 03 | rs1881740 | 10 | q | 811.22 | FRMPD2\|MAPK8 | 49551560 | 1.12E-03 | 0.88 | 0.212 | 0.233 | A | tgccccaccacaacc[A/G]aggacagtgtcttgcc (SEQ ID NO: 0831) |
| 03 | rs7898026 | 10 | q | 811.22 | FRMPD2\|MAPK8 | 49479934 | 5.13E-05 | 0.90 | 0.432 | 0.459 | G | ggaccagtactca[A/G]ggtagcattttgaac (SEQ ID NO: 0832) |
| | | | | | | | | | | | | ctgacgaaggactgc[A/G]gctgaatttcacattt |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | exm822086 | 10 | q | 811.22 | GPRIN2 | 46999130 | 5.78E-20 | 79.75 | 0.008 | 0.000 | A | tggcctccagcactgg[A/G]tcgcgccttgggca (SEQ ID NO: 0833) |
| 03 | rs10509234 | 10 | q | q21.3 | ANXA2P3\|CTNNA3 | 67473973 | 7.69E-03 | 1.15 | 0.098 | 0.086 | A | tttttcaatgctgac[A/G]cagagtgattaaaaa (SEQ ID NO: 0834) |
| 03 | rs4370822 | 10 | q | q21.3 | CTNNA3 | 68072084 | 6.73E-04 | 0.86 | 0.138 | 0.157 | A | ccttggtagctatca[A/G]gtacatgcctaactg (SEQ ID NO: 0835) |
| 02 | exm833170 | 10 | q | q22.1 | SPOCK2 | 73822855 | 1.96E-13 | 17.37 | 0.007 | 0.000 | A | gtgtgaccagagcagc[A/G]gtgactgctgtgtgt (SEQ ID NO: 0836) |
| 02 | exm829854 | 10 | q | q22.1 | SUPV3L1 | 70940052 | 1.26E-07 | Inf | 0.003 | 0.000 | A | tagggcacggagaag[A/G]acatcgaggccgcagg (SEQ ID NO: 0837) |
| 02 | rs7081974 | 10 | q | q22.3 | LOC100132987 | 80215612 | 8.53E-05 | 0.74 | 0.044 | 0.059 | A | ggcagctagggactga[A/G]gcagcgtagcataaca (SEQ ID NO: 0838) |
| 03 | rs16935969 | 10 | q | q22.3 | LOC100132987 | 80220796 | 1.55E-04 | 0.75 | 0.043 | 0.056 | G | gttcgactgcaggaaa[A/G]ccctacagggttgctgg (SEQ ID NO: 0839) |
| 03 | rs12784427 | 10 | q | q22.3 | LOC100132987 | 80207497 | 4.87E-05 | 0.74 | 0.045 | 0.060 | C | ctttcctgggatgct[A/C]attgaggttgaaaga (SEQ ID NO: 0840) |
| 03 | rs4979997 | 10 | q | q22.3 | LOC100132987\|LOC283050 | 80435887 | 1.49E-02 | 1.19 | 0.050 | 0.042 | G | ctggtttcctaatca[A/G]agaaagcttcaaagaa (SEQ ID NO: 0841) |
| 03 | rs288444 | 10 | q | q22.3 | LOC100132987\|LOC283050 | 80348121 | 1.30E-03 | 0.85 | 0.103 | 0.119 | G | tattagcagactcacc[A/G]caaaaggatatgccag (SEQ ID NO: 0842) |
| 03 | rs288450 | 10 | q | q22.3 | LOC100132987\|LOC283050 | 80356268 | 9.03E-03 | 0.87 | 0.102 | 0.115 | A | acagcacaagagaatg[A/G]tgagtgggtatatagt (SEQ ID NO: 0843) |
| 03 | rs288447 | 10 | q | q22.3 | LOC100132987\|LOC283050 | 80359650 | 1.12E-02 | 0.88 | 0.103 | 0.116 | A | gaagcccaggatgaaa[A/C]agggttgttcaatgtc (SEQ ID NO: 0844) |
| 03 | rs288442 | 10 | q | q22.3 | LOC100132987\|LOC283050 | 80348890 | 5.59E-03 | 0.87 | 0.100 | 0.114 | G | cacagacatgcaaatt[A/G]ggatggaaccactt (SEQ ID NO: 0845) |
| 02 | rs1249122 | 10 | q | q22.3 | RPS24\|LOC283050 | 79949403 | 1.28E-02 | 0.89 | 0.367 | 0.393 | T | gggaatagatgcagaa[C/T]ggcaaagaagcaaga (SEQ ID NO: 0846) |
| 03 | rs703990 | 10 | q | q22.3 | ZMIZ1 | 80930439 | 5.80E-04 | 1.14 | 0.224 | 0.202 | A | gcaggcttcatgtgt[A/G]ttaactattaaggctc (SEQ ID NO: 0847) |
| 03 | rs7906565 | 10 | q | q23.31 | LOC119358\|HTR7 | 91922383 | 8.31E-03 | 0.78 | 0.027 | 0.035 | G | aacaaattccatatgt[A/G]ataggatgtacatgc (SEQ ID NO: 0848) |
| 02 | rs6583759 | 10 | q | q23.32 | NUDT9P1\|PCGF5 | 92976570 | 7.20E-05 | 1.27 | 0.074 | 0.059 | C | tccccctaccattcat[A/C]catcatgatttagg (SEQ ID NO: 0849) |
| 03 | rs7894133 | 10 | q | q23.32 | NUDT9P1\|PCGF5 | 92979176 | 8.65E-04 | 1.24 | 0.066 | 0.054 | A | ttgtggtatatataca[A/G]taatatctccaatgc (SEQ ID NO: 0850) |
| 03 | rs1057971 | 10 | q | q23.32 | PCGF5 | 92987510 | 6.66E-04 | 1.24 | 0.067 | 0.054 | G | tggtaggggaggaagt[A/G]taggcagaaaaccagt (SEQ ID NO: 0851) |
| 03 | rs7074612 | 10 | q | q23.32 | PCGF5 | 93041869 | 2.55E-03 | 1.22 | 0.064 | 0.053 | G | atataaatcccatga[A/G]tgaagtratttctata (SEQ ID NO: 0852) |
| 03 | rs7082510 | 10 | q | q23.32 | PCGF5 | 93004825 | 9.19E-04 | 1.23 | 0.067 | 0.055 | A | ccttggtcctttactc[A/G]tgcctctctgtactca (SEQ ID NO: 0853) |
| 03 | rs10882232 | 10 | q | q23.33 | MYOF | 95189263 | 1.29E-02 | 1.08 | 0.416 | 0.397 | G | aagatgttataagtca[A/G]tgattttctgccttc (SEQ ID NO: 0854) |
| 02 | rs2296580 | 10 | q | q24.32 | ACTR1A | 104241683 | 2.32E-05 | 0.88 | 0.265 | 0.292 | A | gcacctgagaattga[A/C]ttgaagttctccttc (SEQ ID NO: 0855) |
| 03 | rs7075281 | 10 | q | q24.32 | C10orf95\|TMEM180 | 104220301 | 1.16E-03 | 0.89 | 0.282 | 0.305 | A | acagcctacattgagc[A/C]aaacaaaactgattt (SEQ ID NO: 0856) |
| 03 | rs7475335 | 10 | q | q24.32 | SUFU | 104343428 | 1.27E-03 | 0.90 | 0.309 | 0.333 | A | (SEQ ID NO: 0857) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2236211 | 10 | q | q24.33 | NEURL | 105349816 | 3.89E-03 | 1.10 | 0.421 | 0.399 | A | tccagcctaaataaat[A/C]cccacccggtttgggg (SEQ ID NO: 0858) |
| 03 | rs7071247 | 10 | q | q24.33 | NEURL | 105257786 | 1.30E-04 | 1.19 | 0.151 | 0.130 | A | ggggaacacaagaaggcc[A/G]ggggagctctcccg (SEQ ID NO: 0859) |
| 03 | rs7918186 | 10 | q | q24.33 | NEURL | 105350447 | 2.46E-03 | 1.10 | 0.420 | 0.397 | A | agatataegctcaagc[A/C]cctccaagccttact (SEQ ID NO: 0860) |
| 03 | rs729952 | 10 | q | q24.33 | NEURL|SH3PXD2A | 105352990 | 6.35E-03 | 1.09 | 0.417 | 0.396 | A | ctagaaacctgcctca[A/G]atggggaaagattagg (SEQ ID NO: 0861) |
| 03 | rs11191750 | 10 | q | q24.33 | SH3PXD2A | 105388286 | 2.73E-04 | 1.17 | 0.174 | 0.153 | A | caacactgtgcctaga[A/C]cttggggccagtctgg (SEQ ID NO: 0862) |
| 03 | rs7918134 | 10 | q | q24.33 | SH3PXD2A | 105391300 | 1.29E-03 | 1.14 | 0.183 | 0.164 | A | ggtgcttgagccagta[A/G]ctcagaaggtaaccct (SEQ ID NO: 0863) |
| 02 | rs11193561 | 10 | q | q25.1 | SORCS1|LOC100128304 | 109374384 | 2.91E-05 | 1.16 | 0.269 | 0.240 | A | gtgatfgttagggggtg[A/G]catcagcaaggactgt (SEQ ID NO: 0864) |
| 03 | rs11195815 | 10 | q | 825.2 | ADRA2A|GPAM | 113859224 | 5.16E-03 | 1.30 | 0.029 | 0.022 | A | gctgtaggcaaacagt[A/G]aatccaatttcctcca (SEQ ID NO: 0865) |
| 03 | rs17129504 | 10 | q | 825.2 | ADRA2A|GPAM | 113855817 | 2.88E-03 | 1.37 | 0.023 | 0.017 | C | crtgtctcaacactg[A/C]acatttcatgtagcttt (SEQ ID NO: 0866) |
| 03 | rs6584993 | 10 | q | q25.2 | DUSP5|SMC3 | 112314670 | 3.83E-03 | 1.20 | 0.070 | 0.059 | A | tccaggaattcagcac[A/G]ttccagccctggagac (SEQ ID NO: 0867) |
| 03 | rs1541466 | 10 | q | q25.3 | ATRNL1 | 117594744 | 3.71E-03 | 0.89 | 0.188 | 0.206 | G | agagagagggagag[A/G]taactgatacatgcta (SEQ ID NO: 0868) |
| 03 | rs2024179 | 10 | q | q25.3 | ATRNL1 | 117591081 | 3.35E-03 | 0.89 | 0.188 | 0.207 | G | cacdgtccctgaattgc[A/G]aaataaggggtgacctt (SEQ ID NO: 0869) |
| 03 | rs7099933 | 10 | q | q25.3 | LOC100286977|LOC100132839 | 115728772 | 6.95E-03 | 1.14 | 0.121 | 0.107 | A | aagcaaaccaattgga[A/G]aggtgttccctgtatt (SEQ ID NO: 0870) |
| 02 | rs2275111 | 10 | q | q26.11 | SFXN4 | 120917445 | 1.11E-06 | 1.14 | 0.527 | 0.494 | G | ccgatagttggtgact[A/G]ttttatttcttgttg (SEQ ID NO: 0871) |
| 02 | rs10749291 | 10 | q | q26.11 | SFXN4 | 120920588 | 3.61E-05 | 0.91 | 0.463 | 0.487 | G | cagagggaaaacctgcc[A/G]agagggggcaaatggat (SEQ ID NO: 0872) |
| 03 | rs12355817 | 10 | q | q26.12 | SEC23IP|PPAPDC1A | 121838912 | 2.46E-03 | 1.18 | 0.092 | 0.079 | A | tctccttaagataca[A/G]gaagcttggaagcgga (SEQ ID NO: 0873) |
| 02 | rs2901297 | 10 | q | q26.13 | ATE1 | 133521484 | 3.23E-05 | 1.08 | 0.125 | 0.117 | A | cccatctgtaaaatgg[A/G]caacctaccattgattc (SEQ ID NO: 0874) |
| 02 | rs1470996 | 10 | q | q26.13 | FAM53B | 126331555 | 2.39E-05 | 1.11 | 0.184 | 0.169 | A | gagggaatggccatta[A/G]gtaaatgctctttaga (SEQ ID NO: 0875) |
| 03 | rs7919338 | 10 | q | q26.2 | ADAM12 | 127731365 | 6.00E-02 | 1.10 | 0.276 | 0.258 | A | caggtcccacgatacc[A/G]tcaggaatgtcgttt (SEQ ID NO: 0876) |
| 02 | rs7076942 | 10 | q | q26.3 | GLRX3|TCERG1L | 132374743 | 2.51E-04 | 1.13 | 0.292 | 0.266 | C | agttaagaaaagtgtc[A/G]caggtcaaggaactgg (SEQ ID NO: 0877) |
| 02 | rs4880419 | 10 | q | q26.3 | INPP5A | 134456109 | 7.78E-03 | 0.92 | 0.411 | 0.432 | A | atfgtagactgcacg[A/C]ggggcgtatgggctc (SEQ ID NO: 0878) |
| 03 | rs2814183 | 10 | q | q26.3 | JAKMIP3 | 133948347 | 4.01E-04 | 0.89 | 0.462 | 0.489 | G | ggggacccgtgtccc[A/G]gaagtgacaggggagga (SEQ ID NO: 0879) |
| 03 | rs12774814 | 10 | #N/A | #N/A | PITRM1 | 3182572 | 1.26E-03 | 0.89 | 0.241 | 0.264 | A | cgcaaccgcgtgaggc[A/G]acagaaccgacgggca (SEQ ID NO: 0880) |
| 03 | rs11038044 | 11 | p | p11.2 | ALX4|CD82 | 44541295 | 5.37E-05 | 0.86 | 0.179 | 0.203 | G | tcaatttcgtccagc[A/G]ttctctgctacactgc (SEQ ID NO: 0881) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 01 | exm2264447 | 11 | p | p11.2 | C11orf49 | 46963196 | 1.45E-20 | 20.92 | 0.004 | 0.000 | A | cacgcctggccaacct[A/C]ttcaccctccaatctaa (SEQ ID NO: 0882) |
| 03 | rs6416127 | 11 | p | p11.2 | PRDM11 | 45339959 | 1.31E-03 | 1.15 | 0.169 | 0.151 | C | tcagcatcactaataa[A/C]agaaacacagcgtagt (SEQ ID NO: 0883) |
| 03 | rs4756204 | 11 | p | p13 | SLC1A2 | 35292312 | 4.58E-03 | 1.10 | 0.418 | 0.396 | A | gaaaatgagtagagai[A/G]aggaaagaaataatat (SEQ ID NO: 0884) |
| 03 | rs11030997 | 11 | p | p14.1 | KCNA4|FSHB | 30206532 | 2.43E-03 | 0.90 | 0.337 | 0.360 | G | ccctattggctatta[A/G]tagattggcatttaaa (SEQ ID NO: 0885) |
| 03 | rs4074516 | 11 | p | p14.1 | LGR4 | 27465591 | 5.78E-05 | 1.10 | 0.441 | 0.418 | G | attgaaaaagcctgt[A/G]gggggtgctttgtgcag (SEQ ID NO: 0886) |
| 02 | rs16916435 | 11 | p | p14.2 | FIBIN|BBOX1 | 27030676 | 1.54E-05 | 1.09 | 0.095 | 0.088 | G | cgttgattctaccct[A/G]tgaacagctgggctta (SEQ ID NO: 0887) |
| 03 | rs1602916 | 11 | p | p14.3 | LUZP2|ANO3 | 25696461 | 4.84E-03 | 1.09 | 0.447 | 0.425 | A | tcaagacctgaattc[A/C]attttatgaatat (SEQ ID NO: 0888) |
| 02 | rs324204 | 11 | p | p14.3 | NELL1|ANO5 | 22001998 | 9.32E-06 | 1.17 | 0.265 | 0.235 | A | tccagttttatggaa[A/G]ctaccatttactcgt (SEQ ID NO: 0889) |
| 02 | rs324172 | 11 | p | p14.3 | NELL1|ANO5 | 21952288 | 3.51E-05 | 1.15 | 0.326 | 0.296 | A | agacccatatcaaaac[A/G]caataagtgtgtgca (SEQ ID NO: 0890) |
| 02 | rs2009912 | 11 | p | p14.3 | NELL1|ANO5 | 21945004 | 5.97E-05 | 1.14 | 0.330 | 0.301 | G | tgcttctagttagctt[A/G]tctatagcttccct (SEQ ID NO: 0891) |
| 02 | rs10833683 | 11 | p | p14.3 | NELL1|ANO5 | 21984498 | 2.53E-05 | 0.87 | 0.429 | 0.462 | A | acctacatcacatal[A/G]ctaaattttttttet (SEQ ID NO: 0892) |
| 03 | rs793283 | 11 | p | p15.1 | E2F8|NAV2 | 19264497 | 1.07E-03 | 0.88 | 0.205 | 0.226 | A | tgtggctcgcagattt[A/G]aaataaagcagaggtc (SEQ ID NO: 0893) |
| 03 | rs7924734 | 11 | p | p15.2 | ARNTL | 13350747 | 8.93E-03 | 1.10 | 0.270 | 0.252 | G | gagagtcacaggaagt[A/G]cccctttacgtcggat (SEQ ID NO: 0894) |
| 03 | rs12290622 | 11 | p | p15.2 | ARNTL | 13314307 | 4.97E-03 | 1.10 | 0.310 | 0.290 | G | agtagatatgtgtcca[A/G]gcctagtatttttaac (SEQ ID NO: 0895) |
| 03 | rs7949336 | 11 | p | p15.2 | ARNTL | 13319894 | 1.22E-02 | 1.09 | 0.273 | 0.255 | G | tccccagaggtgt[A/G]tggctagttagctcac (SEQ ID NO: 0896) |
| 02 | rs10766066 | 11 | p | p15.2 | RASSF10|ARNTL | 13278027 | 2.73E-02 | 1.08 | 0.296 | 0.280 | G | attagtgtcagttac[A/G]tagcttgggcccagac (SEQ ID NO: 0897) |
| 02 | rs11042937 | 11 | p | p15.3 | MRV11|CTR9 | 10745394 | 3.79E-04 | 1.12 | 0.520 | 0.492 | A | cagcacatgaatatgg[A/C]ggccgtgctgtgcca (SEQ ID NO: 0898) |
| 03 | rs10834648 | 11 | p | p15.4 | LOC650368|TRPC2 | 3645345 | 2.92E-03 | 1.11 | 0.325 | 0.303 | G | ctagcctataactaac[A/G]cataagtttcatcat (SEQ ID NO: 0899) |
| 03 | rs17403795 | 11 | p | p15.4 | LYVE1 | 10581217 | 2.51E-03 | 0.86 | 0.106 | 0.122 | A | aaaagattgggctgaat[A/G]gggaaagatgagatg (SEQ ID NO: 0900) |
| 03 | rs4910630 | 11 | p | p15.4 | OR52M1|C11orf40 | 4590639 | 2.59E-04 | 0.89 | 0.393 | 0.421 | A | ccctcctgccccctc[A/G]gtttaggggtttacaag (SEQ ID NO: 0901) |
| 03 | rs12271195 | 11 | p | p15.4 | SYT9 | 7463443 | 2.27E-03 | 0.86 | 0.116 | 0.132 | A | ctcagtgaaaatggct[A/G]aggggaggagcttttc (SEQ ID NO: 0902) |
| 02 | rs1908177 | 11 | p | p15.4 | TRIM68|OR51D1 | 4659419 | 6.34E-06 | 0.87 | 0.389 | 0.424 | A | tctccattcacccc[A/C]acatgcaattcaactt (SEQ ID NO: 0903) |
| 03 | rs1865558 | 11 | p | p15.4 | WEE1|SWAP70 | 9650585 | 1.83E-03 | 1.11 | 0.289 | 0.267 | A | tatatctccatgatat[A/G]taatccaagatatata (SEQ ID NO: 0904) |
| 02 | rs885414 | 11 | p | p15.4 | ZNF195|ART5 | 3644307 | 1.01E-02 | 1.16 | 0.189 | 0.168 | C | cttattgtgagagaa[C/G]aggaaacctcagggtg (SEQ ID NO: 0905) |
| 02 | exm926722 | 11 | q | q13.1 | SCYL1 | 65305309 | 3.44E-14 | 9.50 | 0.010 | 0.001 | A | (SEQ ID NO: 0906) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs10752564 | 11 | q | q13.3 | FGF19\|FGF4 | 69540990 | 1.84E-04 | 1.13 | 0.322 | 0.295 | A | cggtgtccagtcgtc[A/C]tgctggccagcacag (SEQ ID NO: 0907) |
| 02 | exm936578 | 11 | q | q13.3 | PPFIA1 | 70170536 | 1.14E-16 | 5.27 | 0.007 | 0.000 | G | ggaggaagcggctgtc[A/G]cagtggctgggcttag (SEQ ID NO: 0908) |
| 03 | rs11228498 | 11 | q | q13.3 | TPCN2\|MYEOV | 68870298 | 9.14E-05 | 1.11 | 0.508 | 0.482 | A | cttactaaagaactca[A/G]tgtatgcaggaacag (SEQ ID NO: 0909) |
| 03 | rs10751211 | 11 | q | q13.4 | ARAP1 | 72405223 | 3.03E-05 | 1.18 | 0.202 | 0.177 | A | ttgcatttgttttggg[A/G]actgctctgaggttaga (SEQ ID NO: 0910) |
| 02 | exm937263 | 11 | q | q13.4 | DHCR7 | 71155161 | 1.41E-08 | 35.86 | 0.004 | 0.000 | A | tggcagcagtggagat[A/G]gacagagcagagagat (SEQ ID NO: 0911) |
| 02 | rs6592850 | 11 | q | q14.1 | ODZ4 | 79226201 | 9.43E-05 | 1.19 | 0.407 | 0.366 | G | tgaccagtacagctgc[A/C]ccctgactggcccgt (SEQ ID NO: 0912) |
| 03 | rs10831309 | 11 | q | q21 | ENDOD1\|SESN3 | 94881894 | 5.60E-03 | 0.91 | 0.449 | 0.471 | A | aattaagcaataataaa[A/G]atgtgacttttacagc (SEQ ID NO: 0913) |
| 03 | rs16922232 | 11 | q | q21 | LOC100129203\|FAM76B | 95304581 | 8.66E-03 | 1.26 | 0.033 | 0.026 | A | tcatataacttagcta[A/G]gtcattgtgaatttt (SEQ ID NO: 0914) |
| 03 | rs2123325 | 11 | q | q22.1 | CNTN5 | 99959543 | 4.27E-04 | 0.88 | 0.279 | 0.305 | G | catggaacaggtgt[A/G]aacttaagtgcagagcc (SEQ ID NO: 0915) |
| 03 | rs7128754 | 11 | q | q22.1 | JRKL\|CNTN5 | 97618161 | 1.23E-02 | 1.09 | 0.366 | 0.348 | A | tctaccaaacatacaa[A/C]tgtgccttttcacaga (SEQ ID NO: 0916) |
| 03 | rs11212569 | 11 | q | q22.1 | JRKL\|CNTN5 | 97623375 | 7.12E-04 | 1.12 | 0.351 | 0.326 | A | atggtgcttttcaa[A/C]catacccatgaccaat (SEQ ID NO: 0917) |
| 03 | rs12792912 | 11 | q | q22.2 | LOC100288111\|MMP13 | 102801303 | 1.97E-02 | 0.93 | 0.414 | 0.432 | C | ctcacatttaaactga[A/C]gggaatcataaagtaac (SEQ ID NO: 0918) |
| 03 | rs12788925 | 11 | q | q22.2 | LOC100288111\|MMP13 | 102801847 | 1.80E-02 | 0.93 | 0.413 | 0.431 | C | aaaagaaattctgggt[A/G]tctccagagagagggaat (SEQ ID NO: 0919) |
| 02 | rs1784408 | 11 | q | q22.2 | MMP20 | 102469509 | 2.13E-02 | 1.11 | 0.367 | 0.343 | G | aaaagaaggacctttaa[C/G]gctcaacaacaatgcat (SEQ ID NO: 0920) |
| 02 | exm952255 | 11 | q | q22.3 | CASP12 | 104768141 | 5.64E-12 | 6.54 | 0.020 | 0.005 | A | aatgccatctagaaaag[A/G]tcttgatcagcaactt (SEQ ID NO: 0921) |
| 03 | rs10891431 | 11 | q | q23.2 | LOC100132686\|NCAM1 | 112641531 | 1.95E-02 | 0.92 | 0.240 | 0.256 | A | ccagccaatgggagag[A/G]tgaatgctagaggggtt (SEQ ID NO: 0922) |
| 03 | rs2073848 | 11 | q | q23.2 | ZBTB16 | 114051904 | 7.66E-04 | 1.15 | 0.178 | 0.159 | G | agagcccctccatgc[A/G]atttaaagtatgactga (SEQ ID NO: 0923) |
| 03 | rs3782007 | 11 | q | q23.2 | ZBTB16 | 114066438 | 4.47E-04 | 1.15 | 0.207 | 0.186 | A | gataatctcaatatag[A/G]cctcgcatgagagtaag (SEQ ID NO: 0924) |
| 03 | rs11215574 | 11 | q | q23.3 | CADM1 | 115363443 | 3.37E-02 | 0.93 | 0.245 | 0.260 | G | gttttcaccatgggag[A/G]aagaaaaacacaataa (SEQ ID NO: 0925) |
| 02 | exm960718 | 11 | q | q23.3 | PHLDB1 | 118516274 | 5.43E-15 | 33.17 | 0.007 | 0.000 | A | ggggagggtgaagcac[A/C]cctatgatacgctgag (SEQ ID NO: 0926) |
| 01 | rs11217801 | 11 | q | q23.3 | POU2F3 | 120165942 | 2.66E-06 | 1.25 | 0.132 | 0.109 | G | ctaacagatagccgccc[A/G]tggttgaaggcaagca (SEQ ID NO: 0927) |
| 03 | rs17671708 | 11 | q | q24.1 | LOC100128242 | 123306172 | 1.59E-02 | 1.11 | 0.147 | 0.134 | G | ccctctcaattttca[A/G]ctttgtgcagtgaaaa (SEQ ID NO: 0928) |
| 03 | rs10892895 | 11 | q | q24.1 | UBASH3B | 122630672 | 2.34E-02 | 1.14 | 0.086 | 0.076 | G | gtgttcacttcctttgt[A/G]taattccctccctca (SEQ ID NO: 0929) |
| 03 | rs1946091 | 11 | q | q24.2 | KIRREL3 | 126612903 | 3.20E-03 | 1.10 | 0.388 | 0.366 | G | tatctgagatgaggcc[A/G]tcagtgaaggacctcct (SEQ ID NO: 0930) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | exm968612 | 11 | q | q24.2 | RPUSD4 | 126081523 | 1.59E−08 | Inf | 0.003 | 0.000 | A | cgacgcgctccacctg[A/G]gcgccgccatcttaca (SEQ ID NO: 0931) |
| 03 | rs11221660 | 11 | q | q24.3 | RICS\|BARX2 | 129182778 | 1.35E−02 | 0.92 | 0.388 | 0.407 | A | ctgaggtttccgggat[A/G]aggagaagggtgggcg (SEQ ID NO: 0932) |
| 03 | rs7122696 | 11 | q | q25 | NTM | 132001390 | 1.81E−04 | 1.16 | 0.215 | 0.192 | A | acaaggctgcacttc[A/G]tagggttcatcataa (SEQ ID NO: 0933) |
| 03 | rs7310913 | 12 | p | p11.23 | ITPR2 | 26854487 | 1.45E−02 | 1.09 | 0.315 | 0.297 | C | ccagaccatacata[A/C]gaataaaatgttacat (SEQ ID NO: 0934) |
| 03 | rs11048661 | 12 | p | p11.23 | ITPR2 | 26854124 | 1.31E−03 | 1.11 | 0.355 | 0.331 | C | ggcagtgaaagtcatg[A/C]ttgtaccgcaatcaat (SEQ ID NO: 0935) |
| 03 | rs11054439 | 12 | p | p13.2 | ETV6 | 11895308 | 7.91E−05 | 0.88 | 0.336 | 0.366 | A | ataggactcagaaaa[A/G]gcatcattccttcat (SEQ ID NO: 0936) |
| 02 | rs2051525 | 12 | p | p13.2 | ETV6 | 11888423 | 7.12E−05 | 0.88 | 0.345 | 0.375 | A | ccctaataaacaaact[A/G]cttaattgaacagccc (SEQ ID NO: 0937) |
| 02 | rs17181375 | 12 | p | p13.31 | ANO2 | 5678868 | 6.25E−03 | 1.15 | 0.109 | 0.097 | A | gtctcaatccagcca[A/G]gaagtgaataatagatg (SEQ ID NO: 0938) |
| 03 | rs7296720 | 12 | p | p13.32 | TSPAN9 | 3374920 | 2.50E−04 | 1.19 | 0.128 | 0.110 | G | tagaaatttgtcgaac[A/G]tgttttgataaatga (SEQ ID NO: 0939) |
| 03 | rs2429166 | 12 | p | p13.33 | CACNA2D4 | 2025907 | 1.12E−03 | 0.88 | 0.181 | 0.201 | G | gtctcctggattggc[A/G]gaggaagggctttggg (SEQ ID NO: 0940) |
| 03 | rs10774066 | 12 | p | p13.33 | FKBP4\|ITFG2 | 2920736 | 3.61E−04 | 1.18 | 0.144 | 0.125 | G | aaaaaaaatgattct[A/G]ccttatctggatttt (SEQ ID NO: 0941) |
| 03 | rs10848706 | 12 | p | p13.33 | FKBP4\|ITFG2 | 2919701 | 3.45E−04 | 1.18 | 0.144 | 0.125 | G | tgcagatatattctga[A/G]ctgaactgtgttaca (SEQ ID NO: 0942) |
| 03 | rs2286601 | 12 | p | p13.33 | ITFG2 | 2932177 | 2.25E−04 | 1.18 | 0.148 | 0.128 | A | cacttccctttcgaac[A/G]tatccccctgatgtaag (SEQ ID NO: 0943) |
| 03 | rs3759411 | 12 | p | p13.33 | LOC100288472\|LOC728147 | 2901570 | 1.10E−04 | 1.19 | 0.145 | 0.124 | G | catcacctttatctgt[A/G]gctgactcctgctggg (SEQ ID NO: 0944) |
| 03 | rs3814249 | 12 | p | p13.33 | NRIP2 | 2936276 | 1.57E−03 | 1.14 | 0.174 | 0.156 | G | tggaagggcagacacc[A/G]tagtcccccagctacct (SEQ ID NO: 0945) |
| 03 | rs3814250 | 12 | p | p13.33 | NRIP2 | 2936049 | 1.89E−04 | 1.18 | 0.147 | 0.127 | A | ctgcttgggctgggtc[A/G]aaggctctgctgactg (SEQ ID NO: 0946) |
| 03 | rs11062376 | 12 | p | p13.33 | NRIP2\|FOXM1 | 2950208 | 3.76E−04 | 1.17 | 0.146 | 0.127 | A | ttatgtccccaaaccc[A/G]cctggggccagggggt (SEQ ID NO: 0947) |
| 02 | exm997545 | 12 | q | q13.11 | HDAC7 | 48187329 | 6.43E−21 | 12.71 | 0.013 | 0.001 | A | tccccggtgctgcccc[A/G]gggggagccgcccagcc (SEQ ID NO: 0948) |
| 03 | rs7488270 | 12 | q | q13.12 | SPATS2 | 49784365 | 1.05E−04 | 1.24 | 0.087 | 0.071 | A | ttcatcttatttggc[A/G]ttaaagttaacacaa (SEQ ID NO: 0949) |
| 03 | rs7309610 | 12 | q | q13.12 | SPATS2 | 49783814 | 1.61E−04 | 1.24 | 0.087 | 0.071 | A | attttcaactgaacaa[A/G]aaaacaaaggcgttag (SEQ ID NO: 0950) |
| 03 | rs186231 | 12 | q | q13.13 | FIGNL2 | 52212489 | 9.30E−04 | 1.16 | 0.145 | 0.127 | A | ttatgtcccaaaccc[A/G]cctggggccaggggt (SEQ ID NO: 0951) |
| 03 | rs172559 | 12 | q | q13.13 | FLJ33996 | 52204246 | 7.90E−04 | 1.16 | 0.143 | 0.125 | A | tgcacaggaggctgag[A/G]tgggagagagaaaag (SEQ ID NO: 0952) |
| 03 | rs3900362 | 12 | q | q13.13 | SCN8A | 52108030 | 2.18E−04 | 1.19 | 0.135 | 0.116 | G | taatatttggcaaagc[A/G]ttgccacttaccact (SEQ ID NO: 0953) |
| 03 | rs303808 | 12 | q | q13.13 | SCN8A | 52163789 | 2.88E−04 | 1.16 | 0.169 | 0.149 | G | ctgttatagtttccac[A/G]tcacaactaactgttt (SEQ ID NO: 0954) |
| 03 | rs303771 | 12 | q | q13.13 | SCN8A | 52152192 | 8.38E−04 | 1.17 | 0.131 | 0.114 | G | aaagggatgaggagc[A/G]gatggggctgggggacac (SEQ ID NO: 0955) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2280807 | 12 | q | q13.13 | SCN8A | 52174231 | 6.32E-04 | 1.17 | 0.143 | 0.125 | A | gttcgacattttgcaa[A/G]tctctttaatgtctgg (SEQ ID NO: 0956) |
| 03 | rs715930 | 12 | q | q13.3 | B4GALNT1 | 58023981 | 1.85E-03 | 0.88 | 0.190 | 0.210 | A | cctttccttccaggtc[A/G]tttgagtcaagttgaa (SEQ ID NO: 0957) |
| 03 | rs11173855 | 12 | q | q14.1 | LOC100289417\|FAM19A2 | 61637441 | 1.33E-03 | 0.90 | 0.438 | 0.463 | A | ggctgctgaagtgac[A/C]agttgtagttgcctgt (SEQ ID NO: 0958) |
| 03 | rs10784186 | 12 | q | q14.1 | LOC100289417\|FAM19A2 | 61604963 | 2.08E-03 | 0.91 | 0.425 | 0.449 | A | tagactaaaattaata[A/C]agataagagttgaaac (SEQ ID NO: 0959) |
| 02 | rs2270482 | 12 | q | q14.1 | PPM1H | 63087901 | 2.89E-05 | 0.82 | 0.131 | 0.155 | A | attatcattttcttctt[A/C]attattcctagtctg (SEQ ID NO: 0960) |
| 03 | rs2711666 | 12 | q | q14.1 | SLC16A7 | 60132210 | 1.06E-02 | 0.92 | 0.437 | 0.457 | A | tcccataaaggaaga[A/G]gtagtcagtgtggtga (SEQ ID NO: 0961) |
| 03 | rs10431559 | 12 | q | q14.1 | SLC16A7\|LOC100289417 | 60244639 | 7.38E-02 | 0.94 | 0.438 | 0.452 | A | tgggctgctatttctc[A/G]tggaccaataacaaga (SEQ ID NO: 0962) |
| 03 | rs10437957 | 12 | q | q14.1 | SLC16A7\|LOC100289417 | 60202218 | 3.19E-02 | 0.93 | 0.440 | 0.457 | A | attagtcttgggtccca[A/G]attaatttcatgatca (SEQ ID NO: 0963) |
| 03 | rs7307997 | 12 | q | q14.2 | AVPR1A\|DPY19L2 | 63557914 | 8.89E-03 | 0.92 | 0.414 | 0.434 | G | ctaataatctcccctag[A/G]ttttgtccttgtcta (SEQ ID NO: 0964) |
| 03 | rs6581482 | 12 | q | q14.2 | AVPR1A\|DPY19L2 | 63682898 | 1.85E-02 | 0.92 | 0.324 | 0.342 | A | gaattcttgactgcct[A/G]gttgttgttactcttctc (SEQ ID NO: 0965) |
| 03 | rs11612942 | 12 | q | q14.2 | AVPR1A\|DPY19L2 | 63704363 | 1.38E-03 | 1.16 | 0.142 | 0.125 | A | gtaaagattgggaaaa[A/G]cttgcactaacttcca (SEQ ID NO: 0966) |
| 02 | exm1020169 | 12 | q | q15 | CAND1 | 67706476 | 4.89E-10 | 40.9 | 0.004 | 0.000 | A | ctggatgttggggaga[A/G]ttaacttgagttcaga (SEQ ID NO: 0967) |
| 02 | rs1861933 | 12 | q | q15 | LOC100286998\|LOC100288856 | 68842405 | 2.18E-05 | 1.16 | 0.214 | 0.190 | G | ctctctctgcttctg[A/G]aatggttagcagtgct (SEQ ID NO: 0968) |
| 02 | rs7298169 | 12 | q | q15 | LOC100286998\|LOC100288856 | 68854225 | 1.61E-05 | 1.21 | 0.129 | 0.109 | G | aagtaaaggaattata[A/G]actagctgctgcttca (SEQ ID NO: 0969) |
| 02 | rs2216437 | 12 | q | q15 | LOC100286998\|LOC100288856 | 68850924 | 4.99E-05 | 1.19 | 0.097 | 0.082 | G | gccaaagctgtcagaa[A/G]acatcctacaatgcac (SEQ ID NO: 0970) |
| 02 | rs3863373 | 12 | q | q15 | PTPRR | 71288396 | 3.63E-05 | 1.09 | 0.349 | 0.330 | A | acccctgttgagcac[A/G]tggataccttttgaggt (SEQ ID NO: 0971) |
| 03 | rs2035151 | 12 | q | q15 | E2F7 | 77445086 | 8.84E-05 | 1.11 | 0.098 | 0.089 | G | tattttagtaaaata[A/C]taaatacacaccttgt (SEQ ID NO: 0972) |
| 03 | rs12422952 | 12 | q | q21.2 | GLIPR1 | 75881018 | 3.38E-04 | 0.89 | 0.372 | 0.400 | A | tgtctcctcaacccac[A/G]tttgaaaggggctcca (SEQ ID NO: 0973) |
| 03 | rs7969930 | 12 | q | q21.2 | GLIPR1L2\|GLIPR1 | 75867565 | 6.61E-04 | 0.90 | 0.375 | 0.401 | G | ctggagttgcttagg[A/G]gtctgcattttaacaa (SEQ ID NO: 0974) |
| 03 | rs11180540 | 12 | q | q21.2 | GLIPR1L2\|GLIPR1 | 75873161 | 5.42E-04 | 0.89 | 0.375 | 0.402 | A | ttttgacagatagttg[A/G]caacagacatgtacag (SEQ ID NO: 0975) |
| 03 | rs10785190 | 12 | q | q21.2 | GLIPR1L2\|GLIPR1 | 75819844 | 7.57E-04 | 0.90 | 0.375 | 0.401 | G | gctacaggtgtgcctg[A/G]aatgtttcttttacttt (SEQ ID NO: 0976) |
| 03 | rs733880 | 12 | q | q21.2 | KRR1\|LOC100289143 | 75976164 | 7.43E-05 | 1.11 | 0.495 | 0.470 | G | aatacaactagagaga[A/G]tatatatagatacttaa (SEQ ID NO: 0977) |
| 03 | rs6582294 | 12 | q | q21.2 | KRR1\|LOC100289143 | 76034992 | 7.29E-04 | 0.90 | 0.383 | 0.409 | A | taaaattgaccattt[A/G]cagacataatggccaag (SEQ ID NO: 0978) |
| 03 | rs12423804 | 12 | q | q21.31 | PPP1R12A\|C12orf64 | 80580111 | 7.63E-04 | 0.90 | 0.436 | 0.462 | A | gaatgaatcatcccca[A/G]tttgtttcttgctaca (SEQ ID NO: 0979) |
| | | | | | | | | | | | | acctgatgggaagac[A/G]cggctaagtaggaaag |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs4882448 | 12 | q | q21.31 | TMTC2|SLC6A15 | 83746599 | 1.24E-02 | 0.92 | 0.467 | 0.486 | G | tcctctgacatggatg[A/G]ttgtgggcattagtaac (SEQ ID NO: 0980) |
| 03 | rs17790382 | 12 | q | q22 | EEA1 | 93230276 | 4.98E-03 | 0.85 | 0.087 | 0.100 | C | atgcttcatagcttac[A/C]aagtlatttlcagagat (SEQ ID NO: 0981) |
| 03 | rs11829776 | 12 | q | q22 | FGD6 | 95531442 | 2.93E-03 | 0.89 | 0.195 | 0.214 | G | ataggactgaacaaca[A/G]agaattgctgatatct (SEQ ID NO: 0982) |
| 03 | rs12579299 | 12 | q | q22 | NR2C1 | 95442242 | 1.10E-03 | 0.88 | 0.193 | 0.214 | G | cgcaataactgctatt[A/G]taactgacttaacagg (SEQ ID NO: 0983) |
| 02 | rs14121 | 12 | q | q22 | VEZT | 95694394 | 9.10E-06 | 0.85 | 0.262 | 0.294 | G | gaacagacttttggtg[A/G]tgaggaggaagaacaa (SEQ ID NO: 0984) |
| 02 | rs3596 | 12 | q | q22 | VEZT | 95696420 | 8.71E-08 | 1.16 | 0.508 | 0.471 | G | gaagtcagtggttctc[A/G]gttgtatttagtgggt (SEQIDN:0985) |
| 02 | rs10859856 | 12 | q | q22 | VEZT | 95631276 | 5.23E-07 | 1.15 | 0.505 | 0.470 | G | ccctcgtttggtgat[A/G]tcagtgaggctgata (SEQ ID NO: 0986) |
| 02 | rs7959730 | 12 | q | q23.1 | NEDD1|RMST | 97495927 | 3.16E-05 | 1.09 | 0.347 | 0.328 | G | aatgcaaatgaaaaca[A/G]tatgagaagccactac (SEQ ID NO: 0987) |
| 03 | rs10861688 | 12 | q | q23.3 | CRY1 | 107394048 | 9.61E-05 | 0.85 | 0.169 | 0.193 | A | tgtgctgccacaaggac[A/G]actgaaacaaaagaat (SEQ ID NO: 0988) |
| 03 | rs973724 | 12 | q | q23.3 | CRY1|BTBD11 | 107578877 | 4.68E-04 | 0.89 | 0.316 | 0.342 | G | taacaagaatgaccca[A/G]tctatatgatcaactt (SEQ ID NO: 0989) |
| 03 | rs1896058 | 12 | q | q23.3 | LOC100287556|WSCD2 | 108405763 | 7.17E-04 | 1.11 | 0.436 | 0.410 | A | catgaaagtcacta[A/G]aaaactctacctactg (SEQ ID NO: 0990) |
| 02 | rs11068393 | 12 | q | q24.22 | FBXO21 | 117623136 | 3.08E-04 | 0.87 | 0.193 | 0.217 | G | gggaagaaatatct[A/G]tcagtgaacaactgt (SEQ ID NO: 0991) |
| 02 | rs1466852 | 12 | q | q24.22 | FBXO21 | 117591843 | 1.57E-04 | 0.86 | 0.192 | 0.216 | A | atagacactggcccac[A/G]tgtgtgttgaaaagaa (SEQ ID NO: 0992) |
| 01 | rs10431397 | 12 | q | q24.23 | KSR2 | 118106194 | 1.38E-15 | 2.43 | 0.021 | 0.009 | A | cctatgatctgtggaa[A/G]cacctccctctgaa (SEQ ID NO: 0993) |
| 03 | rs10846578 | 12 | q | q24.31 | DNAH10 | 124400278 | 7.08E-04 | 1.12 | 0.306 | 0.282 | A | tgtcgttcatacacc[A/G]gaatatcattcagccc (SEQ ID NO: 0994) |
| 03 | rs7975815 | 12 | q | q24.31 | DNAH10 | 124388129 | 3.30E-03 | 0.72 | 0.019 | 0.026 | G | gtgagagtaggtcact[A/G]ttgaggccccataca (SEQ ID NO: 0995) |
| 02 | exm1044289 | 12 | q | q24.31 | P2RX7 | 121622550 | 1.22E-10 | 6.57 | 0.009 | 0.001 | A | tgccgctgaggatcc[A/G]gaaagagtttcgaag (SEQ ID NO: 0996) |
| 02 | rs4765052 | 12 | q | q24.32 | TMEM132B | 126043965 | 1.91E-03 | 0.87 | 0.140 | 0.158 | A | atcacaaagccatact[A/G]caggtacagggtctga (SEQ ID NO: 0997) |
| 03 | rs4765044 | 12 | q | q24.32 | TMEM132B | 125981136 | 9.73E-04 | 0.90 | 0.375 | 0.400 | A | ctctgggttgcccc[A/G]tccttgagccaatga (SEQ ID NO: 0998) |
| 01 | exm1054045 | 12 | q | q24.33 | POLE | 133263886 | 1.21E-08 | 7.12 | 0.007 | 0.001 | C | catgtctctgaggagc[C/G]gcggggcgcggccgc (SEQ ID NO: 0999) |
| 02 | rs2012359 | 13 | q | q12.12 | PARP4 | 25078073 | 2.11E-02 | 1.16 | 0.135 | 0.119 | G | cacatattgcaagcta[C/G]gatatlattcaatttt (SEQ ID NO: 1000) |
| 03 | rs3117849 | 13 | q | q12.13 | ATP8A2 | 26291179 | 4.22E-03 | 1.34 | 0.025 | 0.018 | A | tgtcctcccagagtct[A/G]tcatctatcaggaagt (SEQ ID NO: 1001) |
| 03 | rs7328428 | 13 | q | q12.3 | HMGB1|USPL1 | 31083678 | 8.44E-04 | 1.24 | 0.062 | 0.051 | A | aatttaagaatattggg[A/G]cacggccaggcgtggt (SEQ ID NO: 1002) |
| 03 | rs1543660 | 13 | q | q12.3 | KIAA0774 | 29855650 | 6.01E-03 | 1.29 | 0.031 | 0.024 | G | ttaagtcactgcataa[A/G]tatcgtcacacaaat (SEQ ID NO: 1003) |
| 03 | rs9506012 | 13 | q | q12.3 | LOC100287487|POMP | 29135021 | 2.97E-04 | 1.16 | 0.183 | 0.161 | G |  (SEQ ID NO: 1004) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs663528 | 13 | q | q12.3 | UBL3\|KATNAL1 | 30607076 | 4.92E-04 | 0.90 | 0.464 | 0.492 | A | ccaagctccctccac[A/G]gcagccaacacacct (SEQ ID NO: 1005) |
| 03 | rs8002871 | 13 | q | q12.3 | UBL3\|KATNAL1 | 30574667 | 4.74E-04 | 1.12 | 0.464 | 0.437 | G | tctgaacaaagatgac[A/C]gggaggagctgccttgg (SEQ ID NO: 1006) |
| 02 | rs9591159 | 13 | q | q13.1 | FRY | 32798953 | 4.76E-05 | 1.16 | 0.230 | 0.204 | A | tgtgattgagtttg[A/G]gcgtcagaaccgcgta (SEQ ID NO: 1007) |
| 02 | rs394307 | 13 | q | q13.1 | LOC122038\|KL | 33569834 | 3.37E-05 | 1.08 | 0.442 | 0.422 | G | tatttccccgaataa[A/G]agcctttatataatgt (SEQ ID NO: 1008) |
| 03 | rs1199994 | 13 | q | q13.3 | CSNK1A1L\|POSTN | 37694027 | 1.50E-03 | 1.23 | 0.063 | 0.052 | G | actgagtagtcatcag[A/G]atatttggttgtttg (SEQ ID NO: 1009) |
| 03 | rs9315468 | 13 | q | q13.3 | FAM48A\|CSNK1A1L | 37667508 | 8.35E-04 | 0.90 | 0.416 | 0.442 | A | caagtactcaataaat[A/G]taaacaaacctgtcat (SEQ ID NO: 1010) |
| 03 | rs9603439 | 13 | q | q13.3 | FREM2 | 39402920 | 9.64E-03 | 1.20 | 0.055 | 0.046 | A | atgaaatagtaaattac[A/C]agcctacactttgaa (SEQ ID NO: 1011) |
| 03 | rs9603442 | 13 | q | q13.3 | FREM2 | 39406629 | 5.34E-03 | 1.21 | 0.055 | 0.046 | A | gagctgggtttatatg[A/C]attgacactgaaaagtt (SEQ ID NO: 1012) |
| 03 | rs2766484 | 13 | q | q14.13 | SIAH3\|ZC3H13 | 46443060 | 1.56E-04 | 1.13 | 0.409 | 0.380 | C | aactggttattcccta[A/G]agctgagattgtgagg (SEQ ID NO: 1013) |
| 03 | rs9567586 | 13 | q | q14.13 | SIAH3\|ZC3H13 | 46431655 | 3.94E-04 | 1.12 | 0.409 | 0.382 | G | attacaagtcagcagt[A/C]acgaagaaaggaacaggg (SEQ ID NO: 1014) |
| 02 | exm1068520 | 13 | q | q14.2 | CYSLTR2 | 49281785 | 5.84E-17 | 5.52 | 0.017 | 0.003 | T | acaaagaatataaaca[A/G]agtacacagaagaagt (SEQ ID NO: 1015) |
| 03 | rs2765760 | 13 | q | q14.2 | FAM10A4\|DLEU7 | 50851577 | 1.59E-04 | 0.83 | 0.123 | 0.145 | A | agtcgtattgcata[A/T]accacttccatgtc (SEQ ID NO: 1016) |
| 03 | rs9591076 | 13 | q | q14.2 | HTR2A\|SUCLA2 | 48127371 | 1.44E-04 | 1.60 | 0.017 | 0.011 | A | ggcacagtcacacgcc[A/C]acgaggccagccctgc (SEQ ID NO: 1017) |
| 03 | rs9596839 | 13 | q | q14.3 | OLFM4\|LOC100287887 | 54264395 | 3.64E-02 | 0.93 | 0.283 | 0.298 | A | ccttcagttctcct[A/G]gggcttcattatggct (SEQ ID NO: 1018) |
| 03 | rs9563182 | 13 | q | q14.3 | OLFM4\|LOC100287887 | 54395310 | 1.71E-02 | 0.90 | 0.155 | 0.169 | G | taattttaattgatcc[A/C]tcacctctactgttg (SEQ ID NO: 1019) |
| 03 | rs9316660 | 13 | q | q14.3 | OLFM4\|LOC100287887 | 54353562 | 2.90E-03 | 0.88 | 0.146 | 0.163 | G | gtaattattaaattac[A/G]tggaagttccttgccc (SEQ ID NO: 1020) |
| 03 | rs9563183 | 13 | q | q14.3 | OLFM4\|LOC100287887 | 54396931 | 1.71E-02 | 0.90 | 0.155 | 0.169 | C | tttacttacctcttac[A/G]tagtcctaagcacaat (SEQ ID NO: 1021) |
| 03 | rs12860689 | 13 | q | q14.3 | OLFM4\|LOC100287887 | 54315805 | 2.89E-03 | 0.88 | 0.146 | 0.163 | G | gaggagctagtgaa[A/C]taaaagcctaagtata (SEQ ID NO: 1022) |
| 03 | rs9568924 | 13 | q | q14.3 | OLFM4\|LOC100287887 | 54360952 | 3.94E-03 | 0.88 | 0.148 | 0.165 | C | tttgggatatagcct[A/G]gaaatgtgactta (SEQ ID NO: 1023) |
| 03 | rs9568902 | 13 | q | q14.3 | OLFM4\|LOC100287887 | 54324954 | 3.15E-03 | 0.88 | 0.145 | 0.162 | A | ctgtattacacattat[A/C]cataatctagaaatga (SEQ ID NO: 1024) |
| 03 | rs2806731 | 13 | q | q14.3 | OLFM4\|LOC100287887 | 54290333 | 3.33E-03 | 0.89 | 0.191 | 0.210 | G | aaagctgttttt[A/G]agaagttctatgctca (SEQ ID NO: 1025) |
| 03 | rs9568919 | 13 | q | q14.3 | OLFM4\|LOC100287887 | 54352229 | 2.71E-03 | 0.88 | 0.146 | 0.163 | C | aacttctgttttact[A/G]ttttctaggcaatgc (SEQ ID NO: 1026) |
| 02 | rs2786266 | 13 | q | q21.32 | LOC730236\|KLHL1 | 68327766 | 2.37E-03 | 1.30 | 0.078 | 0.061 | G | tggtgtctagaaactgc[A/C]tctagcaagtggagg (SEQ ID NO: 1027) |
| 03 | rs287548 | 13 | q | 822.1 | KLF5\|LOC647281 | 73905783 | 1.15E-03 | 0.76 | 0.033 | 0.043 | A | tgctggacaagttgtaa[A/G]gaatctggggtttaga (SEQ ID NO: 1028) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs9543642 | 13 | q | q22.1 | LOC100288208\|LOC647288 | 75008312 | 2.48E-04 | 1.13 | 0.405 | 0.377 | A | tagaagcaacctagc[A/G]tatttaaaacttggag (SEQ ID NO: 1029) |
| 03 | rs9543662 | 13 | q | q22.1 | LOC100288208\|LOC647288 | 75066010 | 1.30E-04 | 0.89 | 0.434 | 0.464 | G | acggatgaatcaaaac[A/G]ttaagctctctaaaag (SEQ ID NO: 1030) |
| 03 | rs1337278 | 13 | q | q31.1 | SLITRK1\|SLITRK6 | 86316853 | 1.97E-02 | 1.08 | 0.406 | 0.388 | G | aaataatccttgatac[A/G]gtactgaatattgt (SEQ ID NO: 1031) |
| 03 | rs4344612 | 13 | q | q31.1 | SPRY2\|SLITRK1 | 81574866 | 3.11E-04 | 1.14 | 0.273 | 0.248 | C | ttatctcaaaaaaaat[A/C]gtaggtataaattg (SEQ ID NO: 1032) |
| 03 | rs7336590 | 13 | q | q31.1 | SPRY2\|SLITRK1 | 81529694 | 3.80E-04 | 0.89 | 0.448 | 0.476 | A | aatccatttgaaattg[A/G]cagtgttttatattt (SEQ ID NO: 1033) |
| 03 | rs12865263 | 13 | q | 831.1 | SPRY2\|SLITRK1 | 81362430 | 8.35E-04 | 1.15 | 0.174 | 0.154 | A | cttcagtcttcgtaca[A/G]aaacacttacttata (SEQ ID NO: 1034) |
| 03 | rs4536348 | 13 | q | 831.1 | SPRY2\|SLITRK1 | 81562924 | 5.42E-03 | 1.13 | 0.165 | 0.149 | G | cctgtaatttgatca[A/G]tcattaagctatcctt (SEQ ID NO: 1035) |
| 03 | rs2348445 | 13 | q | q31.2 | LOC100287432\|LOC144776 | 89846656 | 1.08E-03 | 1.15 | 0.156 | 0.138 | G | tgaagaatttactcac[A/G]tgggggaaataaaggcc (SEQ ID NO: 1036) |
| 03 | rs11616543 | 13 | q | q31.2 | LOC100287432\|LOC144776 | 89297817 | 3.61E-03 | 1.13 | 0.180 | 0.163 | A | tgtattcctagtcag[A/G]ttctattccagcttg (SEQ ID NO: 1037) |
| 03 | rs11620369 | 13 | q | q31.3 | GPC5\|GPC6 | 93873495 | 1.12E-03 | 0.82 | 0.068 | 0.082 | A | tagtattttaggtaac[A/G]atgagtaaatcttaag (SEQ ID NO: 1038) |
| 03 | rs9556267 | 13 | q | q31.3 | GPC5\|GPC6 | 93839833 | 6.97E-04 | 0.81 | 0.067 | 0.082 | G | acagagtctggaaata[A/G]gaccgatgaaaccagg (SEQ ID NO: 1039) |
| 03 | rs7322277 | 13 | q | q31.3 | GPC6 | 94826895 | 7.99E-04 | 0.87 | 0.174 | 0.195 | G | agcacaaactttgct[A/G]aatagcatgtcatcta (SEQ ID NO: 1040) |
| 03 | rs7329232 | 13 | q | q31.3 | GPC6 | 94828678 | 1.97E-03 | 0.86 | 0.113 | 0.130 | G | atatcggttctgctat[A/G]tctatgagttcattc (SEQ ID NO: 1041) |
| 03 | rs9301082 | 13 | q | q33.2 | DAOA\|LOC728192 | 106586930 | 1.40E-03 | 1.12 | 0.302 | 0.279 | A | aatagataaggaagtt[A/G]aagtccaaaaatagtc (SEQ ID NO: 1042) |
| 03 | rs9519858 | 13 | q | q33.2 | DAOA\|LOC728192 | 106583444 | 1.03E-03 | 1.12 | 0.304 | 0.280 | A | aaagtgaatgagaaca[A/G]tactgataataatagc (SEQ ID NO: 1043) |
| 03 | rs958036 | 13 | q | q33.2 | DAOA\|LOC728192 | 106389385 | 8.28E-04 | 1.29 | 0.104 | 0.083 | G | tgcctgtgaccacaata[T/G]tgaaatcttacttaaa (SEQ ID NO: 1044) |
| 02 | rs277836 | 13 | q | q33.3 | MYO16 | 109710600 | 2.10E-05 | 1.15 | 0.394 | 0.362 | G | atgttgaaagggtgcc[A/G]gtgccttggtgatcaa (SEQ ID NO: 1045) |
| 02 | rs12018760 | 13 | #N/A | #N/A | OLFM4\|LOC100287887 | 54308253 | 3.67E-03 | 0.88 | 0.145 | 0.162 | A | ttgattcttaatctgg[A/G]ggtgtttatttcccta (SEQ ID NO: 1046) |
| 02 | exm1085390 | 14 | q | q11.2 | EDDM3A | 21216136 | 2.92E-12 | 9.13 | 0.008 | 0.001 | A | tgcgtagatggatat[A/G]ttgataactagaaga (SEQ ID NO: 1047) |
| 02 | rs227865 | 14 | q | q11.2 | OR4E2\|DAD1 | 22953607 | 4.78E-05 | 1.27 | 0.076 | 0.061 | G | tcgtcaargttttaaa[A/G]ggtaggagttgttaca (SEQ ID NO: 1048) |
| 02 | rs2233859 | 14 | q | q11.2 | RNASE3 | 21359808 | 9.05E-04 | 0.90 | 0.398 | 0.423 | A | ataaccgagaccggat[A/C]ggggagtagttaacttc (SEQ ID NO: 1049) |
| 03 | rs2300850 | 14 | q | q12 | AKAP6 | 33271488 | 9.28E-05 | 1.18 | 0.131 | 0.113 | G | agttcataatcttcca[A/G]gccctccatagtctggt (SEQ ID NO: 1050) |
| 02 | exmrs171111920 | 14 | q | q12 | NOVA1\|LINC00645 | 27406892 | 6.53E-10 | 4.47 | 0.011 | 0.002 | A | tagactaatgcaagca[A/C]aaaatttccatttgct (SEQ ID NO: 1051) |
| 03 | rs8009605 | 14 | q | q12 | PRKD1 | 30254780 | 1.23E-04 | 0.86 | 0.208 | 0.233 | G | ggaagtcttattcgga[A/G]caatcagtcaagaaaa (SEQ ID NO: 1052) |
| 02 | rs17489969 | 14 | q | q12 | STXBP6\|NOVA1 | 26642640 | 7.02E-04 | 1.36 | 0.073 | 0.055 | C | ggaagtcttattcgga[A/G]caatcagtcaagaaaa (SEQ ID NO: 1053) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs17110902 | 14 | q | q12 | STXBP6\|NOVA1 | 26673425 | 9.11E-07 | 1.12 | 0.169 | 0.153 | A | catgcaccgaaatctc[T/C]tcatgatggagaattt (SEQ ID NO: 1054) |
| 02 | rs1012146 | 14 | q | q12 | STXBP6\|NOVA1 | 26678953 | 6.04E-07 | 1.12 | 0.169 | 0.153 | A | ggactgcaaggtaatc[A/G]tcaagggactcttaga (SEQ ID NO: 1055) |
| 03 | rs2899875 | 14 | q | q21.1 | CLEC14A\|LOC283547 | 39001144 | 8.58E-05 | 0.91 | 0.475 | 0.499 | G | ttcattttaatttaca[A/C]ggaaagagtttaaaaaa (SEQ ID NO: 1056) |
| 03 | rs8005701 | 14 | q | q21.2 | LOC644589\|LOC100289583 | 46883709 | 7.79E-03 | 0.92 | 0.419 | 0.439 | A | tatcatgctatttcc[A/G]tgtttggtcaaggcat (SEQ ID NO: 1057) |
| 03 | rs10138214 | 14 | q | q21.2 | LOC644589\|LOC100289583 | 46866809 | 1.36E-02 | 0.92 | 0.418 | 0.437 | A | aaattataacaaaaga[A/G]aattttactcttataa (SEQ ID NO: 1058) |
| 03 | rs1669786 | 14 | q | q21.2 | LOC644589\|LOC100289583 | 46894155 | 8.60E-03 | 0.92 | 0.420 | 0.440 | G | aagtgccagcattcga[A/G]ccataatttttgtgac (SEQ ID NO: 1059) |
| 03 | rs2415982 | 14 | q | q21.2 | LOC644589\|LOC100289583 | 46865899 | 9.90E-03 | 0.92 | 0.417 | 0.437 | A | gggttcaacagtctat[A/G]ttttagcagactgtc (SEQ ID NO: 1060) |
| 03 | rs12883384 | 14 | q | q21.3 | MDGA2 | 47403684 | 6.84E-04 | 1.11 | 0.434 | 0.407 | A | aggcctgcctgtgtat[A/G]actgcaaatattcatt (SEQ ID NO: 1061) |
| 03 | rs11846126 | 14 | q | q21.3 | RPL10L\|MDGA2 | 47294450 | 2.32E-04 | 0.89 | 0.455 | 0.484 | G | tcttgcttgaacfgcl[A/G]aatcttaaaagttaat (SEQ ID NO: 1062) |
| 03 | rs1253706 | 14 | q | q22.1 | GNG2 | 52400377 | 2.84E-04 | 1.12 | 0.456 | 0.427 | A | tgaaatattgtaaatc[A/G]gtggttttgagtgtct (SEQ ID NO: 1063) |
| 03 | rs44271525 | 14 | q | q22.1 | GNG2 | 52408987 | 5.65E-05 | 1.12 | 0.428 | 0.401 | A | aaagaaaatgagagcc[A/G]ctgctcgagtgaaggg (SEQ ID NO: 1064) |
| 03 | rs10498440 | 14 | q | q22.1 | GNG2 | 52413573 | 8.43E-04 | 1.11 | 0.429 | 0.403 | G | ttttcatgatggcttt[A/G]tggctatttattagg (SEQ ID NO: 1065) |
| 03 | rs1618825 | 14 | q | q22.1 | GNG2 | 52407340 | 1.32E-03 | 1.11 | 0.439 | 0.414 | A | aaagtactaggccagc[A/G]ttccaaagaagtgttt (SEQ ID NO: 1066) |
| 03 | rs7157151 | 14 | q | q22.1 | NID2\|PTGDR | 52571583 | 7.51E-04 | 1.12 | 0.311 | 0.287 | A | tgattggaaagagtg[A/G]ctgagtgtgccaaggtg (SEQ ID NO: 1067) |
| 03 | rs941630 | 14 | q | q22.1 | NID2\|PTGDR | 52557650 | 7.32E-03 | 1.10 | 0.236 | 0.218 | A | acgtactcatcaaat[A/G]tatacaatgtagctaa (SEQ ID NO: 1068) |
| 03 | rs34096981 | 14 | q | q22.3 | C14orf34\|LOC100286940 | 56302744 | 6.76E-05 | 1.12 | 0.315 | 0.291 | A | ttgtctatcagttgcc[A/G]tcttccattgccaag (SEQ ID NO: 1069) |
| 03 | rs2342595 | 14 | q | q22.3 | C14orf34\|LOC100286940 | 56271486 | 8.48E-05 | 1.12 | 0.312 | 0.288 | A | ggcagagttacacctc[A/G]taaacaaactattcaa (SEQ ID NO: 1070) |
| 03 | rs1953358 | 14 | q | q22.3 | C14orf34\|LOC100286940 | 56295580 | 5.14E-05 | 0.88 | 0.458 | 0.489 | A | agggccaagctgccaa[A/G]aacttcttgaggtctg (SEQ ID NO: 1071) |
| 02 | rs12896938 | 14 | q | q22.3 | TBPL2\|C14orf33 | 55955102 | 3.40E-05 | 1.12 | 0.236 | 0.216 | G | ggcagcatcaaagtca[A/G]atgactgacccaaggc (SEQ ID NO: 1072) |
| 03 | rs12880763 | 14 | q | q22.3 | TBPL2\|C14orf33 | 55970308 | 9.86E-05 | 1.12 | 0.225 | 0.206 | G | ctatgctctgtttct[A/G]tatttctagaactgt (SEQ ID NO: 1073) |
| 03 | rs12884010 | 14 | q | q22.3 | TBPL2\|C14orf33 | 55944612 | 1.96E-04 | 1.13 | 0.372 | 0.344 | G | taatcttttaaattgtt[A/G]catatttagcaagtgt (SEQ ID NO: 1074) |
| 02 | rs7156144 | 14 | q | q24.1 | TMEM229B | 67979713 | 5.74E-02 | 0.92 | 0.415 | 0.435 | A | gctgctcccagcca[A/G]cagccagaatcaactg (SEQ ID NO: 1075) |
| 03 | rs17104036 | 14 | q | q24.3 | C14orf179\|C14orf118 | 76573554 | 1.38E-02 | 1.18 | 0.060 | 0.051 | A | taaatctgatacaacc[A/G]aaataaacacagtata (SEQ ID NO: 1076) |
| 02 | exm1114136 | 14 | q | q24.3 | COQ6 | 74427993 | 6.12E-12 | Inf | 0.004 | 0.000 | G | cacctagaagaccct[A/G]caaatcaagaaccagag (SEQ ID NO: 1077) |
| | | | | | | | | | | | | gcccccaagcgtagcc[A/G]gggfrggatgccaaaag |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | exm1113959 | 14 | q | q24.3 | ZNF410 | 74388791 | 4.89E-10 | 40.96 | 0.004 | 0.000 | G | aagcctcttcaagcaa[A/G]ctactgccattagtg (SEQ ID NO: 1078) |
| 03 | rs7148059 | 14 | q | q32.11 | KCNK13|PSMC1 | 90657405 | 8.80E-05 | 1.12 | 0.174 | 0.159 | A | gttgtcaatgctaaac[A/G]agaaagggtccctgaa (SEQ ID NO: 1079) |
| 03 | rs1241719 | 14 | q | q32.12 | CPSF2|SLC24A4 | 92673710 | 3.01E-02 | 1.09 | 0.226 | 0.212 | A | tcaaaccagcctgcc[A/G]gtgccctttgtgtccct (SEQ ID NO: 1080) |
| 02 | rs1257415 | 14 | q | q32.2 | BCL11B | 99698931 | 3.94E-05 | 1.14 | 0.525 | 0.493 | C | cactccagggccccca[A/C]gtgagttcccccatcg (SEQ ID NO: 1081) |
| 02 | rs2614459 | 14 | q | q32.2 | BCL11B | 99691180 | 2.49E-06 | 1.15 | 0.314 | 0.285 | C | cattgtggaagctct[A/C]gaagatgggccatcct (SEQ ID NO: 1082) |
| 03 | rs2793321 | 14 | q | q32.2 | BCL11B | 99676623 | 1.04E-04 | 1.14 | 0.326 | 0.298 | A | ctgcagtgcttattct[A/G]tctctttttgttt (SEQ ID NO: 1083) |
| 03 | rs756055 | 14 | q | q32.2 | DEGS2|YY1 | 100691178 | 6.05E-05 | 0.88 | 0.376 | 0.408 | G | atcagggaaaagcat[A/G]aactcaaaatagatga (SEQ ID NO: 1084) |
| 03 | rs7153665 | 14 | q | q32.2 | YY1 | 100730920 | 8.62E-05 | 0.88 | 0.376 | 0.408 | A | aagggcgatgaatcct[A/G]ggccaggctgtgcaga (SEQ ID NO: 1085) |
| 03 | exm1134843 | 14 | q | q32.33 | PACS2 | 105858969 | 1.20E-07 | Inf | 0.003 | 0.000 | A | cagccagggtgcggc[A/G]ccgagctgatggggct (SEQ ID NO: 1086) |
| 02 | rs8179187 | 15 | q | q11.2 | UBE3A | 25652326 | 2.69E-05 | 1.28 | 0.081 | 0.065 | C | gaggtcgcacttca[A/C]aaatgagtcagctggt (SEQ ID NO: 1087) |
| 02 | rs12437614 | 15 | q | q12 | GABRG3 | 27706661 | 2.08E-04 | 1.28 | 0.060 | 0.047 | A | cagcaagagttattgc[A/G]aagaaaacaacaaag (SEQ ID NO: 1088) |
| 03 | rs939981 | 15 | q | q13.1 | LOC727808|LOC100128435 | 30290306 | 3.19E-03 | 1.15 | 0.124 | 0.110 | A | ggtcattctaaaaat[A/G]gtcaccccaatccatc (SEQ ID NO: 1089) |
| 03 | rs12905328 | 15 | q | q13.1 | LOC727808|LOC100128435 | 30239328 | 1.72E-03 | 0.88 | 0.202 | 0.222 | A | attaatattttatgtt[A/G]catgatttagatttat (SEQ ID NO: 1090) |
| 02 | rs12438794 | 15 | q | q14 | MEIS2|TMCO5A | 38146571 | 8.47E-07 | 1.08 | 0.076 | 0.071 | A | tcatggaactaaaagt[A/G]agcatctcaagagact (SEQ ID NO: 1091) |
| 02 | rs8041665 | 15 | q | q14 | MEIS2|TMCO5A | 38150179 | 2.56E-07 | 1.08 | 0.077 | 0.072 | A | agcgtatattatcttc[A/G]aagagcattttattt (SEQ ID NO: 1092) |
| 02 | rs8037309 | 15 | q | q14 | MEIS2|TMCO5A | 38150438 | 2.77E-07 | 1.08 | 0.077 | 0.072 | A | gagcatccaccatccat[A/G]aggctgctgaattcat (SEQ ID NO: 1093) |
| 03 | rs12907066 | 15 | q | q14 | RYR3 | 33990976 | 7.93E-04 | 1.12 | 0.319 | 0.295 | A | tctccagaagatcct[A/G]agcacatgctgaatg (SEQ ID NO: 1094) |
| 03 | rs7165303 | 15 | q | q14 | RYR3 | 33693677 | 2.31E-04 | 0.89 | 0.391 | 0.420 | G | ttcagcactattcagc[A/G]cctatcactgccagct (SEQ ID NO: 1095) |
| 03 | rs2279663 | 15 | q | q14 | RYR3 | 33952326 | 5.80E-03 | 1.13 | 0.157 | 0.142 | A | cccagacattttaacc[A/G]atatggccagtataaa (SEQ ID NO: 1096) |
| 01 | exm1159600 | 15 | q | q21.1 | DUT | 48623812 | 4.41E-08 | 1.65 | 0.010 | 0.000 | A | cgcacggcagagggcc[A/G]aagccgcggractctc (SEQ ID NO: 1097) |
| 03 | rs17645290 | 15 | q | q21.2 | USP8 | 50787955 | 1.92E-02 | 1.10 | 0.191 | 0.177 | G | tacaaacactgccag[A/G]tttagaaacaccgta (SEQ ID NO: 1098) |
| 02 | rs16940167 | 15 | q | q21.3 | AQP9|LIPC | 58683697 | 7.99E-05 | 1.18 | 0.176 | 0.154 | G | ttatgggcccgaatg[A/G]ttccagatcagaattt (SEQ ID NO: 1099) |
| 03 | rs1280415 | 15 | q | q21.3 | CGNL1 | 57749193 | 4.60E-02 | 1.12 | 0.082 | 0.074 | G | tattgaacattctaca[A/G]attttataaaaagg (SEQ ID NO: 1100) |
| 03 | rs1280416 | 15 | q | q21.3 | CGNL1 | 57749300 | 2.10E-03 | 1.24 | 0.055 | 0.045 | A | tattgaacattctaca[A/G]attttataaaaagg (SEQ ID NO: 1101) |
| 03 | rs2017176 | 15 | q | q21.3 | KIAA1370|ONECUT1 | 53006147 | 6.68E-05 | 0.89 | 0.440 | 0.469 | A | tctttgtcagctacc[A/G]ttgctataaaaccttt (SEQ ID NO: 1102) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs17543144 | 15 | q | q21.3 | KIAA1370\|ONECUT1 | 53008923 | 2.07E-05 | 0.88 | 0.438 | 0.468 | A | tgactaattacactgg[A/G]gagtccatcaacatct (SEQ ID NO: 1103) |
| 03 | rs2414407 | 15 | q | q21.3 | RAB27A | 55556228 | 4.27E-03 | 1.14 | 0.131 | 0.117 | A | tggtttgaacatagcc[A/G]tgacagctagccaaca (SEQ ID NO: 1104) |
| 03 | rs1991574 | 15 | q | q21.3 | UNC13C | 54484950 | 6.41E-04 | 0.87 | 0.200 | 0.223 | A | caaacaaacagaaaaa[A/G]taaccctggctatagt (SEQ ID NO: 1105) |
| 03 | rs12440360 | 15 | q | q21.3 | UNC13C | 54491059 | 1.01E-03 | 0.90 | 0.450 | 0.476 | C | gaaggcccagtggga[A/G]ccgagtagtgctacag (SEQ ID NO: 1106) |
| 03 | rs16950635 | 15 | q | q22.33 | SMAD3 | 67418205 | 7.50E-04 | 1.27 | 0.052 | 0.041 | A | atccaaatcaagaaaa[A/C]aatctctgaattgcca (SEQ ID NO: 1107) |
| 03 | rs16951541 | 15 | q | q23 | LOC100286942\|PIAS1 | 68276895 | 2.17E-04 | 1.23 | 0.090 | 0.074 | A | ggggtaattattgcc[A/G]ccgctgcttcaccag (SEQ ID NO: 1108) |
| 02 | exm1173822 | 15 | q | q23 | THSD4 | 72023502 | 9.46E-11 | 17.87 | 0.006 | 0.000 | A | attctgcagacacaca[A/G]tccttttgcctacaa (SEQ ID NO: 1109) |
| 03 | rs1130741 | 15 | q | q24.1 | MPI | 75189930 | 1.47E-04 | 1.13 | 0.477 | 0.448 | A | cgtgcactacgagtac[A/C]tgatcatggggaccaa (SEQ ID NO: 1110) |
| 03 | rs2415251 | 15 | q | q24.2 | COX5A\|RPP25 | 75242155 | 2.06E-04 | 1.12 | 0.502 | 0.473 | A | tggtacaggggacagt[A/G]atagccagcacaccca (SEQ ID NO: 1111) |
| 03 | rs11855944 | 15 | q | q24.3 | LINGO1\|LOC645752 | 78088127 | 8.41E-03 | 1.11 | 0.195 | 0.179 | C | atctgaggccctggt[A/G]ccctgccttggaga (SEQ ID NO: 1112) |
| 03 | rs4075024 | 15 | q | q24.3 | LINGO1\|LOC645752 | 78093898 | 1.18E-02 | 1.10 | 0.198 | 0.183 | G | tgccactgctgccag[A/C]cctggctgaagcaggg (SEQ ID NO: 1113) |
| 03 | rs15939 | 15 | q | q24.3 | RCN2 | 77241542 | 2.36E-02 | 0.89 | 0.105 | 0.117 | G | ttgttttctgattac[A/G]acagaagaacccaaca (SEQ ID NO: 1114) |
| 02 | exm1181151 | 15 | q | q25.1 | ADAMTS7 | 79089098 | 2.26E-09 | Inf | 0.003 | 0.000 | A | gctcatcatgatagaa[A/G]tagtcatcatggaget (SEQ ID NO: 1115) |
| 02 | exm1182536 | 15 | q | q25.1 | IL16 | 81572094 | 1.94E-08 | 34.64 | 0.004 | 0.000 | G | gagtctgcacggagc[A/G]ttgggagcagcggcag (SEQ ID NO: 1116) |
| 03 | rs12905510 | 15 | q | q25.3 | AGBL1\|NCRNA00052 | 87944954 | 1.60E-04 | 1.13 | 0.353 | 0.325 | G | caattacagaatcatg[A/G]tggaagtttctgca (SEQ ID NO: 1117) |
| 03 | rs2016517 | 15 | q | q25.3 | AKAP13 | 86229618 | 1.28E-03 | 1.12 | 0.275 | 0.253 | A | tgataagctggactc[A/G]taaaaactatacacat (SEQ ID NO: 1118) |
| 03 | rs11630274 | 15 | q | q25.3 | AKAP13 | 86288387 | 9.24E-04 | 1.12 | 0.288 | 0.265 | A | catggtaaaatactt[A/G]gctatatttccatcag (SEQ ID NO: 1119) |
| 03 | rs1978391 | 15 | q | q25.3 | KLHL25 | 86311695 | 9.49E-04 | 1.12 | 0.288 | 0.264 | A | tgaccgacgcctggt[A/G]cagactgggccttctt (SEQ ID NO: 1120) |
| 03 | rs3743332 | 15 | q | q25.3 | LOC100288896 | 86303751 | 1.33E-02 | 1.09 | 0.288 | 0.270 | G | ggatgctggttcctcc[A/G]aaaacaaagagcttca (SEQ ID NO: 1121) |
| 03 | rs11634975 | 15 | q | q25.3 | PDE8A | 85606478 | 3.07E-03 | 1.11 | 0.309 | 0.288 | G | accagaaaggtgacca[A/G]gacagatttttaagg (SEQ ID NO: 1122) |
| 03 | rs11629962 | 15 | q | q25.3 | PDE8A | 85530028 | 1.18E-03 | 1.12 | 0.268 | 0.246 | A | aacagtgaccattct[A/G]gtaaacacattacgaa (SEQ ID NO: 1123) |
| 03 | rs6496766 | 15 | q | q25.3 | PDE8A\|LOC728121 | 85702375 | 1.06E-03 | 1.11 | 0.400 | 0.375 | C | agcaagatctcgtctc[A/C]acaaaaaaagttta (SEQ ID NO: 1124) |
| 03 | rs12905479 | 15 | q | q26.1 | LOC390638\|SV2B | 91711209 | 1.44E-02 | 0.93 | 0.431 | 0.450 | A | atgaccaactatatg[A/C]tgtctacaagaaacac (SEQ ID NO: 1125) |
| 02 | exm1190729 | 15 | q | q26.1 | UNC45A | 91486258 | 1.72E-08 | Inf | 0.003 | 0.000 | A | cggcctttggtgct[A/G]tttggtttcatcccca (SEQ ID NO: 1126) |
| | | | | | | | | | | | | tccttgagagactcc[A/G]gggcaccgctttaatc |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs896070 | 15 | q | q26.2 | LOC145820\|NR2F2 | 96428860 | 1.06E−04 | 1.17 | 0.198 | 0.175 | A | aaggctctgaggtttt[A/G]gtaccccagaaagatt (SEQ ID NO: 1127) |
| 03 | rs1025833 | 15 | q | 826.2 | SPATA8\|LOC91948 | 98224547 | 2.07E−04 | 1.25 | 0.073 | 0.059 | A | tattaccatgaactt[A/G]gtaaaagttacaaata (SEQ ID NO: 1128) |
| 02 | rs8024630 | 15 | q | 826.2 | SPATA8\|LOC91948 | 98034118 | 4.66E−05 | 1.14 | 0.526 | 0.494 | A | ttagaaaatctataac[A/G]gtaaaaagtacattag (SEQ ID NO: 1129) |
| 03 | rs12910816 | 15 | q | 826.2 | SPATA8\|LOC91948 | 98249133 | 2.76E−04 | 1.26 | 0.065 | 0.052 | C | aaaacctctcacatga[A/C]taagcttacaaaatag (SEQ ID NO: 1130) |
| 03 | rs8041786 | 15 | q | q26.2 | SPATA8\|LOC91948 | 97896453 | 8.59E−04 | 1.18 | 0.112 | 0.096 | G | ttctatagcagacatt[A/G]gtctctgaacttggt (SEQ ID NO: 1131) |
| 02 | exm1193980 | 15 | q | q26.3 | LRRK1 | 101567912 | 8.37E−13 | Inf | 0.005 | 0.000 | A | ccgcgccgggacgac[A/G]acgtgcagtacctgac (SEQ ID NO: 1132) |
| 03 | rs7173796 | 15 | q | q26.3 | PCSK6\|TM2D3 | 102148666 | 1.66E−05 | 1.22 | 0.134 | 0.113 | A | ggcaggcaggaaacag[A/G]tgattagtaaccaaag (SEQ ID NO: 1133) |
| 01 | exm1194576 | 15 | q | q26.3 | TM2D3 | 102192537 | 1.63E−21 | 46.41 | 0.013 | 0.000 | C | ggtgctcccgctgagg[C/G]gcctccgccgccttgtg (SEQ ID NO: 1134) |
| 03 | rs1132812 | 16 | p | p11.2 | CORO1A | 30198151 | 2.94E−04 | 0.89 | 0.438 | 0.466 | A | aggtgtgggagatccc[A/G]gatggggggcctgatgc (SEQ ID NO: 1135) |
| 03 | rs11859842 | 16 | p | p11.2 | SLC7A5P1\|SPN | 29661217 | 1.65E−04 | 1.13 | 0.497 | 0.467 | A | cagcaaagtctgacca[A/G]tctaaagtaaccactc (SEQ ID NO: 1136) |
| 03 | rs12447415 | 16 | p | p11.2 | SPN\|QPRT | 29682945 | 5.03E−06 | 1.11 | 0.412 | 0.386 | A | agggaccctctaaaal[A/G]gtcactgtgggctggg (SEQ ID NO: 1137) |
| 03 | rs2243605 | 16 | p | p12.1 | TNRC6A\|SLC5A11 | 24848663 | 1.33E−05 | 0.91 | 0.369 | 0.392 | G | gagaacagcctacgca[A/G]catagaaacctgtctct (SEQ ID NO: 1138) |
| 03 | rs7200734 | 16 | p | p12.3 | XYLT1 | 17443347 | 1.00E−02 | 1.08 | 0.495 | 0.475 | A | agtaatacttcccata[A/C]gagatagttgtgaaat (SEQ ID NO: 1139) |
| 02 | exm1219737 | 16 | p | p13.11 | KIAA0430 | 15729650 | 1.26E−07 | Inf | 0.003 | 0.000 | A | ttctgatttcacaagc[A/G]ggggctccagggcattt (SEQ ID NO: 1140) |
| 03 | rs1541702 | 16 | p | p13.13 | C16orf75 | 11445552 | 2.32E−02 | 1.11 | 0.140 | 0.128 | G | atgtccctggagca[A/G]ccccacagcaagttgg (SEQ ID NO: 1141) |
| 03 | rs434762 | 16 | p | p13.13 | GSPT1 | 12009781 | 4.81E−04 | 1.24 | 0.069 | 0.056 | G | tctacaaccatgtcag[A/G]acacaatctaactct (SEQ ID NO: 1142) |
| 03 | rs7204004 | 16 | p | p13.2 | C16orf72\|GRIN2A | 9332745 | 2.64E−04 | 0.86 | 0.168 | 0.190 | A | cagaggcgcggggcggc[A/G]gcagctcaaccctcct (SEQ ID NO: 1143) |
| 02 | rs12443943 | 16 | p | p13.2 | GRIN2A\|LOC100287628 | 10428747 | 2.59E−05 | 1.15 | 0.236 | 0.212 | G | ctccctgaccaggt[A/G]aggcagtgagtaccc (SEQ ID NO: 1144) |
| 02 | exm215795 | 16 | p | p13.3 | ALG1 | 5122041 | 2.22E−15 | 16.45 | 0.008 | 0.001 | A | cacggcttccggtgal[A/C]cctcctggggttctgc (SEQ ID NO: 1145) |
| 02 | exm1207746 | 16 | p | p13.3 | C16orf59 | 2512728 | 1.48E−14 | Inf | 0.005 | 0.000 | A | aggctgcaggagctgc[A/G]tgcaggtgagaccccg (SEQ ID NO: 1146) |
| 02 | rs2171226 | 16 | p | p13.3 | LOC650177\|A2BP1 | 5588451 | 1.22E−06 | 0.88 | 0.427 | 0.458 | A | atcctctcatattc[A/G]tcaaaagccttagtc (SEQ ID NO: 1147) |
| 03 | rs2294619 | 16 | p | p13.3 | MAPK8IP3 | 1814440 | 1.89E−03 | 1.13 | 0.200 | 0.181 | G | gcccaagaggcgcccac[A/G]cgtctcccgagaagaa (SEQ ID NO: 1148) |
| 03 | rs3211995 | 16 | p | p13.3 | SLC9A3R2 | 2089006 | 4.89E−04 | 1.15 | 0.187 | 0.166 | A | gcatgcgcgctctcag[A/G]ataaacaggccctgcc (SEQ ID NO: 1149) |
| 02 | exm1211849 | 16 | p | p13.3 | SLX4 | 3640815 | 8.05E−11 | 43.93 | 0.005 | 0.000 | C | aggggcctctcag[A/G]ataaacaggccctgcc (SEQ ID NO: 1150) |
| 03 | rs13334798 | 16 | q | q12.1 | ABCC11 | 48244717 | 5.74E−05 | 1.18 | 0.080 | 0.069 | G | aggggcacggggagca[C/G]aggccccctgagcagga (SEQ ID NO: 1151) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs7194667 | 16 | q | q12.1 | ABCC11 | 48242898 | 5.35E-05 | 1.18 | 0.080 | 0.068 | C | aaattcaaattttc[A/G]tggagggcaaacacag (SEQ ID NO: 1152) |
| 03 | rs3910446 | 16 | q | q12.1 | LOC388276|TOX3 | 52196841 | 1.68E-03 | 1.11 | 0.369 | 0.345 | A | cccatcccctcagctt[A/C]tattctgagctcaatg (SEQ ID NO: 1153) |
| 03 | rs8052698 | 16 | q | q12.1 | TOX3|CHD9 | 52967995 | 3.62E-04 | 1.12 | 0.474 | 0.446 | A | gagtcacagtgatggc[A/G]gaccggtattctcagc (SEQ ID NO: 1154) |
| 03 | rs4784181 | 16 | q | q12.2 | CDH8|CDH11 | 62346479 | 8.70E-03 | 0.92 | 0.410 | 0.431 | A | tgcgccatcatgccct[A/G]cgcatttcatttaaat (SEQ ID NO: 1155) |
| 03 | rs11861466 | 16 | q | q21 | GOT2|LOC644649 | 59495475 | 7.02E-03 | 1.09 | 0.434 | 0.413 | A | atgagcatgtgatcca[A/G]tgatagtcaatgaaat (SEQ ID NO: 1156) |
| 03 | rs1582600 | 16 | q | q21 | GOT2|LOC644649 | 59314789 | 1.09E-02 | 1.09 | 0.397 | 0.378 | C | gtcaaaaaagcatca[A/G]taaataagtagagagt (SEQ ID NO: 1157) |
| 03 | rs1364204 | 16 | q | q21 | GOT2|LOC644649 | 59411217 | 1.77E-02 | 1.08 | 0.385 | 0.367 | A | taaatgtagtcatggc[A/C]gaaagctgagtgggtg (SEQ ID NO: 1158) |
| 03 | rs7193968 | 16 | q | q22.1 | IL34 | 70672952 | 4.90E-03 | 0.88 | 0.443 | 0.474 | C | tgatcaggttttgggc[A/G]agggtctgcttttttg (SEQ ID NO: 1159) |
| 02 | rs4149499 | 16 | q | q22.2 | CHST4 | 71570413 | 5.95E-06 | 1.36 | 0.057 | 0.042 | A | tgccagcttacaagc[C/G]acagaatcaccaaaac (SEQ ID NO: 1160) |
| 03 | rs150617 | 16 | q | q22.2 | DHX38 | 72139396 | 1.82E-04 | 1.20 | 0.124 | 0.106 | A | caacaatgggcaccagt[A/C]cttctccaaatcattt (SEQ ID NO: 1161) |
| 03 | rs4788591 | 16 | q | q22.2 | PKD1L3 | 72020323 | 1.51E-02 | 1.09 | 0.233 | 0.218 | A | gagcaggacatacagg[A/G]agggaaaatgagtcc (SEQ ID NO: 1162) |
| 03 | rs152828 | 16 | q | q22.2 | TXNL4B | 72123886 | 1.93E-04 | 1.20 | 0.123 | 0.105 | A | tgtgatgtgatacttg[A/G]tagtactgaaggaaac (SEQ ID NO: 1163) |
| 02 | exm1257256 | 16 | q | q22.2 | ZFHX3 | 72821344 | 2.06E-15 | 5.63 | 0.015 | 0.003 | A | tctacccctcagtcata[A/G]gccaggaggaatacca (SEQ ID NO: 1164) |
| 03 | rs12102460 | 16 | q | q23.1 | WWOX | 79093317 | 6.10E-03 | 1.30 | 0.028 | 0.022 | G | gacttcctcggagggt[A/G]gggggaagcggaggag (SEQ ID NO: 1165) |
| 02 | rs9923563 | 16 | q | q23.1 | WWOX | 78615460 | 3.64E-05 | 1.16 | 0.262 | 0.234 | G | tgagatgtagagcttg[A/G]cacctgcatataaagt (SEQ ID NO: 1166) |
| 02 | rs12598440 | 16 | q | q23.1 | WWOX | 78576107 | 1.74E-05 | 1.14 | 0.508 | 0.474 | G | ttcctagaggttcaca[A/G]taaatctaaaaagatc (SEQ ID NO: 1167) |
| 02 | rs11150085 | 16 | q | q23.1 | WWOX | 78567094 | 1.50E-05 | 1.22 | 0.117 | 0.098 | A | tccggcagtgtttacg[A/G]agggctgagatacac (SEQ ID NO: 1168) |
| 03 | rs2943768 | 16 | q | q23.1 | WWOX | 78612914 | 1.77E-03 | 1.13 | 0.206 | 0.187 | C | caggtcagccagttgg[A/G]aacagagttgacggag (SEQ ID NO: 1169) |
| 01 | rs4319778 | 16 | q | q23.1 | WWOX | 78552954 | 1.99E-06 | 1.16 | 0.423 | 0.387 | A | ttacattatacatctt[A/C]gggcatttttttccttt (SEQ ID NO: 1170) |
| 02 | rs2978632 | 16 | q | q23.1 | WWOX | 78559880 | 7.70E-05 | 1.14 | 0.341 | 0.312 | A | tttctaatttaatcctt[A/G]tacatgagacagctat (SEQ ID NO: 1171) |
| 03 | rs16947885 | 16 | q | q23.1 | WWOX | 78551317 | 3.56E-04 | 1.24 | 0.077 | 0.064 | G | gcagatagggatgatac[A/G]tgtgctctgcaaccat (SEQ ID NO: 1172) |
| 03 | rs30405 | 16 | q | q23.2 | LOC729251|MAF | 79621818 | 9.13E-04 | 0.87 | 0.181 | 0.202 | G | caccagaactgaaatt[A/G]tttccagctatgttta (SEQ ID NO: 1173) |
| 01 | rs30428 | 16 | q | q23.2 | LOC729251|MAF | 79598399 | 2.68E-06 | 0.86 | 0.349 | 0.384 | G | gaacacagaaaactgca[A/G]tggcttttggacgcta (SEQ ID NO: 1174) |
| 03 | rs3784925 | 16 | q | q23.2 | LOC729251|MAF | 79605583 | 2.50E-04 | 1.16 | 0.189 | 0.167 | A | atcctcgctctccta[A/G]tcaggcaggataga (SEQ ID NO: 1175) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs173645 | 16 | q | q23.2 | LOC729251\|MAF | 79594409 | 5.42E-04 | 0.88 | 0.243 | 0.267 | G | caaaccattgcatcat[A/G]ttttggactgatagtt (SEQ ID NO: 1176) |
| 03 | rs7206458 | 16 | q | q23.3 | CDH13 | 83446995 | 3.30E-04 | 1.13 | 0.284 | 0.259 | A | ttcccaattattatc[A/C]gtcactcctcctccat (SEQ ID NO: 1177) |
| 02 | rs1013465 | 16 | q | q23.3 | CDH13 | 83412113 | 2.31E-05 | 1.14 | 0.406 | 0.375 | A | tggccaatccaactga[A/C]gggaccccttttattg (SEQ ID NO: 1178) |
| 02 | exm1263172 | 16 | q | q23.3 | OSGIN1 | 83999431 | 1.18E-07 | Inf | 0.003 | 0.000 | G | gcagtggatcctgacc[A/G]gccgctgagcgcaag (SEQ ID NO: 1179) |
| 03 | rs13521 | 16 | q | q23.3 | COTL1 | 84599970 | 5.86E-04 | 0.88 | 0.263 | 0.287 | A | gccaggagctgtgccc[A/G]gtgcctgcagccttca (SEQ ID NO: 1180) |
| 03 | rs11641616 | 16 | q | q24.1 | FOXL1\|LOC100288525 | 86638543 | 6.76E-04 | 1.24 | 0.070 | 0.057 | A | ttaatcaaatatcggg[A/G]ttaaagaatgtatcaa (SEQ ID NO: 1181) |
| 03 | rs7220350 | 16 | q | q24.1 | FOXL1\|LOC100288525 | 86642680 | 1.37E-03 | 1.22 | 0.070 | 0.058 | G | gcagcccccagcaggaa[A/G]gaacagataatcgatt (SEQ ID NO: 1182) |
| 02 | rs11642168 | 16 | q | q24.1 | LOC732275\|FOXF1 | 86520474 | 4.54E-03 | 1.13 | 0.152 | 0.136 | A | aagggaaacggagcc[A/G]gccaaggacaggtgaa (SEQ ID NO: 1183) |
| 03 | rs7186320 | 16 | q | q24.1 | TMEM148\|KIAA0182 | 85577092 | 9.13E-05 | 0.79 | 0.052 | 0.065 | A | acatgggaatgggggt[A/G]tggactctatgggatg (SEQ ID NO: 1184) |
| 03 | rs2274892 | 17 | p | p11.2 | TNFRSF13B | 16852027 | 1.23E-04 | 1.13 | 0.400 | 0.370 | C | cccaaggcaaactgc[A/C]tggtgtcacgcaggt (SEQ ID NO: 1185) |
| 03 | rs17793572 | 17 | p | p11.2 | TNFRSF13B | 16843992 | 5.67E-01 | 1.02 | 0.292 | 0.288 | A | tgctctgatcctg[A/G]aggaagtttgatccat (SEQ ID NO: 1186) |
| 03 | rs4792801 | 17 | p | p11.2 | TNFRSF13B | 16845467 | 6.12E-05 | 1.11 | 0.438 | 0.412 | G | caggtcctcaaaaaac[A/G]aaacagagctattatg (SEQ ID NO: 1187) |
| 02 | rs8072293 | 17 | p | p11.2 | TNFRSF13B | 16855878 | 1.02E-03 | 1.12 | 0.278 | 0.255 | G | cacagggcctgttggac[A/G]gggggtggctatgaagat (SEQ ID NO: 1188) |
| 03 | rs7223652 | 17 | p | p11.2 | TNFRSF13B | 16864559 | 3.60E-05 | 1.22 | 0.325 | 0.283 | G | gttctttgatgttt[G/A]cttaggaagtggaatta (SEQ ID NO: 1189) |
| 03 | rs7504096 | 17 | p | p11.2 | TNFRSF13B\|MPRIP | 16877083 | 2.25E-04 | 1.15 | 0.216 | 0.192 | A | caggccagagccaggaa[A/G]tctatgcacagttaa (SEQ ID NO: 1190) |
| 03 | rs4441330 | 17 | p | p11.2 | ZNF286B | 18562720 | 1.22E-05 | 1.12 | 0.513 | 0.485 | G | cattcatcaagaagtc[A/G]gataaaggggtttaaac (SEQ ID NO: 1191) |
| 02 | rs11078211 | 17 | p | p12 | HS3ST3A1\|CDRT15P | 13836036 | 7.83E-05 | 1.15 | 0.297 | 0.270 | A | ttaactccttcaaac[A/G]atttccttgtatctt (SEQ ID NO: 1192) |
| 02 | rs10852926 | 17 | p | p12 | PIRT\|FLJ45455 | 10778976 | 2.25E-01 | 1.04 | 0.494 | 0.484 | A | aaatagaagacacagcc[A/G]gagtgctggctatgac (SEQ ID NO: 1193) |
| 02 | rs179521 | 17 | p | p12 | PMP22\|TEKT3 | 15173221 | 9.82E-05 | 1.13 | 0.387 | 0.357 | A | catctctgagttcctgt[A/C]accactatcaagtgt (SEQ ID NO: 1194) |
| 02 | rs8068414 | 17 | p | p12 | TEKT3\|LOC100287829 | 15248449 | 9.77E-05 | 1.15 | 0.289 | 0.262 | A | gggagtgtgacacgg[A/G]gctcactgccaggct (SEQ ID NO: 1195) |
| 02 | rs11078672 | 17 | p | p13.1 | EIF5A | 7215142 | 5.26E-05 | 0.87 | 0.306 | 0.336 | A | ctctcctactaggg[A/G]tggcggtggtggcagc (SEQ ID NO: 1196) |
| 03 | rs8072788 | 17 | p | p13.2 | NLRP1\|WSCD1 | 5594285 | 8.70E-03 | 1.11 | 0.200 | 0.184 | A | aaataaaggcctggg[A/G]cctcagttctgtgt (SEQ ID NO: 1197) |
| 02 | rs17804008 | 17 | p | p13.2 | PITPNM3 | 6433659 | 6.08E-06 | 1.12 | 0.369 | 0.344 | G | ctgaccctgactttga[A/G]atttcgtctgtaaaat (SEQ ID NO: 1198) |
| 03 | rs907941 | 17 | p | p13.2 | PITPNM3 | 6362387 | 3.70E-04 | 0.89 | 0.433 | 0.461 | G | (SEQ ID NO: 1199) |
| 03 | rs11078612 | 17 | p | p13.2 | WSCD1\|AIPL1 | 6067298 | 8.12E-03 | 0.87 | 0.101 | 0.114 | G | gggagcagccccttc[A/G]tctggccttccacct (SEQ ID NO: 1200) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs9894371 | 17 | p | p13.2 | WSCD1\|AIPL1 | 6212579 | 1.92E-03 | 0.91 | 0.475 | 0.499 | G | tattgctcatttttt[A/G]tagatgaggaaactgc (SEQ ID NO: 1201) |
| 03 | rs8078781 | 17 | p | p13.3 | OR1D2\|OR1G1 | 3008882 | 8.67E-05 | 1.16 | 0.082 | 0.072 | A | ccttgcttagttcca[A/G]acgtctccctctgta (SEQ ID NO: 1202) |
| 03 | rs9902340 | 17 | q | q11.2 | CCDC55 | 28476458 | 3.06E-02 | 1.07 | 0.503 | 0.486 | C | aacaccatacagcaat[A/G]agcatgaacaacctac (SEQ ID NO: 1203) |
| 03 | rs11080118 | 17 | q | q11.2 | CCDC55 | 28475379 | 3.31E-02 | 1.07 | 0.502 | 0.486 | A | gcaatctractcctct[A/C]tgataacaatagatc (SEQ ID NO: 1204) |
| 03 | rs9896012 | 17 | q | q11.2 | CCDC55 | 28470091 | 3.12E-02 | 1.07 | 0.503 | 0.486 | G | ctatgtctataagrgg[A/G]aaaggctttgtttatt (SEQ ID NO: 1205) |
| 03 | rs9897794 | 17 | q | q11.2 | EFCAB5 | 28296327 | 2.57E-02 | 1.07 | 0.507 | 0.489 | C | gaagcagatgtgtatg[A/G]ttttggagaaacagaa (SEQ ID NO: 1206) |
| 03 | rs3102555 | 17 | q | q11.2 | SSH2 | 28044101 | 5.26E-03 | 0.92 | 0.464 | 0.486 | G | gtgacttcttcatca[A/C]cctctggtaaccagac (SEQ ID NO: 1207) |
| 03 | rs10445384 | 17 | q | q11.2 | SSH2\|EFCAB5 | 28182685 | 1.59E-02 | 1.08 | 0.503 | 0.484 | G | tctctgttaagggc[A/G]gtgggataggtaggt (SEQ ID NO: 1208) |
| 03 | rs10445400 | 17 | q | q11.2 | SSH2\|EFCAB5 | 28183059 | 1.33E-02 | 1.08 | 0.504 | 0.485 | G | tcctagttggatcag[A/G]caacagactatgaaatt (SEQ ID NO: 1209) |
| 03 | rs7219163 | 17 | q | q11.2 | SSH2\|EFCAB5 | 28210703 | 1.11E-02 | 0.92 | 0.466 | 0.486 | A | gatgaggtctgtgcat[A/G]ctccttccccatcaa (SEQ ID NO: 1210) |
| 03 | rs9914342 | 17 | q | q12 | FLJ43826 | 37190141 | 5.71E-04 | 0.88 | 0.238 | 0.262 | G | ttaattctatcctgg[A/C]cagcctaacttctct (SEQ ID NO: 1211) |
| 03 | rs8070269 | 17 | q | q12 | MRM1\|LHX1 | 35134033 | 3.98E-03 | 1.14 | 0.146 | 0.130 | A | gtaaggactttatcca[A/G]aatcacttatgtgtct (SEQ ID NO: 1212) |
| 02 | rs3744474 | 17 | q | 821.31 | C1QL1\|DCAKD | 43100070 | 2.70E-05 | 1.12 | 0.219 | 0.199 | G | tgatagccatcaccca[A/G]ggagaatggttgaaaga (SEQ ID NO: 1213) |
| 03 | rs4793598 | 17 | q | q21.32 | HOXB9\|PRAC | 46743914 | 7.15E-05 | 1.11 | 0.387 | 0.362 | G | ggatgtgtaagaccct[A/G]tagttaacattaacact (SEQ ID NO: 1214) |
| 03 | rs7218921 | 17 | q | q22 | TMEM100 | 53808950 | 4.16E-05 | 1.50 | 0.027 | 0.018 | C | tgctgaactttgtcct[A/G]gcatataattagttac (SEQ ID NO: 1215) |
| 02 | rs12453356 | 17 | q | q22 | DDX5 | 62495009 | 2.05E-03 | 1.21 | 0.071 | 0.059 | A | tagctaacactactac[A/C]caagctaccagaacag (SEQ ID NO: 1216) |
| 02 | rs10512502 | 17 | q | q23.3 | SCN4A | 62028920 | 7.02E-18 | 9.29 | 0.033 | 0.002 | C | taatgacttaatcaggat[A/G]gcaaagctaaccaaaag (SEQ ID NO: 1217) |
| 02 | exm1345526 | 17 | q | q23.3 | SCN4A | 62049749 | 1.33E-12 | 5.07 | 0.013 | 0.003 | A | gacggccccatcca[C/G]cctcgagctggaccac (SEQ ID NO: 1218) |
| 03 | exm1345636 | 17 | q | q24.1 | GNA13\|RGS9 | 63068976 | 3.64E-04 | 0.89 | 0.461 | 0.489 | A | gctgagccctcagc[A/G]tagtcaggcgcgggc (SEQ ID NO: 1219) |
| 03 | rs2907373 | 17 | q | q24.2 | FAM20A | 66533655 | 1.19E-04 | 1.13 | 0.372 | 0.343 | A | tcatgtccttaaccaac[A/G]gaatcaacctggttcc (SEQ ID NO: 1220) |
| 02 | rs8076465 | 17 | q | q24.2 | PRKAR1A | 66513025 | 3.83E-05 | 1.13 | 0.372 | 0.343 | A | gccagagtctggggcc[A/G]actgttccactgggcc (SEQ ID NO: 1221) |
| 03 | rs8080306 | 17 | q | q24.2 | PRKAR1A | 66508243 | 1.62E-05 | 1.16 | 0.314 | 0.284 | C | ttttgaagtcaagtgc[A/G]ttcctggagatccggt (SEQ ID NO: 1222) |
| 03 | rs2952275 | 17 | q | q24.2 | PRKAR1A | 66518663 | 1.33E-04 | 1.13 | 0.372 | 0.344 | A | gagagcgaagagcaggt[A/C]ggaggaacaaaggcga (SEQ ID NO: 1223) |
| 02 | rs2302782 | 17 | q | q24.2 | WIPI1 | 66446803 | 8.10E-05 | 1.14 | 0.334 | 0.306 | G | atggcttgactaatg[A/G]tctttcaagatcaatg (SEQ ID NO: 1224) |
| | | | | | | | | | | | | aaacaaaagatggac[A/G]tctttcaagatcaatg |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2952291 | 17 | q | q24.2 | WIPI1\|PRKAR1A | 66460984 | 1.20E−04 | 1.14 | 0.327 | 0.299 | G | ctattatgaaattctg[A/G]gtctaaagacattgca (SEQ ID NO: 1225) |
| 03 | rs16969749 | 17 | q | q25.2 | SEC14L1 | 75192907 | 2.88E−03 | 0.87 | 0.127 | 0.143 | A | ctaattctgtcagcct[A/G]cttactagaaaccaaa (SEQ ID NO: 1226) |
| 03 | rs4969170 | 17 | q | q25.3 | SOCS3\|PGS1 | 76360538 | 7.40E−03 | 1.09 | 0.358 | 0.338 | A | gtttttagagaccaca[A/G]cctgctttcttctaga (SEQ ID NO: 1227) |
| 02 | rs9957245 | 18 | p | p11.21 | LOC100131500\|LOC644669 | 15102421 | 1.26E−03 | 1.21 | 0.188 | 0.161 | A | tcctaaaagtttcac[G/A]tcaagcataagtttct (SEQ ID NO: 1228) |
| 02 | rs1852893 | 18 | p | p11.21 | LOC100131500\|LOC644669 | 15082789 | 1.12E−04 | 1.14 | 0.282 | 0.256 | G | attatctggagtcagg[A/G]ttcttctttagcagtg (SEQ ID NO: 1229) |
| 02 | rs1893187 | 18 | p | p11.22 | VAPA\|APCDD1 | 10295300 | 2.33E−06 | 1.20 | 0.170 | 0.146 | A | actcacctgtcatca[A/G]aagagaaaggaccatg (SEQ ID NO: 1230) |
| 02 | rs206475 | 18 | p | p11.22 | VAPA\|APCDD1 | 10295284 | 4.30E−04 | 0.89 | 0.444 | 0.472 | A | gggcactaggtgccac[A/G]ctcaccctgtcatcag (SEQ ID NO: 1231) |
| 03 | rs206470 | 18 | p | p11.22 | VAPA\|APCDD1 | 10296623 | 5.55E−04 | 0.89 | 0.316 | 0.341 | A | cattactcagaattat[A/G]tctggagcaataaca (SEQ ID NO: 1232) |
| 02 | rs189982 | 18 | p | p11.22 | VAPA\|APCDD1 | 10302384 | 1.52E−05 | 1.20 | 0.157 | 0.135 | A | cttacaccatgtttct[A/G]tcagtatcaaacaag (SEQ ID NO: 1233) |
| 02 | rs11080401 | 18 | p | p11.22 | VAPA\|APCDD1 | 10304345 | 2.69E−06 | 1.20 | 0.177 | 0.153 | A | ggtttggagtctgatc[A/G]cttggattctggcagg (SEQ ID NO: 1234) |
| 03 | rs475001 | 18 | p | p11.32 | C18orf2\|METTL4 | 2192946 | 8.65E−03 | 1.15 | 0.102 | 0.090 | A | ttcatttgaatgaaac[A/G]ggtcacttaaaaatt (SEQ ID NO: 1235) |
| 03 | rs1507732 | 18 | p | p11.32 | C18orf2\|METTL4 | 1464859 | 1.29E−03 | 1.14 | 0.181 | 0.162 | A | ctgcaaagttccatta[A/G]aaagatggtggacaaa (SEQ ID NO: 1236) |
| 03 | rs561312 | 18 | p | p11.32 | C18orf2\|METTL4 | 2194248 | 7.75E−03 | 1.15 | 0.103 | 0.091 | A | cctgtgccgaagatga[A/G]gcaggaatctccaggg (SEQ ID NO: 1237) |
| 03 | rs2419027 | 18 | q | q12.1 | CDH2\|DSC3 | 27785716 | 4.67E−03 | 1.09 | 0.493 | 0.470 | A | tttactatggcctcc[A/G]ttgaccccagatggga (SEQ ID NO: 1238) |
| 03 | rs954640 | 18 | q | q12.1 | CDH2\|DSC3 | 27688654 | 1.89E−03 | 1.10 | 0.475 | 0.451 | A | tttacagatactgact[A/G]cataaaacaacaatcc (SEQ ID NO: 1239) |
| 03 | rs9967020 | 18 | q | q12.1 | CDH2\|DSC3 | 27681568 | 5.95E−03 | 1.09 | 0.492 | 0.471 | A | caaaaggacgtactgc[A/G]tgatgctaatttataa (SEQ ID NO: 1240) |
| 03 | rs8090231 | 18 | q | q12.1 | CDH2\|DSC3 | 27755950 | 3.86E−03 | 1.10 | 0.468 | 0.446 | A | acagactaagtgaaag[A/G]cccgcattcctacttt (SEQ ID NO: 1241) |
| 03 | rs12456839 | 18 | q | q12.1 | CDH2\|DSC3 | 25895735 | 2.66E−03 | 0.89 | 0.218 | 0.238 | G | aagctaggaagcatta[A/G]aatatgtatactgga (SEQ ID NO: 1242) |
| 03 | rs11564361 | 18 | q | q12.1 | CDH2\|DSC3 | 25904868 | 2.12E−03 | 0.89 | 0.217 | 0.238 | A | aacactagttgagtaa[A/G]tggatacaattgaggt (SEQ ID NO: 1243) |
| 03 | rs9952363 | 18 | q | q12.1 | CDH2\|DSC3 | 27690198 | 6.81E−04 | 1.11 | 0.479 | 0.452 | A | ctagacctactgccat[A/G]agtttgtaagacaca (SEQ ID NO: 1244) |
| 03 | rs12967345 | 18 | q | q12.1 | CDH2\|DSC3 | 27758155 | 2.29E−03 | 1.12 | 0.221 | 0.202 | G | caggacaggcaacaca[A/G]taacttgatacaaaag (SEQ ID NO: 1245) |
| 03 | rs8094149 | 18 | q | q12.2 | BRUNOL4 | 34979873 | 2.11E−04 | 0.89 | 0.365 | 0.394 | C | agtgaggctcactgc[A/C]tgggtgagaaggcgaaa (SEQ ID NO: 1246) |
| 03 | rs1511938 | 18 | q | q12.2 | BRUNOL4\|LOC647946 | 35967920 | 8.63E−04 | 0.90 | 0.461 | 0.488 | G | atgctgagccactg[A/G]taacatctacttgaa (SEQ ID NO: 1247) |
| 03 | rs12604671 | 18 | q | q12.2 | BRUNOL4\|LOC647946 | 36039666 | 4.68E−04 | 1.12 | 0.343 | 0.318 | A | aacgacttggaaatag[A/G]ctataaatgtagaagg (SEQ ID NO: 1248) |
| 03 | rs2625068 | 18 | q | q12.2 | LOC647946 | 37172774 | 1.34E−04 | 0.88 | 0.337 | 0.366 | A | (SEQ ID NO: 1249) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs10502725 | 18 | q | q12.2 | LOC647946 | 37111762 | 4.65E-05 | 0.88 | 0.365 | 0.396 | A | tttaatttaaataat[A/C]acattctgggtgcca (SEQ ID NO: 1250) |
| 03 | rs2852346 | 18 | q | q12.2 | LOC647946 | 37194499 | 7.92E-04 | 0.90 | 0.475 | 0.501 | A | ccaatgacataatatc[A/C]gaccttaaaaaaatga (SEQ ID NO: 1251) |
| 03 | rs2255757 | 18 | q | q12.3 | LOC100131669|SLC14A2 | 42958392 | 1.63E-03 | 1.11 | 0.416 | 0.392 | C | caggtcttatttcttc[A/G]tttacgttatgtgaaa (SEQ ID NO: 1252) |
| 03 | rs2726262 | 18 | q | q12.3 | LOC647946 | 37200183 | 1.99E-04 | 0.89 | 0.351 | 0.379 | A | gccatcccctatctct[A/C]ttgaaaactgactca (SEQ ID NO: 1253) |
| 03 | rs2726267 | 18 | q | q12.3 | LOO647946 | 37208969 | 2.06E-04 | 0.88 | 0.338 | 0.366 | C | cctctcccatgatcca[A/G]tcatctctcccaggc (SEQ ID NO: 1254) |
| 03 | rs2726232 | 18 | q | q12.3 | LOC647946 | 37212167 | 3.33E-04 | 0.89 | 0.465 | 0.493 | G | gtattcaaatcttggc[A/C]aatatccaactagcaa (SEQ ID NO: 1255) |
| 02 | rs10163756 | 18 | q | q12.3 | LOC647946|KC6 | 38325874 | 7.90E-05 | 1.18 | 0.171 | 0.148 | C | gaagaaftgaatgtctt[A/G]ggatacaattaagtga (SEQ ID NO: 1256) |
| 03 | rs981500 | 18 | q | q12.3 | LOC647946|KC6 | 38024748 | 5.32E-04 | 1.17 | 0.151 | 0.133 | C | aaaccattacatagg[A/C]tcaaaatccaaatatt (SEQ ID NO: 1257) |
| 03 | rs16973432 | 18 | q | q12.3 | LOC647946|KC6 | 38041069 | 5.69E-04 | 1.16 | 0.151 | 0.133 | C | aaacatttccagagft[A/C]aagaaagagragaaaa (SEQ ID NO: 1258) |
| 03 | rs4799515 | 18 | q | q12.3 | LOC647946|KC6 | 37387509 | 9.04E-04 | 0.90 | 0.429 | 0.455 | A | gtcatttatgaggtga[A/C]aaaaagaaacaaatgg (SEQ ID NO: 1259) |
| 03 | rs12455503 | 18 | q | q12.3 | LOC647946|KC6 | 37373687 | 4.31E-04 | 0.89 | 0.340 | 0.367 | G | aagcaatcctagctgg[A/G]gtagagctggcatttt (SEQ ID NO: 1260) |
| 03 | rs10502850 | 18 | q | q12.3 | SETBP1 | 42589714 | 1.87E-04 | 1.28 | 0.060 | 0.048 | A | aacacaatggggttga[A/G]catcacctcatattca (SEQ ID NO: 1261) |
| 02 | exm1386239 | 18 | q | q12.1 | C18ORF32 | 47008746 | 1.26E-07 | Inf | 0.003 | 0.000 | A | acctgtctgtttgat[A/G]tgcagactgaggctca (SEQ ID NO: 1262) |
| 03 | rs16949181 | 18 | q | q21.1 | LOC647055 | 45945536 | 1.16E-03 | 0.90 | 0.444 | 0.470 | G | atcacagatttcgtt[A/G]gtccttttgttgtaa (SEQ ID NO: 1263) |
| 03 | rs1377016 | 18 | q | q21.1 | LOXHD1 | 44063598 | 1.14E-02 | 0.92 | 0.314 | 0.333 | A | ttccaggtcccttc[A/G]cttcctgtcfgttgc (SEQ ID NO: 1264) |
| 03 | rs10502876 | 18 | q | q21.1 | LOXHD1|ST8SIA5 | 44257422 | 4.14E-04 | 0.73 | 0.032 | 0.043 | A | ggtctgacatgccag[A/G]caagttctctcttggg (SEQ ID NO: 1265) |
| 03 | rs17681615 | 18 | q | q21.2 | DCC | 50124619 | 2.09E-03 | 0.90 | 0.316 | 0.339 | A | agggaaagtgcttaac[A/G]tagcttgtaaaatgct (SEQ ID NO: 1266) |
| 02 | rs9964201 | 18 | q | q21.2 | DCC | 50600552 | 1.82E-02 | 1.14 | 0.092 | 0.082 | A | cattatactaaatacc[A/G]agggttaagagaataaa (SEQ ID NO: 1267) |
| 03 | rs12327270 | 18 | q | q21.2 | TCF4 | 53168073 | 5.79E-05 | 1.11 | 0.065 | 0.058 | G | agttactatgatttaa[A/C]tgttcattgtgttta (SEQ ID NO: 1268) |
| 03 | rs1506647 | 18 | q | q21.31 | TCF4|TXNL1 | 54136314 | 1.01E-03 | 1.28 | 0.047 | 0.037 | A | gcttcattatatcaca[A/G]agaatgagctcaaata (SEQ ID NO: 1269) |
| 02 | rs1469488 | 18 | q | q21.32 | CCBE1 | 57228450 | 6.44E-05 | 1.26 | 0.085 | 0.069 | A | ctaccttaagaaaca[A/G]gtaaaaaataatgat (SEQ ID NO: 1270) |
| 02 | rs2332079 | 18 | q | q21.32 | LOC728111|CDH20 | 58594189 | 4.68E-05 | 0.90 | 0.416 | 0.443 | G | gcttttgggtacacag[A/G]cccattacatacatga (SEQ ID NO: 1271) |
| 02 | rs17609410 | 18 | q | q21.32 | LOC728111|CDH20 | 58563363 | 1.11E-05 | 0.90 | 0.386 | 0.412 | A | ccaattccttttaaaa[A/G]agaggcttctgaaatt (SEQ ID NO: 1272) |
| 02 | rs1979787 | 18 | q | q21.32 | LOC728111|CDH20 | 58684971 | 2.68E-05 | 0.88 | 0.407 | 0.438 | G | atagcaccctattctg[A/C]agctctcgggactctt (SEQ ID NO: 1273) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs2332197 | 18 | q | q21.32 | LOC728111\|CDH20 | 58717342 | 1.65E-05 | 0.88 | 0.406 | 0.436 | A | ttaaggcagaacaatt[A/G]tcatatctgttcagga (SEQ ID NO: 1274) |
| 03 | rs2850768 | 18 | q | q21.33 | KDSR | 61014410 | 6.16E-03 | 0.90 | 0.190 | 0.208 | G | tacattacagaatgaa[A/G]agaaaaagaggcttgg (SEQ ID NO: 1275) |
| 03 | rs12969516 | 18 | q | q22.2 | SOCS6\|CBLN2 | 68518485 | 6.27E-03 | 0.92 | 0.445 | 0.466 | G | gctgagctctcttt[A/G]aggattcatctttgac (SEQ ID NO: 1276) |
| 03 | rs7235677 | 18 | q | q22.2 | SOCS6\|CBLN2 | 68552596 | 1.23E-03 | 1.14 | 0.200 | 0.181 | G | agaggttgcaagcaca[A/G]gtatttgcacactgt (SEQ ID NO: 1277) |
| 03 | rs4555235 | 18 | q | q22.3 | LOC100289370\|FBXO15 | 71071370 | 6.68E-03 | 1.09 | 0.504 | 0.483 | A | tctctggctttaaaca[A/G]aaagatgactaaaact (SEQ ID NO: 1278) |
| 02 | exm1392554 | 18 | q | q22.3 | TIMM21 | 71816278 | 3.44E-17 | 3.66 | 0.026 | 0.007 | A | aaaagcaaaggaggat[A/G]gcagcaaacaagtgtc (SEQ ID NO: 1279) |
| 03 | rs8084536 | 18 | q | q23 | FLJ44313\|LOC284276 | 74227791 | 1.30E-03 | 1.11 | 0.417 | 0.392 | G | cccaccagcagtatac[A/G]aggcttctcatttcac (SEQ ID NO: 1280) |
| 03 | rs4891030 | 18 | q | q23 | LOC284276\|FLJ44881 | 74295607 | 3.91E-03 | 0.89 | 0.196 | 0.214 | G | agagaaataagtggat[A/G]taacagagtggatctg (SEQ ID NO: 1281) |
| 03 | rs11874114 | 18 | q | q23 | MBP | 74699134 | 1.41E-03 | 1.23 | 0.062 | 0.051 | A | agtggactttgggcc[A/G]tcgtgccgatcctcc (SEQ ID NO: 1282) |
| 03 | rs8086634 | 18 | q | q23 | MBP | 74701192 | 2.52E-04 | 1.23 | 0.087 | 0.072 | A | cgctactcctagcccc[A/G]gaaagggctcacggtg (SEQ ID NO: 1283) |
| 03 | rs11669407 | 19 | p | p13.11 | CHERP\|SLC35E1 | 16654444 | 2.29E-02 | 0.90 | 0.142 | 0.155 | A | aggaagccaagatcaag[A/G]atttttttttctaa (SEQ ID NO: 1284) |
| 02 | exm1442461 | 19 | p | p13.11 | SLC27A1 | 17597661 | 2.51E-20 | 7.24 | 0.017 | 0.002 | A | agcagcgcggcctcca[A/T]tgcccgccttggccagg (SEQ ID NO: 1285) |
| 03 | rs794084 | 19 | p | p13.2 | XAB2 | 7692058 | 4.63E-04 | 1.12 | 0.422 | 0.395 | G | ctggtgacatcctac[A/G]ccggaagctagtgtcaca (SEQ ID NO: 1286) |
| 02 | exm1400852 | 19 | p | p13.3 | APC2 | 1468696 | 1.17E-07 | Inf | 0.003 | 0.000 | A | ctggcacggggtgcc[A/G]ggctgggacgtagat (SEQ ID NO: 1287) |
| 03 | rs313784 | 19 | p | p13.3 | BRUNOL5 | 3293593 | 1.27E-05 | 0.90 | 0.232 | 0.252 | A | ggtggggtgatgcttc[A/G]agaggctacaagaaac (SEQ ID NO: 1288) |
| 03 | rs1610045 | 19 | p | p13.3 | BTBD2 | 1997363 | 1.61E-04 | 0.88 | 0.300 | 0.328 | G | gccagtgcgaaggaaggc[A/G]gccgggttccacgtcgg (SEQ ID NO: 1289) |
| 03 | rs12976454 | 19 | p | p13.3 | C19orf28 | 3544971 | 5.02E-04 | 1.13 | 0.312 | 0.288 | A | ccggggggtggtaccc[A/G]cggtgcctactcatcc (SEQ ID NO: 1290) |
| 03 | rs3916080 | 19 | p | p13.3 | FUT6 | 5832899 | 2.02E-03 | 0.90 | 0.345 | 0.369 | A | cctttctgggtgtc[A/C]ccagactcttcctcaa (SEQ ID NO: 1291) |
| 03 | rs11878982 | 19 | p | p13.3 | KDM4B | 5041049 | 1.37E-04 | 1.15 | 0.252 | 0.227 | A | cacccatgaaagaggc[A/G]ggagggggctdgtcc (SEQ ID NO: 1292) |
| 02 | rs33938520 | 19 | p | p13.3 | KDM4B | 4984588 | 4.40E-05 | 1.15 | 0.292 | 0.264 | A | acctgacgaggcgtac[A/G]gaacaggccggaacag (SEQ ID NO: 1293) |
| 03 | rs4805077 | 19 | q | 813.11 | LSM14A\|KIAA0355 | 34742705 | 2.08E-02 | 1.08 | 0.381 | 0.363 | G | ttccagtgtgaacafg[A/G]catcaagaagaggca (SEQ ID NO: 1294) |
| 03 | rs6510478 | 19 | q | q13.12 | CD22 | 35834621 | 2.20E-04 | 0.87 | 0.234 | 0.260 | G | cccacacctcatagca[A/G]gatctcatctctacaa (SEQ ID NO: 1295) |
| 03 | rs7251526 | 19 | q | q13.12 | CD22 | 35829513 | 4.64E-03 | 0.90 | 0.263 | 0.283 | A | aaaacaagcatctacc[A/G]agcaccctccatgagc (SEQ ID NO: 1296) |
| 02 | rs4806152 | 19 | q | q13.12 | FFAR3\|LOC100128682 | 35886660 | 5.27E-06 | 0.84 | 0.204 | 0.235 | C | caagtgagagcagata[A/C]ggcagcacagggattc (SEQ ID NO: 1297) |
| 03 | rs11669734 | 19 | q | q13.12 | MAG | 35794775 | 1.41E-03 | 0.89 | 0.233 | 0.254 | A | (SEQ ID NO: 1298) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | exm1458802 | 19 | q | q13.12 | WDR62 | 36546015 | 8.28E-18 | 5.91 | 0.017 | 0.003 | A | cgatattccagaggga[A/G]ttgcttaaggaaggg (SEQ ID NO: 1299) |
| 03 | rs234341 | 19 | q | q13.2 | PSMC4 | 40486136 | 1.29E-02 | 1.25 | 0.034 | 0.027 | A | tcggagggcgtcgaga[A/G]tcgcgtcgccgccgt (SEQ ID NO: 1300) |
| 03 | rs17289513 | 19 | q | q13.32 | AP2S1|GRLF1 | 47412622 | 3.06E-03 | 0.85 | 0.087 | 0.101 | A | ctaagggtgggttatc[A/G]tgacagaaggaggta (SEQ ID NO: 1301) |
| 02 | exm1493646 | 19 | q | q13.33 | MYH14 | 50747534 | 4.61E-24 | 95.05 | 0.010 | 0.000 | A | cagtagaactttcaagg[A/G]ctagtaactcgcatgc (SEQ ID NO: 1302) |
| 03 | rs10403102 | 19 | q | q13.33 | TPRX1|CRX | 48317892 | 4.87E-03 | 0.91 | 0.452 | 0.474 | A | ttcaaggcaatgttgc[A/C]aaactgagaactgct (SEQ ID NO: 1303) |
| 03 | rs11881877 | 19 | q | q13.41 | ZNF320|LOC38559 | 53401760 | 1.11E-04 | 0.89 | 0.446 | 0.476 | A | aggtgtcgatcaacg[A/C]cctcagagatgacctg (SEQ ID NO: 1304) |
| 03 | rs6080719 | 20 | p | p12.1 | BFSP1 | 17477592 | 5.89E-03 | 1.11 | 0.254 | 0.236 | A | gattttaaaaaagc[A/G]ttgacattgtaacagt (SEQ ID NO: 1305) |
| 03 | rs1333400 | 20 | p | p12.1 | BTBD3|LOC100289040 | 12693139 | 6.20E-04 | 1.11 | 0.522 | 0.495 | G | tctcagcactgga tcc[A/G]gtgggaaaggtaacgc (SEQ ID NO: 1306) |
| 03 | rs1333383 | 20 | p | p12.1 | BTBD3|LOC100289040 | 12710164 | 5.83E-05 | 0.88 | 0.384 | 0.415 | A | catgcccagatatggt[A/G]tatattgggggaatca (SEQ ID NO: 1307) |
| 03 | rs4814155 | 20 | p | p12.1 | BTBD3|LOC100289040 | 12708838 | 1.08E-04 | 0.88 | 0.374 | 0.403 | G | attgaactgtaacttaa[A/G]acagagcaaacattgt (SEQ ID NO: 1308) |
| 03 | rs6111020 | 20 | p | p12.1 | KIF16B | 16273832 | 7.40E-05 | 1.14 | 0.364 | 0.334 | A | gcctactaacagcaag[A/G]gccttattaatattt (SEQ ID NO: 1309) |
| 03 | rs7263619 | 20 | p | p12.1 | KIF16B | 16447367 | 1.08E-02 | 0.91 | 0.204 | 0.220 | A | accatggttctatc[A/G]atttctgccatatcct (SEQ ID NO: 1310) |
| 03 | rs7275594 | 20 | p | p12.1 | KIF16B | 16302535 | 3.12E-03 | 1.14 | 0.143 | 0.128 | A | gtgtccacctgtatta[A/G]agrgtttcatgtgct (SEQ ID NO: 1311) |
| 03 | rs6111005 | 20 | p | p12.1 | KIF16B | 16256912 | 1.64E-03 | 0.86 | 0.113 | 0.129 | G | cacagttttcccataa[A/G]agctcaaatatcttg (SEQ ID NO: 1312) |
| 03 | rs6043962 | 20 | p | p12.1 | KIF16B | 16438733 | 6.11E-04 | 1.13 | 0.286 | 0.262 | C | gcctaaaggtgtataat[A/G]agaagagaagtaaaag (SEQ ID NO: 1313) |
| 03 | rs8120353 | 20 | p | p12.1 | KIF16B | 16412764 | 1.15E-02 | 0.90 | 0.158 | 0.173 | A | ggtcacagcaaaact[A/C]taccgttttgatctgg (SEQ ID NO: 1314) |
| 03 | rs1028539 | 20 | p | p12.1 | KIF16B | 16445463 | 3.42E-04 | 1.14 | 0.244 | 0.221 | A | gtcagatgggctgat[A/G]tcaagataaggcctac (SEQ ID NO: 1315) |
| 03 | rs8116503 | 20 | p | p12.1 | KIF16B | 16359650 | 8.91E-03 | 0.90 | 0.184 | 0.201 | A | tacttgcatcccaacc[A/G]cctaaaagtgttggtt (SEQ ID NO: 1316) |
| 03 | rs6085463 | 20 | p | p12.3 | FERMT1|BMP2 | 6252538 | 1.46E-02 | 0.92 | 0.388 | 0.407 | A | tggagtccagagagaa[A/G]cagcagagagaggcgc (SEQ ID NO: 1317) |
| 02 | exm1519568 | 20 | p | p13 | TGM3 | 2297721 | 4.47E-11 | Inf | 0.004 | 0.000 | A | cttcaacctcatgtta[A/G]atcagtacttataagc (SEQ ID NO: 1318) |
| 03 | rs4911107 | 20 | q | q11.21 | DNMT3B | 31374991 | 3.21E-03 | 0.91 | 0.378 | 0.401 | A | tctgcccgatcaata[A/G]caatgatgacaatggt (SEQ ID NO: 1319) |
| 02 | exm1534977 | 20 | q | q11.22 | EIF2S2 | 32685262 | 1.32E-35 | Inf | 0.023 | 0.000 | A | ttggtctcgtcacc[A/G]acatcctttgctctgg (SEQ ID NO: 1320) |
| 03 | rs8050 | 20 | q | q11.22 | RB|M12 | 34237224 | 3.52E-03 | 0.73 | 0.021 | 0.028 | A | tgagcctgcccaagca[A/G]ggcctgtctgattact (SEQ ID NO: 1321) |
| 02 | rs16988087 | 20 | q | q12 | LOC339568|MAFB | 38087936 | 3.89E-05 | 1.21 | 0.136 | 0.115 | A | ccatactgtacacaa[A/C]cacagaactccagtaa (SEQ ID NO: 1322) |
| | | | | | | | | | | | | ctaaatcaaatgacaa[A/G]gagaaaagttagcttt |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs7263998 | 20 | q | q12 | LOC339568\|MAFB | 38022796 | 1.65E-04 | 1.19 | 0.135 | 0.116 | A | tctctccccacaca[A/G]gtcattttcttaattc (SEQ ID NO: 1323) |
| 03 | rs6028507 | 20 | q | q12 | LOC339568\|MAFB | 38181661 | 9.17E-04 | 1.14 | 0.187 | 0.168 | G | ccaagaaaagtgccc[A/G]caagaaaaccaaaaca (SEQ ID NO: 1324) |
| 03 | rs11697337 | 20 | q | q12 | LOC339568\|MAFB | 38236027 | 1.06E-02 | 1.25 | 0.035 | 0.028 | A | cacagttactcaagtc[A/G]agaggcaaaaaaaaa (SEQ ID NO: 1325) |
| 03 | rs6101558 | 20 | q | q12 | LOC339568\|MAFB | 38090963 | 8.72E-05 | 1.16 | 0.174 | 0.154 | G | tgtgactaaaccactc[A/G]ctctgtttccccactc (SEQ ID NO: 1326) |
| 02 | rs13044948 | 20 | q | q12 | LOC339568\|MAFB | 38062804 | 1.20E-05 | 1.23 | 0.132 | 0.110 | A | attaaatatttttc[A/G]taataaccagctaga (SEQ ID NO: 1327) |
| 03 | rs2207799 | 20 | q | q12 | LOC339568\|MAFB | 38195894 | 1.99E-04 | 1.26 | 0.069 | 0.055 | A | tattaacattcataaa[A/C]cattcagacaattgct (SEQ ID NO: 1328) |
| 02 | rs13036738 | 20 | q | q12 | LOC339568\|MAFB | 38078988 | 1.64E-05 | 1.22 | 0.132 | 0.110 | C | tgcctatttctaaact[A/C]tgctgggaaagcagg (SEQ ID NO: 1329) |
| 02 | rs13044925 | 20 | q | q12 | LOC339568\|MAFB | 38085378 | 1.81E-05 | 1.22 | 0.133 | 0.111 | G | aggagattagggtgt[A/G]atttccggttcttc (SEQ ID NO: 1330) |
| 03 | rs2143216 | 20 | q | q12 | LOC339568\|MAFB | 38066525 | 1.62E-04 | 1.17 | 0.183 | 0.161 | A | ataaacttgcttact[A/G]tatacacacatgca (SEQ ID NO: 1331) |
| 03 | rs8119002 | 20 | q | q12 | PTPRT | 41072290 | 1.06E-02 | 0.89 | 0.145 | 0.160 | A | ccagggctatgaaacc[A/G]tctcattctgcagcag (SEQ ID NO: 1332) |
| 03 | rs6090639 | 20 | q | q13.12 | EYA2\|ZMYND8 | 45835008 | 2.30E-04 | 1.16 | 0.180 | 0.159 | G | ttttaggggtgtgat[A/G]tctgctatgtgggacac (SEQ ID NO: 1333) |
| 02 | exm2264714 | 20 | q | q13.13 | B4GALT5\|SLC9A8 | 48383467 | 3.26E-10 | Inf | 0.005 | 0.000 | C | ggattacaggcatgag[A/C]caccacatgctgccat (SEQ ID NO: 1334) |
| 03 | rs13041253 | 20 | q | q13.13 | LOC100130589\|LOC284749 | 46773023 | 3.39E-04 | 1.14 | 0.227 | 0.205 | G | atgagttggaagaagt[A/G]ttagaagtcccatcgt (SEQ ID NO: 1335) |
| 03 | rs162076 | 20 | q | q13.13 | LOC100130589\|LOC284749 | 46785499 | 1.17E-04 | 1.13 | 0.461 | 0.431 | G | ggttttcaggaatgca[A/G]aagtctgaagaacac (SEQ ID NO: 1336) |
| 03 | rs927478 | 20 | q | q13.13 | LOC100130589\|LOC284749 | 46761590 | 2.66E-04 | 1.15 | 0.227 | 0.203 | A | taagacaaagataaggt[A/G]tctaatttcattcttt (SEQ ID NO: 1337) |
| 03 | rs852353 | 20 | q | q13.13 | LOC100130589\|LOC284749 | 46833654 | 2.34E-04 | 1.12 | 0.453 | 0.425 | A | aattttcctragaaag[A/C]ctcaacctcagcatac (SEQ ID NO: 1338) |
| 03 | rs852373 | 20 | q | q13.13 | LOC100130589\|LOC284749 | 46841297 | 4.67E-03 | 0.90 | 0.212 | 0.231 | G | ggggtcccttcctgc[A/G]ctctcataagctcccc (SEQ ID NO: 1339) |
| 02 | rs162079 | 20 | q | q13.13 | LOC100130589\|LOC284749 | 46784745 | 8.36E-05 | 1.16 | 0.239 | 0.214 | A | tcgagggctagaagt[A/G]atgagagtgggtgggg (SEQ ID NO: 1340) |
| 02 | rs6023407 | 20 | q | q13.2 | DOK5 | 53221238 | 9.11E-05 | 0.93 | 0.329 | 0.346 | G | atgtatatttaaggta[A/G]gcgttttatttccct (SEQ ID NO: 1341) |
| 02 | rs6064102 | 20 | q | q13.2 | DOK5\|CBLN4 | 53283735 | 7.76E-03 | 0.88 | 0.123 | 0.137 | A | tgcatccctccfatc[A/G]tggttctttgaggagaa (SEQ ID NO: 1342) |
| 02 | exm1550638 | 20 | q | q13.2 | SALL4 | 50408481 | 1.26E-07 | Inf | 0.003 | 0.000 | A | agtggccaaactaat[A/G]tgacttgcaggcact (SEQ ID NO: 1343) |
| 02 | rs6013748 | 20 | q | q13.2 | ZNF217\|SUMO1P1 | 52275163 | 1.44E-05 | 1.17 | 0.177 | 0.156 | A | agcatatttggcctcc[A/G]taatgccgcttaaggt (SEQ ID NO: 1344) |
| 03 | rs6025739 | 20 | q | q13.31 | PMEPA1\|LOC100129869 | 56294313 | 1.40E-03 | 1.18 | 0.100 | 0.086 | G | taaatggcaattgttc[A/G]tgcaataaagaacaat (SEQ ID NO: 1345) |
| 03 | rs170602 | 20 | q | q13.31 | RBM38\|HMGB1L1 | 56019162 | 2.24E-03 | 0.89 | 0.222 | 0.242 | G | ctcatctcttagcc[A/G]gctttcccttacagg (SEQ ID NO: 1346) |
| 03 | rs6129089 | 20 | q | q13.33 | CDH4 | 59850852 | 2.39E-03 | 1.11 | 0.270 | 0.249 | A | (SEQ ID NO: 1347) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2427021 | 20 | q | q13.33 | CDH4 | 59845250 | 1.52E-03 | 1.15 | 0.157 | 0.140 | A | ttccacccccagtgat[A/G]ctcagaatccaggatc (SEQ ID NO: 1348) |
| 03 | rs6010784 | 20 | q | q13.33 | DIDO1 | 61540319 | 1.25E-03 | 0.90 | 0.474 | 0.500 | A | ataaataacgatagcc[A/G]gtaacttacgttcact (SEQ ID NO: 1349) |
| 01 | JBLO001 | 20 | q | q13.33 | LAMA5 | 60892450 | 5.28E-12 | 3.959 | 0.020 | 0.010 | T | ctcatgctgcctgct[A/G]tcagaggccacatctg (SEQ ID NO: 1350) |
| 03 | rs6015653 | 20 | q | q13.33 | LOC729296\|CDH4 | 58692731 | 4.54E-04 | 1.21 | 0.095 | 0.080 | A | tgtgcgtgggcctcgg[C/T]ggcctccactagacgc (SEQ ID NO: 1351) |
| 03 | rs2426990 | 20 | q | q13.33 | LOC729296\|CDH4 | 59788003 | 9.56E-03 | 1.09 | 0.356 | 0.337 | G | actgggttttgtggac[A/C]ctttgcagaggtcggg (SEQ ID NO: 1352) |
| 03 | rs2426983 | 20 | q | q13.33 | LOC729296\|CDH4 | 59777873 | 1.43E-02 | 1.08 | 0.424 | 0.405 | C | gtgcatttaatatat[A/G]gaccacaagctcagag (SEQ ID NO: 1353) |
| 03 | rs6028076 | 20 | q | q13.33 | LOC729296\|CDH4 | 59801421 | 2.54E-02 | 1.08 | 0.359 | 0.343 | G | cattgacacactggca[A/C]actcaatactgtgcac (SEQ ID NO: 1354) |
| 03 | rs2426986 | 20 | q | q13.33 | LOC729296\|CDH4 | 59786367 | 1.33E-02 | 1.11 | 0.167 | 0.149 | G | cccaaaggaaaccct[A/G]aacccaataagcagtc (SEQ ID NO: 1355) |
| 03 | rs6028080 | 20 | q | q13.33 | LOC729296\|CDH4 | 59804478 | 8.27E-04 | 1.15 | 0.168 | 0.254 | G | tgttactgaggtatgc[A/G]atgccatgatttccac (SEQ ID NO: 1356) |
| 03 | rs2427000 | 20 | q | q13.33 | LOC729296\|CDH4 | 59802749 | 2.07E-02 | 1.09 | 0.269 | 0.153 | A | tgtaaatcaccacctc[A/G]ttttgttcctagagct (SEQ ID NO: 1357) |
| 03 | rs2426993 | 20 | q | q13.33 | LOC729296\|CDH4 | 59794418 | 1.03E-02 | 1.12 | 0.167 | 0.153 | G | cccttgccataaattg[A/G]aatccagagctgtaag (SEQ ID NO: 1358) |
| 03 | rs6027379 | 20 | q | q13.33 | LOC729296\|CDH4 | 58747589 | 9.67E-05 | 0.89 | 0.445 | 0.474 | G | acttctactcagcata[A/G]aatgggccgttgccaa (SEQ ID NO: 1359) |
| 02 | rs1023361 | 21 | q | q21.1 | NCAM2\|NCRNA00158 | 23344282 | 3.08E-05 | 1.13 | 0.049 | 0.044 | A | ccataaaaggccggct[A/G]tagactccacatgtttt (SEQ ID NO: 1360) |
| 03 | rs390955 | 21 | q | q21.3 | ADAMTS1\|ADAMTS5 | 28218457 | 8.60E-04 | 0.89 | 0.283 | 0.307 | C | gttttaaatgaaataaa[A/G]catcctcctgtttgcgg (SEQ ID NO: 1361) |
| 03 | rs10482984 | 21 | q | q21.3 | LOC100288252\|NCRNA00113 | 28820729 | 7.34E-04 | 1.22 | 0.075 | 0.062 | G | cgcagccacctcttc[A/C]ccagagaacgacttgt (SEQ ID NO: 1362) |
| 03 | rs12482697 | 21 | q | q22.11 | ATP5O\|FLJ46020 | 35293199 | 2.60E-04 | 0.81 | 0.081 | 0.098 | C | tggaagaagggtaag[A/G]tatctccagagccgct (SEQ ID NO: 1363) |
| 03 | rs11701963 | 21 | q | q22.11 | ATP5O\|FLJ46020 | 35523657 | 1.08E-03 | 0.80 | 0.055 | 0.068 | A | gttttctccctttgccc[A/C]caccactaaaatacag (SEQ ID NO: 1364) |
| 03 | rs2032214 | 21 | q | q22.11 | FLJ46020\|MRPS6 | 35354523 | 2.40E-03 | 0.82 | 0.063 | 0.075 | A | agtccaagcagcacct[A/G]gtaatttaaactgagtc (SEQ ID NO: 1365) |
| 03 | rs2070371 | 21 | q | q22.11 | HUNK | 33368188 | 6.19E-04 | 1.13 | 0.246 | 0.223 | A | gcaaatctatacagac[A/G]gaacacagattcatggt (SEQ ID NO: 1366) |
| 03 | rs198914 | 21 | q | q22.11 | KRTAP6-2\|KRTAP22-1 | 31973405 | 7.04E-04 | 0.89 | 0.275 | 0.299 | A | tctgaatctgtcat[A/G]agcgagcctgagggct (SEQ ID NO: 1367) |
| 03 | rs2834889 | 21 | q | q22.12 | RUNX1\|SETD4 | 36675294 | 4.79E-04 | 0.90 | 0.437 | 0.464 | C | ctcagttgtatagcag[A/G]atcagattctagagtt (SEQ ID NO: 1368) |
| 03 | rs6517494 | 21 | q | q22.2 | FLJ45139\|LOC100289305 | 40330767 | 6.46E-03 | 1.10 | 0.314 | 0.295 | A | agaaaccagccatttg[A/C]atgcgctcaatggaat (SEQ ID NO: 1369) |
| 02 | exm1571045 | 21 | q | q22.2 | LCA5L | 40778182 | 2.87E-10 | 1.47 | 0.127 | 0.090 | A | aaaaagctacgcccac[A/C]tcctaacctccggact (SEQ ID NO: 1370) |
| 02 | rs9981939 | 21 | q | q22.3 | C21orf121\|UMODL1 | 43473602 | 2.00E-05 | 1.13 | 0.259 | 0.236 | C | ggggcagccaatgcc[A/G]gcaacatgaggtacag tataacttcaaaaa[A/C]ttcaacatcatcttcc (SEQ ID NO: 1371) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs467997 | 21 | q | q22.3 | C21orf121\|UMODL1 | 43448016 | 3.66E-05 | 1.16 | 0.279 | 0.251 | A | aaggaaaagtcattc[A/G]gggctgtgataagaaag (SEQ ID NO: 1372) |
| 02 | rs2839452 | 21 | q | q22.3 | C21orf121\|UMODL1 | 43466047 | 1.88E-05 | 1.13 | 0.289 | 0.265 | G | taccactaattccaat[A/G]gtcaagaagagctgac (SEQ ID NO: 1373) |
| 03 | rs220263 | 21 | q | q22.3 | C21orf121\|UMODL1 | 43482161 | 5.74E-05 | 1.13 | 0.471 | 0.440 | G | ccccacgtgaactgc[A/G]gcaggcagagaatcta (SEQ ID NO: 1374) |
| 03 | rs762395 | 21 | q | q22.3 | C21orf136\|FLJ41733 | 44769676 | 5.57E-03 | 1.10 | 0.361 | 0.340 | A | gggctgtttcagaat[A/G]cggttgggcaagttg (SEQ ID NO: 1375) |
| 03 | rs9978582 | 21 | q | 822.3 | COL6A1\|COL6A2 | 47488387 | 2.34E-03 | 0.91 | 0.417 | 0.441 | C | tccgtctacagccacc[A/C]agttaaataacagcgg (SEQ ID NO: 1376) |
| 03 | rs2282527 | 21 | q | q22.3 | RRP1B | 45081426 | 3.72E-03 | 1.10 | 0.357 | 0.336 | A | gttcacctcctgatga[A/C]ataaattcttgaccgt (SEQ ID NO: 1377) |
| 03 | rs3814903 | 21 | q | q22.3 | TMPRSS3\|UBASH3A | 43817117 | 3.43E-04 | 1.12 | 0.363 | 0.336 | A | gggctatttgataggc[A/C]cacggcagctgggtt (SEQ ID NO: 1378) |
| 03 | rs599034 | 22 | q | q11.1 | CECR1\|CECR2 | 17852805 | 1.63E-03 | 1.15 | 0.144 | 0.128 | A | aatccatgagttcagc[A/C]tggtgagatctttccc (SEQ ID NO: 1379) |
| 03 | rs1296795 | 22 | q | q11.21 | CECR2 | 18021760 | 1.19E-04 | 0.87 | 0.235 | 0.262 | G | cattgcgtcattccc[A/G]aagagtctgttccat (SEQ ID NO: 1380) |
| 03 | rs714027 | 22 | q | q12.2 | HORMAD2\|LIF | 30577771 | 4.03E-03 | 1.09 | 0.475 | 0.453 | A | aaagaattttcccca[A/G]tgctctagcaaattgc (SEQ ID NO: 1381) |
| 03 | rs1049536 | 22 | q | q12.2 | THOC5 | 29904354 | 5.88E-03 | 1.11 | 0.245 | 0.227 | A | ggctgtgtattgga[A/G]aatatcaagagtcaca (SEQ ID NO: 1382) |
| 03 | rs2016485 | 22 | q | q12.3 | LARGE | 34086416 | 7.28E-03 | 0.92 | 0.442 | 0.463 | A | gtcattcagccctcc[A/G]gcaacccccagaaatag (SEQ ID NO: 1383) |
| 03 | rs739166 | 22 | q | q13.1 | ELFN2\|MFNG | 37863459 | 9.09E-05 | 1.12 | 0.267 | 0.244 | G | gaagtgaccatctgg[A/G]ccccagaggcaggggc (SEQ ID NO: 1384) |
| 02 | rs1005522 | 22 | q | q13.1 | MAP3K7IP1\|MGAT3 | 39845898 | 7.35E-05 | 1.15 | 0.271 | 0.244 | C | cctcgcaccccctgg[A/C]cctcatggggcacttc (SEQ ID NO: 1385) |
| 02 | exm1609618 | 22 | q | q13.1 | PDGFB | 39621819 | 2.38E-08 | 4.42 | 0.009 | 0.002 | A | ccggcggactcgcacc[A/G]tccgaattggtcaccg (SEQ ID NO: 1386) |
| 03 | rs2187793 | 22 | q | q13.31 | LOC100289420\|FAM19A5 | 47688003 | 2.72E-04 | 0.89 | 0.330 | 0.357 | A | tgcaaaatgcttctga[A/G]atgggtcaaccagaag (SEQ ID NO: 1387) |
| 03 | rs16993202 | 22 | q | q13.31 | PHF21B | 45353413 | 1.02E-03 | 0.84 | 0.097 | 0.113 | G | aaagagagggctgact[A/G]ttgattctgtgcatac (SEQ ID NO: 1388) |
| 03 | rs736490 | 22 | q | q13.31 | PHF21B | 45338213 | 4.34E-04 | 0.82 | 0.078 | 0.094 | A | agaggtgccccagg[A/G]tcctactgtggatcag (SEQ ID NO: 1389) |
| 03 | rs138850 | 22 | q | q13.33 | BRD1 | 50193337 | 1.71E-03 | 1.12 | 0.241 | 0.220 | G | agagggagcaggtgct[A/G]tcaatggaatgggac (SEQ ID NO: 1390) |
| 03 | rs138843 | 22 | q | q13.33 | BRD1 | 50183162 | 3.97E-04 | 1.14 | 0.251 | 0.228 | A | gaagggagcaggtgct[A/G]tcaatggaatgggac (SEQ ID NO: 1391) |

TABLES-continued

Table 1 (Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs5769373 | 22 | q | q13.33 | LOC100128946\|LOC100287247 | 49411595 | 7.63E-02 | 1.06 | 0.413 | 0.399 | A | gaagtcgtaatcaggt[A/G]cgagagctcgggcgg (SEQ ID NO: 1392) |
| 03 | rs5769807 | 22 | q | q13.33 | LOC100128946\|LOC100287247 | 49415539 | 1.58E-02 | 1.09 | 0.303 | 0.285 | G | caagtctccagtgac[A/G]gggccgacacttggtc (SEQ ID NO: 1393) |
| 03 | rs2064542 | 22 | q | q13.33 | LOC100128946\|LOC100287247 | 49430916 | 5.02E-02 | 1.07 | 0.399 | 0.384 | C | aactttctgtaaagca[A/G]tgggagttagggcaac (SEQ ID NO: 1394) |
| 03 | rs1548245 | 22 | q | q13.33 | LOC100128946\|LOC100287247 | 49412197 | 5.13E-02 | 1.07 | 0.249 | 0.236 | A | ctgcctcaaacccga[A/C]gtcttcaagcctgact (SEQ ID NO: 1395) |
| 03 | rs4823969 | 22 | q | q13.33 | LOC100128946\|LOC100287247 | 49416063 | 6.92E-03 | 1.11 | 0.207 | 0.190 | G | gtgtcgtggcagatac[A/C]aggtctcacggaagtc (SEQ ID NO: 1396) |
| 03 | rs5770992 | 22 | q | q13.33 | SHANK3 | 51146139 | 1.21E-04 | 0.81 | 0.092 | 0.111 | G | gtgagctgcacatcct[A/G]cctagaaggacatct (SEQ ID NO: 1397) |
| 02 | rs1007461 | X | p | p22.2 | CLCN4\|MID1 | 10297210 | 1.36E-04 | 1.19 | 0.466 | 0.423 | A | tagctattccaaataa[A/G]ataaaacccaaagaaa (SEQ ID NO: 1398) |
| | | | | | | | | | | | | ccaatgtatgtgaagt[G/A]gctcaaatgaattttg |

What is claimed is:

1. A method of administering an endometriosis altered risk treatment, said method comprising the steps of:
   identifying an endometriosis asymptomatic human female subject,
   obtaining clinical data (CD) and a biological sample of said subject, said CD defining the answers to the questions of "menarche after age 14 (Y/N)", "dysmenorrhea (Y/N)", and "previous pregnancy (Y/N)",
   assigning a raw clinical probability value (RCPV) to said CD,
   assaying said sample,
   detecting in said sample a plurality of endometriosis increased risk associated biomarkers, each endometriosis increased risk associated biomarker defining the minor allele of a biomarker of table 1 having an OR of greater than 1.0 resulting in endometriosis increased risk associated biomarker data,
   performing a statistical analysis using said RCPV and said endometriosis increased risk associated biomarker data to result in an endometriosis condition prognosis of said subject of at least one of an increased risk of endometriosis existence and an increased risk of endometriosis predisposition, and
   administering an endometriosis altered risk treatment to said subject, said endometriosis altered risk treatment defining a hormonal treatment comprising the administration of at least one of an estrogen containing composition, a progesterone containing composition, a progestin containing composition, a testosterone containing composition, a gonadotropin releasing-hormone (GnRH) agonist, and a combination thereof.

2. The method of claim 1, wherein said plurality of endometriosis increased risk associated biomarkers defines all of biomarkers of table 1 having an OR of greater than 1.0.

3. The method of claim 1, wherein said plurality of endometriosis increased risk associated biomarkers defines all of the biomarkers of set 01 of table 1 having an OR of greater than 1.0.

4. The method of claim 1, wherein said plurality of endometriosis increased risk associated biomarkers includes SEQ ID NO:0011.

5. The method of claim 1, wherein said estrogen containing composition is in the form of an oral contraceptive pill, and wherein said progesterone containing composition is in the form of an oral contraceptive pill, and wherein said progestin containing composition is in the form of an oral contraceptive pill, and wherein said GnRH agonist is in the form of an oral contraceptive pill.

6. The method of claim 1, wherein said progesterone further defines at least one progesterone of desogestrel, drospirenone, ethynodiol, levonorgestrel, norethindrone, norgestimate, and norgestrel, and wherein said estrogen defines at least one estrogen of mestranol, estradiol, and ethinyl, and wherein said testosterone defines danazol.

7. The method of claim 1, wherein said GnRH agonist is combined with an add-back therapy to prevent a GnRH agonist side effect.

8. The method of claim 7, wherein said add-back therapy defines a dosage of at least one of estrogen, progestin, and tibolone, and wherein said dosage of at least one of estrogen, progestin, and tibolone is in an amount such that the effectiveness of said GnRH agonist is not substantially reduced.

9. A method of administering an endometriosis altered risk treatment, said method comprising the steps of:
   identifying an endometriosis asymptomatic human female subject,
   obtaining clinical data (CD) and a biological sample of said subject, said CD defining the answers to the questions of "menarche after age 14 (Y/N)", "dysmenorrhea (Y/N)", and "previous pregnancy (Y/N)",
   assigning a raw clinical probability value (RCPV) to said CD,
   assaying said sample,
   detecting in said sample a plurality of endometriosis decreased risk associated biomarkers, each endometriosis decreased risk associated biomarker defining the minor allele of a biomarker of table 1 having an OR of less than 1.0 resulting in endometriosis decreased risk associated biomarker data,
   performing a statistical analysis using said RCPV and said endometriosis decreased risk associated biomarker data to result in an endometriosis condition prognosis of said subject of at least one of a decreased risk of endometriosis existence and a decreased risk of endometriosis predisposition, and
   administering an endometriosis altered risk treatment to said subject, said endometriosis altered risk treatment defining the cancellation of a planned administration of at least one of an estrogen containing composition, a progesterone containing composition, a progestin containing composition, a GnRH agonist, and a combination thereof.

10. The method of claim 9, wherein said plurality of endometriosis decreased risk associated biomarkers defines all of the biomarkers of table 1 having an OR of less than 1.0.

11. The method of claim 9, wherein said plurality of endometriosis decreased risk associated biomarkers defines all of the biomarkers of set 01 of table 1 having an OR of less than 1.0.

12. The method of claim 9, wherein said plurality of endometriosis decreased risk associated biomarkers includes SEQ ID NO: 0786.

13. The method of claim 9, wherein said estrogen containing composition is in the form of an oral contraceptive pill, and wherein said progesterone containing composition is in the form of an oral contraceptive pill, and wherein said progestin containing composition is in the form of an oral contraceptive pill, and wherein said GnRH agonist is in the form of an oral contraceptive pill.

14. The method of claim 9, wherein said progesterone further defines at least one progesterone of desogestrel, drospirenone, ethynodiol, levonorgestrel, norethindrone, norgestimate, and norgestrel, and wherein said estrogen defines at least one estrogen of mestranol, estradiol, and ethinyl, and wherein said testosterone defines danazol.

15. A method of administering a hormonal treatment, said method comprising the steps of:
   identifying an endometriosis asymptomatic human female subject,
   obtaining clinical data (CD) of said subject,
   detecting in the DNA of said subject at least one endometriosis altered risk associated biomarker (EAB) defining the minor allele of at least one biomarker of table 1 having an OR of greater than 1.0, and
   administering a hormonal treatment to said subject.

16. The method of claim 15, wherein said at least one EAB defines all of the biomarkers of table 1 having an OR of greater than 1.0.

17. The method of claim 15, wherein said at least one EAB defines all of the biomarkers of set 01 of table 1 having an OR of greater than 1.0.

18. The method of claim 15, wherein said hormonal treatment defines at least one of a drug that alters a hormone level, a surgical procedure that alters a hormone level, and a combination thereof.

19. A method comprising applying an endometriosis increased risk therapeutic to a patient based on at least one endometriosis increased risk associated biomarker defining the minor allele of a biomarker of table 1 having an OR of greater than 1.0 known to be present in the DNA of said patient.

20. The method of claim 19, wherein said at least one endometriosis increased risk associated biomarker includes all of biomarkers of table 1 having an OR of greater than 1.0.

21. The method of claim 19, wherein said endometriosis increased risk therapeutic defines administering a hormonal treatment to said patient.

22. The method of claim 21, wherein said hormonal treatment defines at least one of administering a composition to said subject in an amount effective to alter the hormone level of said subject, performing a surgical procedure on said subject, and a combination thereof.

23. The method of claim 22, wherein said composition defines a defines at least one of an estrogen containing composition, a progesterone containing composition, a progestin containing composition, a gonadotropin releasing-hormone (GnRH) agonist, and a combination thereof.

24. The method of claim 19, wherein said at least one endometriosis increased risk associated biomarker defines all of the biomarkers of set 01 of table 1 having an OR of greater than 1.0.

25. The method of claim 19, wherein said endometriosis increased risk associated biomarker includes SEQ ID NO:0011.

26. The method of claim 19, wherein said applying step is preceded by the step of obtaining clinical data (CD) of said patient.

27. The method of claim 19, wherein said patient defines an endometriosis asymptomatic human female.

28. A method comprising applying an endometriosis decreased risk therapeutic to a patient based on at least one endometriosis decreased risk associated biomarker defining the minor allele of a biomarker of table 1 having an OR of less than 1.0 known to be present in the DNA of said patient.

29. The method of claim 28, wherein said endometriosis decreased risk associated biomarker includes all of biomarkers of table 1 having an OR of less than 1.0.

30. The method of claim 28, wherein said decreased risk therapeutic defines canceling a contemplated hormonal treatment of said patient.

31. The method of claim 30, wherein said hormonal treatment defines at least one of administering a composition to said subject in an amount effective to alter the hormone level of said subject, performing a surgical procedure on said subject, and a combination thereof.

32. The method of claim 31, wherein said composition defines a defines at least one of an estrogen containing composition, a progesterone containing composition, a progestin containing composition, a gonadotropin releasing-hormone (GnRH) agonist, and a combination thereof.

33. The method of claim 28, wherein said at least one endometriosis decreased risk associated biomarker defines the minor allele of all of the biomarkers of set 01 of table 1 having an OR of less than 1.0.

34. The method of claim 28, wherein said endometriosis decreased risk associated biomarker includes SEQ ID NO:0786.

35. The method of claim 28, wherein said applying step is preceded by the step of obtaining clinical data (CD) of said patient.

36. The method of claim 28, wherein said patient defines an endometriosis asymptomatic human female.

* * * * *